(12) United States Patent
Morrison et al.

(10) Patent No.: US 10,182,984 B2
(45) Date of Patent: Jan. 22, 2019

(54) TARGETED INTERFERONS DEMONSTRATE POTENT APOPTOTIC AND ANTI-TUMOR ACTIVITIES

(71) Applicant: The Regents of the University of California, Oakland, CA (US)

(72) Inventors: Sherie L. Morrison, Los Angeles, CA (US); Tzu-Hsuan Huang, Libertyville, IL (US); Caiyun Xuan, Newton, MA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/359,456

(22) Filed: Nov. 22, 2016

(65) Prior Publication Data

US 2017/0151342 A1   Jun. 1, 2017

Related U.S. Application Data

(63) Continuation of application No. 14/015,838, filed on Aug. 30, 2013, now Pat. No. 9,534,033, which is a continuation of application No. 12/985,122, filed on Jan. 5, 2011, now Pat. No. 8,563,692, which is a continuation of application No. 12/650,329, filed on Dec. 30, 2009, now Pat. No. 8,258,263, which is a continuation-in-part of application No. PCT/US2008/077074, filed on Sep. 19, 2008.

(60) Provisional application No. 60/994,717, filed on Sep. 21, 2007.

(51) Int. Cl.
| | |
|---|---|
| *A61K 38/00* | (2006.01) |
| *A61K 38/21* | (2006.01) |
| *A61K 39/00* | (2006.01) |
| *A61K 47/68* | (2017.01) |
| *C07K 14/56* | (2006.01) |
| *C07K 14/555* | (2006.01) |
| *C07K 14/565* | (2006.01) |
| *C07K 16/28* | (2006.01) |
| *C07K 16/32* | (2006.01) |
| *A61K 9/00* | (2006.01) |

(52) U.S. Cl.
CPC .......... *A61K 9/0019* (2013.01); *A61K 38/212* (2013.01); *A61K 38/215* (2013.01); *A61K 47/6813* (2017.08); *A61K 47/6851* (2017.08); *A61K 47/6855* (2017.08); *A61K 47/6875* (2017.08); *C07K 14/555* (2013.01); *C07K 14/56* (2013.01); *C07K 14/565* (2013.01); *C07K 16/2863* (2013.01); *C07K 16/2887* (2013.01); *C07K 16/32* (2013.01); *A61K 38/00* (2013.01); *A61K 2039/505* (2013.01); *C07K 2317/24* (2013.01); *C07K 2317/622* (2013.01); *C07K 2319/33* (2013.01)

(58) Field of Classification Search
CPC .... A61K 38/00; A61K 38/212; A61K 38/215; A61K 2039/505; A61K 39/39558; A61K 47/6813; A61K 47/6851; A61K 47/6855; A61K 47/6875; C07K 2317/24; C07K 14/56; C07K 16/2887; C07K 16/32; C07K 2319/33; C07K 16/2863; C07K 14/565; C07K 2317/622; C07K 14/555
See application file for complete search history.

(56) References Cited

U.S. PATENT DOCUMENTS

| | | |
|---|---|---|
| 5,696,237 A | 12/1997 | Fitzgerald et al. |
| 5,824,782 A | 10/1998 | Hölzer et al. |
| 5,980,895 A | 11/1999 | Pastan et al. |
| 6,428,788 B1 | 8/2002 | Debinski et al. |
| 6,800,735 B2 | 10/2004 | Whitty et al. |
| 6,893,625 B1 | 5/2005 | Robinson et al. |
| 7,005,498 B1 | 2/2006 | Steinaa et al. |
| 7,151,164 B2 | 12/2006 | Hansen et al. |
| 7,919,078 B2 | 4/2011 | Schreiber et al. |
| 8,258,263 B2 | 9/2012 | Morrison et al. |
| 8,563,692 B2 | 10/2013 | Morrison et al. |
| 9,139,634 B2 | 9/2015 | Morrison et al. |
| 9,534,033 B2 | 1/2017 | Morrison et al. |
| 9,803,021 B2 | 10/2017 | Morrison |
| 2002/0193569 A1 | 12/2002 | Hanna |
| 2003/0219433 A1 | 11/2003 | Hansen et al. |
| 2004/0005647 A1 | 1/2004 | Denardo et al. |
| 2005/0008649 A1 | 1/2005 | Shin et al. |
| 2005/0079154 A1 | 4/2005 | Yarkoni et al. |
| 2005/0232931 A1 | 10/2005 | Ma et al. |
| 2006/0228300 A1 | 10/2006 | Chang et al. |
| 2006/0263368 A1 | 11/2006 | Rosenblum et al. |
| 2006/0287509 A1 | 12/2006 | Marks et al. |
| 2008/0166319 A1 | 7/2008 | Schreiber et al. |

(Continued)

FOREIGN PATENT DOCUMENTS

| | | |
|---|---|---|
| CN | 1751122 A | 3/2006 |
| JP | 11-505132 A | 5/1999 |

(Continued)

OTHER PUBLICATIONS

Theofilopoulos, A.N., et al. Type I interferons (alpha/beta) in immunity and autoimmunity. Annual Reviews of Immunology, vol. 23, p. 307-336.*

(Continued)

*Primary Examiner* — Robert S Landsman
*Assistant Examiner* — Bruce D. Hissong
(74) *Attorney, Agent, or Firm* — Tom Hunter; Weaver Austin Villeneuve & Sampson LLP

(57) ABSTRACT

Novel chimeric moieties that show significant efficacy against cancers are provided. In certain embodiments the chimeric moieties comprise a targeting moiety attached to an interferon. In certain embodiments, the chimeric moieties comprise fusion proteins where an antibody that specifically binds to a cancer marker is fused to interferon alpha (IFN-α) or interferon beta (IFN-β).

17 Claims, 32 Drawing Sheets

Specification includes a Sequence Listing.

(56) References Cited

U.S. PATENT DOCUMENTS

| | | |
|---|---|---|
| 2010/0047164 A1 | 2/2010 | Bigner et al. |
| 2010/0172868 A1 | 7/2010 | Morrison et al. |
| 2010/0297076 A1 | 11/2010 | Morrison et al. |
| 2011/0104112 A1 | 5/2011 | Morrison et al. |
| 2011/0123554 A1 | 5/2011 | Osterroth et al. |
| 2011/0165122 A1 | 7/2011 | Shahangian et al. |
| 2011/0171229 A1 | 7/2011 | Ferrone et al. |
| 2012/0237442 A1 | 9/2012 | Rossi et al. |
| 2012/0258073 A1 | 10/2012 | Gerdes et al. |
| 2014/0079668 A1 | 3/2014 | Morrison et al. |
| 2016/0115239 A1 | 4/2016 | Morrison |
| 2016/0115242 A1 | 4/2016 | Morrison et al. |

FOREIGN PATENT DOCUMENTS

| | | |
|---|---|---|
| JP | 11-513669 A | 11/1999 |
| JP | 2003-508023 A | 3/2003 |
| JP | 2003-535908 A | 12/2003 |
| JP | 2004-93527 A | 3/2004 |
| JP | 2004-528014 A | 9/2004 |
| JP | 2005-520853 A | 7/2005 |
| JP | 2006-500904 A | 1/2006 |
| JP | 2008-505174 A | 2/2008 |
| JP | 2009-511495 A | 3/2009 |
| JP | 5591701 B2 | 9/2014 |
| WO | WO 97/13529 A1 | 4/1997 |
| WO | WO 97/24137 | 7/1997 |
| WO | WO 01/03737 A1 | 1/2001 |
| WO | WO 01/097844 A1 | 12/2001 |
| WO | WO 02/46227 A2 | 6/2002 |
| WO | WO 03/068821 A2 | 8/2003 |
| WO | WO 2003/080106 A1 | 10/2003 |
| WO | WO 2004/074486 A2 | 9/2004 |
| WO | WO 2006/000448 A2 | 1/2006 |
| WO | WO 2006/010891 A2 | 2/2006 |
| WO | WO 2006/019447 A1 | 2/2006 |
| WO | WO 2006/127757 A2 | 11/2006 |
| WO | WO 2007/027106 A1 | 3/2007 |
| WO | WO 2007/044616 A2 | 4/2007 |
| WO | WO 2009/039409 A1 | 3/2009 |
| WO | WO 2009/134870 A1 | 11/2009 |
| WO | WO 2012/075324 A1 | 6/2012 |
| WO | WO 2013/050725 A1 | 4/2013 |
| WO | WO 2014/089354 A1 | 6/2014 |
| WO | WO 2014/194100 A1 | 12/2014 |

OTHER PUBLICATIONS

U.S. Office Action [Requirement for Restriction/Election] dated May 13, 2016 issued in U.S. Appl. No. 14/649,888.
U.S. Office Action dated Oct. 3, 2016 issued in U.S. Appl. No. 14/649,888.
U.S. Notice of Allowance dated Jun. 16, 2017 issued in U.S. Appl. No. 14/649,888.
U.S. Office Action [Requirement for Restriction/Election] dated Mar. 10, 2011 issued in U.S. Appl. No. 12/678,981.
U.S. Office Action dated Jul. 5, 2011 issued in U.S. Appl. No. 12/678,981.
U.S. Office Action dated Jun. 14, 2012 issued in U.S. Appl. No. 12/678,981.
U.S. Final Office Action dated Mar. 26, 2013 issued in U.S. Appl. No. 12/678,981.
U.S. Office Action dated Jun. 17, 2014 issued in U.S. Appl. No. 12/678,981.
U.S. Ex Parte Quayle Action dated Mar. 3, 2015 issued in U.S. Appl. No. 12/678,981.
U.S. Notice of Allowance dated May 14, 2015 issued in U.S. Appl. No. 12/678,981.
U.S. Office Action dated Feb. 1, 2011 issued in U.S. Appl. No. 12/650,329.
U.S. Office Action dated Aug. 8, 2011 issued in U.S. Appl. No. 12/650,329.
U.S. Final Office Action dated Apr. 30, 2012 issued in U.S. Appl. No. 12/650,329.
U.S. Notice of Allowance dated Jun. 18, 2012 issued in U.S. Appl. No. 12/650,329.
U.S. Office Action dated Jul. 6, 2012 issued in U.S. Appl. No. 12/985,122.
U.S. Final Office Action dated Apr. 2, 2013 issued in U.S. Appl. No. 12/985,122.
U.S. Notice of Allowance dated Aug. 9, 2013 issued in U.S. Appl. No. 12/985,122.
U.S. Office Action dated Mar. 19, 2015 issued in U.S. Appl. No. 14/015,838.
U.S. Final Office Action dated Dec. 18, 2015 issued in U.S. Appl. No. 14/015,838.
U.S. Notice of Allowance dated Aug. 24, 2016 issued in U.S. Appl. No. 14/015,838.
PCT International Search Report and Written Opinion dated Mar. 18, 2014 issued in PCT/US2013/073410.
PCT International Preliminary Report on Patentability and Written Opinion dated Jun. 18, 2015 issued in PCT/US2013/073410.
PCT International Search Report and Written Opinion dated Jan. 12, 2009 issued in PCT/US08/77074 (WO2009/039409).
PCT International Preliminary Report on Patentability dated Mar. 24, 2010 issued in PCT/US08/77074 (WO2009/039409).
PCT International Search Report and Written Opinion dated Oct. 1, 2014 issued in PCT/US2014/040036.
PCT International Report on Patentability and Written Opinion dated Dec. 10, 2015 issued in PCT/US2014/040036.
Australian Office Action dated Feb. 26, 2013 issued in 2008302111.
Canadian Examiner's Report dated Feb. 4, 2015 issued in 2,699,944.
Canadian Examiner's Report dated Mar. 10, 2016 issued in 2,699,944.
Canadian Examiner's Report dated Nov. 22, 2016 issued in 2,699,944.
Chinese First Office Action dated May 2, 2012 issued in CN200880117225.8.
Chinese Second Office Action dated Feb. 4, 2013 issued in CN200880117225.8.
Chinese Third Office Action dated Jul. 15, 2013 issued in CN200880117225.8.
Chinese Final Rejection dated Jan. 6, 2014 issued in CN200880117225.8.
Chinese First Office Action dated Jul. 17, 2015 issued in CN201410160383.9.
Chinese Second Office Action dated Jun. 6, 2016 issued in CN201410160383.9.
Chinese Third Office Action dated Feb. 16, 2017 issued in CN201410160383.9.
European Extended Search Report dated Apr. 26, 2012 issued in EP08831632.8.
European Office Action dated Feb. 8, 2013 issued in EP08831632.8.
European Summons to attend Oral Proceedings dated Oct. 14, 2013 issued in EP08831632.8.
European Response [EP Summons to attend Oral Proceedings dated Oct. 14, 2013] dated Jan. 7, 2014 for EP08831632.8.
European Findings upon submission relating to Oral Proceedings dated Jan. 13, 2014 issued in EP08831632.8.
European Brief Communication [regarding the Oral Proceedings of Mar. 13, 2014] dated Jan. 16, 2014 issued in EP08831632.8.
European Written Submission [response to Communication dated Jan. 16, 2014] dated Jan. 29, 2014 issued in EP08831632.8.
European Findings upon submission relating to Oral Proceedings dated Feb. 10, 2014 issued in EP08831632.8.
European Notification relating to Oral Proceedings dated Feb. 13, 2014 issued in EP08831632.8.
European Communication regarding Intention to Grant dated Mar. 4, 2014 issued in EP08831632.8.
European Communication regarding Intention to Grant dated Oct. 2, 2014 issued in EP08831632.8.
European Communication regarding Decision to Grant dated Jan. 15, 2015 issued in EP08831632.8.
European Extended Search Report dated Feb. 26, 2015 issued in EP 14 180 412.0.
European Office Action dated Dec. 11, 2015 issued in EP 14 180 412.0.

(56) References Cited

OTHER PUBLICATIONS

European Reply to Communication from Examining Division dated Mar. 29, 2016 for EP 14 180 412.0.
European Intention to Grant dated Jun. 24, 2016 issued in EP 14 180 412.0.
European Decision to Grant dated Nov. 10, 2016 issued in EP 14 180 412.0.
European Extended Search Report dated Feb. 24, 2017 issued in EP 16 19 5608.1.
Israeli Office Action dated Apr. 5, 2012 issued in IL-204644.
Israeli Office Action dated Apr. 17, 2013 issued in IL-204644.
Israeli Office Action dated Apr. 19, 2015 issued in IL-233305.
Israeli Office Action dated Nov. 24, 2016 issued in IL-233305.
Indian Office Action dated Dec. 30, 2016 issued in IN-1404/KOLNP/2010.
Japanese Office Action dated Jan. 29, 2013 issued in JP 2010-526011.
Japanese Final Office Action dated Mar. 10, 2014 issued in JP 2010-526011.
Japanese First Office Action dated Jul. 6, 2015 issued in JP 2014-154820.
Japanese Second Office Action dated Jul. 4, 2016 issued in JP 2014-154820.
Japanese Notice of Allowance [No Translation] dated Jan. 4, 2017 issued in JP 2014-154820.
Korean Office Action dated Mar. 27, 2015 issued in KR 2010-7008737.
Korean Final Rejection dated Feb. 25, 2016 issued in KR 2010-7008737.
Korean Office Action dated Jun. 21, 2016 issued in KR 2016-7014105.
Mexican Office Action [no translation] dated May 7, 2013 issued in MX/a/2010/003099.
Mexican Office Action [no translation] dated Feb. 12, 2014 issued in MX/a/2010/003099.
Mexican Office Action [brief description in English] dated Apr. 25, 2016 issued in MX/a/2014/010567.
Mexican Second Office Action [no translation] dated Nov. 10, 2016 issued in MX/a/2014/010567.
NCBI, GenBank accession No. CAP17327.1, "interferon gamma [*Homo sapiens*]", (Oct. 15, 2008), 2pp.
Alfthan et al. (1995) "Properties of a single-chain antibody containing different linker peptides," *Protein Engineering* 8(7):725-731.
Arai et al. (Aug. 2001) "Design of the linkers which effectively separate domains of a bifunctional fusion protein," *Protein Engineering*, 14(8):529-532.
Bai et al. (Sep. 2006) "Improving the oral efficacy of recombinant granulocyte colony stimulating factor and transferrin fusion protein by spacer optimization," *Pharmaceutical Research*, 23(9):2116-2121.
Berger et al. (2002) "Licensure of Gemtuzumab Ozogamicin for the Treatment of Selected Patients 60 Years of Age or Older with Acute Myeloid Leukemia in First Relapse," *Invest. New Drugs*, 20(4):395-406.
Bird et al. (1988) "Single-Chain Antigen-Binding Proteins," *Science*, 242:423-426.
Bosly et al. (2004) "Role of anti-CD20 monoclonal antibody in association with immunomodulatory agents," *Pathologic Biologie* 52:39-42 [English Abstract Only].
Cheng et al. (2008) "Antibody-fused interferons as an effective approach to enhance target specificity and antiviral efficacy of type I interferons," *Cell Research* 18:1230-1232.
Curtis et al. (1991) "Enhanced hematopoietic activity of a human granulocyte/macrophage colony-stimulating factor-interleukin 3 fusion protein," *Proc. Natl. Acad. Sci. USA*, 88:5809-5813.
Dela Cruz et al. (2004) "Antibody-cytokine fusion proteins: innovative weapons in the war against cancer," *Clin Exp Med*, 4:57-64.

Ebbinghaus et al. (2004) "An Antibody-Interferon Gamma Fusion Protein for Cancer Therapy," *A dissertation submitted to the Swiss Federal Institute of Technology Zurich for the degree of Doctor of Natural Sciences* pp. 1-137.
Ebbinghaus et al. (2005) "Engineered vascular-targeting antibody-interferon-γ fusion protein for cancer therapy," *Int. J Cancer*, 116(2):304-313.
Field-Smith et al. (2006) "Bortezomib (Velcade™) in the treatment of multiple myeloma," *Therapeutics and Clinical Risk Management*, 2(3):271-279.
Flannery et al. (1984) "Immunomodulation: NK cells activated by interferon-conjugated monoclonal antibody against human osteosarcoma," *Eur J Cancer Clin Oncol.*, 20(6):791-798.
Frey et al. (2011) "Antibody-Based Targeting of Tumor Vasculature and Stroma," *The Tumor Microenvironment 4* Part VI Chapter 22:419-450.
Frey et al. (2011) "Antibody-based targeting of interferon-alpha to the tumor neovasculature: a critical evaluation," *Integr. Biol.*, 3:468-478.
Goldstein et al. (1988) "The role of interferon in cancer therapy: A current perspective," *CA Cancer J. Clin.*, 38(5):258-277.
Helguera et al. (2006) "Cytokines fused to antibodies and their combinations as therapeutic agents against different peritoneal HER2/neu expressing tumors," *Molecular Cancer Therapeutics, American Association of Cancer Research*, 5(4): 1029-1040.
Heuser et al. (2003) "Anti-CD30-IL-12 Antibody-Cytokine Fusion Protein That Induces IFN-Γ Secretion of T Cells and NK Cell-Mediated Lysis of Hodgkin's Lymphoma-Derived Tumor Cells," *Int. J. Cancer*, 106:545-552.
Huang et al. (2006) "Fusion of anti-HER2/ neu with inflammatory cytokines IFN-alpha and TNF-alpha results in molecules that elicit an anti-tumor response or potentiate wound healing," *Dissertation*, pp. 1-120 XP009158273.
Huang et al. (2007) "Targeting IFN-α to B cell lymphoma by a tumor-specific antibody elicits potent antitumor activities," *Journal of Immunology*, 179(10):6881-6888.
Huston et al. (1988) "Protein engineering of antibody binding sites: Recovery of specific activity in an anti-digoxin single-chain Fv analogue produced in *Escherichia coli,*" *Proc. Natl. Acad. Sci.*, 85:5879-5883.
Jain et al. (2007) "Engineering antibodies for clinical applications," *Trends in Biotechnology*, 25(7):307-316.
Kaspar et al. (2007) "The Antibody-Mediated Targeted Delivery of Interleukin-15 and GM-CSF to the Tumor Neovasculature Inhibits Tumor Growth and Metastasis," *Cancer Res*, 67(10):4940-4948.
Klimka et al. (2003) "Construction of proteolysis resistant human interleukin-2 by fusion to its protective single chain antibody," *Cytokine*, 22:134-141.
McCarron et al. (2005) "Antibody Conjugates and Therapeutic Strategies," *Molecular Interventions*, 5(6):368-380.
Marshall et al. (2001) "Engineering and Characterization of a Novel Fusion Protein Incorporating B7.2 and an Anti-ErbB-2 Single-Chain Antibody Fragment for the Activation of Jurkat T Cells," *J. Immunotherapy*, 24(1):27-36.
Mickle, John E.; Ph.D. et al. (2000) "Genotype-Phenotype Relationships in Cystic Fibrosis," *Med. Clin. N. America*, 84(3):597-607.
Mizokami et al. (2003) "Chimeric TNT-3 Antibody/Murine Interferon-γ Fusion Protein for the Immunotherapy of Solid Malignancies," *Hybridoma and Hybridomics*, 22(4): 197-207.
Ozzello et al. (1998) "Conjugation of interferon alpha to a humanized monoclonal antibody (HuBrE-3v1) enhances the selective localization and antitumor effects of interferon in breast cancer xenografts," *Breast Cancer Res Treat.*, 48(2):135-47.
Peng et al. (1999) "A Single-Chain IL-12 IgG3 Antibody Fusion Protein Retains Antibody Specificity and IL-12 Bioactivity and Demonstrates Antitumor Activity," *J. Immunol.*, 163:250-258.
Portlock et al. (2006) "Pegylated interferon plus rituximab in advanced stage, indolent lymphoma: is there CD20 antigen upregulation?" *Leukemia & Lymphoma*, 47(7): 1260-1264.
Rossi et al. (2009) "CD20-targeted tetrameric interferon-, a novel and potent immunocytokine for the therapy of B-cell lymphomas," *Blood*, 114:3864-3871.

(56) References Cited

OTHER PUBLICATIONS

Rossi et al. (2010) "A Bispecific Antibody-IFNα2b Immunocytokine Targeting CD20 and HLA-DR Is Highly Toxic to Human Lymphoma and Multiple Myeloma Cells," *Cancer Res.*, 70:7600-7609.
Scharma et al. (2006) "Antibody targeted drugs as cancer therapeutics," *Nature Reviews Drug Discovery*, 5:147-159.
Seyfried et al. (2008) "Up-regulation of NG2 proteoglycan and interferon induced transmembrane proteins 1 and 3 in mouse astrocytoma: A membrane proteomics approach," *Cancer Letters*, 263(2):243-252.
Song et al. (2007) "Construction of Expression Vector of Anti-HBsAg dsFv and Alpha-IFN Fusion Gene," *Chinese Journal of Public Health*, 23(9):1096-1099 [English Abstract].
Takaoka et al. (Jul. 31, 2003) "Integration of interferon-α/β signalling to p53 responses in tumour suppression and antiviral defence," *Nature*, 424(6948):516-523.
von Gabain, A., et al. (1990) "Three human interferon-α2 subvariants disclose structural and functional differences," *Eur. J Biochem.*, 190:257-261.
Wei et al. (1998) "Clone and expression of a fusion protein consisting of anti-HBsAg Fab fragment and interferon-α in *E. coli*," *Chinese Journal of Hepatology*, 6(4):229-231 [Abstract Only].
Wells, J.A., (Sep. 18, 1990) "Additivity of Mutational Effects in Proteins," *Biochemistry*, 29(37):8509-8517.
Xuan et al. (2010) "Targeted delivery of interferon-alpha via fusion to anti-CD20 results in potent antitumor activity against B-cell lymphoma," *Blood*, 115(14):2864-2871.
Yoo et al. (Dec. 11, 2012) Anti-CD138-IFNα Fusion Proteins are Effective in Treating Multiple Myeloma, In: *54th American Society of Hematology Annual Meeting and Exposition*, Atlanta, GA, Abstract No. 939, 1 page.
Zaidi et al. (2011) "The two faces of interferon-gamma in cancer," *Clin. Cancer Res.*, 17(19):1-7.
Zheng et al. (1998) "The Construction and Expression of a Fusion Protein Consisting of anti-HBsAg Antibody Fragment Fab and interferon-αA in *E. coli*," *Chinese Journal of Hepatology*, 6(4):229-231 [English Abstract Only].
U.S. Office Action dated Aug. 10, 2017 issued in U.S. Appl. No. 14/893,912.
European Office Action dated Nov. 29, 2017 issued in EP 16 19 5608.1.
Indian Office Action (Hearing Notice) dated Nov. 29, 2017 issued in IN-1404/KOLNP/2010.
Japanese First Office Action dated Jul. 31, 2017 issued in JP 2016-215048.
Ozzello et al. (1993) "The use of natural interferon alpha conjugated to a monoclonal antibody anti mammary epithelial mucin (Mc5) for the treatment of human breast cancer xenografts," *Breast Cancer Res Treat.*, 25(3):265-276.
Pallela et al. (2000) "Interferon-α-2b immunoconjugate for improving immunoscintigraphy and immunotherapy," *The Journal of Nuclear Medicine*, 41(6): 1108-1113.
Thakur et al. (1997) "Improved antibody targeting with interferon-α-2b conjugate," *Journal of Immunotherapy*, 20(3): 194-201.
Theofilopoulos et al. (2014) "Type I interferons (alpha/beta) in immunity and autoimmunity." *Annual Reviews of Immunology*, 23: 307-336.

\* cited by examiner

Anti-HER2/neu IgG3 heavy chain IFNα

```
M G W S W V M H L S P V S N C G V H S Q V Q L V Q S G A E V K K
P G E S L K I S C K G S G Y S F T S Y W I A W V R Q M P G K G L
E Y M G L I Y P G D S D T K Y S P S F Q G Q V T I S V D K S V S
T A Y L Q W S S L K P S D S A V Y F C A R H D V G Y C T D R T C
A K W P E Y F Q H W G Q G T L V T V S S A S T K G P S V F P L A
P C S R S T S G G T A A L G C L V K D Y F P E P V T V S W N S G
A L T S G V H T F P A V L Q S S G L Y S L S S V V T V P S S S L
G T Q T Y T C N V N H K P S N T K V D K R V E L K T P L G D T T
H T C P R C P E P K S C D T P P P C P R C P E P K S C D T P P P
C P R C P E P K S C D T P P P C P R C P A P E L L G G P S V F L
F P P K P K D T L M I S R T P E V T C V V V D V S H E D P E V Q
F K W Y V D G V E V H N A K T K L R E E Q Y N S T F R V V S V L
T V L H Q D W L N G K E Y K C K V S N K A L P A P I E K T I S K
A K G Q P R E P Q V Y T L P P S R E E M T K N Q V S L T C L V K
G F Y P S D I A V E W E S N G Q P E N N Y N T T P P M L D S D G
S F F L Y S K L T V D K S R W Q Q G N I F S C S V M H E A L H N
H Y T Q K S L S L S P G K S G G G G S G G G G S G G G G S C D L
P Q T H N L R N K R A L T L L V Q M R R L S P L S C L K D R K D
F G F P Q E K V D A Q Q I K K A Q A I P V L S E L T Q Q I L N I
F T S K D S S A A W N A T L L D S F C N D L H Q Q L N D L Q G C
L M Q Q V G V Q E F P L T Q E D A L L A V R K Y F H R I T V Y L
R E K K H S P C A W E V V R A E V W R A L S S A N V L G R L R
E E K
```

Anti-HER2/neu IgG3-IFNα light chain sequence

αCD20-IgG3-huIFNα Gly₄Ser linker - nucleic acid sequence

```
ATGTACTTGGGACTGAACTGTGTAATCATAGTTTTTCTCTTAAAAGGTGTCCAGAGTCAGGTACAACTG
CAGCAGCCTGGGGCTGAGCTGGTGAAGCCTGGGGCCTCAGTGAAGATGTCCTGCAAGGCTTCTGGCTAC
ACATTTACCAGTTACAATATGCACTGGGTAAAACAGACACCTGGTCGGGGCCTGGAATGGATTGGAGCT
ATTTATCCCGGAAATGGTGATACTTCCTACAATCAGAAGTTCAAAGGCAAGGCCACATTGACTGCAGAC
AAATCCTCCAGCACAGCCTACATGCAGCTCAGCAGCCTGACATCTGAGGACTCTGCGGTCTATTACTGT
GCAAGATCGACTTACTACGGCGGTGACTGGTACTTCAATGTCTGGGGCGCAGGGACCACGGTCACCGTC
TCTGCAGCTAGCACCAAGGGCCCATCGGTCTTCCCCCTGGCGCCCTGCTCCAGGAGCACCTCTGGGGGC
ACAGCGGCCCTGGGCTGCCTGGTCAAGGACTACTTCCCCGAACCGGTGACGGTGTCGTGGAACTCAGGC
GCCCTGACCAGCGGCGTGCACACCTTCCCGGCTGTCCTACAGTCCTCAGGACTCTACTCCCTCAGCAGC
GTGGTGACCGTGCCCTCCAGCAGCTTGGGCACCCAGACCTACACCTGCAACGTGAATCACAAGCCCAGC
AACACCAAGGTGGACAAGAGAGTTGAGCTCAAAACCCCACTTGGTGACACAACTCACACATGCCCACGG
TGCCCAGAGCCCAAATCTTGTGACACACCTCCCCCGTGCCCAAGGTGCCCAGAGCCCAAATCTTGTGAC
ACACCTCCCCGTGCCCAAGGTGCCCAGAGCCCAAATCTTGTGACACACCTCCCCGTGCCCAAGGTGC
CCAGCACCTGAACTCCTGGGAGGACCGTCAGTCTTCCTCTTCCCCCCAAAACCCAAGGATACCCTTATG
ATTTCCCGGACCCCTGAGGTCACGTGCGTGGTGGTGGACGTGAGCCACGAAGACCCCGAGGTCCAGTTC
AAGTGGTACGTGGACGGCGTGGAGGTGCATAATGCCAAGACAAAGCTGCGGGAGGAGCAGTACAACAGC
ACGTTCCGTGTGGTCAGCGTCCTCACCGTCCTGCACCAGGACTGGCTGAACGGCAAGGAGTACAAGTGC
AAGGTCTCCAACAAAGCCCTCCCAGCCCCCATCGAGAAAACCATCTCCAAAGCCAAAGGACAGCCCCGA
GAACCACAGGTGTACACCCTGCCCCCATCCCGGGAGGAGATGACCAAGAACCAGGTCAGCCTGACCTGC
CTGGTCAAAGGCTTCTACCCCAGCGACATCGCCGTGGAGTGGGAGAGCAATGGGCAGCCGGAGAACAAC
TACAACACCACGCCTCCCATGCTGGACTCCGACGGCTCCTTCTTCCTCTACAGCAAGCTCACCGTGGAC
AAGAGCAGGTGGCAGCAGGGGAACATCTTCTCATGCTCCGTGATGCATGAGGCTCTGCACAACCACTAC
ACGCAGAAGAGCCTCTCCCTGTCTCCGGGTAAATCTGGTGGCGGTGGATCCTGTGATCTGCCTCAAACC
CACAGCCTGGGTAGCAGGAGGACCTTGATGCTCCTGGCACAGATGAGGAGAATCTCTCTTTTCTCCTGC
TTGAAGGACAGACATGACTTTGGATTTCCCCAGGAGGAGTTTGGCAACCAGTTCCAAAAGGCTGAAACC
ATCCCTGTCCTCCATGAGATGATCCAGCAGATCTTCAATCTCTTCAGCACAAAGGACTCATCTGCTGCT
TGGGATGAGACCCTCCTAGACAAATTCTACACTGAACTCTACCAGCAGCTGAATGACCTGGAAGCCTGT
GTGATACAGGGGGTGGGGGTGACAGAGACTCCCCTGATGAAGGAGGACTCCATTCTGGCTGTGAGGAAA
TACTTCCAAAGAATCACTCTCTATCTGAAAGAGAAGAAATACAGCCCTTGTGCCTGGGAGGTTGTCAGA
GCAGAAATCATGAGATCTTTTTCTTTGTCAACAAACTTGCAAGAAAGTTTAAGAAGTAAGGAA
```

αCD20-IgG3-huIFNα Gly₄Ser linker - amino acid sequence

```
MYLGLNCVIIVFLLKGVQSQVQLQQPGAELVKPGASVKMSCKASGYTFTSYNMHWVKQTPGRGLEWIGA
IYPGNGDTSYNQKFKGKATLTADKSSSTAYMQLSSLTSEDSAVYYCARSTYYGGDWYFNVWGAGTTVTV
SAASTKGPSVFPLAPCSRSTSGGTAALGCLVKDYFPEPVTVSWNSGALTSGVHTFPAVLQSSGLYSLSS
VVTVPSSSLGTQTYTCNVNHKPSNTKVDKRVELKTPLGDTTHTCPRCPEPKSCDTPPPCPRCPEPKSCD
TPPPCPRCPEPKSCDTPPPCPRCPAPELLGGPSVFLFPPKPKDTLMISRTPEVTCVVVDVSHEDPEVQF
KWYVDGVEVHNAKTKLREEQYNSTFRVVSVLTVLHQDWLNGKEYKCKVSNKALPAPIEKTISKAKGQPR
EPQVYTLPPSREEMTKNQVSLTCLVKGFYPSDIAVEWESNGQPENNYNTTPPMLDSDGSFFLYSKLTVD
KSRWQQGNIFSCSVMHEALHNHYTQKSLSLSPGKSGGGGSCDLPQTHSLGSRRTLMLLAQMRRISLFSC
LKDRHDFGFPQEEFGNQFQKAETIPVLHEMIQQIFNLFSTKDSSAAWDETLLDKFYTELYQQLNDLEAC
VIQGVGVTETPLMKEDSILAVRKYFQRITLYLKEKKYSPCAWEVVRAEIMRSFSLSTNLQESLRSKE
```

Fig. 1B

1. CFSE control  2. PBS or anti-HER2-IgG3
3. IgG3-IFN  4. anti-HER2-IgG3-IFN 3 copy Gly₃Ser ⟶ 1 copy Gly₃Ser

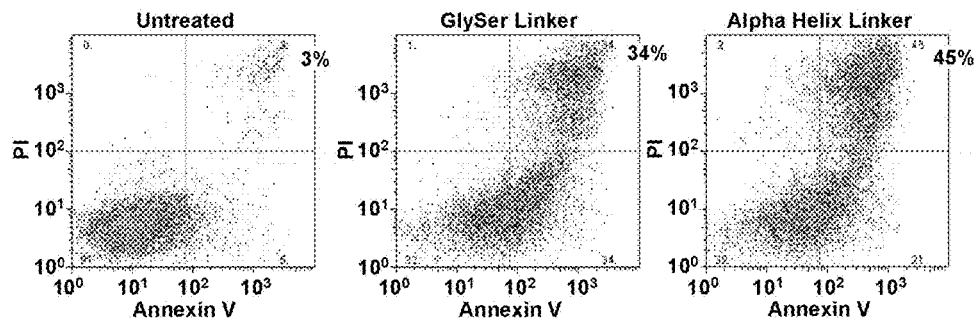

*Fig. 21*

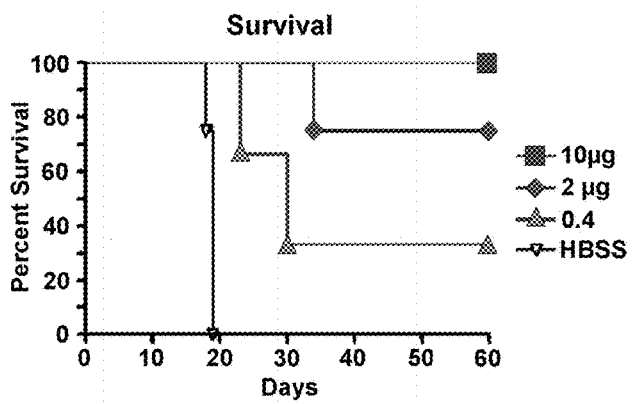

| Comparison of Survival curves | HBSS vs 10 ug | Comparison of Survival curves | HBSS vs 2 ug |
|---|---|---|---|
| Logrank Test | | Logrank Test | |
| Chi square | 6.628 | Chi square | 6.628 |
| df | 1 | df | 1 |
| P value | 0.0100 | P value | 0.0100 |
| P value summary | * | P value summary | * |
| Are the survival curves different? | yes | Are the survival curves different? | yes |
| Comparison of Survival curves | HBSS vs 0.4 ug | Comparison of Survival curves | 0.4 ug vs 2 ug |
| Logrank Test | | Logrank Test | |
| Chi square | 6.352 | Chi square | 3.282 |
| df | 1 | df | 1 |
| P value | 0.0207 | P value | 0.0701 |
| P value summary | * | P value summary | ns |
| Are the survival curves different? | yes | Are the survival curves different? | no |

*Fig. 22*

SEQUENCE LISTING

<160> NUMBER OF SEQ ID NOS: 82

<210> SEQ ID NO 1
<211> LENGTH: 707
<212> TYPE: PRT
<213> ORGANISM: Artificial
<220> FEATURE:
<223> OTHER INFORMATION: Fusion protein anti-HER2/neu IgG3 heavy chain-IFN

<400> SEQUENCE: 1

```
Met Gly Trp Ser Trp Val Met His Leu Ser Pro Val Ser Asn Cys Gly
  1               5                  10                  15

Val His Ser Gln Val Gln Leu Val Gln Ser Gly Ala Glu Val Lys Lys
             20                  25                  30

Pro Gly Glu Ser Leu Lys Ile Ser Cys Lys Gly Ser Gly Tyr Ser Phe
         35                  40                  45

Thr Ser Tyr Trp Ile Ala Trp Val Arg Gln Met Pro Gly Lys Gly Leu
     50                  55                  60

Glu Tyr Met Gly Leu Ile Tyr Pro Gly Asp Ser Asp Thr Lys Tyr Ser
 65                  70                  75                  80

Pro Ser Phe Gln Gly Gln Val Thr Ile Ser Val Asp Lys Ser Val Ser
                 85                  90                  95

Thr Ala Tyr Leu Gln Trp Ser Ser Leu Lys Pro Ser Asp Ser Ala Val
            100                 105                 110

Tyr Phe Cys Ala Arg His Asp Val Gly Tyr Cys Thr Asp Arg Thr Cys
        115                 120                 125

Ala Lys Trp Pro Glu Tyr Phe Gln His Trp Gly Gln Gly Thr Leu Val
    130                 135                 140

Thr Val Ser Ser Ala Ser Thr Lys Gly Pro Ser Val Phe Pro Leu Ala
145                 150                 155                 160

Pro Cys Ser Arg Ser Thr Ser Gly Gly Thr Ala Ala Leu Gly Cys Leu
                165                 170                 175

Val Lys Asp Tyr Phe Pro Glu Pro Val Thr Val Ser Trp Asn Ser Gly
            180                 185                 190

Ala Leu Thr Ser Gly Val His Thr Phe Pro Ala Val Leu Gln Ser Ser
        195                 200                 205

Gly Leu Tyr Ser Leu Ser Ser Val Val Thr Val Pro Ser Ser Ser Leu
    210                 215                 220

Gly Thr Gln Thr Tyr Thr Cys Asn Val Asn His Lys Pro Ser Asn Thr
225                 230                 235                 240

Lys Val Asp Lys Arg Val Glu Leu Lys Thr Pro Leu Gly Asp Thr Thr
                245                 250                 255

His Thr Cys Pro Arg Cys Pro Glu Pro Lys Ser Cys Asp Thr Pro Pro
            260                 265                 270

Pro Cys Pro Arg Cys Pro Glu Pro Lys Ser Cys Asp Thr Pro Pro Pro
        275                 280                 285

Cys Pro Arg Cys Pro Glu Pro Lys Ser Cys Asp Thr Pro Pro Pro Cys
    290                 295                 300

Pro Arg Cys Pro Ala Pro Glu Leu Leu Gly Gly Pro Ser Val Phe Leu
305                 310                 315                 320

Phe Pro Pro Lys Pro Lys Asp Thr Leu Met Ile Ser Arg Thr Pro Glu
                325                 330                 335

Val Thr Cys Val Val Val Asp Val Ser His Glu Asp Pro Glu Val Gln
            340                 345                 350
```

```
Phe Lys Trp Tyr Val Asp Gly Val Glu Val His Asn Ala Lys Thr Lys
            355                 360                 365

Leu Arg Glu Glu Gln Tyr Asn Ser Thr Phe Arg Val Val Ser Val Leu
    370                 375                 380

Thr Val Leu His Gln Asp Trp Leu Asn Gly Lys Glu Tyr Lys Cys Lys
385                 390                 395                 400

Val Ser Asn Lys Ala Leu Pro Ala Pro Ile Glu Lys Thr Ile Ser Lys
                405                 410                 415

Ala Lys Gly Gln Pro Arg Glu Pro Gln Val Tyr Thr Leu Pro Pro Ser
            420                 425                 430

Arg Glu Glu Met Thr Lys Asn Gln Val Ser Leu Thr Cys Leu Val Lys
            435                 440                 445

Gly Phe Tyr Pro Ser Asp Ile Ala Val Glu Trp Glu Ser Asn Gly Gln
            450                 455                 460

Pro Glu Asn Asn Tyr Asn Thr Thr Pro Pro Met Leu Asp Ser Asp Gly
465                 470                 475                 480

Ser Phe Phe Leu Tyr Ser Lys Leu Thr Val Asp Lys Ser Arg Trp Gln
                485                 490                 495

Gln Gly Asn Ile Phe Ser Cys Ser Val Met His Glu Ala Leu His Asn
            500                 505                 510

His Tyr Thr Gln Lys Ser Leu Ser Leu Ser Pro Gly Lys Ser Gly Gly
            515                 520                 525

Gly Gly Ser Gly Gly Gly Ser Gly Gly Gly Ser Cys Asp Leu
            530                 535                 540

Pro Gln Thr His Asn Leu Arg Asn Lys Arg Ala Leu Thr Leu Leu Val
545                 550                 555                 560

Gln Met Arg Arg Leu Ser Pro Leu Ser Cys Leu Lys Asp Arg Lys Asp
            565                 570                 575

Phe Gly Phe Pro Gln Glu Lys Val Asp Ala Gln Gln Ile Lys Lys Ala
            580                 585                 590

Gln Ala Ile Pro Val Leu Ser Glu Leu Thr Gln Gln Ile Leu Asn Ile
            595                 600                 605

Phe Thr Ser Lys Asp Ser Ser Ala Ala Trp Asn Ala Thr Leu Leu Asp
            610                 615                 620

Ser Phe Cys Asn Asp Leu His Gln Gln Leu Asn Asp Leu Gln Gly Cys
625                 630                 635                 640

Leu Met Gln Gln Val Gly Val Gln Glu Phe Pro Leu Thr Gln Glu Asp
                645                 650                 655

Ala Leu Leu Ala Val Arg Lys Tyr Phe His Arg Ile Thr Val Tyr Leu
            660                 665                 670

Arg Glu Lys Lys His Ser Pro Cys Ala Trp Glu Val Val Arg Ala Glu
            675                 680                 685

Val Trp Arg Ala Leu Ser Ser Ala Asn Val Leu Gly Arg Leu Arg
            690                 695                 700

Glu Glu Lys
705

<210> SEQ ID NO 2
<211> LENGTH: 237
<212> TYPE: PRT
<213> ORGANISM: Artificial
<220> FEATURE:
<223> OTHER INFORMATION: Antibody anti-HER2/neu IgG3 light chain
```

```
<400> SEQUENCE: 2

Met Gly Trp Ser Trp Val Ile Leu Phe Leu Leu Ser Val Thr Ala Gly
1               5                   10                  15

Val His Ser Gln Ser Val Leu Thr Gln Pro Pro Ser Val Ser Ala Ala
                20                  25                  30

Pro Gly Gln Lys Val Thr Ile Ser Cys Ser Gly Ser Ser Ser Asn Ile
            35                  40                  45

Gly Asn Asn Tyr Val Ser Trp Tyr Gln Gln Leu Pro Gly Thr Ala Pro
50                      55                  60

Lys Leu Leu Ile Tyr Asp His Thr Asn Arg Pro Ala Gly Val Pro Asp
65                  70                  75                  80

Arg Phe Ser Gly Ser Lys Ser Gly Thr Ser Ala Ser Leu Ala Ile Ser
                85                  90                  95

Gly Phe Arg Ser Glu Asp Glu Ala Asp Tyr Tyr Cys Ala Ser Trp Asp
            100                 105                 110

Tyr Thr Leu Ser Gly Trp Val Phe Gly Gly Gly Thr Lys Val Thr Val
        115                 120                 125

Leu Gly Arg Thr Val Ala Ala Pro Ser Val Phe Ile Phe Pro Pro Ser
130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 3
<211> LENGTH: 2064
<212> TYPE: DNA
<213> ORGANISM: Artificial
<220> FEATURE:
<223> OTHER INFORMATION: DNA encoding fusion protein anti-CD20-IgG3-
      huIFN

<400> SEQUENCE: 3
atgtacttgg gactgaactg tgtaatcata gttttctct  taaaggtgt  ccagagtcag    60 gtacaactgc agcagcctgg ggctgagctg gtgaagcctg gggcctcagt gaagatgtcc   120
tgcaaggctt ctggctacac atttaccagt tacaatatgc actgggtaaa acagacacct   180
ggtcggggcc tggaatggat tggagctatt tatcccggaa atggtgatac ttcctacaat   240
cagaagttca aggcaaggc cacattgact gcagacaaat cctccagcac agcctacatg    300
cagctcagca gcctgacatc tgaggactct gcggtctatt actgtgcaag atcgacttac   360
tacggcggtg actggtactt caatgtctgg ggcgcaggga ccacggtcac cgtctctgca   420
gctagcacca agggcccatc ggtcttcccc ctggcgccct gctccaggag cacctctggg   480
ggcacagcgg ccctgggctg cctggtcaag gactacttcc ccgaaccggt gacggtgtcg   540
tggaactcag cgccctgac cagcggcgtg cacaccttcc cggctgtcct acagtcctca   600
ggactctact ccctcagcag cgtggtgacc gtgccctcca gcagcttggg cacccagacc   660
```

```
tacacctgca acgtgaatca caagcccagc aacaccaagg tggacaagag agttgagctc    720
aaaaccccac ttggtgacac aactcacaca tgcccacggt gcccagagcc caaatcttgt    780
gacacacctc ccccgtgccc aaggtgccca gagcccaaat cttgtgacac acctcccccg    840
tgcccaaggt gcccagagcc caaatcttgt gacacacctc ccccgtgccc aaggtgccca    900
gcacctgaac tcctgggagg accgtcagtc ttcctcttcc ccccaaaacc caaggatacc    960
cttatgattt cccggacccc tgaggtcacg tgcgtggtgg tggacgtgag ccacgaagac   1020
cccgaggtcc agttcaagtg gtacgtggac ggcgtggagg tgcataatgc caagacaaag   1080
ctgcgggagg agcagtacaa cagcacgttc cgtgtggtca gcgtcctcac cgtcctgcac   1140
caggactggc tgaacggcaa ggagtacaag tgcaaggtct ccaacaaagc cctcccagcc   1200
cccatcgaga aaaccatctc caaagccaaa ggacagcccc gagaaccaca ggtgtacacc   1260
ctgcccccat cccgggagga gatgaccaag aaccaggtca gcctgacctg cctggtcaaa   1320
ggcttctacc ccagcgacat cgccgtggag tgggagagca atgggcagcc ggagaacaac   1380
tacaacacca cgcctcccat gctggactcc gacggctcct tcttcctcta cagcaagctc   1440
accgtggaca gagcaggtg gcagcagggg aacatcttct catgctccgt gatgcatgag   1500
gctctgcaca accactacac gcagaagagc ctctccctgt ctccgggtaa atctggtggc   1560
ggtggatcct gtgatctgcc tcaaacccac agcctgggta gcaggaggac cttgatgctc   1620
ctggcacaga tgaggagaat ctctcttttc tcctgcttga aggacagaca tgactttgga   1680
tttccccagg aggagtttgg caaccagttc caaaaggctg aaaccatccc tgtcctccat   1740
gagatgatcc agcagatctt caatctcttc agcacaaagg actcatctgc tgcttgggat   1800
gagacccctc tagacaaatt ctacactgaa ctctaccagc agctgaatga cctggaagcc   1860
tgtgtgatac agggggtggg ggtgacagag actcccctga tgaaggagga ctccattctg   1920
gctgtgagga aatacttcca aagaatcact ctctatctga agagaagaa atacagccct   1980
tgtgcctggg aggttgtcag agcagaaatc atgagatctt tttctttgtc aacaaacttg   2040
caagaaagtt taagaagtaa ggaa                                           2064
```

<210> SEQ ID NO 4
<211> LENGTH: 688
<212> TYPE: PRT
<213> ORGANISM: Artificial
<220> FEATURE:
<223> OTHER INFORMATION: Fusion protein for anti-CD20-IgG3-huIFN

<400> SEQUENCE: 4

```
Met Tyr Leu Gly Leu Asn Cys Val Ile Ile Val Phe Leu Leu Lys Gly
1               5                   10                  15

Val Gln Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110
```

```
Tyr Tyr Cys Ala Arg Ser Thr Tyr Tyr Gly Gly Asp Trp Tyr Phe Asn
            115                 120                 125

Val Trp Gly Ala Gly Thr Thr Val Thr Val Ser Ala Ala Ser Thr Lys
130                 135                 140

Gly Pro Ser Val Phe Pro Leu Ala Pro Cys Ser Arg Ser Thr Ser Gly
145                 150                 155                 160

Gly Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Thr Cys Asn
        210                 215                 220

Val Asn His Lys Pro Ser Asn Thr Lys Val Asp Lys Arg Val Glu Leu
225                 230                 235                 240

Lys Thr Pro Leu Gly Asp Thr Thr His Thr Cys Pro Arg Cys Pro Glu
            245                 250                 255

Pro Lys Ser Cys Asp Thr Pro Pro Cys Pro Arg Cys Pro Glu Pro
        260                 265                 270

Lys Ser Cys Asp Thr Pro Pro Cys Pro Arg Cys Pro Glu Pro Lys
        275                 280                 285

Ser Cys Asp Thr Pro Pro Cys Pro Arg Cys Pro Ala Pro Glu Leu
    290                 295                 300

Leu Gly Gly Pro Ser Val Phe Leu Phe Pro Lys Pro Lys Asp Thr
305                 310                 315                 320

Leu Met Ile Ser Arg Thr Pro Glu Val Thr Cys Val Val Val Asp Val
            325                 330                 335

Ser His Glu Asp Pro Glu Val Gln Phe Lys Trp Tyr Val Asp Gly Val
        340                 345                 350

Glu Val His Asn Ala Lys Thr Lys Leu Arg Glu Gln Tyr Asn Ser
    355                 360                 365

Thr Phe Arg Val Val Ser Val Leu Thr Val Leu His Gln Asp Trp Leu
            370                 375                 380

Asn Gly Lys Glu Tyr Lys Cys Lys Val Ser Asn Lys Ala Leu Pro Ala
385                 390                 395                 400

Pro Ile Glu Lys Thr Ile Ser Lys Ala Lys Gly Gln Pro Arg Glu Pro
            405                 410                 415

Gln Val Tyr Thr Leu Pro Pro Ser Arg Glu Glu Met Thr Lys Asn Gln
                420                 425                 430

Val Ser Leu Thr Cys Leu Val Lys Gly Phe Tyr Pro Ser Asp Ile Ala
            435                 440                 445

Val Glu Trp Glu Ser Asn Gly Gln Pro Glu Asn Asn Tyr Asn Thr Thr
        450                 455                 460

Pro Pro Met Leu Asp Ser Asp Gly Ser Phe Phe Leu Tyr Ser Lys Leu
465                 470                 475                 480

Thr Val Asp Lys Ser Arg Trp Gln Gln Gly Asn Ile Phe Ser Cys Ser
            485                 490                 495

Val Met His Glu Ala Leu His Asn His Tyr Thr Gln Lys Ser Leu Ser
        500                 505                 510

Leu Ser Pro Gly Lys Ser Gly Gly Gly Ser Cys Asp Leu Pro Gln
    515                 520                 525
```

```
Thr His Ser Leu Gly Ser Arg Arg Thr Leu Met Leu Leu Ala Gln Met
            530                 535                 540

Arg Arg Ile Ser Leu Phe Ser Cys Leu Lys Asp Arg His Asp Phe Gly
545                 550                 555                 560

Phe Pro Gln Glu Glu Phe Gly Asn Gln Phe Gln Lys Ala Glu Thr Ile
                565                 570                 575

Pro Val Leu His Glu Met Ile Gln Gln Ile Phe Asn Leu Phe Ser Thr
            580                 585                 590

Lys Asp Ser Ser Ala Ala Trp Asp Glu Thr Leu Leu Asp Lys Phe Tyr
            595                 600                 605

Thr Glu Leu Tyr Gln Gln Leu Asn Asp Leu Glu Ala Cys Val Ile Gln
            610                 615                 620

Gly Val Gly Val Thr Glu Thr Pro Leu Met Lys Glu Asp Ser Ile Leu
625                 630                 635                 640

Ala Val Arg Lys Tyr Phe Gln Arg Ile Thr Leu Tyr Leu Lys Glu Lys
                645                 650                 655

Lys Tyr Ser Pro Cys Ala Trp Glu Val Val Arg Ala Glu Ile Met Arg
            660                 665                 670

Ser Phe Ser Leu Ser Thr Asn Leu Gln Glu Ser Leu Arg Ser Lys Glu
            675                 680                 685
```

<210> SEQ ID NO 5
<211> LENGTH: 15
<212> TYPE: PRT
<213> ORGANISM: Artificial
<220> FEATURE:
<223> OTHER INFORMATION: Peptide linker

<400> SEQUENCE: 5

```
Gly Gly Gly Gly Ser Gly Gly Gly Gly Ser Gly Gly Gly Gly Ser
1               5                   10                  15
```

<210> SEQ ID NO 6
<211> LENGTH: 5
<212> TYPE: PRT
<213> ORGANISM: Artificial
<220> FEATURE:
<223> OTHER INFORMATION: Peptide linker

<400> SEQUENCE: 6

```
Gly Gly Gly Gly Ser
1               5
```

<210> SEQ ID NO 7
<211> LENGTH: 12
<212> TYPE: PRT
<213> ORGANISM: Artificial
<220> FEATURE:
<223> OTHER INFORMATION: Peptide linker

<400> SEQUENCE: 7

```
Ala Glu Ala Ala Ala Lys Glu Ala Ala Ala Lys Ala
1               5                   10
```

<210> SEQ ID NO 8
<211> LENGTH: 375
<212> TYPE: DNA
<213> ORGANISM: Artificial
<220> FEATURE:
<223> OTHER INFORMATION: Nucleic acid encoding alpha CD20 light chain

<400> SEQUENCE: 8

```
atgaagttgc ctgttaggct gttggtgctg atgttctgga ttcctgcttc cagcagtcaa      60
attgttctct cccagtctcc agcaatcctg tctgcatctc caggggagaa ggtcacaatg     120
acttgcaggg ccagctcaag tgtaagttac atccactggt tccagcagaa gccaggatcc     180
tcccccaaac cctggattta tgccacatcc aacctggctt ctggagtccc tgttcgcttc     240
agtggcagtg ggtctgggac ttcttactct ctcacaatca gcagagtgga ggctgaagat     300
gctgccactt attactgcca gcagtggact agtaacccac ccacgttcgg agggggggacc   360 aagctggaaa tcaaa                                                     375
```

<210> SEQ ID NO 9
<211> LENGTH: 125
<212> TYPE: PRT
<213> ORGANISM: Artificial
<220> FEATURE:
<223> OTHER INFORMATION: Antibody alpha CD20 light chain

<400> SEQUENCE: 9

Met Lys Leu Pro Val Arg Leu Leu Val Leu Met Phe Trp Ile Pro Ala
1               5                   10                  15

Ser Ser Ser Gln Ile Val Leu Ser Gln Ser Pro Ala Ile Leu Ser Ala
            20                  25                  30

Ser Pro Gly Glu Lys Val Thr Met Thr Cys Arg Ala Ser Ser Ser Val
        35                  40                  45

Ser Tyr Ile His Trp Phe Gln Gln Lys Pro Gly Ser Ser Pro Lys Pro
    50                  55                  60

Trp Ile Tyr Ala Thr Ser Asn Leu Ala Ser Gly Val Pro Val Arg Phe
65                  70                  75                  80

Ser Gly Ser Gly Ser Gly Thr Ser Tyr Ser Leu Thr Ile Ser Arg Val
                85                  90                  95

Glu Ala Glu Asp Ala Ala Thr Tyr Tyr Cys Gln Gln Trp Thr Ser Asn
            100                 105                 110

Pro Pro Thr Phe Gly Gly Gly Thr Lys Leu Glu Ile Lys
        115                 120                 125

<210> SEQ ID NO 10
<211> LENGTH: 2067
<212> TYPE: DNA
<213> ORGANISM: Artificial
<220> FEATURE:
<223> OTHER INFORMATION: Nucleic acid encoding fusion protein alpha
      CD20-IgG3-muIFN with Gly4Ser linker

<400> SEQUENCE: 10

```
atgtacttgg gactgaactg tgtaatcata gttttctctct taaaggtgt ccagagtcag      60 gtacaactgc agcagcctgg ggctgagctg gtgaagcctg gggcctcagt gaagatgtcc     120
tgcaaggctt ctggctacac atttaccagt tacaatatgc actgggtaaa acagacacct     180
ggtcggggcc tggaatggat tggagctatt tatcccggaa atggtgatac ttcctacaat     240
cagaagttca aaggcaaggc cacattgact gcagacaaat cctccagcac agcctacatg     300
cagctcagca gcctgacatc tgaggactct gcggtctatt actgtgcaag atcgacttac     360
tacggcggtg actggtactt caatgtctgg ggcgcaggga ccacggtcac cgtctctgca     420
gctagcacca agggcccatc ggtcttcccc ctggcgccct gctccaggag cacctctggg     480
ggcacagcgg ccctgggctg cctggtcaag gactacttcc ccgaaccggt gacggtgtcg     540
tggaactcag gcgccctgac cagcggcgtg cacaccttcc cggctgtcct acagtcctca     600

```
ggactctact ccctcagcag cgtggtgacc gtgccctcca gcagcttggg cacccagacc      660
tacacctgca acgtgaatca caagcccagc aacaccaagg tggacaagag agttgagctc      720
aaaaccccac ttggtgacac aactcacaca tgcccacggt gcccagagcc caaatcttgt      780
gacacacctc cccgtgccc aaggtgccca gagcccaaat cttgtgacac acctcccccg      840
tgcccaaggt gcccagagcc caaatcttgt gacacacctc cccgtgccc aaggtgccca      900 gcacctgaac tcctgggagg accgtcagtc ttcctcttcc ccccaaaacc caaggatacc      960
cttatgattt cccggacccc tgaggtcacg tgcgtggtgg tggacgtgag ccacgaagac     1020
cccgaggtcc agttcaagtg gtacgtggac ggcgtggagg tgcataatgc caagacaaag     1080
ctgcgggagg agcagtacaa cagcacgttc cgtgtggtca gcgtcctcac cgtcctgcac     1140
caggactggc tgaacggcaa ggagtacaag tgcaaggtct ccaacaaagc cctcccagcc     1200
cccatcgaga aaccatctc caaagccaaa ggacagcccc gagaaccaca ggtgtacacc     1260
ctgcccccat cccgggagga gatgaccaag aaccaggtca gcctgacctg cctggtcaaa     1320
ggcttctacc ccagcgacat cgccgtggag tgggagagca tgggcagcc ggagaacaac     1380 tacaacacca cgcctcccat gctggactcc gacggctcct tcttcctcta cagcaagctc     1440
accgtggaca agagcaggtg gcagcagggg aacatcttct catgctccgt gatgcatgag     1500
gctctgcaca accactacac gcagaagagc ctctccctgt ctccgggtaa atctggtggc     1560
ggtggatcct gtgacctgcc tcagactcat aacctcagga caagagagc cttgacactc     1620 ctggtacaaa tgaggagact ctcccctctc tcctgcctga aggacaggaa ggactttgga     1680
ttcccgcagg agaaggtgga tgcccagcag atcaagaagg ctcaagccat ccctgtcctg     1740
agtgagctga cccagcagat cctgaacatc ttcacatcaa aggactcatc tgctgcttgg     1800
aatgcaaccc tcctagactc attctgcaat gacctccacc agcagctcaa tgacctgcaa     1860
ggttgtctga tgcagcaggt gggggtgcag gaatttcccc tgacccagga agatgccctg     1920
ctggctgtga ggaaatactt ccacaggatc actgtgtacc tgagagagaa gaaacacagc     1980
ccctgtgcct gggaggtggt cagagcagaa gtctggagag ccctgtcttc ctctgccaat     2040
gtgctgggaa gactgagaga agagaaa                                         2067
```

<210> SEQ ID NO 11
<211> LENGTH: 689
<212> TYPE: PRT
<213> ORGANISM: Artificial
<220> FEATURE:
<223> OTHER INFORMATION: Fusion protein alpha CD20-IgG3-muIFN with
      Gly4Ser linker

<400> SEQUENCE: 11

```
Met Tyr Leu Gly Leu Asn Cys Val Ile Ile Val Phe Leu Leu Lys Gly
1               5                   10                  15

Val Gln Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95
```

```
Thr Ala Tyr Met Gln Leu Ser Ser Leu Thr Ser Glu Asp Ser Ala Val
            100                 105                 110
Tyr Tyr Cys Ala Arg Ser Thr Tyr Tyr Gly Gly Asp Trp Tyr Phe Asn
        115                 120                 125
Val Trp Gly Ala Gly Thr Thr Val Thr Val Ser Ala Ala Ser Thr Lys
    130                 135                 140
Gly Pro Ser Val Phe Pro Leu Ala Pro Cys Ser Arg Ser Thr Ser Gly
145                 150                 155                 160
Gly Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
            180                 185                 190
Phe Pro Ala Val Leu Gln Ser Ser Gly Leu Tyr Ser Leu Ser Ser Val
        195                 200                 205
Val Thr Val Pro Ser Ser Ser Leu Gly Thr Gln Thr Tyr Thr Cys Asn
    210                 215                 220
Val Asn His Lys Pro Ser Asn Thr Lys Val Asp Lys Arg Val Glu Leu
225                 230                 235                 240
Lys Thr Pro Leu Gly Asp Thr Thr His Thr Cys Pro Arg Cys Pro Glu
                245                 250                 255
Pro Lys Ser Cys Asp Thr Pro Pro Cys Pro Arg Cys Pro Glu Pro
            260                 265                 270
Lys Ser Cys Asp Thr Pro Pro Cys Pro Arg Cys Pro Glu Pro Lys
        275                 280                 285
Ser Cys Asp Thr Pro Pro Cys Pro Arg Cys Pro Ala Pro Glu Leu
    290                 295                 300
Leu Gly Gly Pro Ser Val Phe Leu Phe Pro Pro Lys Pro Lys Asp Thr
305                 310                 315                 320
Leu Met Ile Ser Arg Thr Pro Glu Val Thr Cys Val Val Val Asp Val
                325                 330                 335
Ser His Glu Asp Pro Glu Val Gln Phe Lys Trp Tyr Val Asp Gly Val
            340                 345                 350
Glu Val His Asn Ala Lys Thr Lys Leu Arg Glu Glu Gln Tyr Asn Ser
        355                 360                 365
Thr Phe Arg Val Val Ser Val Leu Thr Val Leu His Gln Asp Trp Leu
    370                 375                 380
Asn Gly Lys Glu Tyr Lys Cys Lys Val Ser Asn Lys Ala Leu Pro Ala
385                 390                 395                 400
Pro Ile Glu Lys Thr Ile Ser Lys Ala Lys Gly Gln Pro Arg Glu Pro
                405                 410                 415
Gln Val Tyr Thr Leu Pro Pro Ser Arg Glu Glu Met Thr Lys Asn Gln
            420                 425                 430
Val Ser Leu Thr Cys Leu Val Lys Gly Phe Tyr Pro Ser Asp Ile Ala
        435                 440                 445
Val Glu Trp Glu Ser Asn Gly Gln Pro Glu Asn Tyr Asn Thr Thr
    450                 455                 460
Pro Pro Met Leu Asp Ser Asp Gly Ser Phe Phe Leu Tyr Ser Lys Leu
465                 470                 475                 480
Thr Val Asp Lys Ser Arg Trp Gln Gln Gly Asn Ile Phe Ser Cys Ser
                485                 490                 495
Val Met His Glu Ala Leu His Asn His Tyr Thr Gln Lys Ser Leu Ser
            500                 505                 510
Leu Ser Pro Gly Lys Ser Gly Gly Gly Gly Ser Cys Asp Leu Pro Gln
```

```
                515                 520                 525
Thr His Asn Leu Arg Asn Lys Arg Ala Leu Thr Leu Leu Val Gln Met
            530                 535                 540
Arg Arg Leu Ser Pro Leu Ser Cys Leu Lys Asp Arg Lys Asp Phe Gly
545                 550                 555                 560
Phe Pro Gln Glu Lys Val Asp Ala Gln Gln Ile Lys Lys Ala Gln Ala
                565                 570                 575
Ile Pro Val Leu Ser Glu Leu Thr Gln Gln Ile Leu Asn Ile Phe Thr
            580                 585                 590
Ser Lys Asp Ser Ser Ala Ala Trp Asn Ala Thr Leu Leu Asp Ser Phe
595                 600                 605
Cys Asn Asp Leu His Gln Gln Leu Asn Asp Leu Gln Gly Cys Leu Met
            610                 615                 620
Gln Gln Val Gly Val Gln Glu Phe Pro Leu Thr Gln Glu Asp Ala Leu
625                 630                 635                 640
Leu Ala Val Arg Lys Tyr Phe His Arg Ile Thr Val Tyr Leu Arg Glu
                645                 650                 655
Lys Lys His Ser Pro Cys Ala Trp Glu Val Val Arg Ala Glu Val Trp
            660                 665                 670
Arg Ala Leu Ser Ser Ser Ala Asn Val Leu Gly Arg Leu Arg Glu Glu
        675                 680                 685
Lys

<210> SEQ ID NO 12
<211> LENGTH: 2091
<212> TYPE: DNA
<213> ORGANISM: Artificial
<220> FEATURE:
<223> OTHER INFORMATION: Nucleic acid encoding alpha CD20-IgG3-muIFN
      with helical linker

<400> SEQUENCE: 12
atgtacttgg gactgaactg tgtaatcata gttttttctct taaaaggtgt ccagagtcag    60
gtacaactgc agcagcctgg ggctgagctg gtgaagcctg ggccctcagt gaagatgtcc   120
tgcaaggctt ctggctacac atttaccagt acaatatgca ctgggtaaaa cagacacct   180 ggtcggggcc tggaatggat tggagctatt tatcccggaa atggtgatac ttcctacaat   240
cagaagttca aggcaaggc cacattgact gcagacaaat cctccagcac agcctacatg   300
cagctcagca gcctgacatc tgaggactct gcggtctatt actgtgcaag atcgacttac   360
tacggcggtg actggtactt caatgtctgg ggcgcaggga ccacggtcac cgtctctgca   420
gctagcacca agggcccatc ggtcttcccc ctggcgccct gctccaggag cacctctggg   480
ggcacagcgg ccctgggctg cctggtcaag gactacttcc ccgaaccggt gacggtgtcg   540
tggaactcag gcgccctgac cagcggcgtg cacaccttcc cggctgtcct acagtcctca   600
ggactctact ccctcagcag cgtggtgacc gtgccctcca gcagcttggg cacccagacc   660
tacacctgca acgtgaatca caagcccagc aacaccaagg tggacaagag agttgagctc   720
aaaaccccac ttggtgacac aactcacaca tgcccacggt gcccagagcc caaatcttgt   780
gacacacctc cccgtgccc aaggtgccca gagcccaaat cttgtgacac acctcccccg   840
tgcccaaggt gcccagagcc caaatcttgt gacacacctc cccgtgccc aaggtgccca   900 gcacctgaac tcctgggagg accgtcagtc ttcctcttcc cccaaaaacc caaggatacc   960
cttatgattt cccggacccc tgaggtcacg tgcgtggtgg tggacgtgag ccacgaagac  1020
```

```
cccgaggtcc agttcaagtg gtacgtggac ggcgtggagg tgcataatgc caagacaaag    1080
ctgcgggagg agcagtacaa cagcacgttc cgtgtggtca gcgtcctcac cgtcctgcac    1140
caggactggc tgaacggcaa ggagtacaag tgcaaggtct ccaacaaagc cctcccagcc    1200
cccatcgaga aaaccatctc caaagccaaa ggacagcccc gagaaccaca ggtgtacacc    1260
ctgcccccat cccgggagga gatgaccaag aaccaggtca gcctgacctg cctggtcaaa    1320
ggcttctacc ccagcgacat cgccgtggag tgggagagca atgggcagcc ggagaacaac    1380
tacaacacca cgcctcccat gctggactcc gacggctcct tcttcctcta cagcaagctc    1440
accgtggaca gagcaggtg gcagcagggg aacatcttct catgctccgt gatgcatgag    1500
```

-continued

```
Val Thr Val Ser Trp Asn Ser Gly Ala Leu Thr Ser Gly Val His Thr
            180                 185                 190
Phe Pro Ala Val Leu Gln Ser Ser Gly Leu Tyr Ser Leu Ser Ser Val
            195                 200                 205
Val Thr Val Pro Ser Ser Leu Gly Thr Gln Thr Tyr Thr Cys Asn
210                 215                 220
Val Asn His Lys Pro Ser Asn Thr Lys Val Asp Lys Arg Val Glu Leu
225                 230                 235                 240
Lys Thr Pro Leu Gly Asp Thr Thr His Thr Cys Pro Arg Cys Pro Glu
            245                 250                 255
Pro Lys Ser Cys Asp Thr Pro Pro Cys Pro Arg Cys Pro Glu Pro
            260                 265                 270
Lys Ser Cys Asp Thr Pro Pro Cys Pro Arg Cys Pro Glu Pro Lys
            275                 280                 285
Ser Cys Asp Thr Pro Pro Cys Pro Arg Cys Pro Ala Pro Glu Leu
            290                 295                 300
Leu Gly Gly Pro Ser Val Phe Leu Phe Pro Pro Lys Pro Lys Asp Thr
305                 310                 315                 320
Leu Met Ile Ser Arg Thr Pro Glu Val Thr Cys Val Val Val Asp Val
            325                 330                 335
Ser His Glu Asp Pro Glu Val Gln Phe Lys Trp Tyr Val Asp Gly Val
            340                 345                 350
Glu Val His Asn Ala Lys Thr Lys Leu Arg Glu Glu Gln Tyr Asn Ser
            355                 360                 365
Thr Phe Arg Val Val Ser Val Leu Thr Val Leu His Gln Asp Trp Leu
370                 375                 380
Asn Gly Lys Glu Tyr Lys Cys Lys Val Ser Asn Lys Ala Leu Pro Ala
385                 390                 395                 400
Pro Ile Glu Lys Thr Ile Ser Lys Ala Lys Gly Gln Pro Arg Glu Pro
            405                 410                 415
Gln Val Tyr Thr Leu Pro Pro Ser Arg Glu Glu Met Thr Lys Asn Gln
            420                 425                 430
Val Ser Leu Thr Cys Leu Val Lys Gly Phe Tyr Pro Ser Asp Ile Ala
            435                 440                 445
Val Glu Trp Glu Ser Asn Gly Gln Pro Glu Asn Asn Tyr Asn Thr Thr
            450                 455                 460
Pro Pro Met Leu Asp Ser Asp Gly Ser Phe Phe Leu Tyr Ser Lys Leu
465                 470                 475                 480
Thr Val Asp Lys Ser Arg Trp Gln Gln Gly Asn Ile Phe Ser Cys Ser
                485                 490                 495
Val Met His Glu Ala Leu His Asn His Tyr Thr Gln Lys Ser Leu Ser
            500                 505                 510
Leu Ser Pro Gly Lys Ala Glu Ala Ala Lys Glu Ala Ala Lys
            515                 520                 525
Ala Gly Ser Cys Asp Leu Pro Gln Thr His Asn Leu Arg Asn Lys Arg
            530                 535                 540
Ala Leu Thr Leu Leu Val Gln Met Arg Arg Leu Ser Pro Leu Ser Cys
545                 550                 555                 560
Leu Lys Asp Arg Lys Asp Phe Gly Phe Pro Gln Glu Lys Val Asp Ala
            565                 570                 575
Gln Gln Ile Lys Lys Ala Gln Ala Ile Pro Val Leu Ser Glu Leu Thr
            580                 585                 590
```

```
Gln Gln Ile Leu Asn Ile Phe Thr Ser Lys Asp Ser Ala Ala Trp
            595                 600                 605
Asn Ala Thr Leu Leu Asp Ser Phe Cys Asn Asp Leu His Gln Gln Leu
    610                 615                 620
Asn Asp Leu Gln Gly Cys Leu Met Gln Gln Val Gly Val Gln Glu Phe
625                 630                 635                 640
Pro Leu Thr Gln Glu Asp Ala Leu Leu Ala Val Arg Lys Tyr Phe His
                645                 650                 655
Arg Ile Thr Val Tyr Leu Arg Glu Lys Lys His Ser Pro Cys Ala Trp
            660                 665                 670
Glu Val Val Arg Ala Glu Val Trp Arg Ala Leu Ser Ser Ser Ala Asn
    675                 680                 685
Val Leu Gly Arg Leu Arg Glu Glu Lys
    690                 695

<210> SEQ ID NO 14
<211> LENGTH: 2064
<212> TYPE: DNA
<213> ORGANISM: Artificial
<220> FEATURE:
<223> OTHER INFORMATION: Nucleic acid encoding susion protein alpha
      CD20-IgG3-huIFN with Gly4Ser linker

<400> SEQUENCE: 14
atgtacttgg gactgaactg tgtaatcata gtttttctct taaaaggtgt ccagagtcag     60
gtacaactgc agcagcctgg ggctgagctg gtgaagcctg ggcctcagt gaagatgtcc    120 tgcaaggctt ctggctacac atttaccagt tacaatatgc actgggtaaa acagacacct    180
ggtcggggcc tggaatggat tggagctatt tatcccggaa atggtgatac ttcctacaat    240
cagaagttca aggcaaggc cacattgact gcagacaaat cctccagcac agcctacatg    300
cagctcagca gcctgacatc tgaggactct gcggtctatt actgtgcaag atcgacttac    360
tacggcggtg actggtactt caatgtctgg ggcgcaggga ccacggtcac cgtctctgca    420
gctagcacca agggcccatc ggtcttcccc ctggcgccct gctccaggag cacctctggg    480
ggcacagcgg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgacc gtgccctcca gcagcttggg cacccagacc    660
tacacctgca acgtgaatca caagcccagc aacaccaagg tggacaagag agttgagctc    720
aaaaccccac ttggtgacac aactcacaca tgcccacggt gcccagagcc caaatcttgt    780
gacacacctc ccccgtgccc aaggtgccca gagcccaaat cttgtgacac acctccccg    840 tgcccaaggt gccagagcc caaatcttgt gacacacctc ccccgtgccc aaggtgccca    900
gcacctgaac tcctgggagg accgtcagtc ttcctcttcc cccaaaaacc caaggatacc    960
cttatgattt cccggacccc tgaggtcacg tgcgtggtgg tggacgtgag ccacgaagac   1020
cccgaggtcc agttcaagtg gtacgtggac ggcgtggagg tgcataatgc caagacaaag   1080
ctgcgggagg agcagtacaa cagcacgttc cgtgtggtca gcgtcctcac cgtcctgcac   1140
caggactggc tgaacggcaa ggagtacaag tgcaaggtct ccaacaaagc cctcccagcc   1200
cccatcgaga aaaccatctc caaagccaaa ggacagcccc gagaaccaca ggtgtacacc   1260 ctgccccat cccgggagga gatgaccaag aaccaggtca gcctgacctg cctggtcaaa   1320
ggcttctacc ccagcgacat cgccgtggag tgggagagca atgggcagcc ggagaacaac   1380
tacaacacca cgcctcccat gctggactcc gacggctcct tcttcctcta cagcaagctc   1440
```

```
accgtggaca agagcaggtg gcagcagggg aacatcttct catgctccgt gatgcatgag   1500
gctctgcaca accactacac gcagaagagc ctctccctgt ctccgggtaa atctggtggc   1560
ggtggatcct gtgatctgcc tcaaacccac agcctgggta gcaggaggac cttgatgctc   1620
ctggcacaga tgaggagaat ctctcttttc tcctgcttga aggacagaca tgactttgga   1680
tttccccagg aggagtttgg caaccagttc caaaaggctg aaaccatccc tgtcctccat   1740
gagatgatcc agcagatctt caatctcttc agcacaaagg actcatctgc tgcttgggat   1800
gagaccctcc tagacaaatt ctacactgaa ctctaccagc agctgaatga cctggaagcc   1860
tgtgtgatac aggggtgggg ggtgacagag actcccctga tgaaggagga ctccattctg   1920
gctgtgagga atacttcca aagaatcact ctctatctga agagaagaa atacagccct   1980 tgtgcctggg aggttgtcag agcagaaatc atgagatctt tttctttgtc aacaaacttg   2040
caagaaagtt taagaagtaa ggaa                                          2064
```

<210> SEQ ID NO 15
<211> LENGTH: 688
<212> TYPE: PRT
<213> ORGANISM: Artificial
<220> FEATURE:
<223> OTHER INFORMATION: Fusion protein alpha CD20-IgG3-huIFN with
      Gly4Ser linker

<400> SEQUENCE: 15

Met Tyr Leu Gly Leu Asn Cys Val Ile Ile Val Phe Leu Leu Lys Gly
1               5                   10                  15

Val Gln Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ala Ala Ser Thr Lys
    130                 135                 140

Gly Pro Ser Val Phe Pro Leu Ala Pro Cys Ser Arg Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Thr Cys Asn
    210                 215                 220

Val Asn His Lys Pro Ser Asn Thr Lys Val Asp Lys Arg Val Glu Leu
225                 230                 235                 240

```
Lys Thr Pro Leu Gly Asp Thr Thr His Thr Cys Pro Arg Cys Pro Glu
                245                 250                 255

Pro Lys Ser Cys Asp Thr Pro Pro Cys Pro Arg Cys Pro Glu Pro
            260                 265                 270

Lys Ser Cys Asp Thr Pro Pro Cys Pro Arg Cys Pro Glu Pro Lys
        275                 280                 285

Ser Cys Asp Thr Pro Pro Cys Pro Arg Cys Pro Ala Pro Glu Leu
    290                 295                 300

Leu Gly Gly Pro Ser Val Phe Leu Phe Pro Pro Lys Pro Lys Asp Thr
305                 310                 315                 320

Leu Met Ile Ser Arg Thr Pro Glu Val Thr Cys Val Val Val Asp Val
                325                 330                 335

Ser His Glu Asp Pro Glu Val Gln Phe Lys Trp Tyr Val Asp Gly Val
            340                 345                 350

Glu Val His Asn Ala Lys Thr Lys Leu Arg Glu Gln Tyr Asn Ser
        355                 360                 365

Thr Phe Arg Val Val Ser Val Leu Thr Val Leu His Gln Asp Trp Leu
    370                 375                 380

Asn Gly Lys Glu Tyr Lys Cys Lys Val Ser Asn Lys Ala Leu Pro Ala
385                 390                 395                 400

Pro Ile Glu Lys Thr Ile Ser Lys Ala Lys Gly Gln Pro Arg Glu Pro
                405                 410                 415

Gln Val Tyr Thr Leu Pro Pro Ser Arg Glu Glu Met Thr Lys Asn Gln
            420                 425                 430

Val Ser Leu Thr Cys Leu Val Lys Gly Phe Tyr Pro Ser Asp Ile Ala
        435                 440                 445

Val Glu Trp Glu Ser Asn Gly Gln Pro Glu Asn Asn Tyr Asn Thr Thr
    450                 455                 460

Pro Pro Met Leu Asp Ser Asp Gly Ser Phe Phe Leu Tyr Ser Lys Leu
465                 470                 475                 480

Thr Val Asp Lys Ser Arg Trp Gln Gln Gly Asn Ile Phe Ser Cys Ser
                485                 490                 495

Val Met His Glu Ala Leu His Asn His Tyr Thr Gln Lys Ser Leu Ser
            500                 505                 510

Leu Ser Pro Gly Lys Ser Gly Gly Gly Ser Cys Asp Leu Pro Gln
        515                 520                 525

Thr His Ser Leu Gly Ser Arg Arg Thr Leu Met Leu Leu Ala Gln Met
    530                 535                 540

Arg Arg Ile Ser Leu Phe Ser Cys Leu Lys Asp Arg His Asp Phe Gly
545                 550                 555                 560

Phe Pro Gln Glu Glu Phe Gly Asn Gln Phe Gln Lys Ala Glu Thr Ile
                565                 570                 575

Pro Val Leu His Glu Met Ile Gln Gln Ile Phe Asn Leu Phe Ser Thr
            580                 585                 590

Lys Asp Ser Ser Ala Ala Trp Asp Glu Thr Leu Leu Asp Lys Phe Tyr
        595                 600                 605

Thr Glu Leu Tyr Gln Gln Leu Asn Asp Leu Glu Ala Cys Val Ile Gln
    610                 615                 620

Gly Val Gly Val Thr Glu Thr Pro Leu Met Lys Glu Asp Ser Ile Leu
625                 630                 635                 640

Ala Val Arg Lys Tyr Phe Gln Arg Ile Thr Leu Tyr Leu Lys Glu Lys
                645                 650                 655

Lys Tyr Ser Pro Cys Ala Trp Glu Val Val Arg Ala Glu Ile Met Arg
```

```
                660               665              670
Ser Phe Ser Leu Ser Thr Asn Leu Gln Glu Ser Leu Arg Ser Lys Glu
        675              680              685
```

<210> SEQ ID NO 16
<211> LENGTH: 2088
<212> TYPE: DNA
<213> ORGANISM: Artificial
<220> FEATURE:
<223> OTHER INFORMATION: Nucleic acid encoding fusion protein alpha
      CD20-IgG3-huIFN with helical linker

<400> SEQUENCE: 16

| | |
|---|---|
| atgtacttgg gactgaactg tgtaatcata gtttttctct taaaaggtgt ccagagtcag | 60 |
| gtacaactgc agcagcctgg ggctgagctg gtgaagcctg gggcctcagt gaagatgtcc | 120 |
| tgcaaggctt ctggctacac atttaccagt tacaatatgc actgggtaaa acagacacct | 180 |
| ggtcggggcc tggaatggat tggagctatt tatcccggaa atggtgatac ttcctacaat | 240 |
| cagaagttca aggcaaggc cacattgact gcagacaaat cctccagcac agcctacatg | 300 |
| cagctcagca gcctgacatc tgaggactct gcggtctatt actgtgcaag atcgacttac | 360 |
| tacggcggtg actggtactt caatgtctgg ggcgcaggga ccacggtcac cgtctctgca | 420 |
| gctagcacca agggcccatc ggtcttcccc ctggcgccct gctccaggag cacctctggg | 480 |
| ggcacagcgg ccctgggctg cctggtcaag gactacttcc ccgaaccggt gacggtgtcg | 540 |
| tggaactcag gcgccctgac cagcggcgtg cacaccttcc cggctgtcct acagtcctca | 600 |
| ggactctact ccctcagcag cgtggtgacc gtgccctcca gcagcttggg cacccagacc | 660 |
| tacacctgca acgtgaatca caagcccagc aacaccaagg tggacaagag agttgagctc | 720 |
| aaaaccccac ttggtgacac aactcacaca tgcccacggt gcccagagcc caaatcttgt | 780 |
| gacacacctc cccgtgccc aaggtgccca gagcccaaat cttgtgacac acctcccccg | 840 |
| tgcccaaggt gcccagagcc caaatcttgt gacacacctc cccgtgccc aaggtgccca | 900 |
| gcacctgaac tcctgggagg accgtcagtc ttcctcttcc ccccaaaacc caaggatacc | 960 |
| cttatgattt cccggacccc tgaggtcacg tgcgtggtgg tggacgtgag ccacgaagac | 1020 |
| cccgaggtcc agttcaagtg gtacgtggac ggcgtggagg tgcataatgc caagacaaag | 1080 |
| ctgcgggagg agcagtacaa cagcacgttc cgtgtggtca gcgtcctcac cgtcctgcac | 1140 |
| caggactggc tgaacggcaa ggagtacaag tgcaaggtct ccaacaaagc cctcccagcc | 1200 |
| cccatcgaga aaaccatctc caaagccaaa ggacagcccc gagaaccaca ggtgtacacc | 1260 |
| ctgcccccat cccgggagga gatgaccaag aaccaggtca gcctgacctg cctggtcaaa | 1320 |
| ggcttctacc ccagcgacat cgccgtggag tgggagagca atgggcagcc ggagaacaac | 1380 |
| tacaacacca cgcctcccat gctggactcc gacggctcct tcttcctcta cagcaagctc | 1440 |
| accgtggaca agagcaggtg gcagcagggg aacatcttct catgctccgt gatgcatgag | 1500 |
| gctctgcaca accactacac gcagaagagc ctctccctgt ctccgggtaa agcagaggcc | 1560 |
| gcagctaaag aggccgcagc caaagcggga tcctgtgatc tgcctcaaac ccacagcctg | 1620 |
| ggtagcagga ggaccttgat gctcctggca cagatgagga gaatctctct ttttctcctgc | 1680 |
| ttgaaggaca gacatgactt tggatttccc caggaggagt ttggcaacca gttccaaaag | 1740 |
| gctgaaacca tccctgtcct ccatgagatg atccagcaga tcttcaatct cttcagcaca | 1800 |
| aaggactcat ctgctgcttg ggatgagacc ctcctagaca aattctacac tgaactctac | 1860 |
| cagcagctga atgacctgga agcctgtgtg atacagggg tggggtgac agagactccc | 1920 |

```
ctgatgaagg aggactccat tctggctgtg aggaaatact tccaaagaat cactctctat  1980
ctgaaagaga agaaatacag cccttgtgcc tgggaggttg tcagagcaga aatcatgaga  2040 tcttttttctt tgtcaacaaa cttgcaagaa agtttaagaa gtaaggaa             2088
```

<210> SEQ ID NO 17
<211> LENGTH: 696
<212> TYPE: PRT
<213> ORGANISM: Artificial
<220> FEATURE:
<223> OTHER INFORMATION: Fusion protein alpha CD20-IgG3-huIFN with
      helical linker

<400> SEQUENCE: 17

```
Met Tyr Leu Gly Leu Asn Cys Val Ile Ile Val Phe Leu Leu Lys Gly
1               5                   10                  15

Val Gln Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ala Ala Ser Thr Lys
    130                 135                 140

Gly Pro Ser Val Phe Pro Leu Ala Pro Cys Ser Arg Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Thr Cys Asn
    210                 215                 220

Val Asn His Lys Pro Ser Asn Thr Lys Val Asp Lys Arg Val Glu Leu
225                 230                 235                 240

Lys Thr Pro Leu Gly Asp Thr Thr His Thr Cys Pro Arg Cys Pro Glu
                245                 250                 255

Pro Lys Ser Cys Asp Thr Pro Pro Pro Cys Pro Arg Cys Pro Glu Pro
            260                 265                 270

Lys Ser Cys Asp Thr Pro Pro Pro Cys Pro Arg Cys Pro Glu Pro Lys
        275                 280                 285

Ser Cys Asp Thr Pro Pro Pro Cys Pro Arg Cys Pro Ala Pro Glu Leu
    290                 295                 300

Leu Gly Gly Pro Ser Val Phe Leu Phe Pro Pro Lys Pro Lys Asp Thr
305                 310                 315                 320

Leu Met Ile Ser Arg Thr Pro Glu Val Thr Cys Val Val Val Asp Val
```

```
                    325                 330                 335
Ser His Glu Asp Pro Glu Val Gln Phe Lys Trp Tyr Val Asp Gly Val
                340                 345                 350
Glu Val His Asn Ala Lys Thr Lys Leu Arg Glu Glu Gln Tyr Asn Ser
                355                 360                 365
Thr Phe Arg Val Val Ser Val Leu Thr Val Leu His Gln Asp Trp Leu
            370                 375                 380
Asn Gly Lys Glu Tyr Lys Cys Lys Val Ser Asn Lys Ala Leu Pro Ala
385                 390                 395                 400
Pro Ile Glu Lys Thr Ile Ser Lys Ala Lys Gly Gln Pro Arg Glu Pro
                405                 410                 415
Gln Val Tyr Thr Leu Pro Pro Ser Arg Glu Glu Met Thr Lys Asn Gln
                420                 425                 430
Val Ser Leu Thr Cys Leu Val Lys Gly Phe Tyr Pro Ser Asp Ile Ala
            435                 440                 445
Val Glu Trp Glu Ser Asn Gly Gln Pro Glu Asn Asn Tyr Asn Thr Thr
            450                 455                 460
Pro Pro Met Leu Asp Ser Asp Gly Ser Phe Phe Leu Tyr Ser Lys Leu
465                 470                 475                 480
Thr Val Asp Lys Ser Arg Trp Gln Gln Gly Asn Ile Phe Ser Cys Ser
                485                 490                 495
Val Met His Glu Ala Leu His Asn His Tyr Thr Gln Lys Ser Leu Ser
            500                 505                 510
Leu Ser Pro Gly Lys Ala Glu Ala Ala Lys Glu Ala Ala Ala Lys
            515                 520                 525
Ala Gly Ser Cys Asp Leu Pro Gln Thr His Ser Leu Gly Ser Arg Arg
        530                 535                 540
Thr Leu Met Leu Leu Ala Gln Met Arg Arg Ile Ser Leu Phe Ser Cys
545                 550                 555                 560
Leu Lys Asp Arg His Asp Phe Gly Phe Pro Gln Glu Glu Phe Gly Asn
                565                 570                 575
Gln Phe Gln Lys Ala Glu Thr Ile Pro Val Leu His Glu Met Ile Gln
                580                 585                 590
Gln Ile Phe Asn Leu Phe Ser Thr Lys Asp Ser Ser Ala Ala Trp Asp
            595                 600                 605
Glu Thr Leu Leu Asp Lys Phe Tyr Thr Glu Leu Tyr Gln Gln Leu Asn
        610                 615                 620
Asp Leu Glu Ala Cys Val Ile Gln Gly Val Gly Val Thr Glu Thr Pro
625                 630                 635                 640
Leu Met Lys Glu Asp Ser Ile Leu Ala Val Arg Lys Tyr Phe Gln Arg
                645                 650                 655
Ile Thr Leu Tyr Leu Lys Glu Lys Lys Tyr Ser Pro Cys Ala Trp Glu
                660                 665                 670
Val Val Arg Ala Glu Ile Met Arg Ser Phe Ser Leu Ser Thr Asn Leu
            675                 680                 685
Gln Glu Ser Leu Arg Ser Lys Glu
            690                 695

<210> SEQ ID NO 18
<211> LENGTH: 1926
<212> TYPE: DNA
<213> ORGANISM: Artificial
<220> FEATURE:
<223> OTHER INFORMATION: Nucleic acid encoding fusion protein alpha
      CD20-IgG1-muIFN with Gly4Ser linker
```

<400> SEQUENCE: 18

```
atgtacttgg gactgaactg tgtaatcata gttttctct taaaaggtgt ccagagtcag      60
gtacaactgc agcagcctgg ggctgagctg gtgaagcctg gggcctcagt gaagatgtcc    120
tgcaaggctt ctggctacac atttaccagt tacaatatgc actgggtaaa acagacacct    180
ggtcggggcc tggaatggat tggagctatt tatcccggaa atggtgatac ttcctacaat    240
cagaagttca aggcaaggc cacattgact gcagacaaat cctccagcac agcctacatg    300
cagctcagca gcctgacatc tgaggactct gcggtctatt actgtgcaag atcgacttac    360
tacggcggtg actggtactt caatgtctgg ggcgcaggga ccacggtcac cgtctctgca    420
gctagcacca agggcccatc ggtcttcccc ctggcaccct cctccaagag cacctctggg    480
ggcacagcgg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgacc gtgccctcca gcagcttggg cacccagacc    660
tacatctgca acgtgaatca caagcccagc aacaccaagg tggacaagaa agttgagccc    720
aaatcttgtg acaaaactca cacatgccca ccgtgcccag cacctgaact cctgggggga    780
ccgtcagtct tcctcttccc cccaaaaccc aaggacaccc tcatgatctc ccggacccct    840
gaggtcacat gcgtggtggt ggacgtgagc cacgaagacc ctgaggtcaa gttcaactgg    900
tacgtggacg gcgtggaggt gcataatgcc aagacaaagc cgcgggagga gcagtacaac    960
agcacgtacc gtgtggtcag cgtcctcacc gtcctgcacc aggactggct gaatggcaag   1020
gagtacaagt gcaaggtctc caacaaagcc ctcccagccc catcgagaa aaccatctcc   1080
aaagccaaag gcagccccg agaaccacag gtgtacaccc tgcccccatc ccgggatgag   1140
ctgaccaaga accaggtcag cctgacctgc ctggtcaaag gcttctatcc cagcgacatc   1200
gccgtggagt gggagagcaa tgggcagccg gagaacaact acaagaccac gcctcccgtg   1260
ctggactccg acggctcctt cttcctctac agcaagctca ccgtggacaa gagcaggtgg   1320
cagcagggga acgtcttctc atgctccgtg atgcatgagg ctctgcacaa ccactacacg   1380
cagaagagcc tctccctgtc tccgggtaaa tctggtggcg gtggatcctg tgacctgcct   1440
cagactcata acctcaggaa caagagagcc ttgacactcc tggtacaaat gaggagactc   1500
tcccctctct cctgcctgaa ggacaggaag gactttggat tcccgcagga aaggtggat   1560
gcccagcaga tcaagaaggc tcaagccatc cctgtcctga gtgagctgac ccagcagatc   1620
ctgaacatct tcacatcaaa ggactcatct gctgcttgga atgcaaccct cctagactca   1680
ttctgcaatg acctccacca gcagctcaat gacctgcaag gttgtctgat gcagcaggtg   1740
ggggtgcagg aatttcccct gacccaggaa gatgccctgc tggctgtgag gaaatacttc   1800
cacaggatca ctgtgtacct gagagagaag aaacacagcc cctgtgcctg ggaggtggtc   1860
agagcagaag tctggagagc cctgtcttcc tctgccaatg tgctgggaag actgagagaa   1920
gagaaa                                                              1926
```

<210> SEQ ID NO 19
<211> LENGTH: 642
<212> TYPE: PRT
<213> ORGANISM: Artificial
<220> FEATURE:
<223> OTHER INFORMATION: Fusion protein alpha CD20-IgG1-muIFN with Gly4Ser linker

<400> SEQUENCE: 19

-continued

```
Met Tyr Leu Gly Leu Asn Cys Val Ile Ile Val Phe Leu Leu Lys Gly
 1               5                  10                  15

Val Gln Ser Gln Val Gln Leu Gln Gln Pro Gly Ala Glu Leu Val Lys
             20                  25                  30

Pro Gly Ala Ser Val Lys Met Ser Cys Lys Ala Ser Gly Tyr Thr Phe
             35                  40                  45

Thr Ser Tyr Asn Met His Trp Val Lys Gln Thr Pro Gly Arg Gly Leu
         50                  55                  60

Glu Trp Ile Gly Ala Ile Tyr Pro Gly Asn Gly Asp Thr Ser Tyr Asn
 65                  70                  75                  80

Gln Lys Phe Lys Gly Lys Ala Thr Leu Thr Ala Asp Lys Ser Ser Ser
             85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
            115                 120                 125

Val Trp Gly Ala Gly Thr Thr Val Thr Val Ser Ala Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
            245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415
```

```
Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys Ser Gly Gly Gly Ser Cys Asp Leu Pro
465                 470                 475                 480

Gln Thr His Asn Leu Arg Asn Lys Arg Ala Leu Thr Leu Leu Val Gln
                485                 490                 495

Met Arg Arg Leu Ser Pro Leu Ser Cys Leu Lys Asp Arg Lys Asp Phe
            500                 505                 510

Gly Phe Pro Gln Glu Lys Val Asp Ala Gln Gln Ile Lys Lys Ala Gln
        515                 520                 525

Ala Ile Pro Val Leu Ser Glu Leu Thr Gln Gln Ile Leu Asn Ile Phe
    530                 535                 540

Thr Ser Lys Asp Ser Ser Ala Ala Trp Asn Ala Thr Leu Leu Asp Ser
545                 550                 555                 560

Phe Cys Asn Asp Leu His Gln Gln Leu Asn Asp Leu Gln Gly Cys Leu
                565                 570                 575

Met Gln Gln Val Gly Val Gln Glu Phe Pro Leu Thr Gln Glu Asp Ala
            580                 585                 590

Leu Leu Ala Val Arg Lys Tyr Phe His Arg Ile Thr Val Tyr Leu Arg
        595                 600                 605

Glu Lys Lys His Ser Pro Cys Ala Trp Glu Val Val Arg Ala Glu Val
    610                 615                 620

Trp Arg Ala Leu Ser Ser Ser Ala Asn Val Leu Gly Arg Leu Arg Glu
625                 630                 635                 640

Glu Lys

<210> SEQ ID NO 20
<211> LENGTH: 1953
<212> TYPE: DNA
<213> ORGANISM: Artificial
<220> FEATURE:
<223> OTHER INFORMATION: Nucleic acid encoding alpha CD20-IgG1-muIFN
      with alpha helical linker

<400> SEQUENCE: 20
atgtacttgg gactgaactg tgtaatcata gttttctct  taaaaggtgt ccagagtcag    60
gtacaactgc agcagcctgg ggctgagctg gtgaagcctg gggcctcagt gaagatgtcc   120
tgcaaggctt ctggctacac atttaccagt tacaatatgc actgggtaaa acagacacct   180
ggtcggggcc tggaatggat tggagctatt tatcccggaa atggtgatac ttcctacaat   240
cagaagttca aggcaaggc cacattgact gcagacaaat cctccagcac agcctacatg   300
cagctcagca gcctgacatc tgaggactct gcggtctatt actgtgcaag atcgacttac   360
tacggcggtg actggtactt caatgtctgg ggcgcaggga ccacggtcac cgtctctgca   420
gctagcacca aggcccatc  ggtcttcccc ctggcaccct cctccaagag cacctctggg   480
ggcacagcgg ccctgggctg cctggtcaag gactacttcc ccgaaccggt gacggtgtcg   540
tggaactcag gcgccctgac cagcggcgtg cacaccttcc cggctgtcct acagtcctca   600
ggactctact ccctcagcag cgtggtgacc gtgccctcca gcagcttggg cacccagacc   660
tacatctgca acgtgaatca caagcccagc aacaccaagg tggacaagaa agttgagccc   720
```

```
aaatcttgtg acaaaactca cacatgccca ccgtgcccag cacctgaact cctgggggga      780
ccgtcagtct tcctcttccc cccaaaaccc aaggacaccc tcatgatctc ccggacccct      840
gaggtcacat gcgtggtggt ggacgtgagc cacgaagacc ctgaggtcaa gttcaactgg      900
tacgtggacg gcgtggaggt gcataatgcc aagacaaagc cgcggaggga gcagtacaac      960
agcacgtacc gggtggtcag cgtcctcacc gtcctgcacc aggactggct gaatggcaag     1020
gagtacaagt gcaaggtctc caacaaagcc ctcccagccc ccatcgagaa aaccatctcc     1080
aaagccaaag ggcagccccg agaaccacag gtgtacaccc tgcccccatc ccgggatgag     1140
ctgaccaaga accaggtcag cctgacctgc ctggtcaaag gcttctatcc cagcgacatc     1200
gccgtggagt gggagagcaa tgggcagccg gagaacaact acaagaccac gcctcccgtg     1260
ctggactccg acggctcctt cttcctctac agcaagctca ccgtggacaa gagcaggtgg     1320
cagcagggga acgtcttctc atgctccgtg atgcatgagg ctctgcacaa ccactacacg     1380
cagaagagcc tctccctgtc tccgggtaaa gcagaggccg cagctaaaga ggccgcagcc     1440
aaagcgggat cctgtgacct gcctcagact cataacctca ggaacaagag agccttgaca     1500
ctcctggtac aaatgaggag actctcccct ctctcctgcc tgaaggacag gaaggacttt     1560
ggattcccgc aggagaaggt ggatgcccag cagatcaaga aggctcaagc catccctgtc     1620
ctgagtgagc tgacccagca gatcctgaac atcttcacat caaggactc atctgctgct     1680 tggaatgcaa ccctcctaga ctcattctgc aatgacctcc accagcagct caatgacctg     1740
caaggttgtc tgatgcagca ggtgggggtg caggaatttc ccctgaccca ggaagatgcc     1800
ctgctggctg tgaggaaata cttccacagg atcactgtgt acctgagaga aaagaaacac     1860
agcccctgtg cctgggaggt ggtcagagca gaagtctgga gagccctgtc ttcctctgcc     1920
aatgtgctgg gaagactgag agaagagaaa tga                                  1953
```

<210> SEQ ID NO 21
<211> LENGTH: 650
<212> TYPE: PRT
<213> ORGANISM: Artificial
<220> FEATURE:
<223> OTHER INFORMATION: Fusion protein alpha CD20-IgG1-muIFN with alpha helical linker

<400> SEQUENCE: 21

```
Met Tyr Leu Gly Leu Asn Cys Val Ile Ile Val Phe Leu Leu Lys Gly
1               5                   10                  15

Val Gln Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ala Ala Ser Thr Lys
    130                 135                 140
```

```
Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
        180                 185                 190

Phe Pro Ala Val Leu Gln Ser Ser Gly Leu Tyr Ser Leu Ser Ser Val
    195                 200                 205

Val Thr Val Pro Ser Ser Leu Gly Thr Gln Thr Tyr Ile Cys Asn
210                 215                 220

Val Asn His Lys Pro Ser Asn Thr Lys Val Asp Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys Ala Glu Ala Ala Lys Glu Ala Ala
465                 470                 475                 480

Lys Ala Gly Ser Cys Asp Leu Pro Gln Thr His Asn Leu Arg Asn Lys
                485                 490                 495

Arg Ala Leu Thr Leu Leu Val Gln Met Arg Arg Leu Ser Pro Leu Ser
            500                 505                 510

Cys Leu Lys Asp Arg Lys Asp Phe Gly Phe Pro Gln Glu Lys Val Asp
        515                 520                 525

Ala Gln Gln Ile Lys Lys Ala Gln Ala Ile Pro Val Leu Ser Glu Leu
    530                 535                 540

Thr Gln Gln Ile Leu Asn Ile Phe Thr Ser Lys Asp Ser Ser Ala Ala
545                 550                 555                 560
```

```
Trp Asn Ala Thr Leu Leu Asp Ser Phe Cys Asn Asp Leu His Gln Gln
            565                 570                 575

Leu Asn Asp Leu Gln Gly Cys Leu Met Gln Gln Val Gly Val Gln Glu
        580                 585                 590

Phe Pro Leu Thr Gln Glu Asp Ala Leu Leu Ala Val Arg Lys Tyr Phe
            595                 600                 605

His Arg Ile Thr Val Tyr Leu Arg Glu Lys Lys His Ser Pro Cys Ala
        610                 615                 620

Trp Glu Val Val Arg Ala Glu Val Trp Arg Ala Leu Ser Ser Ser Ala
625                 630                 635                 640

Asn Val Leu Gly Arg Leu Arg Glu Glu Lys
            645                 650

<210> SEQ ID NO 22
<211> LENGTH: 1923
<212> TYPE: DNA
<213> ORGANISM: Artificial
<220> FEATURE:
<223> OTHER INFORMATION: Nucleic acid encoding fusion protein alpha
      CD20-IgG1-huIFN with Gly4Ser linker

<400> SEQUENCE: 22
```

| | | | | | |
|---|---|---|---|---|---|
| atgtacttgg | gactgaactg | tgtaatcata | gttttctct | taaaggtgt | ccagagtcag | 60 |
| gtacaactgc | agcagcctgg | ggctgagctg | gtgaagcctg | gggcctcagt | gaagatgtcc | 120 |
| tgcaaggctt | ctggctacac | atttaccagt | tacaatatgc | actgggtaaa | acagacacct | 180 |
| ggtcggggcc | tggaatggat | tggagctatt | tatcccggaa | atggtgatac | ttcctacaat | 240 |
| cagaagttca | aggcaaggc | cacattgact | gcagacaaat | cctccagcac | agcctacatg | 300 |
| cagctcagca | gcctgacatc | tgaggactct | gcggtctatt | actgtgcaag | atcgacttac | 360 |
| tacggcggtg | actggtactt | caatgtctgg | ggcgcaggga | ccacggtcac | cgtctctgca | 420 |
| gctagcacca | agggcccatc | ggtcttcccc | ctggcaccct | cctccaagag | cacctctggg | 480 |
| ggcacagcgg | ccctgggctg | cctggtcaag | gactacttcc | ccgaaccggt | gacggtgtcg | 540 |
| tggaactcag | gcgccctgac | cagcggcgtg | cacaccttcc | cggctgtcct | acagtcctca | 600 |
| ggactctact | ccctcagcag | cgtggtgacc | gtgccctcca | gcagcttggg | cacccagacc | 660 |
| tacatctgca | acgtgaatca | caagcccagc | aacaccaagg | tggacaagaa | agttgagccc | 720 |
| aaatcttgtg | acaaaactca | cacatgccca | ccgtgcccag | cacctgaact | cctgggggga | 780 |
| ccgtcagtct | tcctcttccc | cccaaaaccc | aaggacaccc | tcatgatctc | ccggacccct | 840 |
| gaggtcacat | gcgtggtggt | ggacgtgagc | cacgaagacc | ctgaggtcaa | gttcaactgg | 900 |
| tacgtggacg | gcgtggaggt | gcataatgcc | aagacaaagc | cgcgggagga | gcagtacaac | 960 |
| agcacgtacc | gtgtggtcag | cgtcctcacc | gtcctgcacc | aggactggct | gaatggcaag | 1020 |
| gagtacaagt | gcaaggtctc | caacaaagcc | ctcccagccc | ccatcgagaa | aaccatctcc | 1080 |
| aaagccaaag | ggcagccccg | agaaccacag | gtgtacaccc | tgcccccatc | ccgggatgag | 1140 |
| ctgaccaaga | accaggtcag | cctgacctgc | ctggtcaaag | gcttctatcc | cagcgacatc | 1200 |
| gccgtggagt | gggagagcaa | tgggcagccg | gagaacaact | acaagaccac | gcctcccgtg | 1260 |
| ctggactccg | acggctcctt | cttcctctac | agcaagctca | ccgtggacaa | gagcaggtgg | 1320 |
| cagcagggga | acgtcttctc | atgctccgtg | atgcatgagg | ctctgcacaa | ccactacacg | 1380 |
| cagaagagcc | tctccctgtc | tccgggtaaa | tctggtggcg | gtggatcctg | tgatctgcct | 1440 |
| caaacccaca | gcctgggtag | caggaggacc | ttgatgctcc | tggcacagat | gaggagaatc | 1500 |

-continued

```
tctctttttct cctgcttgaa ggacagacat gactttggat ttccccagga ggagtttggc      1560
aaccagttcc aaaaggctga aaccatccct gtcctccatg agatgatcca gcagatcttc      1620
aatctcttca gcacaaagga ctcatctgct gcttgggatg agaccctcct agacaaattc      1680
tacactgaac tctaccagca gctgaatgac ctggaagcct gtgtgataca gggggtgggg      1740
gtgacagaga ctcccctgat gaaggaggac tccattctgg ctgtgaggaa atacttccaa      1800
agaatcactc tctatctgaa agagaagaaa tacagccctt gtgcctggga ggttgtcaga      1860
gcagaaatca tgagatcttt ttctttgtca acaaacttgc aagaaagttt aagaagtaag      1920
gaa                                                                    1923
```

<210> SEQ ID NO 23
<211> LENGTH: 641
<212> TYPE: PRT
<213> ORGANISM: Artificial
<220> FEATURE:
<223> OTHER INFORMATION: Fusion protein alpha CD20-IgG1-huIFN with
      Gly4Ser linker

<400> SEQUENCE: 23

```
Met Tyr Leu Gly Leu Asn Cys Val Ile Ile Val Phe Leu Leu Lys Gly
1               5                   10                  15

Val Gln Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ala Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
```

```
                    275                 280                 285
        Val Ser His Glu Asp Pro Glu Val Lys Phe Asn Trp Tyr Val Asp Gly
                    290                 295                 300
        Val Glu Val His Asn Ala Lys Thr Lys Pro Arg Glu Glu Gln Tyr Asn
        305                 310                 315                 320
        Ser Thr Tyr Arg Val Val Ser Val Leu Thr Val Leu His Gln Asp Trp
                        325                 330                 335
        Leu Asn Gly Lys Glu Tyr Lys Cys Lys Val Ser Asn Lys Ala Leu Pro
                    340                 345                 350
        Ala Pro Ile Glu Lys Thr Ile Ser Lys Ala Lys Gly Gln Pro Arg Glu
                    355                 360                 365
        Pro Gln Val Tyr Thr Leu Pro Pro Ser Arg Asp Glu Leu Thr Lys Asn
                    370                 375                 380
        Gln Val Ser Leu Thr Cys Leu Val Lys Gly Phe Tyr Pro Ser Asp Ile
        385                 390                 395                 400
        Ala Val Glu Trp Glu Ser Asn Gly Gln Pro Glu Asn Asn Tyr Lys Thr
                        405                 410                 415
        Thr Pro Pro Val Leu Asp Ser Asp Gly Ser Phe Phe Leu Tyr Ser Lys
                    420                 425                 430
        Leu Thr Val Asp Lys Ser Arg Trp Gln Gln Gly Asn Val Phe Ser Cys
                    435                 440                 445
        Ser Val Met His Glu Ala Leu His Asn His Tyr Thr Gln Lys Ser Leu
        450                 455                 460
        Ser Leu Ser Pro Gly Lys Ser Gly Gly Gly Gly Ser Cys Asp Leu Pro
        465                 470                 475                 480
        Gln Thr His Ser Leu Gly Ser Arg Arg Thr Leu Met Leu Leu Ala Gln
                        485                 490                 495
        Met Arg Arg Ile Ser Leu Phe Ser Cys Leu Lys Asp Arg His Asp Phe
                    500                 505                 510
        Gly Phe Pro Gln Glu Glu Phe Gly Asn Gln Phe Gln Lys Ala Glu Thr
                    515                 520                 525
        Ile Pro Val Leu His Glu Met Ile Gln Gln Ile Phe Asn Leu Phe Ser
                    530                 535                 540
        Thr Lys Asp Ser Ser Ala Ala Trp Asp Glu Thr Leu Leu Asp Lys Phe
        545                 550                 555                 560
        Tyr Thr Glu Leu Tyr Gln Gln Leu Asn Asp Leu Glu Ala Cys Val Ile
                        565                 570                 575
        Gln Gly Val Gly Val Thr Glu Thr Pro Leu Met Lys Glu Asp Ser Ile
                    580                 585                 590
        Leu Ala Val Arg Lys Tyr Phe Gln Arg Ile Thr Leu Tyr Leu Lys Glu
                    595                 600                 605
        Lys Lys Tyr Ser Pro Cys Ala Trp Glu Val Val Arg Ala Glu Ile Met
                    610                 615                 620
        Arg Ser Phe Ser Leu Ser Thr Asn Leu Gln Glu Ser Leu Arg Ser Lys
        625                 630                 635                 640

Glu

<210> SEQ ID NO 24
<211> LENGTH: 1950
<212> TYPE: DNA
<213> ORGANISM: Artificial
<220> FEATURE:
<223> OTHER INFORMATION: Nucleic acid encoding alpha CD20-IgG1-huIFN
      with alpha helical linker
```

<400> SEQUENCE: 24

```
atgtacttgg gactgaactg tgtaatcata gtttttctct taaaaggtgt ccagagtcag      60
gtacaactgc agcagcctgg ggctgagctg tgaagcctg gggcctcagt gaagatgtcc     120
tgcaaggctt ctggctacac atttaccagt tacaatatgc actgggtaaa acagacacct    180
ggtcggggcc tggaatggat tggagctatt tatcccggaa atggtgatac ttcctacaat    240
cagaagttca aggcaaggc acattgact gcagacaaat cctccagcac agcctacatg      300
cagctcagca gcctgacatc tgaggactct gcggtctatt actgtgcaag atcgacttac    360
tacggcggtg actggtactt caatgtctgg ggcgcaggga ccacggtcac cgtctctgca    420
gctagcacca agggcccatc ggtcttcccc ctggcaccct cctccaagag cacctctggg    480
ggcacagcgg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgacc gtgccctcca gcagcttggg cacccagacc    660
tacatctgca acgtgaatca caagcccagc aacaccaagg tggacaagaa agttgagccc    720
aaatcttgtg acaaaactca cacatgccca ccgtgcccag cacctgaact cctggggga    780
ccgtcagtct tcctcttccc cccaaaaccc aaggacaccc tcatgatctc ccggacccct    840
gaggtcacat gcgtggtggt ggacgtgagc cacgaagacc ctgaggtcaa gttcaactgg    900
tacgtggacg gcgtggaggt gcataatgcc aagacaaagc cgcggagga gcagtacaac    960
agcacgtacc gtgtggtcag cgtcctcacc gtcctgcacc aggactggct gaatggcaag   1020
gagtacaagt gcaaggtctc caacaaagcc ctcccagccc ccatcgagaa aaccatctcc   1080
aaagccaaag gcagccccg agaaccacag gtgtacaccc tgcccccatc ccgggatgag    1140
ctgaccaaga accaggtcag cctgacctgc ctggtcaaag gcttctatcc cagcgacatc   1200
gccgtggagt gggagagcaa tgggcagccg gagaacaact acaagaccac gcctcccgtg   1260
ctggactccg acggctcctt cttcctctac agcaagctca ccgtggacaa gagcaggtgg   1320
cagcagggga acgtcttctc atgctccgtg atgcatgagg ctctgcacaa ccactacacg   1380
cagaagagcc tctccctgtc tccgggtaaa gcagaggccg cagctaaaga ggccgcagcc   1440
aaagcgggat cctgtgatct gcctcaaacc cacagcctgg gtagcaggag gaccttgatg   1500
ctcctggcac agatgaggag aatctctctt ttctcctgct tgaaggacag acatgacttt   1560
ggatttcccc aggaggagtt tggcaaccag ttccaaaagg ctgaaaccat ccctgtcctc   1620
catgagatga tccagcagat cttcaatctc ttcagcacaa aggactcatc tgctgcttgg   1680
gatgagaccc tcctagacaa attctacact gaactctacc agcagctgaa tgacctggaa   1740
gcctgtgtga tacaggggt gggggtgaca gagactcccc tgatgaagga ggactccatt   1800
ctggctgtga ggaaatactt ccaaagaatc actctctatc tgaaagagaa gaaatacagc   1860
ccttgtgcct gggaggttgt cagagcagaa atcatgagat ctttttcttt gtcaacaaac   1920
ttgcaagaaa gtttaagaag taaggaatga                                     1950
```

<210> SEQ ID NO 25
<211> LENGTH: 649
<212> TYPE: PRT
<213> ORGANISM: Artificial
<220> FEATURE:
<223> OTHER INFORMATION: Fusion protein alpha CD20-IgG1-huIFN with alpha helical linker

<400> SEQUENCE: 25

```
Met Tyr Leu Gly Leu Asn Cys Val Ile Ile Val Phe Leu Leu Lys Gly
1               5                   10                  15

Val Gln Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
            35                  40                  45

Thr Ser Tyr Asn Met His Trp Val Lys Gln Thr Pro Gly Arg Gly Leu
        50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
            115                 120                 125

Val Trp Gly Ala Gly Thr Thr Val Thr Val Ser Ala Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
```

```
                420               425               430
Leu Thr Val Asp Lys Ser Arg Trp Gln Gln Gly Asn Val Phe Ser Cys
                435               440               445
Ser Val Met His Glu Ala Leu His Asn His Tyr Thr Gln Lys Ser Leu
                450               455               460
Ser Leu Ser Pro Gly Lys Ala Glu Ala Ala Lys Glu Ala Ala Ala
465             470              475                 480
Lys Ala Gly Ser Cys Asp Leu Pro Gln Thr His Ser Leu Gly Ser Arg
                485               490               495
Arg Thr Leu Met Leu Leu Ala Gln Met Arg Arg Ile Ser Leu Phe Ser
                500               505               510
Cys Leu Lys Asp Arg His Asp Phe Gly Phe Pro Gln Glu Glu Phe Gly
                515               520               525
Asn Gln Phe Gln Lys Ala Glu Thr Ile Pro Val Leu His Glu Met Ile
                530               535               540
Gln Gln Ile Phe Asn Leu Phe Ser Thr Lys Asp Ser Ser Ala Ala Trp
545             550               555                 560
Asp Glu Thr Leu Leu Asp Lys Phe Tyr Thr Glu Leu Tyr Gln Gln Leu
                565               570               575
Asn Asp Leu Glu Ala Cys Val Ile Gln Gly Val Gly Val Thr Glu Thr
                580               585               590
Pro Leu Met Lys Glu Asp Ser Ile Leu Ala Val Arg Lys Tyr Phe Gln
                595               600               605
Arg Ile Thr Leu Tyr Leu Lys Glu Lys Lys Tyr Ser Pro Cys Ala Trp
                610               615               620
Glu Val Val Arg Ala Glu Ile Met Arg Ser Phe Ser Leu Ser Thr Asn
625             630               635                 640
Leu Gln Glu Ser Leu Arg Ser Lys Glu
                645
```

<210> SEQ ID NO 26
<211> LENGTH: 714
<212> TYPE: DNA
<213> ORGANISM: Artificial
<220> FEATURE:
<223> OTHER INFORMATION: Nucleic acid encoding antibody alpha Her2/neu
      light chain

<400> SEQUENCE: 26

```
atgggatgga gctgggtaat cctctttctc ctgtcagtaa ctgcaggtgt ccactcccag    60
tctgtgttga cgcagccgcc ctcagtgtct gcggccccag gacagaaggt caccatctcc   120
tgctctggaa gcagctccaa cattgggaat aattatgtat cctggtacca gcagctccca   180
ggaacagccc ccaaactcct catctatgat cacaccaatc ggcccgcagg ggtccctgac   240
cgattctctg gctccaagtc tggcacctca gcctccctgg ccatcagtgg gttccggtcc   300
gaggatgagg ctgattatta ctgtgcctcc tgggactaca ccctctcggg ctgggtgttc   360
ggaggaggga ccaaggtcac cgtcctaggt cgaactgtgg ctgcaccatc tgtcttcatc   420
ttcccgccat ctgatgagca gttgaaatct ggaactgcct ctgttgtgtg cctgctgaat   480
aacttctatc ccagagaggc caaagtacag tggaaggtgg ataacgccct ccaatcgggt   540
aactcccagg agagtgtcac agagcaggac agcaaggaca gcacctacag cctcagcagc   600
accctgacgc tgagcaaagc agactacgag aaacacaaag tctacgcctg cgaagtcacc   660
catcagggcc tgagctcgcc cgtcacaaag agcttcaaca ggggagagtg ttag          714
```

<210> SEQ ID NO 27
<211> LENGTH: 237
<212> TYPE: PRT
<213> ORGANISM: Artificial
<220> FEATURE:
<223> OTHER INFORMATION: Antibody alpha Her2/neu light chain

<400> SEQUENCE: 27

```
Met Gly Trp Ser Trp Val Ile Leu Phe Leu Ser Val Thr Ala Gly
1               5                   10                  15

Val His Ser Gln Ser Val Leu Thr Gln Pro Pro Ser Val Ser Ala Ala
            20                  25                  30

Pro Gly Gln Lys Val Thr Ile Ser Cys Ser Gly Ser Ser Ser Asn Ile
        35                  40                  45

Gly Asn Asn Tyr Val Ser Trp Tyr Gln Gln Leu Pro Gly Thr Ala Pro
    50                  55                  60

Lys Leu Leu Ile Tyr Asp His Thr Asn Arg Pro Ala Gly Val Pro Asp
65                  70                  75                  80

Arg Phe Ser Gly Ser Lys Ser Gly Thr Ser Ala Ser Leu Ala Ile Ser
                85                  90                  95

Gly Phe Arg Ser Glu Asp Glu Ala Asp Tyr Tyr Cys Ala Ser Trp Asp
            100                 105                 110

Tyr Thr Leu Ser Gly Trp Val Phe Gly Gly Gly Thr Lys Val Thr Val
        115                 120                 125

Leu Gly Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 28
<211> LENGTH: 1950
<212> TYPE: DNA
<213> ORGANISM: Artificial
<220> FEATURE:
<223> OTHER INFORMATION: Nucleic acid encoding fusion protein alpha Her2/neu-IgG1-muIFN with Gly4Ser linker

<400> SEQUENCE: 28

| | |
|---|---|
| atgggatgga gctgggtaat gcatctttct cctgtcagta actgcggtgt ccactcccag | 60 |
| gtccagctgg tgcagtctgg ggcagaggtg aaaaagcccg gggagtctct gaagatctcc | 120 |
| tgtaagggtt ctggatacag ctttaccagc tactggatcg cctgggtgcg ccagatgccc | 180 |
| gggaaaggcc tggagtacat ggggctcatc tatcctggtg actctgacac caaatacagc | 240 |
| ccgtccttcc aaggccaggt caccatctca gtcgacaagt ccgtcagcac tgcctacttg | 300 |
| caatggagca gtctgaagcc ctcggacagc gccgtgtatt tttgtgcgag acatgacgtg | 360 |
| ggatattgca ccgaccggac ttgcgcaaag tggcctgaat acttccagca ttggggccag | 420 |

```
ggcaccctgg tcaccgtctc ctcagctagc accagggcc catcggtctt ccccctggca    480
ccctcctcca agagcacctc tgggggcaca gcggccctgg gctgcctggt caaggactac    540
ttccccgaac cggtgacggt gtcgtggaac tcaggcgccc tgaccagcgg cgtgcacacc    600
ttcccggctg tcctacagtc ctcaggactc tactccctca gcagcgtggt gaccgtgccc    660
tccagcagct gggcaccca gacctacatc tgcaacgtga atcacaagcc cagcaacacc    720
aaggtggaca agaaagttga gcccaaatct tgtgacaaaa ctcacacatg cccaccgtgc    780
ccagcacctg aactcctggg gggaccgtca gtcttcctct tccccccaaa acccaaggac    840
accctcatga tctcccggac ccctgaggtc acatgcgtgg tggtggacgt gagccacgaa    900
gaccctgagg tcaagttcaa ctggtacgtg gacggcgtgg aggtgcataa tgccaagaca    960
aagccgcggg aggagcagta caacagcacg taccgtgtgg tcagcgtcct caccgtcctg   1020
caccaggact ggctgaatgg caaggagtac aagtgcaagg tctccaacaa agccctccca   1080
gcccccatcg agaaaaccat ctccaaagcc aaagggcagc cccgagaacc acaggtgtac   1140
accctgcccc catcccggga tgagctgacc aagaaccagg tcagcctgac ctgcctggtc   1200
aaaggcttct atcccagcga catcgccgtg gagtgggaga gcaatgggca gccggagaac   1260
aactacaaga ccacgcctcc cgtgctggac tccgacggct ccttcttcct ctacagcaag   1320
ctcaccgtgg acaagagcag gtggcagcag gggaacgtct tctcatgctc cgtgatgcat   1380
gaggctctgc acaaccacta cacgcagaag agcctctccc tgtctccggg taaatctggt   1440
ggcggtggat cctgtgacct gcctcagact cataacctca ggaacaagag agccttgaca   1500
ctcctggtac aaatgaggag actctcccct ctctcctgcc tgaaggacag aaggactttt   1560
ggattcccgc aggagaaggt ggatgcccag cagatcaaga aggctcaagc catccctgtc   1620
ctgagtgagc tgacccagca gatcctgaac atcttcacat caaggactc atctgctgct   1680
tggaatgcaa ccctcctaga ctcattctgc aatgacctcc accagcagct caatgacctg   1740
caaggttgtc tgatgcagca ggtggggtg caggaatttc ccctgaccca ggaagatgcc   1800
ctgctggctg tgaggaaata cttccacagg atcactgtgt acctgagaga gaagaaacac   1860
agcccctgtg cctgggaggt ggtcagagca gaagtctgga gagccctgtc ttcctctgcc   1920
aatgtgctgg gaagactgag agaagagaaa                                    1950
```

<210> SEQ ID NO 29  
<211> LENGTH: 650  
<212> TYPE: PRT  
<213> ORGANISM: Artificial  
<220> FEATURE:  
<223> OTHER INFORMATION: Fusion protein alpha Her2/neu-IgG1-muIFN with Gly4Ser linker

<400> SEQUENCE: 29

```
Met Gly Trp Ser Trp Val Met His Leu Ser Pro Val Ser Asn Cys Gly
1               5                   10                  15

Val His Ser Gln Val Gln Leu Val Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Thr Ser Tyr Trp Ile Ala Trp Val Arg Gln Met Pro Gly Lys Gly Leu
    50                  55                  60

Glu Tyr Met Gly Leu Ile Tyr Pro Gly Asp Ser Asp Thr Lys Tyr Ser
65                  70                  75                  80
```

-continued

```
Pro Ser Phe Gln Gly Gln Val Thr Ile Ser Val Asp Lys Ser Val Ser
                85                  90                  95
Thr Ala Tyr Leu Gln Trp Ser Ser Leu Lys Pro Ser Asp Ser Ala Val
            100                 105                 110
Tyr Phe Cys Ala Arg His Asp Val Gly Tyr Cys Thr Asp Arg Thr Cys
        115                 120                 125
Ala Lys Trp Pro Glu Tyr Phe Gln His Trp Gly Gln Gly Thr Leu Val
    130                 135                 140
Thr Val Ser Ser Ala Ser Thr Lys Gly Pro Ser Val Phe Pro Leu Ala
145                 150                 155                 160
Pro Ser Ser Lys Ser Thr Ser Gly Gly Thr Ala Ala Leu Gly Cys Leu
                165                 170                 175
Val Lys Asp Tyr Phe Pro Glu Pro Val Thr Val Ser Trp Asn Ser Gly
            180                 185                 190
Ala Leu Thr Ser Gly Val His Thr Phe Pro Ala Val Leu Gln Ser Ser
        195                 200                 205
Gly Leu Tyr Ser Leu Ser Ser Val Val Thr Val Pro Ser Ser Ser Leu
    210                 215                 220
Gly Thr Gln Thr Tyr Ile Cys Asn Val Asn His Lys Pro Ser Asn Thr
225                 230                 235                 240
Lys Val Asp Lys Lys Val Glu Pro Lys Ser Cys Asp Lys Thr His Thr
                245                 250                 255
Cys Pro Pro Cys Pro Ala Pro Glu Leu Leu Gly Gly Pro Ser Val Phe
            260                 265                 270
Leu Phe Pro Pro Lys Pro Lys Asp Thr Leu Met Ile Ser Arg Thr Pro
        275                 280                 285
Glu Val Thr Cys Val Val Val Asp Val Ser His Glu Asp Pro Glu Val
    290                 295                 300
Lys Phe Asn Trp Tyr Val Asp Gly Val Glu Val His Asn Ala Lys Thr
305                 310                 315                 320
Lys Pro Arg Glu Glu Gln Tyr Asn Ser Thr Tyr Arg Val Val Ser Val
                325                 330                 335
Leu Thr Val Leu His Gln Asp Trp Leu Asn Gly Lys Glu Tyr Lys Cys
            340                 345                 350
Lys Val Ser Asn Lys Ala Leu Pro Ala Pro Ile Glu Lys Thr Ile Ser
        355                 360                 365
Lys Ala Lys Gly Gln Pro Arg Glu Pro Gln Val Tyr Thr Leu Pro Pro
    370                 375                 380
Ser Arg Asp Glu Leu Thr Lys Asn Gln Val Ser Leu Thr Cys Leu Val
385                 390                 395                 400
Lys Gly Phe Tyr Pro Ser Asp Ile Ala Val Glu Trp Glu Ser Asn Gly
                405                 410                 415
Gln Pro Glu Asn Asn Tyr Lys Thr Thr Pro Pro Val Leu Asp Ser Asp
            420                 425                 430
Gly Ser Phe Phe Leu Tyr Ser Lys Leu Thr Val Asp Lys Ser Arg Trp
        435                 440                 445
Gln Gln Gly Asn Val Phe Ser Cys Ser Val Met His Glu Ala Leu His
    450                 455                 460
Asn His Tyr Thr Gln Lys Ser Leu Ser Leu Ser Pro Gly Lys Ser Gly
465                 470                 475                 480
Gly Gly Gly Ser Cys Asp Leu Pro Gln Thr His Asn Leu Arg Asn Lys
                485                 490                 495
Arg Ala Leu Thr Leu Leu Val Gln Met Arg Arg Leu Ser Pro Leu Ser
```

```
            500             505             510
Cys Leu Lys Asp Arg Lys Asp Phe Gly Phe Pro Gln Glu Lys Val Asp
        515             520             525

Ala Gln Gln Ile Lys Lys Ala Gln Ala Ile Pro Val Leu Ser Glu Leu
    530             535             540

Thr Gln Gln Ile Leu Asn Ile Phe Thr Ser Lys Asp Ser Ser Ala Ala
545             550             555             560

Trp Asn Ala Thr Leu Leu Asp Ser Phe Cys Asn Asp Leu His Gln Gln
                565             570             575

Leu Asn Asp Leu Gln Gly Cys Leu Met Gln Gln Val Gly Val Gln Glu
            580             585             590

Phe Pro Leu Thr Gln Glu Asp Ala Leu Leu Ala Val Arg Lys Tyr Phe
        595             600             605

His Arg Ile Thr Val Tyr Leu Arg Glu Lys Lys His Ser Pro Cys Ala
    610             615             620

Trp Glu Val Val Arg Ala Glu Val Trp Arg Ala Leu Ser Ser Ser Ala
625             630             635             640

Asn Val Leu Gly Arg Leu Arg Glu Glu Lys
                645             650

<210> SEQ ID NO 30
<211> LENGTH: 1974
<212> TYPE: DNA
<213> ORGANISM: Artificial
<220> FEATURE:
<223> OTHER INFORMATION: Nucleic acid encoding fusion protein alpha
      Her2/neu-IgG1-muIFNa with alpha helix linker

<400> SEQUENCE: 30
atgggatgga gctgggtaat gcatctttct cctgtcagta actgcggtgt ccactcccag      60
gtccagctgg tgcagtctgg ggcagaggtg aaaaagcccg ggagtctct gaagatctcc     120 tgtaagggtt ctggatacag ctttaccagc tactggatcg cctgggtgcg ccagatgccc     180
gggaaaggcc tggagtacat ggggctcatc tatcctggtg actctgacac caaatacagc     240
ccgtccttcc aaggccaggt caccatctca gtcgacaagt ccgtcagcac tgcctacttg     300
caatggagca gtctgaagcc ctcggacagc gccgtgtatt tttgtgcgag acatgacgtg     360
ggatattgca ccgaccggac ttgcgcaaag tggcctgaat acttccagca ttggggccag     420
ggcaccctgg tcaccgtctc ctcagctagc accaagggcc catcggtctt ccccctggca     480
ccctcctcca agagcacctc tgggggcaca gcggccctgg gctgcctggt caaggactac     540
ttccccgaac cggtgacggt gtcgtggaac tcaggcgccc tgaccagcgg cgtgcacacc     600
ttccggctgt cctacagtc ctcaggactc tactccctca gcagcgtggt gaccgtgccc     660
tccagcagct gggcaccca gacctacatc tgcaacgtga atcacaagcc cagcaacacc     720
aaggtggaca gaaagttga gcccaaatct tgtgacaaaa ctcacacatg cccaccgtgc     780
ccagcacctg aactcctggg gggaccgtca gtcttcctct tccccccaaa acccaaggac     840
accctcatga tctcccggac ccctgaggtc acatgcgtgg tggtggacgt gagccacgaa     900
gaccctgagg tcaagttcaa ctggtacgtg gacggcgtgg aggtgcataa tgccaagaca     960
aagccgcggg aggagcagta caacagcacg taccgtgtgg tcagcgtcct caccgtcctg    1020
caccaggact ggctgaatgg caaggagtac aagtgcaagg tctccaacaa agccctccca    1080
gcccccatcg agaaaaccat ctccaaagcc aaagggcagc ccgagaacc acaggtgtac    1140 accctgcccc catcccggga tgagctgacc aagaaccagg tcagcctgac ctgcctggtc    1200
```

```
aaaggcttct atcccagcga catcgccgtg gagtgggaga gcaatgggca gccggagaac   1260
aactacaaga ccacgcctcc cgtgctggac tccgacggct ccttcttcct ctacagcaag   1320
ctcaccgtgg acaagagcag gtggcagcag gggaacgtct tctcatgctc cgtgatgcat   1380
gaggctctgc acaaccacta cacgcagaag agcctctccc tgtctccggg taaagcagag   1440
gccgcagcta agaggccgc agccaaagcg ggatcctgtg acctgcctca gactcataac   1500
ctcaggaaca agagagcctt gacactcctg gtacaaatga ggagactctc ccctctctcc   1560
tgcctgaagg acaggaagga ctttggattc ccgcaggaga aggtggatgc ccagcagatc   1620
aagaaggctc aagccatccc tgtcctgagt gagctgaccc agcagatcct gaacatcttc   1680
acatcaaagg actcatctgc tgcttggaat gcaaccctcc tagactcatt ctgcaatgac   1740
ctccaccagc agctcaatga cctgcaaggt tgtctgatgc agcaggtggg ggtgcaggaa   1800
tttcccctga cccaggaaga tgccctgctg ctgtgagga aatacttcca caggatcact   1860
gtgtacctga gagaagaa acacagcccc tgtgcctggg aggtggtcag agcagaagtc   1920
tggagagccc tgtcttcctc tgccaatgtg ctgggaagac tgagagaaga gaaa        1974
```

<210> SEQ ID NO 31
<211> LENGTH: 658
<212> TYPE: PRT
<213> ORGANISM: Artificial
<220> FEATURE:
<223> OTHER INFORMATION: Fusion protein alpha Her2/neu-IgG1-muIFNa with
      alpha helix linker

<400> SEQUENCE: 31

```
Met Gly Trp Ser Trp Val Met His Leu Ser Pro Val Ser Asn Cys Gly
1               5                   10                  15

Val His Ser Gln Val Gln Leu Val Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Thr Ser Tyr Trp Ile Ala Trp Val Arg Gln Met Pro Gly Lys Gly Leu
    50                  55                  60

Glu Tyr Met Gly Leu Ile Tyr Pro Gly Asp Ser Asp Thr Lys Tyr Ser
65                  70                  75                  80

Pro Ser Phe Gln Gly Gln Val Thr Ile Ser Val Asp Lys Ser Val Ser
                85                  90                  95

Thr Ala Tyr Leu Gln Trp Ser Ser Leu Lys Pro Ser Asp Ser Ala Val
            100                 105                 110

Tyr Phe Cys Ala Arg His Asp Val Gly Tyr Cys Thr Asp Arg Thr Cys
        115                 120                 125

Ala Lys Trp Pro Glu Tyr Phe Gln His Trp Gly Gln Gly Thr Leu Val
    130                 135                 140

Thr Val Ser Ser Ala Ser Thr Lys Gly Pro Ser Val Phe Pro Leu Ala
145                 150                 155                 160

Pro Ser Ser Lys Ser Thr Ser Gly Gly Thr Ala Ala Leu Gly Cys Leu
                165                 170                 175

Val Lys Asp Tyr Phe Pro Glu Pro Val Thr Val Ser Trp Asn Ser Gly
            180                 185                 190

Ala Leu Thr Ser Gly Val His Thr Phe Pro Ala Val Leu Gln Ser Ser
        195                 200                 205

Gly Leu Tyr Ser Leu Ser Ser Val Val Thr Val Pro Ser Ser Ser Leu
    210                 215                 220
```

```
Gly Thr Gln Thr Tyr Ile Cys Asn Val Asn His Lys Pro Ser Asn Thr
225                 230                 235                 240

Lys Val Asp Lys Lys Val Glu Pro Lys Ser Cys Asp Lys Thr His Thr
            245                 250                 255

Cys Pro Pro Cys Pro Ala Pro Glu Leu Leu Gly Gly Pro Ser Val Phe
        260                 265                 270

Leu Phe Pro Pro Lys Pro Lys Asp Thr Leu Met Ile Ser Arg Thr Pro
    275                 280                 285

Glu Val Thr Cys Val Val Val Asp Val Ser His Glu Asp Pro Glu Val
    290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
            325                 330                 335

Leu Thr Val Leu His Gln Asp Trp Leu Asn Gly Lys Glu Tyr Lys Cys
        340                 345                 350

Lys Val Ser Asn Lys Ala Leu Pro Ala Pro Ile Glu Lys Thr Ile Ser
    355                 360                 365

Lys Ala Lys Gly Gln Pro Arg Glu Pro Gln Val Tyr Thr Leu Pro Pro
370                 375                 380

Ser Arg Asp Glu Leu Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
            405                 410                 415

Gln Pro Glu Asn Asn Tyr Lys Thr Thr Pro Pro Val Leu Asp Ser Asp
        420                 425                 430

Gly Ser Phe Phe Leu Tyr Ser Lys Leu Thr Val Asp Lys Ser Arg Trp
    435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly Lys Ala Glu
465                 470                 475                 480

Ala Ala Ala Lys Glu Ala Ala Ala Lys Ala Gly Ser Cys Asp Leu Pro
            485                 490                 495

Gln Thr His Asn Leu Arg Asn Lys Arg Ala Leu Thr Leu Leu Val Gln
        500                 505                 510

Met Arg Arg Leu Ser Pro Leu Ser Cys Leu Lys Asp Arg Lys Asp Phe
    515                 520                 525

Gly Phe Pro Gln Glu Lys Val Asp Ala Gln Gln Ile Lys Lys Ala Gln
    530                 535                 540

Ala Ile Pro Val Leu Ser Glu Leu Thr Gln Gln Ile Leu Asn Ile Phe
545                 550                 555                 560

Thr Ser Lys Asp Ser Ser Ala Ala Trp Asn Ala Thr Leu Leu Asp Ser
            565                 570                 575

Phe Cys Asn Asp Leu His Gln Gln Leu Asn Asp Leu Gln Gly Cys Leu
        580                 585                 590

Met Gln Gln Val Gly Val Gln Glu Phe Pro Leu Thr Gln Glu Asp Ala
    595                 600                 605

Leu Leu Ala Val Arg Lys Tyr Phe His Arg Ile Thr Val Tyr Leu Arg
    610                 615                 620

Glu Lys Lys His Ser Pro Cys Ala Trp Glu Val Val Arg Ala Glu Val
625                 630                 635                 640
```

Trp Arg Ala Leu Ser Ser Ser Ala Asn Val Leu Gly Arg Leu Arg Glu
                645                 650                 655

Glu Lys

<210> SEQ ID NO 32
<211> LENGTH: 1947
<212> TYPE: DNA
<213> ORGANISM: Artificial
<220> FEATURE:
<223> OTHER INFORMATION: Nucleic acid encoding fusion protein alpha
      Her2/neu-IgG2hIFN with Gly4Ser linker

<400> SEQUENCE: 32

| | | | | | |
|---|---|---|---|---|---|
| atgggatgga | gctgggtaat | gcatctttct | cctgtcagta | actgcggtgt | ccactcccag | 60 |
| gtccagctgg | tgcagtctgg | ggcagaggtg | aaaaagcccg | gggagtctct | gaagatctcc | 120 |
| tgtaagggtt | ctggatacag | ctttaccagc | tactggatcg | cctgggtgcg | ccagatgccc | 180 |
| gggaaaggcc | tggagtacat | ggggctcatc | tatcctggtg | actctgacac | caaatacagc | 240 |
| ccgtccttcc | aaggccaggt | caccatctca | gtcgacaagt | ccgtcagcac | tgcctacttg | 300 |
| caatggagca | gtctgaagcc | ctcggacagc | gccgtgtatt | tttgtgcgag | acatgacgtg | 360 |
| ggatattgca | ccgaccggac | ttgcgcaaag | tggcctgaat | acttccagca | ttggggccag | 420 |
| ggcaccctgg | tcaccgtctc | ctcagctagc | accaagggcc | catcggtctt | cccctggca | 480 |
| ccctcctcca | gagcacctc | tgggggcaca | gcggccctgg | gctgcctggt | caaggactac | 540 |
| ttccccgaac | cggtgacggt | gtcgtggaac | tcaggcgccc | tgaccagcgg | cgtgcacacc | 600 |
| ttcccggctg | tcctacagtc | ctcaggactc | tactccctca | gcagcgtggt | gaccgtgccc | 660 |
| tccagcagct | tgggcaccca | gacctacatc | tgcaacgtga | atcacaagcc | cagcaacacc | 720 |
| aaggtggaca | agaaagttga | gcccaaatct | tgtgacaaaa | ctcacacatg | cccaccgtgc | 780 |
| ccagcacctg | aactcctggg | gggaccgtca | gtcttcctct | tccccccaaa | acccaaggac | 840 |
| accctcatga | tctcccggac | ccctgaggtc | acatgcgtgg | tggtggacgt | gagccacgaa | 900 |
| gaccctgagg | tcaagttcaa | ctggtacgtg | gacggcgtgg | aggtgcataa | tgccaagaca | 960 |
| aagccgcggg | aggagcagta | caacagcacg | taccgtgtgg | tcagcgtcct | caccgtcctg | 1020 |
| caccaggact | ggctgaatgg | caaggagtac | aagtgcaagg | tctccaacaa | agccctccca | 1080 |
| gcccccatcg | agaaaaccat | ctccaaagcc | aagggcagc | ccgagaacc | acaggtgtac | 1140 |
| accctgcccc | catcccggga | tgagctgacc | aagaaccagg | tcagcctgac | ctgcctggtc | 1200 |
| aaaggcttct | atcccagcga | catcgccgtg | gagtgggaga | gcaatgggca | gccggagaac | 1260 |
| aactacaaga | ccacgcctcc | cgtgctggac | tccgacggct | ccttcttcct | ctacagcaag | 1320 |
| ctcaccgtgg | acaagagcag | gtggcagcag | gggaacgtct | tctcatgctc | cgtgatgcat | 1380 |
| gaggctctgc | acaaccacta | cacgcagaag | agcctctccc | tgtctccggg | taaatctggt | 1440 |
| ggcggtggat | cctgtgatct | gcctcaaacc | cacagcctgg | gtagcaggag | gaccttgatg | 1500 |
| ctcctggcac | agatgaggag | aatctctctt | ttctcctgct | tgaaggacag | acatgacttt | 1560 |
| ggatttcccc | aggaggagtt | tggcaaccag | ttccaaaagg | ctgaaaccat | ccctgtcctc | 1620 |
| catgagatga | tccagcagat | cttcaatctc | ttcagcacaa | aggactcatc | tgctgcttgg | 1680 |
| gatgagaccc | tcctagacaa | attctacact | gaactctacc | agcagctgaa | tgacctggaa | 1740 |
| gcctgtgtga | tacaggggt | ggggtgaca | gagactcccc | tgatgaagga | ggactccatt | 1800 |
| ctggctgtga | ggaaatactt | ccaaagaatc | actctctatc | tgaaagagaa | gaaatacagc | 1860 |
| ccttgtgcct | gggaggttgt | cagagcagaa | atcatgagat | cttttcttt | gtcaacaaac | 1920 |

```
ttgcaagaaa gtttaagaag taaggaa                                         1947
```

<210> SEQ ID NO 33
<211> LENGTH: 649
<212> TYPE: PRT
<213> ORGANISM: Artificial
<220> FEATURE:
<223> OTHER INFORMATION: Fusion protein alpha Her2/neu-IgG2hIFN with
      Gly4Ser linker

<400> SEQUENCE: 33

```
Met Gly Trp Ser Trp Val Met His Leu Ser Pro Val Ser Asn Cys Gly
1               5                   10                  15

Val His Ser Gln Val Gln Leu Val Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Thr Ser Tyr Trp Ile Ala Trp Val Arg Gln Met Pro Gly Lys Gly Leu
    50                  55                  60

Glu Tyr Met Gly Leu Ile Tyr Pro Gly Asp Ser Asp Thr Lys Tyr Ser
65                  70                  75                  80

Pro Ser Phe Gln Gly Gln Val Thr Ile Ser Val Asp Lys Ser Val Ser
                85                  90                  95

Thr Ala Tyr Leu Gln Trp Ser Ser Leu Lys Pro Ser Asp Ser Ala Val
            100                 105                 110

Tyr Phe Cys Ala Arg His Asp Val Gly Tyr Cys Thr Asp Arg Thr Cys
        115                 120                 125

Ala Lys Trp Pro Glu Tyr Phe Gln His Trp Gly Gln Gly Thr Leu Val
    130                 135                 140

Thr Val Ser Ser Ala Ser Thr Lys Gly Pro Ser Val Phe Pro Leu Ala
145                 150                 155                 160

Pro Ser Ser Lys Ser Thr Ser Gly Gly Thr Ala Ala Leu Gly Cys Leu
                165                 170                 175

Val Lys Asp Tyr Phe Pro Glu Pro Val Thr Val Ser Trp Asn Ser Gly
            180                 185                 190

Ala Leu Thr Ser Gly Val His Thr Phe Pro Ala Val Leu Gln Ser Ser
        195                 200                 205

Gly Leu Tyr Ser Leu Ser Ser Val Val Thr Val Pro Ser Ser Ser Leu
    210                 215                 220

Gly Thr Gln Thr Tyr Ile Cys Asn Val Asn His Lys Pro Ser Asn Thr
225                 230                 235                 240

Lys Val Asp Lys Lys Val Glu Pro Lys Ser Cys Asp Lys Thr His Thr
                245                 250                 255

Cys Pro Pro Cys Pro Ala Pro Glu Leu Leu Gly Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335

Leu Thr Val Leu His Gln Asp Trp Leu Asn Gly Lys Glu Tyr Lys Cys
            340                 345                 350
```

```
Lys Val Ser Asn Lys Ala Leu Pro Ala Pro Ile Glu Lys Thr Ile Ser
            355                 360                 365

Lys Ala Lys Gly Gln Pro Arg Glu Pro Gln Val Tyr Thr Leu Pro Pro
        370                 375                 380

Ser Arg Asp Glu Leu Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
            420                 425                 430

Gly Ser Phe Phe Leu Tyr Ser Lys Leu Thr Val Asp Lys Ser Arg Trp
        435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly Lys Ser Gly
465                 470                 475                 480

Gly Gly Gly Ser Cys Asp Leu Pro Gln Thr His Ser Leu Gly Ser Arg
                485                 490                 495

Arg Thr Leu Met Leu Leu Ala Gln Met Arg Arg Ile Ser Leu Phe Ser
            500                 505                 510

Cys Leu Lys Asp Arg His Asp Phe Gly Phe Pro Gln Glu Glu Phe Gly
        515                 520                 525

Asn Gln Phe Gln Lys Ala Glu Thr Ile Pro Val Leu His Glu Met Ile
    530                 535                 540

Gln Gln Ile Phe Asn Leu Phe Ser Thr Lys Asp Ser Ser Ala Ala Trp
545                 550                 555                 560

Asp Glu Thr Leu Leu Asp Lys Phe Tyr Thr Glu Leu Tyr Gln Gln Leu
                565                 570                 575

Asn Asp Leu Glu Ala Cys Val Ile Gln Gly Val Gly Val Thr Glu Thr
            580                 585                 590

Pro Leu Met Lys Glu Asp Ser Ile Leu Ala Val Arg Lys Tyr Phe Gln
        595                 600                 605

Arg Ile Thr Leu Tyr Leu Lys Glu Lys Lys Tyr Ser Pro Cys Ala Trp
    610                 615                 620

Glu Val Val Arg Ala Glu Ile Met Arg Ser Phe Ser Leu Ser Thr Asn
625                 630                 635                 640

Leu Gln Glu Ser Leu Arg Ser Lys Glu
                645
```

<210> SEQ ID NO 34
<211> LENGTH: 1974
<212> TYPE: DNA
<213> ORGANISM: Artificial
<220> FEATURE:
<223> OTHER INFORMATION: Nucleic acid encoding fusion protein alpha
      Her2/neu-IgG1-huIFN with alpha helix linker

<400> SEQUENCE: 34
atgggatgga gctgggtaat gcatctttct cctgtcagta actgcggtgt ccactcccag      60
gtccagctgg tgcagtctgg ggcagaggtg aaaaagcccg ggagtctct gaagatctcc      120 tgtaagggtt ctggatacag ctttaccagc tactggatcg cctgggtgcg ccagatgccc      180
gggaaaggcc tggagtacat ggggctcatc tatcctggtg actctgacac caaatacagc      240
ccgtccttcc aaggccaggt caccatctca gtcgacaagt ccgtcagcac tgcctacttg      300

```
caatggagca gtctgaagcc ctcggacagc gccgtgtatt tttgtgcgag acatgacgtg      360
ggatattgca ccgaccggac ttgcgcaaag tggcctgaat acttccagca ttggggccag      420
ggcaccctgg tcaccgtctc ctcagctagc accaagggcc catcggtctt ccccctggca      480
ccctcctcca agagcacctc tgggggcaca gcggccctgg gctgcctggt caaggactac      540
ttccccgaac cggtgacggt gtcgtggaac tcaggcgccc tgaccagcgg cgtgcacacc      600
ttcccggctg tcctacagtc ctcaggactc tactccctca gcagcgtggt gaccgtgccc      660
tccagcagct tgggcaccca gacctacatc tgcaacgtga atcacaagcc cagcaacacc      720
aaggtggaca gaaagttga gcccaaatct tgtgacaaaa ctcacacatg cccaccgtgc       780
ccagcacctg aactcctggg gggaccgtca gtcttcctct tccccccaaa acccaaggac      840
accctcatga tctcccggac ccctgaggtc acatgcgtgg tggtggacgt gagccacgaa      900
gaccctgagg tcaagttcaa ctggtacgtg gacggcgtgg aggtgcataa tgccaagaca      960
aagccgcggg aggagcagta caacagcacg taccgggtgg tcagcgtcct caccgtcctg     1020
caccaggact ggctgaatgg caaggagtac aagtgcaagg tctccaacaa agccctccca     1080
gcccccatcg agaaaaccat ctccaaagcc aaagggcagc cccgagaacc acaggtgtac     1140
accctgcccc catcccggga tgagctgacc aagaaccagg tcagcctgac ctgcctggtc     1200
aaaggcttct atcccagcga catcgccgtg gagtgggaga gcaatgggca gccggagaac     1260
aactacaaga ccacgcctcc cgtgctggac tccgacggct ccttcttcct ctacagcaag     1320
ctcaccgtgg acaagagcag gtggcagcag gggaacgtct tctcatgctc cgtgatgcat     1380
gaggctctgc acaaccacta cacgcagaag agcctctccc tgtctccggg taaagcagag     1440
gccgcagcta agaggccgc agccaaagcg ggatcctgtg atctgcctca aacccacagc     1500
ctgggtagca ggaggacctt gatgctcctg cacagatga ggagaatctc tctttctcc      1560
tgcttgaagg acagacatga ctttggattt ccccaggagg agtttggcaa ccagttccaa     1620
aaggctgaaa ccatccctgt cctccatgag atgatccagc agatcttcaa tctcttcagc     1680
acaaaggact catctgctgc ttgggatgag accctcctag acaaattcta cactgaactc     1740
taccagcagc tgaatgacct ggaagcctgt gtgatacagg gggtggggt gacagagact     1800
cccctgatga aggaggactc cattctggct gtgaggaaat acttccaaag aatcactctc     1860
tatctgaaag agaagaaata cagcccttgt gcctgggagg ttgtcagagc agaaatcatg     1920
agatcttttt ctttgtcaac aaacttgcaa gaaagttaa gaagtaagga atga             1974
```

<210> SEQ ID NO 35
<211> LENGTH: 657
<212> TYPE: PRT
<213> ORGANISM: Artificial
<220> FEATURE:
<223> OTHER INFORMATION: Fusion protein alpha Her2/neu-IgG1-huIFN with alpha helix linker

<400> SEQUENCE: 35

```
Met Gly Trp Ser Trp Val Met His Leu Ser Pro Val Ser Asn Cys Gly
1               5                   10                  15

Val His Ser Gln Val Gln Leu Val Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Thr Ser Tyr Trp Ile Ala Trp Val Arg Gln Met Pro Gly Lys Gly Leu
    50                  55                  60
```

-continued

Glu Tyr Met Gly Leu Ile Tyr Pro Gly Asp Ser Asp Thr Lys Tyr Ser
65                  70                  75                  80

Pro Ser Phe Gln Gly Gln Val Thr Ile Ser Val Asp Lys Ser Val Ser
            85                  90                  95

Thr Ala Tyr Leu Gln Trp Ser Ser Leu Lys Pro Ser Asp Ser Ala Val
            100                 105                 110

Tyr Phe Cys Ala Arg His Asp Val Gly Tyr Cys Thr Asp Arg Thr Cys
            115                 120                 125

Ala Lys Trp Pro Glu Tyr Phe Gln His Trp Gly Gln Gly Thr Leu Val
130                 135                 140

Thr Val Ser Ser Ala Ser Thr Lys Gly Pro Ser Val Phe Pro Leu Ala
145                 150                 155                 160

Pro Ser Ser Lys Ser Thr Ser Gly Gly Thr Ala Ala Leu Gly Cys Leu
            165                 170                 175

Val Lys Asp Tyr Phe Pro Glu Pro Val Thr Val Ser Trp Asn Ser Gly
            180                 185                 190

Ala Leu Thr Ser Gly Val His Thr Phe Pro Ala Val Leu Gln Ser Ser
            195                 200                 205

Gly Leu Tyr Ser Leu Ser Ser Val Val Thr Val Pro Ser Ser Ser Leu
210                 215                 220

Gly Thr Gln Thr Tyr Ile Cys Asn Val Asn His Lys Pro Ser Asn Thr
225                 230                 235                 240

Lys Val Asp Lys Lys Val Glu Pro Lys Ser Cys Asp Lys Thr His Thr
            245                 250                 255

Cys Pro Pro Cys Pro Ala Pro Glu Leu Leu Gly Gly Pro Ser Val Phe
            260                 265                 270

Leu Phe Pro Pro Lys Pro Lys Asp Thr Leu Met Ile Ser Arg Thr Pro
            275                 280                 285

Glu Val Thr Cys Val Val Val Asp Val Ser His Glu Asp Pro Glu Val
290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
            325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
            355                 360                 365

Lys Ala Lys Gly Gln Pro Arg Glu Pro Gln Val Tyr Thr Leu Pro Pro
370                 375                 380

Ser Arg Asp Glu Leu Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
            405                 410                 415

Gln Pro Glu Asn Asn Tyr Lys Thr Thr Pro Pro Val Leu Asp Ser Asp
            420                 425                 430

Gly Ser Phe Phe Leu Tyr Ser Lys Leu Thr Val Asp Lys Ser Arg Trp
            435                 440                 445

Gln Gln Gly Asn Val Phe Ser Cys Ser Val Met His Glu Ala Leu His
            450                 455                 460

Asn His Tyr Thr Gln Lys Ser Leu Ser Leu Ser Pro Gly Lys Ala Glu
465                 470                 475                 480

Ala Ala Ala Lys Glu Ala Ala Ala Lys Ala Gly Ser Cys Asp Leu Pro

```
                485              490              495
Gln Thr His Ser Leu Gly Ser Arg Arg Thr Leu Met Leu Leu Ala Gln
            500              505              510

Met Arg Arg Ile Ser Leu Phe Ser Cys Leu Lys Asp Arg His Asp Phe
            515              520              525

Gly Phe Pro Gln Glu Glu Phe Gly Asn Gln Phe Gln Lys Ala Glu Thr
            530              535              540

Ile Pro Val Leu His Glu Met Ile Gln Gln Ile Phe Asn Leu Phe Ser
545              550              555              560

Thr Lys Asp Ser Ser Ala Ala Trp Asp Glu Thr Leu Leu Asp Lys Phe
            565              570              575

Tyr Thr Glu Leu Tyr Gln Gln Leu Asn Asp Leu Glu Ala Cys Val Ile
            580              585              590

Gln Gly Val Gly Val Thr Glu Thr Pro Leu Met Lys Glu Asp Ser Ile
            595              600              605

Leu Ala Val Arg Lys Tyr Phe Gln Arg Ile Thr Leu Tyr Leu Lys Glu
610              615              620

Lys Lys Tyr Ser Pro Cys Ala Trp Glu Val Val Arg Ala Glu Ile Met
625              630              635              640

Arg Ser Phe Ser Leu Ser Thr Asn Leu Gln Glu Ser Leu Arg Ser Lys
            645              650              655

Glu
```

<210> SEQ ID NO 36
<211> LENGTH: 1929
<212> TYPE: DNA
<213> ORGANISM: Artificial
<220> FEATURE:
<223> OTHER INFORMATION: Nucleic acid encoding fusion protein anti-CD20
    IgG1 GS1 human IFN beta

<400> SEQUENCE: 36

```
atgtacttgg gactgaactg tgtaatcata gttttctctc taaaaggtgt ccagagtcag    60
gtacaactgc agcagcctgg ggctgagctg gtgaagcctg ggcctcagt gaagatgtcc    120 tgcaaggctt ctggctacac atttaccagt tacaatatgc actgggtaaa acagacacct    180
ggtcggggcc tggaatggat tggagctatt tatcccggaa atggtgatac ttcctacaat    240
cagaagttca aggcaaggc cacattgact gcagacaaat cctccagcac agcctacatg    300
cagctcagca gcctgacatc tgaggactct gcggtctatt actgtgcaag atcgacttac    360
tacggcggtg actggtactt caatgtctgg ggcgcaggga ccacggtcac cgtctctgca    420
gctagcacca agggcccatc ggtcttcccc ctggcaccct cctccaagag cacctctggg    480
ggcacagcgg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgacc gtgccctcca gcagcttggg cacccagacc    660
tacatctgca acgtgaatca caagcccagc aacaccaagg tggacaagaa agttgagccc    720
aaatcttgtg acaaaactca cacatgccca ccgtgccag cacctgaact cctgggggga    780
ccgtcagtct tcctcttccc cccaaaaccc aaggacaccc tcatgatctc ccggaccct    840 gaggtcacat gcgtggtggt ggacgtgagc cacgaagacc ctgaggtcaa gttcaactgg    900
tacgtggacg gcgtggaggt gcataatgcc aagacaaagc cgcgggagga gcagtacaac    960
agcacgtacc gggtggtcag cgtcctcacc gtcctgcacc aggactggct gaatggcaag    1020
```

```
gagtacaagt gcaaggtctc caacaaagcc ctcccagccc ccatcgagaa aaccatctcc    1080
aaagccaaag gcagccccg agaaccacag gtgtacaccc tgcccccatc ccgggatgag    1140
ctgaccaaga accaggtcag cctgacctgc ctggtcaaag gcttctatcc cagcgacatc    1200
gccgtggagt gggagagcaa tgggcagccg gagaacaact acaagaccac gcctcccgtg    1260
ctggactccg acggctcctt cttcctctac agcaagctca ccgtggacaa gagcaggtgg    1320
cagcagggga acgtcttctc atgctccgtg atgcatgagg ctctgcacaa ccactacacg    1380
cagaagagcc tctccctgtc tccgggtaaa tctggtggcg gtggatccat gagctacaac    1440
ttgcttggat tcctacaaag aagcagcaat tttcagtgtc agaagctcct gtggcaattg    1500
aatgggaggc ttgaatactg cctcaaggac aggatgaact ttgacatccc tgaggagatt    1560
aagcagctgc agcagttcca gaaggaggac gccgcattga ccatctatga gatgctccag    1620
aacatctttg ctattttcag acaagattca tctagcactg gctggaatga gactattgtt    1680
gagaacctcc tggctaatgt ctatcatcag ataaaccatc tgaagacagt cctggaagaa    1740
aaactggaga agaagatttt caccagggga aaactcatga gcagtctgca cctgaaaaga    1800
tattatggga ggattctgca ttacctgaag gccaaggagt acagtcactg tgcctggacc    1860
atagtcagag tggaaatcct aaggaacttt tacttcatta acagacttac aggttacctc    1920
cgaaactga                                                          1929
```

```
<210> SEQ ID NO 37
<211> LENGTH: 642
<212> TYPE: PRT
<213> ORGANISM: Artificial
<220> FEATURE:
<223> OTHER INFORMATION: Fusion protein anti-CD20 IgG1 GS1 human IFN
      beta

<400> SEQUENCE: 37
```

```
Met Tyr Leu Gly Leu Asn Cys Val Ile Ile Val Phe Leu Leu Lys Gly
1               5                   10                  15

Val Gln Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ala Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190
```

-continued

```
Phe Pro Ala Val Leu Gln Ser Gly Leu Tyr Ser Leu Ser Ser Val
            195                 200                 205
Val Thr Val Pro Ser Ser Leu Gly Thr Gln Thr Tyr Ile Cys Asn
    210                 215                 220
Val Asn His Lys Pro Ser Asn Thr Lys Val Asp Lys Lys Val Glu Pro
225                 230                 235                 240
Lys Ser Cys Asp Lys Thr His Thr Cys Pro Pro Cys Pro Ala Pro Glu
                245                 250                 255
Leu Leu Gly Gly Pro Ser Val Phe Leu Phe Pro Pro Lys Pro Lys Asp
            260                 265                 270
Thr Leu Met Ile Ser Arg Thr Pro Glu Val Thr Cys Val Val Val Asp
        275                 280                 285
Val Ser His Glu Asp Pro Glu Val Lys Phe Asn Trp Tyr Val Asp Gly
    290                 295                 300
Val Glu Val His Asn Ala Lys Thr Lys Pro Arg Glu Glu Gln Tyr Asn
305                 310                 315                 320
Ser Thr Tyr Arg Val Val Ser Val Leu Thr Val Leu His Gln Asp Trp
                325                 330                 335
Leu Asn Gly Lys Glu Tyr Lys Cys Lys Val Ser Asn Lys Ala Leu Pro
            340                 345                 350
Ala Pro Ile Glu Lys Thr Ile Ser Lys Ala Lys Gly Gln Pro Arg Glu
        355                 360                 365
Pro Gln Val Tyr Thr Leu Pro Pro Ser Arg Asp Glu Leu Thr Lys Asn
    370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Val Leu Asp Ser Asp Gly Ser Phe Phe Leu Tyr Ser Lys
            420                 425                 430
Leu Thr Val Asp Lys Ser Arg Trp Gln Gln Gly Asn Val Phe Ser Cys
        435                 440                 445
Ser Val Met His Glu Ala Leu His Asn His Tyr Thr Gln Lys Ser Leu
    450                 455                 460
Ser Leu Ser Pro Gly Lys Ser Gly Gly Gly Ser Met Ser Tyr Asn
465                 470                 475                 480
Leu Leu Gly Phe Leu Gln Arg Ser Ser Asn Phe Gln Cys Gln Lys Leu
                485                 490                 495
Leu Trp Gln Leu Asn Gly Arg Leu Glu Tyr Cys Leu Lys Asp Arg Met
            500                 505                 510
Asn Phe Asp Ile Pro Glu Glu Ile Lys Gln Leu Gln Gln Phe Gln Lys
        515                 520                 525
Glu Asp Ala Ala Leu Thr Ile Tyr Glu Met Leu Gln Asn Ile Phe Ala
    530                 535                 540
Ile Phe Arg Gln Asp Ser Ser Ser Thr Gly Trp Asn Glu Thr Ile Val
545                 550                 555                 560
Glu Asn Leu Leu Ala Asn Val Tyr His Gln Ile Asn His Leu Lys Thr
                565                 570                 575
Val Leu Glu Glu Lys Leu Glu Lys Glu Asp Phe Thr Arg Gly Lys Leu
            580                 585                 590
Met Ser Ser Leu His Leu Lys Arg Tyr Tyr Gly Arg Ile Leu His Tyr
        595                 600                 605
Leu Lys Ala Lys Glu Tyr Ser His Cys Ala Trp Thr Ile Val Arg Val
```

Glu Ile Leu Arg Asn Phe Tyr Phe Ile Asn Arg Leu Thr Gly Tyr Leu
625                 630                 635                 640

Arg Asn

<210> SEQ ID NO 38
<211> LENGTH: 2070
<212> TYPE: DNA
<213> ORGANISM: Artificial
<220> FEATURE:
<223> OTHER INFORMATION: Nucleic acid encoding fusion protein anti-CD20
      IgG3 GS1 human IFN beta

<400> SEQUENCE: 38

| | | | | | |
|---|---|---|---|---|---|
| atgtacttgg | gactgaactg | tgtaatcata | gttttctct | taaaaggtgt | ccagagtcag | 60 |
| gtacaactgc | agcagcctgg | ggctgagctg | gtgaagcctg | ggcctcagt | gaagatgtcc | 120 |
| tgcaaggctt | ctggctacac | atttaccagt | tacaatatgc | actgggtaaa | acagacacct | 180 |
| ggtcggggcc | tggaatggat | tggagctatt | tatcccggaa | atggtgatac | ttcctacaat | 240 |
| cagaagttca | aggcaaggc | cacattgact | gcagacaaat | cctccagcac | agcctacatg | 300 |
| cagctcagca | gcctgacatc | tgaggactct | gcggtctatt | actgtgcaag | atcgacttac | 360 |
| tacggcggtg | actggtactt | caatgtctgg | ggcgcaggga | ccacggtcac | cgtctctgca | 420 |
| gctagcacca | agggcccatc | ggtcttcccc | ctggcgccct | gctccaggag | cacctctggg | 480 |
| ggcacagcgg | ccctgggctg | cctggtcaag | gactacttcc | ccgaaccggt | gacggtgtcg | 540 |
| tggaactcag | gcgccctgac | cagcggcgtg | cacaccttcc | cggctgtcct | acagtcctca | 600 |
| ggactctact | ccctcagcag | cgtggtgacc | gtgccctcca | gcagcttggg | cacccagacc | 660 |
| tacacctgca | acgtgaatca | caagcccagc | aacaccaagg | tggacaagag | agttgagctc | 720 |
| aaaacccac | ttggtgacac | aactcacaca | tgcccacggt | gcccagagcc | caaatcttgt | 780 |
| gacacacctc | cccgtgccc | aaggtgccca | gagcccaaat | cttgtgacac | acctccccg | 840 |
| tgcccaaggt | gcccagagcc | caaatcttgt | gacacacctc | cccgtgccc | aaggtgccca | 900 |
| gcacctgaac | tcctggggagg | accgtcagtc | ttcctcttcc | ccccaaaacc | caaggatacc | 960 |
| cttatgattt | cccggacccc | tgaggtcacg | tgcgtggtgg | tggacgtgag | ccacgaagac | 1020 |
| cccgaggtcc | agttcaagtg | gtacgtggac | ggcgtggagg | tgcataatgc | caagacaaag | 1080 |
| ctgcgggagg | agcagtacaa | cagcacgttc | cgtgtggtca | gcgtcctcac | cgtcctgcac | 1140 |
| caggactggc | tgaacggcaa | ggagtacaag | tgcaaggtct | ccaacaaagc | cctcccagcc | 1200 |
| cccatcgaga | aaaccatctc | caaagccaaa | ggacagcccc | gagaaccaca | ggtgtacacc | 1260 |
| ctgcccccat | cccgggagga | gatgaccaag | aaccaggtca | gcctgacctg | cctggtcaaa | 1320 |
| ggcttctacc | ccagcgacat | cgccgtggag | tgggagagca | atgggcagcc | ggagaacaac | 1380 |
| tacaacacca | cgcctcccat | gctggactcc | gacggctcct | tcttcctcta | cagcaagctc | 1440 |
| accgtggaca | agagcaggtg | gcagcagggg | aacatcttct | catgctccgt | gatgcatgag | 1500 |
| gctctgcaca | accactacac | gcagaagagc | ctctccctgt | ctccgggtaa | atctggtggc | 1560 |
| ggtggatcca | tgagctacaa | cttgcttgga | ttcctacaaa | gaagcagcaa | ttttcagtgt | 1620 |
| cagaagctcc | tgtggcaatt | gaatgggagg | cttgaatact | gcctcaagga | caggatgaac | 1680 |
| tttgacatcc | ctgaggagat | taagcagctg | cagcagttcc | agaaggagga | cgccgcattg | 1740 |
| accatctatg | agatgctcca | gaacatcttt | gctattttca | gacaagattc | atctagcact | 1800 |
| ggctggaatg | agactattgt | tgagaacctc | ctggctaatg | tctatcatca | gataaaccat | 1860 |

```
ctgaagacag tcctggaaga aaaactggag aaagaagatt tcaccagggg aaaactcatg      1920
agcagtctgc acctgaaaag atattatggg aggattctgc attacctgaa ggccaaggag      1980
tacagtcact gtgcctggac catagtcaga gtggaaatcc taaggaactt ttacttcatt      2040
aacagactta caggttacct ccgaaactga                                        2070

<210> SEQ ID NO 39
<211> LENGTH: 689
<212> TYPE: PRT
<213> ORGANISM: Artificial
<220> FEATURE:
<223> OTHER INFORMATION: Fusion protein anti-CD20 IgG3 GS1 human IFN

```
Leu Met Ile Ser Arg Thr Pro Glu Val Thr Cys Val Val Asp Val
            325                 330                 335

Ser His Glu Asp Pro Glu Val Gln Phe Lys Trp Tyr Val Asp Gly Val
        340                 345                 350

Glu Val His Asn Ala Lys Thr Lys Leu Arg Glu Glu Gln Tyr Asn Ser
            355                 360                 365

Thr Phe Arg Val Val Ser Val Leu Thr Val Leu His Gln Asp Trp Leu
    370                 375                 380

Asn Gly Lys Glu Tyr Lys Cys Lys Val Ser Asn Lys Ala Leu Pro Ala
385                 390                 395                 400

Pro Ile Glu Lys Thr Ile Ser Lys Ala Lys Gly Gln Pro Arg Glu Pro
                405                 410                 415

Gln Val Tyr Thr Leu Pro Pro Ser Arg Glu Glu Met Thr Lys Asn Gln
            420                 425                 430

Val Ser Leu Thr Cys Leu Val Lys Gly Phe Tyr Pro Ser Asp Ile Ala
        435                 440                 445

Val Glu Trp Glu Ser Asn Gly Gln Pro Glu Asn Asn Tyr Asn Thr Thr
    450                 455                 460

Pro Pro Met Leu Asp Ser Asp Gly Ser Phe Phe Leu Tyr Ser Lys Leu
465                 470                 475                 480

Thr Val Asp Lys Ser Arg Trp Gln Gln Gly Asn Ile Phe Ser Cys Ser
                485                 490                 495

Val Met His Glu Ala Leu His Asn His Tyr Thr Gln Lys Ser Leu Ser
            500                 505                 510

Leu Ser Pro Gly Lys Ser Gly Gly Gly Ser Met Ser Tyr Asn Leu
        515                 520                 525

Leu Gly Phe Leu Gln Arg Ser Ser Asn Phe Gln Cys Gln Lys Leu Leu
    530                 535                 540

Trp Gln Leu Asn Gly Arg Leu Glu Tyr Cys Leu Lys Asp Arg Met Asn
545                 550                 555                 560

Phe Asp Ile Pro Glu Glu Ile Lys Gln Leu Gln Gln Phe Gln Lys Glu
                565                 570                 575

Asp Ala Ala Leu Thr Ile Tyr Glu Met Leu Gln Asn Ile Phe Ala Ile
            580                 585                 590

Phe Arg Gln Asp Ser Ser Ser Thr Gly Trp Asn Glu Thr Ile Val Glu
    595                 600                 605

Asn Leu Leu Ala Asn Val Tyr His Gln Ile Asn His Leu Lys Thr Val
610                 615                 620

Leu Glu Glu Lys Leu Glu Lys Glu Asp Phe Thr Arg Gly Lys Leu Met
625                 630                 635                 640

Ser Ser Leu His Leu Lys Arg Tyr Tyr Gly Arg Ile Leu His Tyr Leu
                645                 650                 655

Lys Ala Lys Glu Tyr Ser His Cys Ala Trp Thr Ile Val Arg Val Glu
            660                 665                 670

Ile Leu Arg Asn Phe Tyr Phe Ile Asn Arg Leu Thr Gly Tyr Leu Arg
    675                 680                 685

Asn
```

<210> SEQ ID NO 40
<211> LENGTH: 2055
<212> TYPE: DNA
<213> ORGANISM: Artificial
<220> FEATURE:
<223> OTHER INFORMATION: Nucleic acid encoding fusion protein anti-CD20

IgG3 GS1 murine IFN beta

<400> SEQUENCE: 40

```
atgtacttgg gactgaactg tgtaatcata gttttctct taaaaggtgt ccagagtcag    60
gtacaactgc agcagcctgg ggctgagctg gtgaagcctg ggcctcagt gaagatgtcc   120
tgcaaggctt ctggctacac atttaccagt tacaatatgc actgggtaaa acagacacct   180
ggtcggggcc tggaatggat tgagctatt tatcccggaa atggtgatac ttcctacaat   240
cagaagttca aggcaaggc cacattgact gcagacaaat cctccagcac agcctacatg   300
cagctcagca gcctgacatc tgaggactct gcggtctatt actgtgcaag atcgacttac   360
tacggcggtg actggtactt caatgtctgg ggcgcaggga ccacggtcac cgtctctgca   420
gctagcacca agggcccatc ggtcttcccc ctggcgccct gctccaggag cacctctggg   480
ggcacagcgg ccctgggctg cctggtcaag gactacttcc ccgaaccggt gacggtgtcg   540
tggaactcag cgccctgac cagcggcgtg cacaccttcc cggctgtcct acagtcctca   600
ggactctact ccctcagcag cgtggtgacc gtgcctcca gcagcttggg cacccagacc   660
tacacctgca acgtgaatca caagcccagc aacaccaagg tggacaagag agttgagctc   720
aaaaccccac ttggtgacac aactcacaca tgcccacggt gcccagagcc caaatcttgt   780
gacacacctc ccccgtgccc aaggtgccca gagcccaaat cttgtgacac acctcccccg   840
tgcccaaggt gcccagagcc caaatcttgt gacacacctc ccccgtgccc aaggtgccca   900
gcacctgaac tcctgggagg accgtcagtc ttcctcttcc ccccaaaacc caaggatacc   960
cttatgattt cccggacccc tgaggtcacg tgcgtggtgg tggacgtgag ccacgaagac  1020
cccgaggtcc agttcaagtg gtacgtggac ggcgtggagg tgcataatgc caagacaaag  1080
ctgcgggagg agcagtacaa cagcacgttc cgtgtggtca gcgtcctcac cgtcctgcac  1140
caggactggc tgaacggcaa ggagtacaag tgcaaggtct ccaacaaagc cctcccagcc  1200
cccatcgaga aaaccatctc caaagccaaa ggacagcccc gagaaccaca ggtgtacacc  1260
ctgcccccat cccgggagga tgaccaag aaccaggtca gcctgacctg cctggtcaaa  1320
ggcttctacc ccagcgacat cgccgtggag tgggagagca atgggcagcc ggagaacaac  1380
tacaacacca cgcctcccat gctggactcc gacggctcct tcttcctcta cagcaagctc  1440
accgtggaca gagcaggtg gcagcagggg aacatcttct catgctccgt gatgcatgag  1500
gctctgcaca accactacac gcagaagagc ctctccctgt ctccgggtaa atctggtggc  1560
ggtggatcca tcaactataa gcagctccag ctccaagaaa ggacgaacat tcggaaatgt  1620
caggagctcc tggagcagct gaatggaaag atcaacctca cctacaggc ggactttaag  1680
atccctatgg agatgacgga gaagatgcag aagagttaca ctgcctttgc catccaagag  1740
atgctccaga atgtctttct tgtcttcaga aacaatttct ccagcactgg gtggaatgag  1800
actattgttg tacgtctcct ggatgaactc caccagcaga cagtgtttct gaagacagta  1860
ctagaggaaa agcaagagga aagattgacg tgggagatgt cctcaactgc tctccacttg  1920
aagagctatt actggagggt gcaaaggtac cttaaactca tgaagtacaa cagctacgcc  1980
tggatggtgg tccagcagaga gatcttcagg aactttctca tcattcgaag acttaccaga  2040
aacttccaaa actga                                                   2055
```

<210> SEQ ID NO 41
<211> LENGTH: 684
<212> TYPE: PRT
<213> ORGANISM: Artificial

<220> FEATURE:
<223> OTHER INFORMATION: Fusion protein anti-CD20 IgG3 GS1 murine IFN
      beta

<400> SEQUENCE: 41

Met Tyr Leu Gly Leu Asn Cys Val Ile Ile Val Phe Leu Leu Lys Gly
1               5                   10                  15

Val Gln Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ala Ala Ser Thr Lys
    130                 135                 140

Gly Pro Ser Val Phe Pro Leu Ala Pro Cys Ser Arg Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Thr Cys Asn
    210                 215                 220

Val Asn His Lys Pro Ser Asn Thr Lys Val Asp Lys Arg Val Glu Leu
225                 230                 235                 240

Lys Thr Pro Leu Gly Asp Thr Thr His Thr Cys Pro Arg Cys Pro Glu
                245                 250                 255

Pro Lys Ser Cys Asp Thr Pro Pro Pro Cys Pro Arg Cys Pro Glu Pro
            260                 265                 270

Lys Ser Cys Asp Thr Pro Pro Pro Cys Pro Arg Cys Pro Glu Pro Lys
        275                 280                 285

Ser Cys Asp Thr Pro Pro Pro Cys Pro Arg Cys Pro Ala Pro Glu Leu
    290                 295                 300

Leu Gly Gly Pro Ser Val Phe Leu Phe Pro Pro Lys Pro Lys Asp Thr
305                 310                 315                 320

Leu Met Ile Ser Arg Thr Pro Glu Val Thr Cys Val Val Val Asp Val
                325                 330                 335

Ser His Glu Asp Pro Glu Val Gln Phe Lys Trp Tyr Val Asp Gly Val
            340                 345                 350

Glu Val His Asn Ala Lys Thr Lys Leu Arg Glu Gln Tyr Asn Ser
        355                 360                 365

Thr Phe Arg Val Val Ser Val Leu Thr Val Leu His Gln Asp Trp Leu
    370                 375                 380

Asn Gly Lys Glu Tyr Lys Cys Lys Val Ser Asn Lys Ala Leu Pro Ala

Pro Ile Glu Lys Thr Ile Ser Lys Ala Lys Gly Gln Pro Arg Glu Pro
385                 390                 395                 400
                405                 410                 415

Gln Val Tyr Thr Leu Pro Pro Ser Arg Glu Glu Met Thr Lys Asn Gln
                420                 425                 430

Val Ser Leu Thr Cys Leu Val Lys Gly Phe Tyr Pro Ser Asp Ile Ala
                435                 440                 445

Val Glu Trp Glu Ser Asn Gly Gln Pro Glu Asn Asn Tyr Asn Thr Thr
450                 455                 460

Pro Pro Met Leu Asp Ser Asp Gly Ser Phe Phe Leu Tyr Ser Lys Leu
465                 470                 475                 480

Thr Val Asp Lys Ser Arg Trp Gln Gln Gly Asn Ile Phe Ser Cys Ser
                485                 490                 495

Val Met His Glu Ala Leu His Asn His Tyr Thr Gln Lys Ser Leu Ser
                500                 505                 510

Leu Ser Pro Gly Lys Ser Gly Gly Gly Ser Ile Asn Tyr Lys Gln
                515                 520                 525

Leu Gln Leu Gln Glu Arg Thr Asn Ile Arg Lys Cys Gln Glu Leu Leu
530                 535                 540

Glu Gln Leu Asn Gly Lys Ile Asn Leu Thr Tyr Arg Ala Asp Phe Lys
545                 550                 555                 560

Ile Pro Met Glu Met Thr Glu Lys Met Gln Lys Ser Tyr Thr Ala Phe
                565                 570                 575

Ala Ile Gln Glu Met Leu Gln Asn Val Phe Leu Val Phe Arg Asn Asn
                580                 585                 590

Phe Ser Ser Thr Gly Trp Asn Glu Thr Ile Val Val Arg Leu Leu Asp
                595                 600                 605

Glu Leu His Gln Gln Thr Val Phe Leu Lys Thr Val Leu Glu Glu Lys
                610                 615                 620

Gln Glu Glu Arg Leu Thr Trp Glu Met Ser Ser Thr Ala Leu His Leu
625                 630                 635                 640

Lys Ser Tyr Tyr Trp Arg Val Gln Arg Tyr Leu Lys Leu Met Lys Tyr
                645                 650                 655

Asn Ser Tyr Ala Trp Met Val Val Arg Ala Glu Ile Phe Arg Asn Phe
                660                 665                 670

Leu Ile Ile Arg Arg Leu Thr Arg Asn Phe Gln Asn
                675                 680

```
<210> SEQ ID NO 42
<211> LENGTH: 1923
<212> TYPE: DNA
<213> ORGANISM: Artificial
<220> FEATURE:
<223> OTHER INFORMATION: Nucleic acid encoding fusion protein anti-HER2/
      neu IgG1 G/S hIFN alpha

<400> SEQUENCE: 42
atggaatgca gctgggtaat gctctttctc ctgtcagtaa ctgcaggtgt ccactccgag      60
gttcagctgg tggagtctgg cggtggcctg gtgcagccag ggggctcact ccgtttgtcc    120
tgtgcagctt ctggcttcaa cattaaagac acctatatac actgggtgcg tcaggccccg    180
ggtaagggcc tggaatgggt tgcaaggatt tatcctacga atggttatac tagatatgcc    240
gatagcgtca aggccgtttt cactataagc gcagacacat ccaaaaacac agcctacctg    300
cagatgaaca gcctgcgtgc tgaggacact gccgtctatt attgttctag atgggggaggg    360
```

```
gacggcttct atgctatgga ctactggggt caaggaaccc tggtcaccgt ctcctcggct    420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttcccccc aaaacccaag gacaccctca tgatctcccg gacccctgag    840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccggg tggtcagcgt cctcaccgtc ctgcaccagg actggctgaa tggcaaggag   1020
tacaagtgca aggtctccaa caaagccctc ccagccccca tcgagaaaac catctccaaa   1080
gccaaagggc agccccgaga accacaggtg tacaccctgc ccccatcccg ggatgagctg   1140
accaagaacc aggtcagcct gacctgcctg gtcaaaggct tctatcccag cgacatcgcc   1200
gtggagtggg agagcaatgg gcagccggag aacaactaca agaccacgcc tcccgtgctg   1260
gactccgacg gctccttctt cctctacagc aagctcaccg tggacaagag caggtggcag   1320
caggggaacg tcttctcatg ctccgtgatg catgaggctc tgcacaacca ctacacgcag   1380
aagagcctct ccctgtctcc gggtaaatct ggtggcggtg gatcctgtga tctgcctcaa   1440
acccacagcc tgggtagcag gaggaccttg atgctcctgg cacagatgag gagaatctct   1500
cttttctcct gcttgaagga cagacatgac tttggatttc cccaggagga gtttggcaac   1560
cagttccaaa aggctgaaac catccctgtc ctccatgaga tgatccagca gatcttcaat   1620
ctcttcagca caaaggactc atctgctgct tgggatgaga ccctcctaga caaattctac   1680
actgaactct accagcagct gaatgacctg gaagcctgtg tgatacaggg ggtgggggtg   1740
acagagactc ccctgatgaa ggaggactcc attctggctg tgaggaaata cttccaaaga   1800
atcactctct atctgaaaga gaagaaatac agcccttgtg cctgggaggt tgtcagagca   1860
gaaatcatga gatcttttc tttgtcaaca aacttgcaag aaagtttaag aagtaaggaa   1920
tga                                                                 1923
```

<210> SEQ ID NO 43
<211> LENGTH: 640
<212> TYPE: PRT
<213> ORGANISM: Artificial
<220> FEATURE:
<223> OTHER INFORMATION: Fusion protein anti-HER2/neu IgG1 G/S hIFN alpha

<400> SEQUENCE: 43

```
Met Glu Cys Ser Trp Val Met Leu Phe Leu Leu Ser Val Thr Ala Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80
```

```
Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys Ser Gly Gly Gly Ser Cys Asp Leu Pro Gln
465                 470                 475                 480

Thr His Ser Leu Gly Ser Arg Arg Thr Leu Met Leu Leu Ala Gln Met
                485                 490                 495
```

```
Arg Arg Ile Ser Leu Phe Ser Cys Leu Lys Asp Arg His Asp Phe Gly
            500                 505                 510
Phe Pro Gln Glu Glu Phe Gly Asn Gln Phe Gln Lys Ala Glu Thr Ile
        515                 520                 525
Pro Val Leu His Glu Met Ile Gln Gln Ile Phe Asn Leu Phe Ser Thr
    530                 535                 540
Lys Asp Ser Ser Ala Ala Trp Asp Glu Thr Leu Leu Asp Lys Phe Tyr
545                 550                 555                 560
Thr Glu Leu Tyr Gln Gln Leu Asn Asp Leu Glu Ala Cys Val Ile Gln
                565                 570                 575
Gly Val Gly Val Thr Glu Thr Pro Leu Met Lys Glu Asp Ser Ile Leu
            580                 585                 590
Ala Val Arg Lys Tyr Phe Gln Arg Ile Thr Leu Tyr Leu Lys Glu Lys
        595                 600                 605
Lys Tyr Ser Pro Cys Ala Trp Glu Val Val Arg Ala Glu Ile Met Arg
    610                 615                 620
Ser Phe Ser Leu Ser Thr Asn Leu Gln Glu Ser Leu Arg Ser Lys Glu
625                 630                 635                 640

<210> SEQ ID NO 44
<211> LENGTH: 1926
<212> TYPE: DNA
<213> ORGANISM: Artificial
<220> FEATURE:
<223> OTHER INFORMATION: Nucleotide sequence encoding fusion protein
      anti-HER/neu IgG1 G/S huIFN beta

<400> SEQUENCE: 44
atggaatgca gctgggtaat gctctttctc ctgtcagtaa ctgcaggtgt ccactccgag      60
gttcagctgg tggagtctgg cggtggcctg gtgcagccag ggggctcact ccgtttgtcc     120
tgtgcagctt ctggcttcaa cattaaagac acctatatac actgggtgcg tcaggccccg     180
ggtaagggcc tggaatgggt tgcaaggatt tatcctacga atggttatac tagatatgcc     240
gatagcgtca agggccgttt cactataagc gcagacacat ccaaaaacac agcctacctg     300
cagatgaaca gcctgcgtgc tgaggacact gccgtctatt attgttctag atggggaggg     360
gacggcttct atgctatgga ctactggggt caaggaaccc tggtcaccgt ctcctcggct     420
agcaccaagg gcccatcggt cttccccctg gcaccctcct ccaagagcac ctctgggggc     480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttcccccc aaaacccaag gacaccctca tgatctcccg gacccctgag     840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccggg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc ccccatcccg ggatgagctg    1140
accaagaacc aggtcagcct gacctgcctg gtcaaaggct tctatccag cgacatcgcc    1200 gtggagtggg agagcaatgg gcagccggag aacaactaca agaccacgcc tcccgtgctg    1260
```

-continued

```
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatct ggtggcggtg gatccatgag ctacaacttg    1440
cttggattcc tacaaagaag cagcaatttt cagtgtcaga agctcctgtg gcaattgaat    1500
gggaggcttg aatactgcct caaggacagg atgaactttg acatccctga ggagattaag    1560
cagctgcagc agttccagaa ggaggacgcc gcattgacca tctatgagat gctccagaac    1620
atctttgcta ttttcagaca agattcatct agcactggct ggaatgagac tattgttgag    1680
aacctcctgg ctaatgtcta tcatcagata accatctga agacagtcct ggaagaaaaa    1740
ctggagaaag aagatttcac caggggaaaa ctcatgagca gtctgcacct gaaaagatat    1800
tatgggagga ttctgcatta cctgaaggcc aaggagtaca gtcactgtgc ctggaccata    1860
gtcagagtgg aaatcctaag gaactttttac ttcattaaca gacttacagg ttacctccga    1920
aactga                                                               1926
```

<210> SEQ ID NO 45
<211> LENGTH: 641
<212> TYPE: PRT
<213> ORGANISM: Artificial
<220> FEATURE:
<223> OTHER INFORMATION: Fusion protein anti-HER/neu IgG1 G/S huIFN beta

<400> SEQUENCE: 45

```
Met Glu Cys Ser Trp Val Met Leu Phe Leu Leu Ser Val Thr Ala Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240
```

Ser Cys Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp Thr
        260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
        290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys Ser Gly Gly Gly Ser Met Ser Tyr Asn Leu
465                 470                 475                 480

Leu Gly Phe Leu Gln Arg Ser Ser Asn Phe Gln Cys Gln Lys Leu Leu
            485                 490                 495

Trp Gln Leu Asn Gly Arg Leu Glu Tyr Cys Leu Lys Asp Arg Met Asn
        500                 505                 510

Phe Asp Ile Pro Glu Glu Ile Lys Gln Leu Gln Gln Phe Gln Lys Glu
    515                 520                 525

Asp Ala Ala Leu Thr Ile Tyr Glu Met Leu Gln Asn Ile Phe Ala Ile
530                 535                 540

Phe Arg Gln Asp Ser Ser Ser Thr Gly Trp Asn Glu Thr Ile Val Glu
545                 550                 555                 560

Asn Leu Leu Ala Asn Val Tyr His Gln Ile Asn His Leu Lys Thr Val
            565                 570                 575

Leu Glu Glu Lys Leu Glu Lys Glu Asp Phe Thr Arg Gly Lys Leu Met
        580                 585                 590

Ser Ser Leu His Leu Lys Arg Tyr Tyr Gly Arg Ile Leu His Tyr Leu
    595                 600                 605

Lys Ala Lys Glu Tyr Ser His Cys Ala Trp Thr Ile Val Arg Val Glu
    610                 615                 620

Ile Leu Arg Asn Phe Tyr Phe Ile Asn Arg Leu Thr Gly Tyr Leu Arg
625                 630                 635                 640

Asn

<210> SEQ ID NO 46
<211> LENGTH: 1947
<212> TYPE: DNA
<213> ORGANISM: Artificial
<220> FEATURE:
<223> OTHER INFORMATION: Nucleic acid encoding fusion protein anti-her2/
neu IgG1 huIFN alpha joine with alpha helical linker

<400> SEQUENCE: 46

```
atggaatgca gctgggtaat gctctttctc ctgtcagtaa ctgcaggtgt ccactccgag      60
gttcagctgg tggagtctgg cggtggcctg gtgcagccag ggggctcact ccgtttgtcc     120
tgtgcagctt ctggcttcaa cattaaagac acctatatac actgggtgcg tcaggccccg     180
ggtaagggcc tggaatgggt tgcaaggatt tatcctacga atggttatac tagatatgcc     240
gatagcgtca agggccgttt cactataagc gcagacacat ccaaaaacac agcctacctg     300
cagatgaaca gcctgcgtgc tgaggacact gccgtctatt attgttctag atggggaggg     360
gacggcttct atgctatgga ctactgggg caaggaaccc tggtcaccgt ctcctcggct     420
agcaccaagg gcccatcggt cttccccctg gcaccctcct ccaagagcac ctctgggggc     480
acagcggccc tgggctgcct ggtcaaggac tacttcccg aaccggtgac ggtgtcgtgg      540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttcccccc aaaacccaag gacaccctca tgatctcccg gacccctgag     840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccggg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc cccatcccg ggatgagctg     1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaagca gaggccgcag ctaaagaggc cgcagccaaa    1440
gcgggatcct gtgatctgcc tcaaacccac agcctgggta gcaggaggac cttgatgctc    1500
ctggcacaga tgaggagaat ctctcttttc tcctgcttga aggacagaca tgactttgga    1560
tttccccagg aggagtttgg caaccagttc caaaaggctg aaaccatccc tgtcctccat    1620
gagatgatcc agcagatctt caatctcttc agcacaaagg actcatctgc tgcttgggat    1680
gagaccctcc tagacaaatt ctacactgaa ctctaccagc agctgaatga cctggaagcc    1740
tgtgtgatac agggggtggg ggtgacagag actcccctga tgaaggagga ctccattctg    1800
gctgtgagga aatacttcca aagaatcact ctctatctga agagaagaa atacagccct     1860
tgtgcctggg aggttgtcag agcagaaatc atgagatctt tttctttgtc aacaaacttg    1920
caagaaagtt taagaagtaa ggaatga                                        1947
```

<210> SEQ ID NO 47
<211> LENGTH: 648

<212> TYPE: PRT
<213> ORGANISM: Artificial
<220> FEATURE:
<223> OTHER INFORMATION: Fusion protein anti-her2/neu IgG1 huIFN alpha joine with alpha helical linker

<400> SEQUENCE: 47

```
Met Glu Cys Ser Trp Val Met Leu Phe Leu Leu Ser Val Thr Ala Gly
 1               5                  10                  15

Val His Ser Glu Val Gln Leu Val Glu Ser Gly Gly Gly Leu Val Gln
             20                  25                  30

Pro Gly Gly Ser Leu Arg Leu Ser Cys Ala Ala Ser Gly Phe Asn Ile
         35                  40                  45

Lys Asp Thr Tyr Ile His Trp Val Arg Gln Ala Pro Gly Lys Gly Leu
 50                  55                  60

Glu Trp Val Ala Arg Ile Tyr Pro Thr Asn Gly Tyr Thr Arg Tyr Ala
 65                  70                  75                  80

Asp Ser Val Lys Gly Arg Phe Thr Ile Ser Ala Asp Thr Ser Lys Asn
                 85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
370                 375                 380
```

```
Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
        420                 425                 430

Thr Val Asp Lys Ser Arg Trp Gln Gln Gly Asn Val Phe Ser Cys Ser
    435                 440                 445

Val Met His Glu Ala Leu His Asn His Tyr Thr Gln Lys Ser Leu Ser
450                 455                 460

Leu Ser Pro Gly Lys Ala Glu Ala Ala Lys Glu Ala Ala Ala Lys
465                 470                 475                 480

Ala Gly Ser Cys Asp Leu Pro Gln Thr His Ser Leu Gly Ser Arg Arg
            485                 490                 495

Thr Leu Met Leu Leu Ala Gln Met Arg Arg Ile Ser Leu Phe Ser Cys
        500                 505                 510

Leu Lys Asp Arg His Asp Phe Gly Phe Pro Gln Glu Glu Phe Gly Asn
    515                 520                 525

Gln Phe Gln Lys Ala Glu Thr Ile Pro Val Leu His Glu Met Ile Gln
530                 535                 540

Gln Ile Phe Asn Leu Phe Ser Thr Lys Asp Ser Ser Ala Ala Trp Asp
545                 550                 555                 560

Glu Thr Leu Leu Asp Lys Phe Tyr Thr Glu Leu Tyr Gln Gln Leu Asn
            565                 570                 575

Asp Leu Glu Ala Cys Val Ile Gln Gly Val Gly Val Thr Glu Thr Pro
        580                 585                 590

Leu Met Lys Glu Asp Ser Ile Leu Ala Val Arg Lys Tyr Phe Gln Arg
    595                 600                 605

Ile Thr Leu Tyr Leu Lys Glu Lys Lys Tyr Ser Pro Cys Ala Trp Glu
610                 615                 620

Val Val Arg Ala Glu Ile Met Arg Ser Phe Ser Leu Ser Thr Asn Leu
625                 630                 635                 640

Gln Glu Ser Leu Arg Ser Lys Glu
            645

<210> SEQ ID NO 48
<211> LENGTH: 702
<212> TYPE: DNA
<213> ORGANISM: Artificial
<220> FEATURE:
<223> OTHER INFORMATION: Nucleic acid encoding anti-HER2/neu antibody
      light chain

<400> SEQUENCE: 48
atggaatgga gctgtgtcat gctctttctc ctgtcagtaa ctgcaggtgt ccactccgac      60
atccagatga cccagtcccc gagctccctg tccgcctctg tgggcgatag ggtcaccatc     120
acctgccgtg ccagtcagga tgtgaatact gctgtagcct ggtatcaaca gaaaccagga     180
aaagctccga aactactgat ttactcggca tccttcctct actctggagt cccttctcgc     240
ttctctggat ccagatctgg gacggatttc actctgacca tcagcagtct gcagccggaa     300
gacttcgcaa cttattactg tcagcaacat tatactactc ctcccacgtt cggacagggt     360
accaaggtgg agatcaaacg aactgtggct gcaccatctg tcttcatctt cccgccatct     420
gatgagcagt tgaaatctgg aactgcctct gttgtgtgcc tgctgaataa cttctatccc     480
```

```
agagaggcca aagtacagtg gaaggtggat aacgccctcc aatcgggtaa ctcccaggag    540
agtgtcacag agcaggacag caaggacagc acctacagcc tcagcagcac cctgacgctg    600
agcaaagcag actacgagaa acacaaagtc tacgcctgcg aagtcaccca tcagggcctg    660
agctcgcccg tcacaaagag cttcaacagg ggagagtgtt ag                      702
```

<210> SEQ ID NO 49
<211> LENGTH: 233
<212> TYPE: PRT
<213> ORGANISM: Artificial
<220> FEATURE:
<223> OTHER INFORMATION: Anti-HER2/neu antibody light chain
<400> SEQUENCE: 49

```
Met Glu Trp Ser Cys Val Met Leu Phe Leu Leu Ser Val Thr Ala Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Asp Val
        35                  40                  45

Asn Thr Ala Val Ala Trp Tyr Gln Gln Lys Pro Gly Lys Ala Pro Lys
    50                  55                  60

Leu Leu Ile Tyr Ser Ala Ser Phe Leu Tyr Ser Gly Val Pro Ser Arg
65                  70                  75                  80

Phe Ser Gly Ser Arg Ser Gly Thr Asp Phe Thr Leu Thr Ile Ser Ser
                85                  90                  95

Leu Gln Pro Glu Asp Phe Ala Thr Tyr Tyr Cys Gln Gln His Tyr Thr
            100                 105                 110

Thr Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 50
<211> LENGTH: 184
<212> TYPE: PRT
<213> ORGANISM: Artificial
<220> FEATURE:
<223> OTHER INFORMATION: Truncated interferon
<400> SEQUENCE: 50

```
Met Gly Lys Met Ala Ser Leu Phe Ala Thr Phe Leu Val Val Leu Val
1               5                   10                  15

Ser Leu Ser Leu Ala Ser Glu Ser Ala Cys Asp Leu Pro Gln Thr
            20                  25                  30
```

His Ser Leu Gly Ser Arg Arg Thr Leu Met Leu Leu Ala Gln Met Arg
        35                  40                  45

Arg Ile Ser Leu Phe Ser Cys Leu Lys Asp Arg His Asp Phe Gly Phe
    50                  55                  60

Pro Gln Glu Glu Phe Gly Asn Gln Phe Gln Lys Ala Glu Thr Ile Pro
65                  70                  75                  80

Val Leu His Glu Met Ile Gln Gln Ile Phe Asn Leu Phe Ser Thr Lys
                85                  90                  95

Asp Ser Ser Ala Ala Trp Asp Glu Thr Leu Leu Asp Lys Phe Tyr Thr
                100                 105                 110

Glu Leu Tyr Gln Gln Leu Asn Asp Leu Glu Ala Cys Val Ile Gln Gly
            115                 120                 125

Val Gly Val Thr Glu Thr Pro Leu Met Lys Glu Asp Ser Ile Leu Ala
        130                 135                 140

Val Arg Lys Tyr Phe Gln Arg Ile Thr Leu Tyr Leu Lys Glu Lys Lys
145                 150                 155                 160

Tyr Ser Pro Cys Ala Trp Glu Val Val Arg Ala Glu Ile Met Arg Ser
                165                 170                 175

Phe Ser Leu Ser Thr Asn Leu Gln
                180

<210> SEQ ID NO 51
<211> LENGTH: 183
<212> TYPE: PRT
<213> ORGANISM: Artificial
<220> FEATURE:
<223> OTHER INFORMATION: Truncated interferon

<400> SEQUENCE: 51

Met Gly Lys Met Ala Ser Leu Phe Ala Thr Phe Leu Val Val Leu Val
1               5                   10                  15

Ser Leu Ser Leu Ala Ser Glu Ser Ser Ala Cys Asp Leu Pro Gln Thr
            20                  25                  30

His Ser Leu Gly Ser Arg Arg Thr Leu Met Leu Leu Ala Gln Met Arg
        35                  40                  45

Arg Ile Ser Leu Phe Ser Cys Leu Lys Asp Arg His Asp Phe Gly Phe
    50                  55                  60

Pro Gln Glu Glu Phe Gly Asn Gln Phe Gln Lys Ala Glu Thr Ile Pro
65                  70                  75                  80

Val Leu His Glu Met Ile Gln Gln Ile Phe Asn Leu Phe Ser Thr Lys
                85                  90                  95

Asp Ser Ser Ala Ala Trp Asp Glu Thr Leu Leu Asp Lys Phe Tyr Thr
                100                 105                 110

Glu Leu Tyr Gln Gln Leu Asn Asp Leu Glu Ala Cys Val Ile Gln Gly
            115                 120                 125

Val Gly Val Thr Glu Thr Pro Leu Met Lys Glu Asp Ser Ile Leu Ala
        130                 135                 140

Val Arg Lys Tyr Phe Gln Arg Ile Thr Leu Tyr Leu Lys Glu Lys Lys
145                 150                 155                 160

Tyr Ser Pro Cys Ala Trp Glu Val Val Arg Ala Glu Ile Met Arg Ser
                165                 170                 175

Phe Ser Leu Ser Thr Asn Leu
                180

```
<210> SEQ ID NO 52
<211> LENGTH: 182
<212> TYPE: PRT
<213> ORGANISM: Artificial
<220> FEATURE:
<223> OTHER INFORMATION: Truncated interferon

<400> SEQUENCE: 52

Met Gly Lys Met Ala Ser Leu Phe Ala Thr Phe Leu Val Val Leu Val
1               5                   10                  15

Ser Leu Ser Leu Ala Ser Glu Ser Ser Ala Cys Asp Leu Pro Gln Thr
            20                  25                  30

His Ser Leu Gly Ser Arg Arg Thr Leu Met Leu Leu Ala Gln Met Arg
        35                  40                  45

Arg Ile Ser Leu Phe Ser Cys Leu Lys Asp Arg His Asp Phe Gly Phe
    50                  55                  60

Pro Gln Glu Glu Phe Gly Asn Gln Phe Gln Lys Ala Glu Thr Ile Pro
65                  70                  75                  80

Val Leu His Glu Met Ile Gln Gln Ile Phe Asn Leu Phe Ser Thr Lys
                85                  90                  95

Asp Ser Ser Ala Ala Trp Asp Glu Thr Leu Leu Asp Lys Phe Tyr Thr
            100                 105                 110

Glu Leu Tyr Gln Gln Leu Asn Asp Leu Glu Ala Cys Val Ile Gln Gly
        115                 120                 125

Val Gly Val Thr Glu Thr Pro Leu Met Lys Glu Asp Ser Ile Leu Ala
    130                 135                 140

Val Arg Lys Tyr Phe Gln Arg Ile Thr Leu Tyr Leu Lys Glu Lys Lys
145                 150                 155                 160

Tyr Ser Pro Cys Ala Trp Glu Val Val Arg Ala Glu Ile Met Arg Ser
                165                 170                 175

Phe Ser Leu Ser Thr Asn
            180

<210> SEQ ID NO 53
<211> LENGTH: 10
<212> TYPE: PRT
<213> ORGANISM: Artificial
<220> FEATURE:
<223> OTHER INFORMATION: Peptide linker

<400> SEQUENCE: 53

Gly Gly Gly Gly Ser Gly Gly Gly Gly Ser
1               5                   10

<210> SEQ ID NO 54
<211> LENGTH: 7
<212> TYPE: PRT
<213> ORGANISM: Artificial
<220> FEATURE:
<223> OTHER INFORMATION: Peptide linker

<400> SEQUENCE: 54

Ala Glu Ala Ala Ala Lys Ala
1               5

<210> SEQ ID NO 55
<211> LENGTH: 12
<212> TYPE: PRT
<213> ORGANISM: Artificial
<220> FEATURE:
<223> OTHER INFORMATION: Peptide linker
```

```
<400> SEQUENCE: 55

Ala Glu Ala Ala Ala Lys Glu Ala Ala Ala Lys Ala
1               5                   10

<210> SEQ ID NO 56
<211> LENGTH: 17
<212> TYPE: PRT
<213> ORGANISM: Artificial
<220> FEATURE:
<223> OTHER INFORMATION: Peptide linker

<400> SEQUENCE: 56

Ala Glu Ala Ala Ala Lys Glu Ala Ala Ala Lys Glu Ala Ala Ala Lys
1               5                   10                  15

Ala

<210> SEQ ID NO 57
<211> LENGTH: 22
<212> TYPE: PRT
<213> ORGANISM: Artificial
<220> FEATURE:
<223> OTHER INFORMATION: Peptide linker

<400> SEQUENCE: 57

Ala Glu Ala Ala Ala Lys Glu Ala Ala Ala Lys Glu Ala Ala Ala Lys
1               5                   10                  15

Glu Ala Ala Ala Lys Ala
            20

<210> SEQ ID NO 58
<211> LENGTH: 27
<212> TYPE: PRT
<213> ORGANISM: Artificial
<220> FEATURE:
<223> OTHER INFORMATION: Peptide linker

<400> SEQUENCE: 58

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25

<210> SEQ ID NO 59
<211> LENGTH: 5
<212> TYPE: PRT
<213> ORGANISM: Artificial
<220> FEATURE:
<223> OTHER INFORMATION: Peptide linker

<400> SEQUENCE: 59

Gly Gly Gly Gly Gly
1               5

<210> SEQ ID NO 60
<211> LENGTH: 8
<212> TYPE: PRT
<213> ORGANISM: Artificial
<220> FEATURE:
<223> OTHER INFORMATION: Peptide linker

<400> SEQUENCE: 60

Gly Gly Gly Gly Gly Gly Gly Gly
1               5
```

```
<210> SEQ ID NO 61
<211> LENGTH: 5
<212> TYPE: PRT
<213> ORGANISM: Artificial
<220> FEATURE:
<223> OTHER INFORMATION: Peptide linker

<400> SEQUENCE: 61

Gly Gly Ala Gly Gly
1               5

<210> SEQ ID NO 62
<211> LENGTH: 10
<212> TYPE: PRT
<213> ORGANISM: Artificial
<220> FEATURE:
<223> OTHER INFORMATION: Peptide linker

<400> SEQUENCE: 62

Gly Ala Gly Ala Gly Ala Gly Ala Gly Ala
1               5                   10

<210> SEQ ID NO 63
<211> LENGTH: 18
<212> TYPE: PRT
<213> ORGANISM: Artificial
<220> FEATURE:
<223> OTHER INFORMATION: Peptide linker

<400> SEQUENCE: 63

Arg Pro Leu Ser Tyr Arg Pro Pro Phe Pro Phe Gly Phe Pro Ser Val
1               5                   10                  15

Arg Pro

<210> SEQ ID NO 64
<211> LENGTH: 18
<212> TYPE: PRT
<213> ORGANISM: Artificial
<220> FEATURE:
<223> OTHER INFORMATION: Peptide linker

<400> SEQUENCE: 64

Tyr Pro Arg Ser Ile Tyr Ile Arg Arg Arg His Pro Ser Pro Ser Leu
1               5                   10                  15

Thr Thr

<210> SEQ ID NO 65
<211> LENGTH: 18
<212> TYPE: PRT
<213> ORGANISM: Artificial
<220> FEATURE:
<223> OTHER INFORMATION: Peptide linker

<400> SEQUENCE: 65

Thr Pro Ser His Leu Ser His Ile Leu Pro Ser Phe Gly Leu Pro Thr
1               5                   10                  15

Phe Asn

<210> SEQ ID NO 66
<211> LENGTH: 18
<212> TYPE: PRT
<213> ORGANISM: Artificial
<220> FEATURE:
<223> OTHER INFORMATION: Peptide linker
```

```
<400> SEQUENCE: 66

Arg Pro Val Ser Pro Phe Thr Phe Pro Arg Leu Ser Asn Ser Trp Leu
1               5                   10                  15

Pro Ala

<210> SEQ ID NO 67
<211> LENGTH: 18
<212> TYPE: PRT
<213> ORGANISM: Artificial
<220> FEATURE:
<223> OTHER INFORMATION: Peptide linker

<400> SEQUENCE: 67

Ser Pro Ala Ala His Phe Pro Arg Ser Ile Pro Arg Pro Gly Pro Ile
1               5                   10                  15

Arg Thr

<210> SEQ ID NO 68
<211> LENGTH: 18
<212> TYPE: PRT
<213> ORGANISM: Artificial
<220> FEATURE:
<223> OTHER INFORMATION: Peptide linker

<400> SEQUENCE: 68

Ala Pro Gly Pro Ser Ala Pro Ser His Arg Ser Leu Pro Ser Arg Ala
1               5                   10                  15

Phe Gly

<210> SEQ ID NO 69
<211> LENGTH: 18
<212> TYPE: PRT
<213> ORGANISM: Artificial
<220> FEATURE:
<223> OTHER INFORMATION: Peptide linker

<400> SEQUENCE: 69

Pro Arg Asn Ser Ile His Phe Leu His Pro Leu Leu Val Ala Pro Leu
1               5                   10                  15

Gly Ala

<210> SEQ ID NO 70
<211> LENGTH: 18
<212> TYPE: PRT
<213> ORGANISM: Artificial
<220> FEATURE:
<223> OTHER INFORMATION: Peptide linker

<400> SEQUENCE: 70

Met Pro Ser Leu Ser Gly Val Leu Gln Val Arg Tyr Leu Ser Pro Pro
1               5                   10                  15

Asp Leu

<210> SEQ ID NO 71
<211> LENGTH: 18
<212> TYPE: PRT
<213> ORGANISM: Artificial
<220> FEATURE:
<223> OTHER INFORMATION: Peptide linker
```

```
<400> SEQUENCE: 71

Ser Pro Gln Tyr Pro Ser Pro Leu Thr Leu Thr Leu Pro Pro His Pro
1               5                   10                  15

Ser Leu

<210> SEQ ID NO 72
<211> LENGTH: 18
<212> TYPE: PRT
<213> ORGANISM: Artificial
<220> FEATURE:
<223> OTHER INFORMATION: Peptide linker

<400> SEQUENCE: 72

Asn Pro Ser Leu Asn Pro Pro Ser Tyr Leu His Arg Ala Pro Ser Arg
1               5                   10                  15

Ile Ser

<210> SEQ ID NO 73
<211> LENGTH: 17
<212> TYPE: PRT
<213> ORGANISM: Artificial
<220> FEATURE:
<223> OTHER INFORMATION: Peptide linker

<400> SEQUENCE: 73

Leu Pro Trp Arg Thr Ser Leu Leu Pro Ser Leu Pro Leu Arg Arg Arg
1               5                   10                  15

Pro

<210> SEQ ID NO 74
<211> LENGTH: 18
<212> TYPE: PRT
<213> ORGANISM: Artificial
<220> FEATURE:
<223> OTHER INFORMATION: Peptide linker

<400> SEQUENCE: 74

Pro Pro Leu Phe Ala Lys Gly Pro Val Gly Leu Leu Ser Arg Ser Phe
1               5                   10                  15

Pro Pro

<210> SEQ ID NO 75
<211> LENGTH: 18
<212> TYPE: PRT
<213> ORGANISM: Artificial
<220> FEATURE:
<223> OTHER INFORMATION: Peptide linker

<400> SEQUENCE: 75

Val Pro Pro Ala Pro Val Val Ser Leu Arg Ser Ala His Ala Arg Pro
1               5                   10                  15

Pro Tyr

<210> SEQ ID NO 76
<211> LENGTH: 17
<212> TYPE: PRT
<213> ORGANISM: Artificial
<220> FEATURE:
<223> OTHER INFORMATION: Peptide linker
```

```
<400> SEQUENCE: 76

Leu Arg Pro Thr Pro Arg Val Arg Ser Tyr Thr Cys Cys Pro Thr
1               5                   10                  15

Pro

<210> SEQ ID NO 77
<211> LENGTH: 18
<212> TYPE: PRT
<213> ORGANISM: Artificial
<220> FEATURE:
<223> OTHER INFORMATION: Peptide linker

<400> SEQUENCE: 77

Pro Asn Val Ala His Val Leu Pro Leu Leu Thr Val Pro Trp Asp Asn
1               5                   10                  15

Leu Arg

<210> SEQ ID NO 78
<211> LENGTH: 18
<212> TYPE: PRT
<213> ORGANISM: Artificial
<220> FEATURE:
<223> OTHER INFORMATION: Peptide linker

<400> SEQUENCE: 78

Cys Asn Pro Leu Leu Pro Leu Cys Ala Arg Ser Pro Ala Val Arg Thr
1               5                   10                  15

Phe Pro

<210> SEQ ID NO 79
<211> LENGTH: 28
<212> TYPE: DNA
<213> ORGANISM: Artificial
<220> FEATURE:
<223> OTHER INFORMATION: PCR primer

<400> SEQUENCE: 79
cgcggatcct gtgacctgcc tcagactc                                          28

<210> SEQ ID NO 80
<211> LENGTH: 31
<212> TYPE: DNA
<213> ORGANISM: Artificial
<220> FEATURE:
<223> OTHER INFORMATION: PCR primer

<400> SEQUENCE: 80
gctctagatc atttctcttc tctcagtctt c                                      31

<210> SEQ ID NO 81
<211> LENGTH: 6
<212> TYPE: PRT
<213> ORGANISM: Artificial
<220> FEATURE:
<223> OTHER INFORMATION: Peptide linker

<400> SEQUENCE: 81

Ser Gly Gly Gly Gly Ser
1               5

<210> SEQ ID NO 82
<211> LENGTH: 14
<212> TYPE: PRT
<213> ORGANISM: Artificial
```

```
<220> FEATURE:
<223> OTHER INFORMATION: Peptide linker

<400> SEQUENCE: 82

Ala Glu Ala Ala Ala Lys Glu Ala Ala Ala Lys Ala Gly Ser
1               5                   10
```

TARGETED INTERFERONS DEMONSTRATE POTENT APOPTOTIC AND ANTI-TUMOR ACTIVITIES

CROSS-REFERENCE TO RELATED APPLICATIONS

This application is a Continuation of U.S. Ser. No. 14/015,838, filed on Aug. 30, 2013, which is a Continuation of U.S. Ser. No. 12/985,122, filed on Jan. 5, 2011, U.S. Pat. No. 8,563,692, issued on Oct. 22, 2013, which is a Continuation of U.S. Ser. No. 12/650,329, filed on Dec. 30, 2009, U.S. Pat. No. 8,258,263, issued on Sep. 4, 2012, which is a Continuation-in-Part of PCT/US2008/077074 (WO 2009/039409), filed on Sep. 19, 2008, which claims priority to and benefit of U.S. Ser. No. 60/994,717, filed on Sep. 21, 2007, all of which are incorporated herein by reference in their entirety for all purposes.

STATEMENT OF GOVERNMENTAL SUPPORT

This invention was made with Government support under Grant No. CA087990 awarded by the National Institutes of Health. The Government has certain rights in the invention.

FIELD OF THE INVENTION

This invention pertains to the field of oncology. Chimeric constructs are provided that have significant anti-cancer activity.

BACKGROUND OF THE INVENTION

Although spontaneous immune responses against tumor-associated antigens (TAAs) (Hrouda et al. (1999) *Semin. Oncol.* 26: 455-471) can be detected (Disis et al. (1997) *J. Clin. Oncol.* 15: 3363-3367), malignant cells causing disease fail to elicit an immune response that leads to rejection. Many studies have demonstrated that it is possible to enhance the immunogenicity of tumor cells by introducing immunostimulatory molecules such as cytokines and costimulatory molecules into them (Dranoff and Mulligan (1995) *Adv. Immunol.* 58: 417-454; Hrouda et al. (1999) *Semin. Oncol.* 26: 455-471; Hurford et al. (1995) *Nat. Genet.* 10: 430-435); however, effective gene transfer still remains a challenge. In addition, eradication of residual cancer cells may require the targeting of widely scattered micrometastatic tumor deposits that are not accessible to direct gene transfer.

Both the innate and the adaptive immune responses are essential for providing protection against infectious pathogens and tumors. The cross-talk between innate and adaptive immunity is regulated by interactions between cells and cytokines. Cytokines produced by cells of the innate immune system can, directly or indirectly, activate the cells of the adaptive immune response and can play an important role in eliciting protective antitumor immunity (Belardelli and Ferrantini (2002) *Trends Immunol.* 23: 201-208). Central to the activation of the innate immune system is the detection of bacterial products or "danger" signals that lead to the release of proinflammatory cytokines, such as IFN-α, TNF-α, and IL-1.

IFN-α is a proinflammatory cytokine with potent antiviral and immunomodulatory activities and is a stimulator of differentiation and activity of dendritic cells (DCs) (Santini et al. (2000) *J. Exp. Med.* 191: 1777-1788). Type I IFNs (IFN-α and IFN-β) have multiple effects on the immune response (Theofilopoulos et al. (2005) *Annu. Rev. Immunol.* 23: 307-336). IFN-α plays a role in the differentiation of Th1 cells (Finkelman et al. (1991) *J. Exp. Med.* 174: 1179-1188) and the long-term survival of CD8+ T cells in response to specific antigens (Tough et al. (1996) *Science* 272: 1947-1950).

Multiple studies have shown that IFNs are also capable of exerting antitumor effects in both animal models (Ferrantini et al. (1994) *J. Immunol.* 153: 4604-4615) and cancer patients (14. Gutterman et al. (1980) *Ann. Intern. Med.* 93: 399-406). In addition to enhancing the adaptive antitumor immune response, IFN-α can increase expression of the tumor suppressor gene P53 (Takaoka et al. (2003) *Nature* 424: 516-523), inhibit angiogenesis (Sidky and Borden (1987) *Cancer Res.* 47: 5155-5161), and prime apoptosis (Rodriguez-Villanueva and McDonnell (1995) *Int. J. Cancer* 61: 110-11417) in tumor cells. Although these properties suggest that IFN-α should be an effective therapeutic for the treatment of cancer, its short half-life and systemic toxicity have limited its usage.

SUMMARY OF THE INVENTION

In various embodiments this invention pertains to the discovery that attaching an interferon to a targeting moiety (e.g., a molecule that specifically and/or preferentially binds a marker on or associated with a cell) substantially improves the therapeutic efficacy of the interferon and appears to reduce systemic toxicity. Accordingly, in various embodiments, this invention provides constructs comprising an interferon attached to a targeting moiety and uses of such constructs to specifically and/or preferentially inhibit the growth or proliferation or even to kill certain target cells (e.g., cancer cells).

Accordingly, in certain embodiments, a chimeric construct is provided where the construct comprises an interferon (e.g., interferon-alpha, interferon-beta, interferon-gamma, etc.) attached to a targeting moiety that binds to a tumor associated antigen (TAA), where the construct when contacted to a tumor cell results in the killing or inhibition of growth or proliferation of the tumor cell. In certain embodiments a chimeric construct is provided where the construct comprises an interferon attached to a targeting moiety that binds to a cell surface marker or a cell-associated marker, where the targeting is not attached to the interferon by a (Gly$_4$Ser)$_3$ (SEQ ID NO:5) linker. In various embodiments the interferon is a type 1 interferon. In various embodiments the interferon is a type 2 interferon. In various embodiments the interferon is an interferon alpha, an interferon-beta, or an interferon-gamma. In certain embodiments the targeting moiety is an antibody that binds a tumor associated antigen. In certain embodiments the targeting moiety is chemically coupled to the interferon. In certain embodiments the targeting moiety is joined to the interferon with a peptide linker. In certain embodiments the peptide linker is fewer than 15, fewer than 14, fewer than 12, fewer than 11, fewer than 10, fewer than 9, fewer than 8, fewer than 7, fewer than 6, fewer than 5, fewer than 4, fewer than 3, or fewer than 2 amino acids in length. In certain embodiments the linker is 15, 14, 13, 12, 11, 10, 9, 8, 7, 6, 5, 4, 3, 2, or 1 amino acid in length. In certain embodiments the linker is not (Gly$_4$Ser)$_3$ (SEQ ID NO:5). In certain embodiments the linker is a linker that is resistant or substantially resistant to proteolysis. In certain embodiments the peptide linker is Gly$_4$Ser (SEQ ID NO:6). In certain embodiments the linker comprises or consists of an amino acid sequence found in Table 4. In certain embodiments the construct is a recombinantly expressed fusion protein. In certain embodiments the antibody specifically binds a marker selected from the group consisting of EGFR, HER4, HER3, HER2/neu, MUC-1, G250, mesothelin, gp100, tyrosinase, and MAGE. In certain embodiments the targeting moiety is an antibody that binds CD20. In certain embodiments the targeting moiety is a single chain antibody that comprises the CDRS and/or the variable regions from an antibody selected from the group consisting of anti-CD20 (rituximab), Ibritumomab tiuxetan, tositumomab, AME-133v, OCRELIZUMAB, OFATUMUMAB, TRU-015, IMMU-106, and the like. In various embodiments the targeting moiety is an antibody that binds HER2. In certain embodiments the antibody is a C6 antibody. In certain embodiments the antibody comprises the VH and VL CDRs or VH and VL domains of C6MH3-B1. In various embodiments the antibody is an IgG (e.g., IgG1, IgG3, etc.), an IgE, a single chain Fv (scFv), a FAB, a (Fab')$_2$, an (ScFv)$_2$, and the like. In certain embodiments the antibody is an antibody selected form the group consisting of RITUXAN®, IF5, B1, 1H4, CD19, B4, B43, FVS191, hLL2, LL2, RFB4, M195, HuM195, AT13/5, HERCEPTIN®, 4D5, HuCC49, HUCC39ΔCH2 B72.3, 12C10, IG5, H23, BM-2, BM-7, 12H12, MAM-6, and HMFG-1. In certain embodiments the antibody is an antibody that binds a member of the EGF receptor family. In certain embodiments the antibody is selected from the group consisting of C6.5, C6ML3-9, C6MH3-B1, C6-B1D2, F5, HER3.A5, HER3.F4, HER3.H1, HER3.H3, HER3.E12, HER3.B12, EGFR.E12, EGFR.C10, EGFR.B11, EGFR.E8, HER4.B4, HER4.G4, HER4.F4, HER4.A8, HER4.B6, HER4.D4, HER4.D7, HER4.D11, HER4.D12, HER4.E3, HER4.E7, HER4.F8 and HER4.C7. In certain embodiments the construct comprises an anti-HER2 IgG1 antibody attached to an interferon.

Also provided are pharmaceutical formulations. In various embodiments the formulations comprise a chimeric construct comprising an interferon attached to a targeting moiety. In certain embodiments the chimeric construct comprises a construct as described above (and/or herein below) (e.g., an anti-CD20-Interferon, and anti-HER2-interferon, etc.). In certain embodiments the formulation is a unit dosage formulation. In certain embodiments the formulation is a formulated for parenteral administration. In certain embodiments the formulation is a formulated for administration via a route selected from the group consisting of oral administration, intravenous administration, intramuscular administration, direct tumor administration, inhalation, rectal administration, vaginal administration, transdermal administration, and subcutaneous depot administration.

In various embodiments methods are provided for inhibiting growth and/or proliferation of a cancer cell. The methods typically involve contacting the cancer cell with a chimeric construct as described herein. In certain embodiments the cancer cell is a metastatic cell, and/or a cell is in a solid tumor. In certain embodiments the cancer cell is a breast cancer cell. In certain embodiments the cancer cell is a B cell lymphoma. In certain embodiments the cancer cell is cell produced by a cancer selected from the group consisting of a B cell lymphoma, lung cancer, a bronchus cancer, a colorectal cancer, a prostate cancer, a breast cancer, a pancreas cancer, a stomach cancer, an ovarian cancer, a urinary bladder cancer, a brain or central nervous system cancer, a peripheral nervous system cancer, an esophageal cancer, a cervical cancer, a melanoma, a uterine or endometrial cancer, a cancer of the oral cavity or pharynx, a liver cancer, a kidney cancer, a biliary tract cancer, a small bowel or appendix cancer, a salivary gland cancer, a thyroid gland cancer, a adrenal gland cancer, an osteosarcoma, a chondrosarcoma, a liposarcoma, a testes cancer, and a malignant fibrous histiocytoma. In various embodiments the contacting comprises systemically administering the chimeric moiety to a mammal. In certain embodiments the contacting comprises administering the chimeric moiety directly into a tumor site. In certain embodiments the contacting comprises intravenous administration of the chimeric moiety. In certain embodiments the cancer cell is a cancer cell in a human or in a non-human mammal.

In certain embodiments nucleic acids are provided that encode the chimeric constructs described herein. In various embodiments the nucleic acid encodes a fusion protein comprising an interferon attached to an anti-EGFR family member antibody, an anti-HER2 antibody, an anti-C6 single-chain antibody, or to an anti-CD20 single chain antibody. In various embodiments the interferon encoded by the nucleic acid is a type I interferon. In certain embodiments the interferon is IFN-α or interferon-β. In various embodiments the nucleic acid encodes an antibody that comprises the VH and VL CDRs of C6MH3-B1. In various embodiments nucleic acid encodes a peptide linker (e.g., as described herein) attaching the antibody to the interferon. In certain embodiments the nucleic acid encodes the CDRs and/or the variable regions for anti-CD20 (rituximab).

Also provided is a cell comprising a nucleic acid as described above, that encodes a chimeric construct. In certain embodiments the cell expresses the chimeric construct.

In various embodiments this invention provides the use of a chimeric construct as described herein in the manufacture of a medicament to inhibit the growth and/or proliferation of a cancer cell.

In certain embodiments, the methods and constructs of this invention specifically exclude constructs using any of the antibodies disclosed in U.S. Patent Publication No: US 2002/0193569 A1. In certain embodiments the methods and constructs of this invention specifically exclude constructs incorporating an anti-CD20 antibody. In certain embodiments the methods and constructs of this invention specifically exclude constructs incorporating antibodies that bind to any of the following targets: CD19, CD20, CD22, CD33, CD38, EGF-R, HM1.24, phosphatidyl serine antigen, HER-2, TAG-72, and/or MUC-1. In certain embodiments the constructs described herein can be used in the treatment of pathologies such as multiple sclerosis, HCV mediated vasculitis, and the like.

Definitions

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide. Preferred "peptides", "polypeptides", and "proteins" are chains of amino acids whose alpha carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to peptide mimetics such as amino acids joined by an ether as opposed to an amide bond.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these regions of the light and heavy chains respectively.

Antibodies exist as intact immunoglobulins or as a number of well characterized fragments produced by digestion with various peptidases or expressed de novo. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into an Fab' monomer. The Fab' monomer is essentially an Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies, including, but are not limited to, Fab'$_2$, IgG, IgM, IgA, IgE, scFv, dAb, nanobodies, unibodies, and diabodies. In various embodiments preferred antibodies include, but are not limited to Fab'$_2$, IgG, IgM, IgA, IgE, and single chain antibodies, more preferably single chain Fv (scFv) antibodies in which a variable heavy and a variable light chain are joined together (directly or through a peptide linker) to form a continuous polypeptide.

In certain embodiments antibodies and fragments used in the constructs of the present invention can be bispecific. Bispecific antibodies or fragments can be of several configurations. For example, bispecific antibodies may resemble single antibodies (or antibody fragments) but have two different antigen binding sites (variable regions). In various embodiments bispecific antibodies can be produced by chemical techniques (Kranz et al. (1981) *Proc. Natl. Acad. Sci., USA*, 78: 5807), by "polydoma" techniques (see, e.g., U.S. Pat. No. 4,474,893), or by recombinant DNA techniques. In certain embodiments bispecific antibodies of the present invention can have binding specificities for at least two different epitopes at least one of which is a tumor associate antigen. In various embodiments the antibodies and fragments can also be heteroantibodies. Heteroantibodies are two or more antibodies, or antibody binding fragments (e.g., Fab) linked together, each antibody or fragment having a different specificity.

An "antigen-binding site" or "binding portion" refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al. *Sequences of proteins of immunological interest*, 4th ed. U.S. Dept. Health and Human Services, Public Health Services, Bethesda, Md. (1987).

The term "interferon" refers to a full-length interferon or to an interferon fragment (truncated interferon) or interferon mutant, that substantially retains the biological activity of the full length wild-type interferon (e.g., retains at least 80%, preferably at least 90%, more preferably at least 95%, 98%, or 99% of the full-length interferon). Interferons include type I interferons (e.g., interferon-alpha and interferon-beta) as well as type II inteferons (e.g., interferon-gamma). The interferon (e.g., IFN-α) can be from essentially any mammalian species. In certain preferred embodiments, the interferon is from a species selected from the group consisting of human, equine, bovine, rodent, porcine, lagomorph, feline, canine, murine, caprine, ovine, a non-human primate, and the like. In various embodiments the mutated interferon comprises one or more amino acid substitutions, insertions, and/or deletions.

An anti-HER2/neu antibody is an antibody that specifically or preferentially binds a HER2/neu receptor.

As used herein, the term "subject" refers to a human or non-human animal, including, but not limited to, a cat, dog, horse, pig, cow, sheep, goat, rabbit, mouse, rat, or monkey.

The term "C6 antibody", as used herein refers to antibodies derived from C6.5 whose sequence is expressly provided, for example, in U.S. Pat. Nos. 6,512,097 and 5,977,322, and in PCT Publication WO 97/00271. C6 antibodies preferably have a binding affinity of about $1.6 \times 10^{-8}$ or better for HER2/neu. In certain embodiments C6 antibodies are derived by screening (for affinity to c-erbB-2/HER2/neu) a phage display library in which a known C6 variable heavy ($V_H$) chain is expressed in combination with a multiplicity of variable light ($V_L$) chains or conversely a known C6 variable light chain is expressed in combination with a multiplicity of variable heavy ($V_H$) chains. C6 antibodies also include those antibodies produced by the introduction of mutations into the variable heavy or variable light complementarity determining regions (CDR1, CDR2 or CDR3), e.g., as described in U.S. Pat. Nos. 6,512,097 and 5,977,322, and in PCT Publication WO 97/00271. In addition, C6 antibodies include those antibodies produced by any combination of these modification methods as applied to C6.5 and its derivatives.

An "anti-EGFR family antibody" refers to an antibody that specifically binds to a member of the epidermal growth factor receptor family (e.g., an antibody that binds to ErbB-1, also named epidermal growth factor receptor (EGFR), ErbB-2, also named HER2 in humans and neu in rodents, ErbB-3, also named HER3, and/or to ErbB-4, also named HER4). Illustrative anti-EGFR family antibodies include, but are not limited to antibodies such as C6.5, C6ML3-9, C6MH3-B1, C6-B1D2, F5, HER3.A5, HER3.F4, HER3.H1, HER3.H3, HER3.E12, HER3.B12, EGFR.E12, EGFR.C10, EGFR.B11, EGFR.E8, HER4.B4, HER4.G4, HER4.F4, HER4.A8, HER4.B6, HER4.D4, HER4.D7, HER4.D11, HER4.D12, HER4.E3, HER4.E7, HER4.F8 and HER4.C7 and the like (see, e.g., U.S. Patent publications US 2006/0099205 A1 and US 2004/0071696 A1 which are incorporated herein by reference).

A single chain Fv ("sFv" or "scFv") polypeptide is a covalently linked $V_H$: $V_L$ heterodimer which, in certain embodiments, may be expressed from a nucleic acid including $V_H$- and $V_L$-encoding sequences either joined directly or joined by a peptide-encoding linker. Huston, et al. *Proc. Nat. Acad. Sci. USA*, 85: 5879-5883 (1988). A number of structures for converting the naturally aggregated, but chemically separated light and heavy polypeptide chains from an antibody V region into an sFv molecule that will fold into a three dimensional structure substantially similar to the structure of an antigen-binding site. See, e.g. U.S. Pat. Nos. 5,091,513 and 5,132,405, and 4,956,778.

"CD20" is a non-glycosylated phosphoprotein expressed on the surface of mature B-cells (see, e.g., Cragg et al. (2005) *Curr. Dir. Autoimmun.*, 8: 140-174). It is also found on B-cell lymphomas, hairy cell leukemia, B-cell chronic lymphocytic leukemia on skin/melanoma cancer stem cells, and the like.

The phrase "inhibition of growth and/or proliferation" of a cancer cell refers to decrease in the growth rate and/or proliferation rate of a cancer cell. In certain embodiments this includes death of a cancer cell (e.g. via apoptosis). In certain embodiments this term also refers to inhibiting the growth and/or proliferation of a solid tumor and/or inducing tumor size reduction or elimination of the tumor.

The term "cancer marker" refers to biomolecules such as proteins, carbohydrates, glycoproteins, and the like that are exclusively or preferentially or differentially expressed on a cancer cell and/or are found in association with a cancer cell and thereby provide targets preferential or specific to the cancer. In various embodiments the preferential expression can be preferential expression as compared to any other cell in the organism, or preferential expression within a particular area of the organism (e.g. within a particular organ or tissue).

BRIEF DESCRIPTION OF THE DRAWINGS

FIGS. 1A and 1B illustrate nucleic acid and amino acid sequences for various constructs described herein. FIG. 1A shows amino acid sequences for anti-HER2/neu IgG3 heavy chain-IFNα (SEQ ID NO:1) and anti-HER2/neu IgG3 light chain (SEQ ID NO:2). Single underline is linker, double underline is murine IFN-α, no underline is anti-HER2/neu. FIG. 1B shows a nucleic acid sequence (SEQ ID NO:3) and an amino acid sequence (SEQ ID NO:4) for anti-CD20-IgG3-huIFNα with a Gly$_4$Ser (SEQ ID NO:6) linker. It will be appreciated that while the constructs in this figure are shown with particular targeting moieties, particular linkers, and particular interferons, in certain embodiments other targeting moieties, linkers, and interferons can be substituted therefore as described herein.

FIG. 2A: Schematic diagram of anti-HER2/neu-IgG3-IFN-α. Solid areas represent anti-HER2/neu variable regions. Open areas represent human IgG3 and κ constant regions. White circle regions represent murine IFN-α. FIG. 2B: SDS-PAGE of purified anti-HER2/neu-IgG3 (lanes 1 and 4), IgG3-IFN-α (lanes 2 and 5), and anti-HER2/neu-IgG3-IFN-α (lanes 3 and 6) under nonreducing (lanes 1-3) or reducing (lanes 4-6) conditions. The molecular mass marker proteins are shown at the left of each gel. FIG. 2C: Anti-HER2/neu-IgG3 and anti-HER2/neu-IgG3-IFN-α bind HER2/neu. CT26/HER2, a murine colonic cell line expressing high levels of human HER2/neu, was reacted with anti-HER2/neu-IgG3, IgG3-IFN-α, or anti-HER2/neu-IgG3-IFN-α with or without heparin followed by PE-labeled rabbit anti-human IgG. Dashed lines represent signal from cells without addition of recombinant protein. FIG. 2D: The protective activity of the IFN-α standard and different IFN-α fusion proteins against VSV. Dilutions of 1 U of IFN-α standard, 0.21 ng (10 pM) of anti-HER2/neu-IgG3-IFN-α, 0.21 ng (10 pM) of IgG3-IFN-α, or 0.17 ng (10 pM) of anti-HER2/neu-IgG3 in 100 μl were prepared and added to L-929 cells. After a 24-h incubation, 4000 PFU of VSV were added. Forty-eight hours later, viable cells were stained with crystal violet dye, dissolved by methanol, and solubilized dye was detected using an ELISA reader at 570 nm.

FIG. 4A: Mice were treated with 9600 U of rIFN-α or 9600 U (4 μg) of IgG3-IFN-α at days 1 and 3 after tumor challenge. Animals were followed for survival and sacrificed when the diameter of the s.c. tumor reached 15 mm. FIG. 4B: Groups of three C3H/HeN mice were injected i.p. with 66 μCi of $^{125}$I-labeled rIFN-α, IgG3-IFN-α or anti-HER2/neu-IgG3-IFN-α. At various intervals after injection of the $^{125}$I-labeled proteins residual radioactivity was measured using a mouse whole body counter. The results represent the mean of three mice. Bars, SD.

FIG. 5C: IFN-α fusion proteins induce apoptosis in 38C13/HER2 cells. In brief, 1×10$^6$ 38C13/HER2 cells were incubated with 1 nM of the indicated proteins for 72 h. The cells were then washed, stained with Alexa Fluor 488, annexin V, and PI and were analyzed by flow cytometry. The percentage of cells located in each quadrant is indicated at the corner. FIG. 5D: IFN-α fusion proteins inhibited proliferation of surviving 38C13/HER2 cells. In brief, 1×10$^6$ 38C13/HER2 cells were labeled with 2.5 µM CFSE and immediately fixed (dash line), or treated with PBS (thin black line), or 1 nM of either anti-HER2/neu IgG3 (thin black line, overlaps with PBS control), IgG3-IFN-α (thick black line), or anti-HER2/neu-IgG3-IFN-α (black area) for 48 h. The cells were then washed and analyzed by flow cytometry. The histogram was obtained by gating on the population of live cells.

Figure 6A:
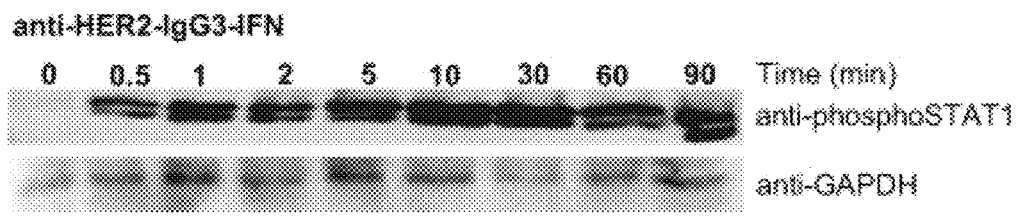
Figure 6B:
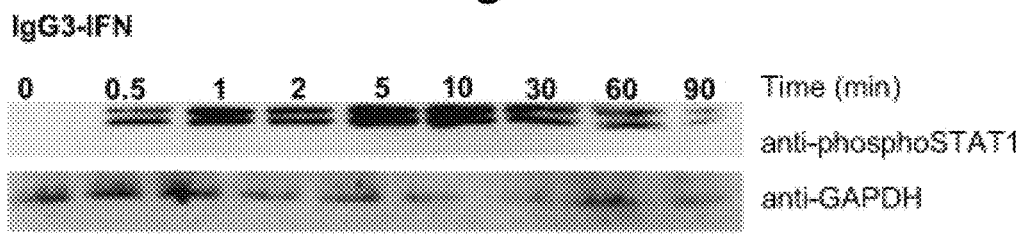
Figure 6C:
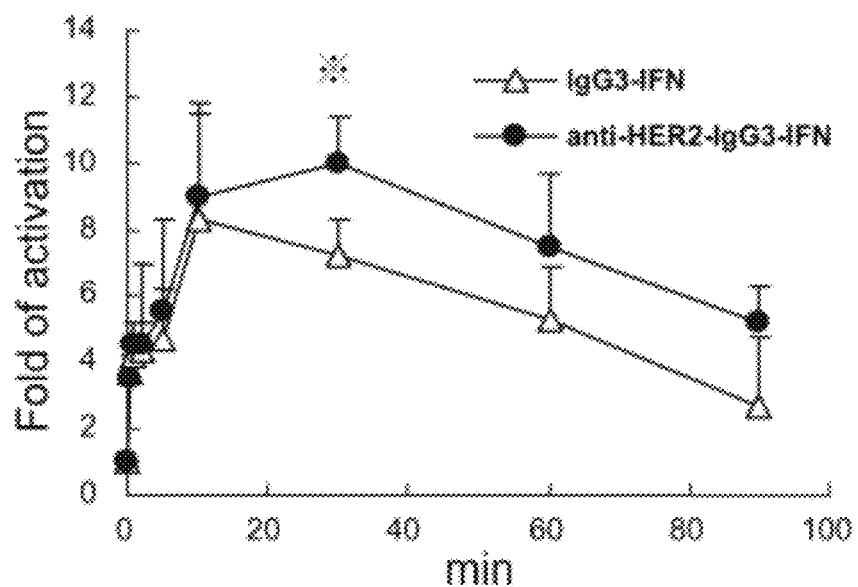

FIGS. 6A, 6B, and 6C show that IFN-α fusion proteins induced STAT1 activation in 38C13/HER2 cells. In brief, $1\times10^7$ 38C13/HER2 cells were treated with 1000 U/ml of either anti-HER2/neu-IgG3-IFN-α (FIG. 6A) or IgG3-IFN-α (FIG. 6B) for the indicated times. The cell lysates were separated by SDS-PAGE and analyzed by Western blot using a polyclonal rabbit anti-phosphoSTAT1. To confirm equal loading of protein samples, blots were probed with a HRPconjugated rabbit polyclonal Ab against GAPDH. FIG. 6C: The intensity of antiphosphoSTAT1 was normalized with the intensity of anti-GAPDH for each indicated time point, and the values obtained were divided by the value at time 0 to obtain the fold activation for STAT1. These experiments were performed twice; error bars, SD of the measurements. *, Only point where the two groups differ with a $p<0.05$.

Figure 7:
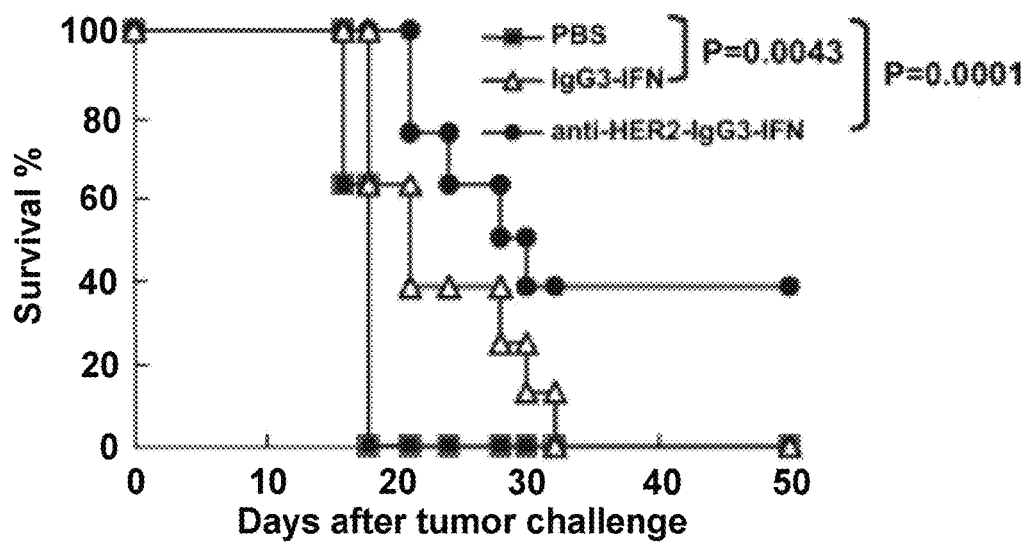

FIG. 7 IFN-α fusion proteins inhibit the growth of established tumor. C3H/HeN mice were injected s.c. with $1\times10^3$ 38C13/HER2 cells. After 12 days, mice were treated i.p. with 5 µg of the indicated protein for 3 consecutive days. The tumor volume of each mouse is measured. Animals were sacrificed when the diameter of the s.c. tumor reached 15 mm.

Figure 8:
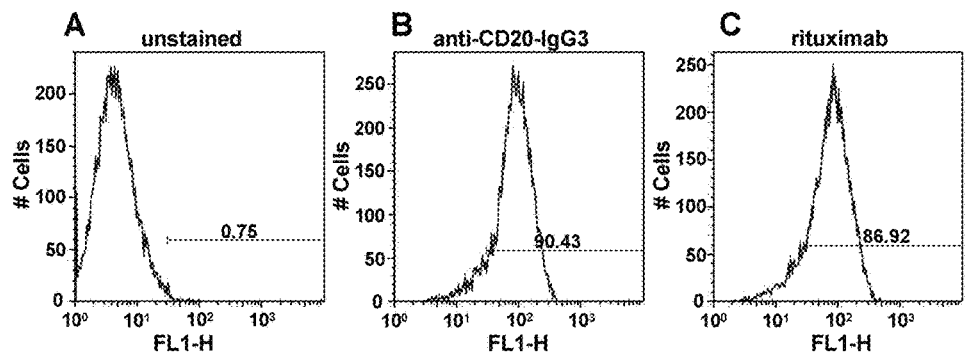

FIG. 8 shows binding of recombinant antibodies to human cells expressing CD20. Daudi cells were incubated with either recombinant IgG3 or rituximab followed by biotinylated rat anti-human IgG and PE-labeled strepavidin and analyzed by flow-cytometry. A, cells with only the secondary antibody; B, cells with recombinant IgG3; C, cells with rituximab.

Figure 9:
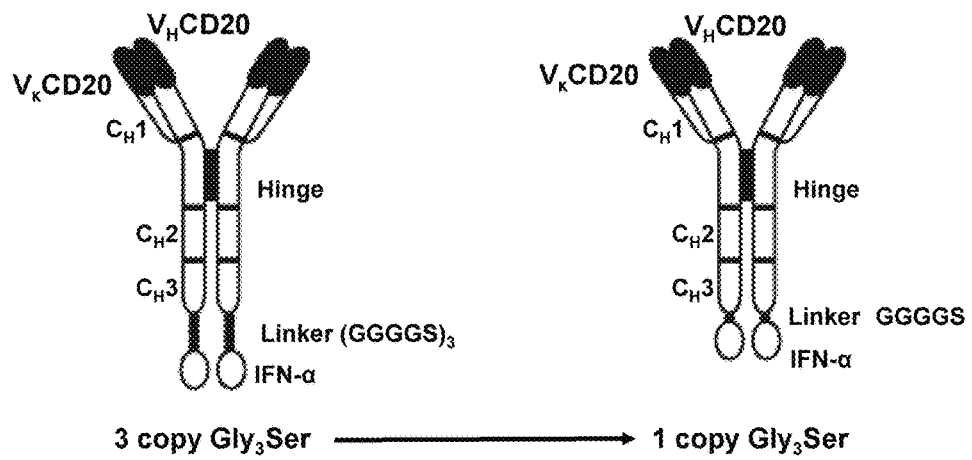

FIG. 9 shows a diagram of the heavy chain of the antibody-IFN-α fusion protein. In particular, the figure illustrates shortening of the $(Gly_4Ser)_3$ (SEQ ID NO:5) to a $Gly_4Ser$ (SEQ ID NO:6) linker enables production of full-length αCD20-IgG3-mIFNα.

Figure 10:
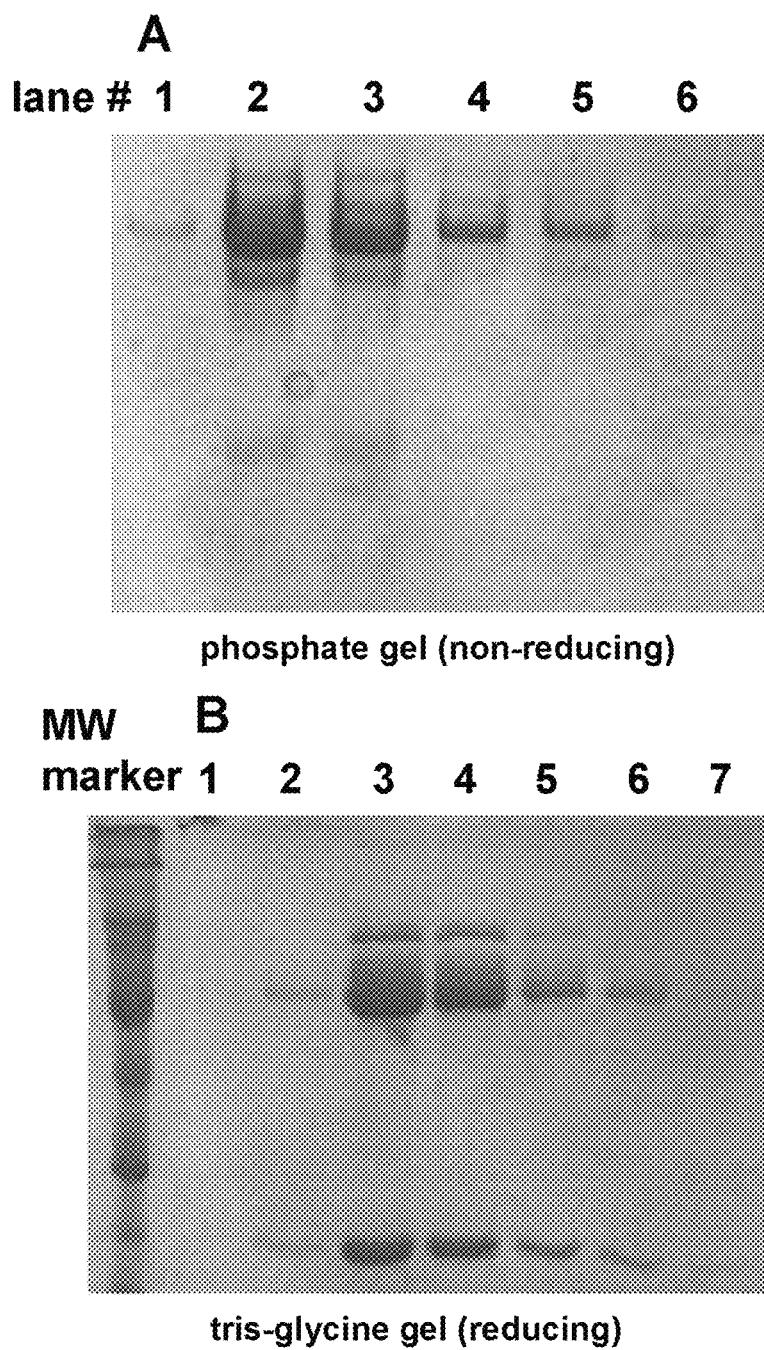

FIG. 10 shows SDS-PAGE analysis of fractions eluted from protein A Sepharose. Culture supernatants from cells expressing anti-CD-20-IgG3-IFNα with the $(Gly_4Ser)_3$ (SEQ ID NO:5) linker were passed through the protein A Sepharose and the fusion protein bound prior to elution. A. Proteins were run without reduction. Lane 1, IgG3; Lanes 2-6, fractions eluted from protein A Sepharose. B. Proteins were reduced prior to analysis. Lane 2, IgG3; Lanes 3-7, fractions eluted from protein A Sepharose.

Figure 11:
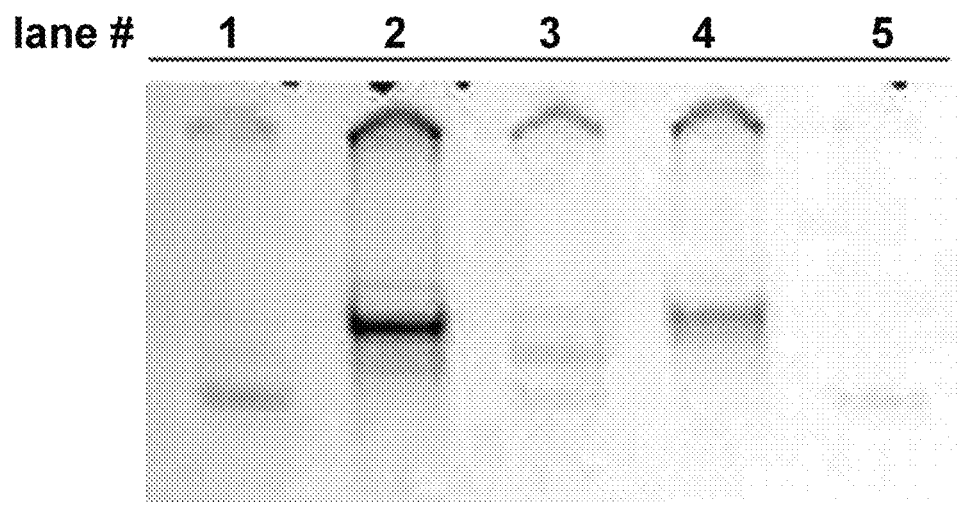

FIG. 11 shows SDS-PAGE analysis of proteins made by transient expression in HEK293T cells. Lane 1, anti-CD20-IgG3-huIFNα☐ with extended $(Gly_4Ser)_3$ (SEQ ID NO:5) linker; Lane 2, anti-CD20-IgG3 huIFNα☐ with shortened $Gly_4Ser$ (SEQ ID NO:6) linker; Lane 3, anti-CD20-IgG3-muIFNα☐ with extended $(Gly_4Ser)_3$ (SEQ ID NO:5) linker; Lane 4, anti-CD20-IgG3-muIFNα☐ with shortened $Gly_3Ser$ linker; Lane 5, anti-CD20 IgG3.

Figure 12:
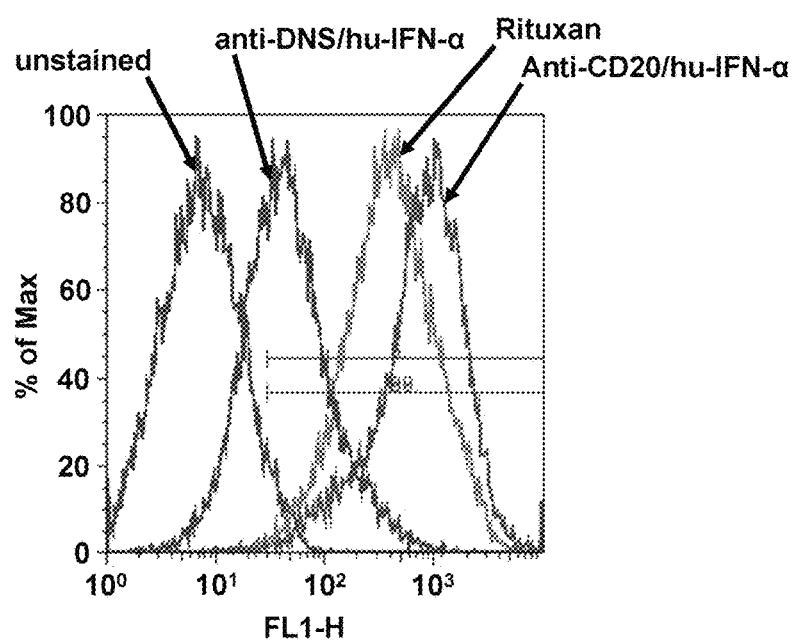

FIG. 12 was shows an analysis of protein binding to Daudi cells using FLOW cytometry. $1\times10^6$ Daudi cells were stained with 1 µg of fusion protein containing human IFN-α or RITUXAN®.

Figure 13:
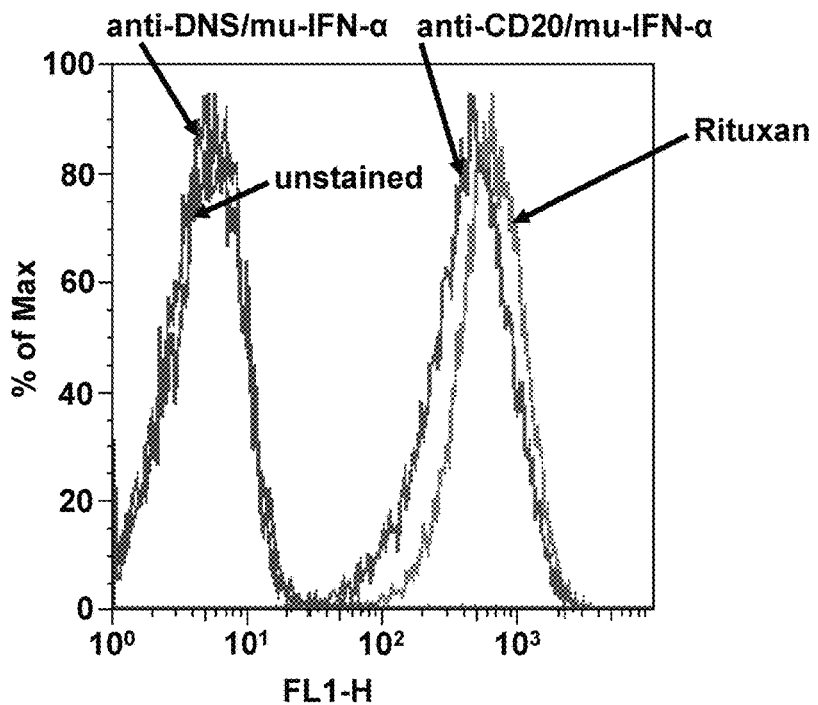

FIG. 13 shows an analysis of protein binding to 38C13/CD20 by FLOW cytometry.

Figure 14:
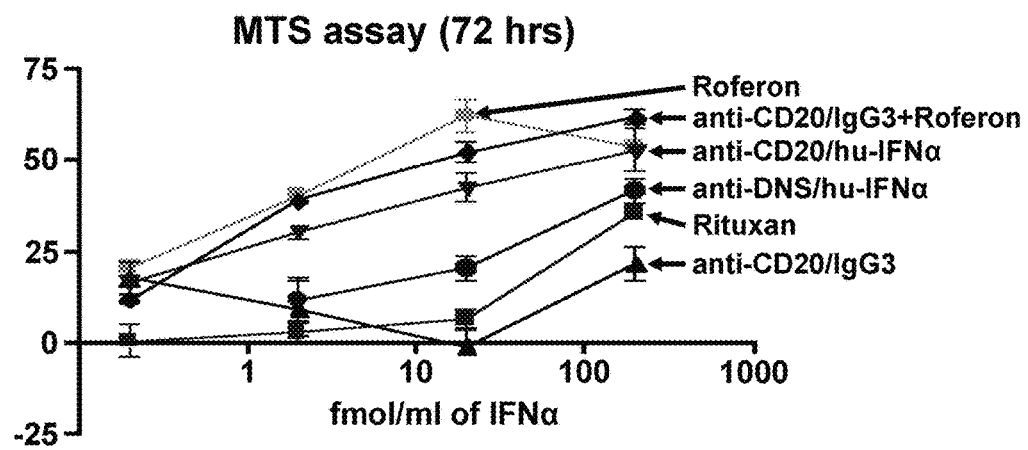

FIG. 14. Daudi cells were incubated with various concentrations of IFN-α, antibody or fusion protein for 72 hrs. Growth inhibition was assessed using the CellTiter 96 AQueous cell proliferation assay.

Figure 15:
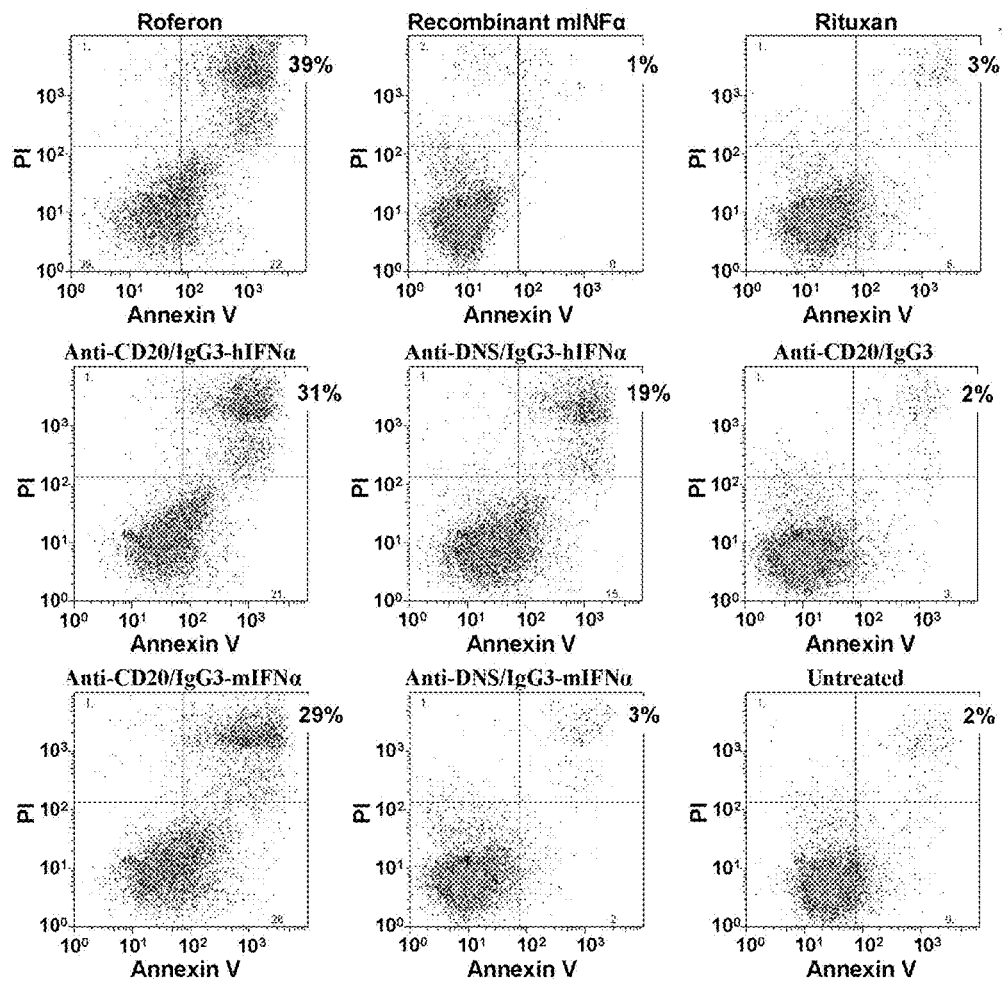

FIG. 15. Daudi cells were treated with 10 pM of the indicated proteins for 72 hours. Cell viability and apoptosis was determined following staining with Annexin V and PI and analysis by FLOW cytometry.

Figure 16:
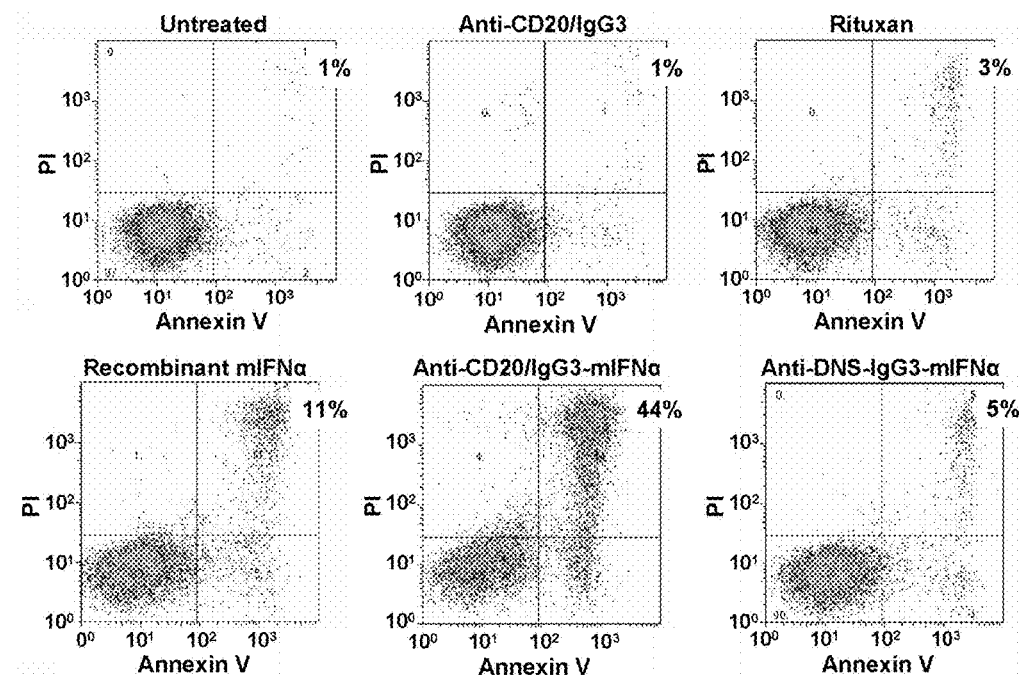

FIG. 16. 38C13/CD20 cells were treated with 10 pM of the indicated proteins for 48 hours. Cell viability and apoptosis was determined following staining with Annexin V and PI and analysis by FLOW cytometry.

Figure 17:
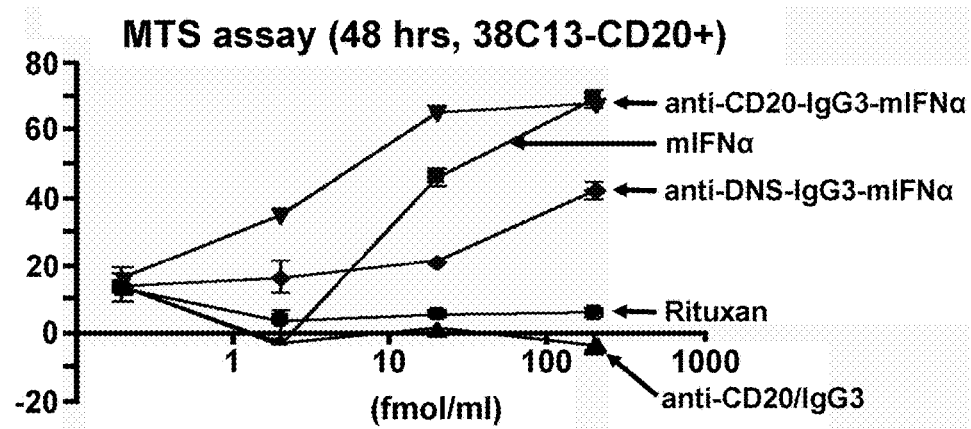

FIG. 17 shows inhibition of cell proliferation following treatment with different proteins at varying concentrations. 38C13-CD20 cells were treated with the indicated proteins at varying concentrations for 48 hours. After treatment the extent of proliferation was monitored using the MTS assay.

Figure 18:
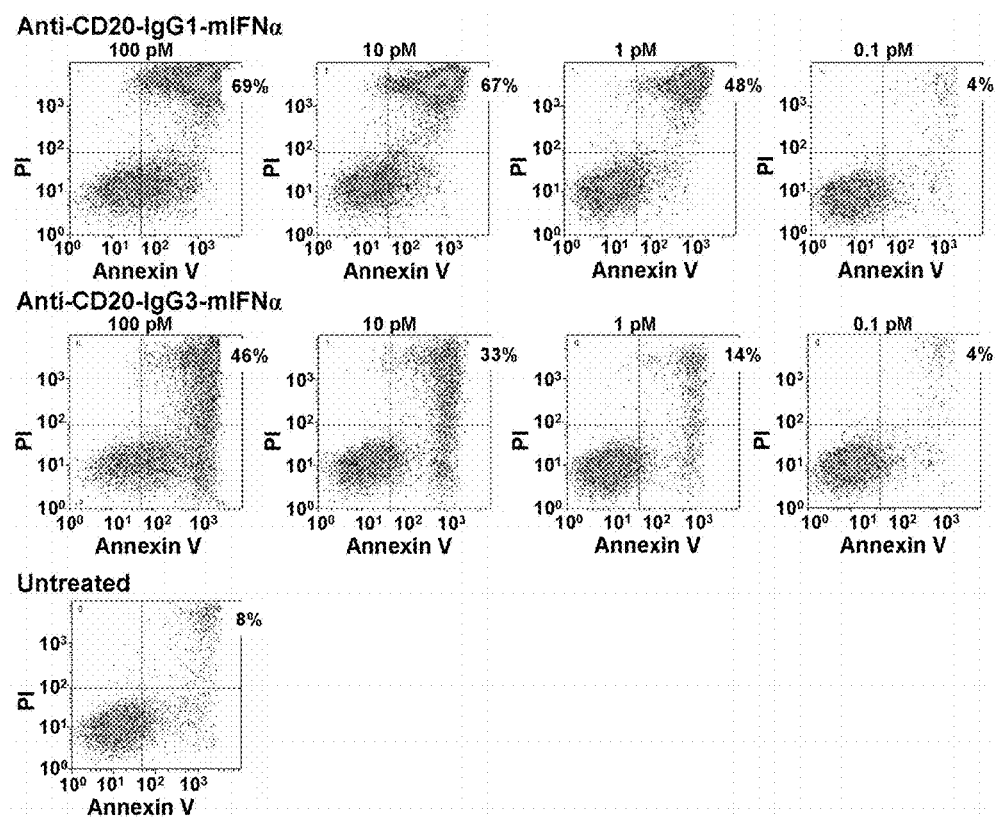

FIG. 18. 38C13/CD20 cells were treated with the different concentrations of the indicated proteins for 48 hours. Cell viability and apoptosis was determined following staining with Annexin V and PI and analysis by FLOW cytometry.

Figure 19:
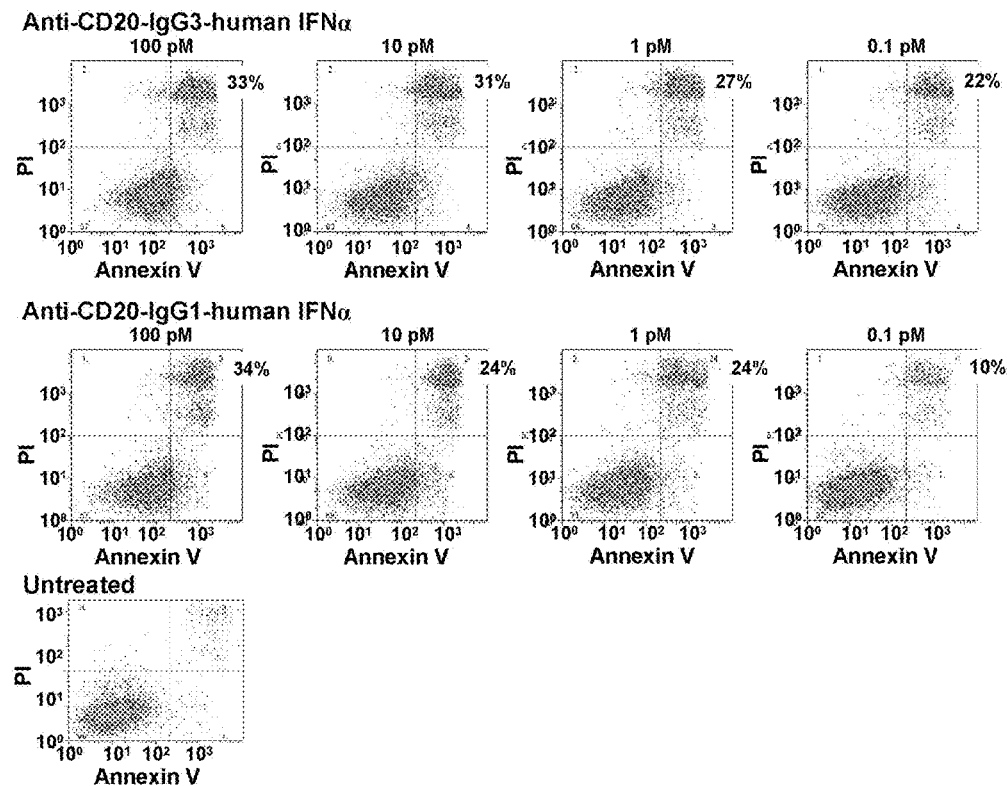

FIG. 19. Daudi cells were incubated for 72 hours with different concentrations of the fusion protein. Cell viability and apoptosis was determined following staining with Annexin V and PI and analysis by FLOW cytometry.

Figure 20:
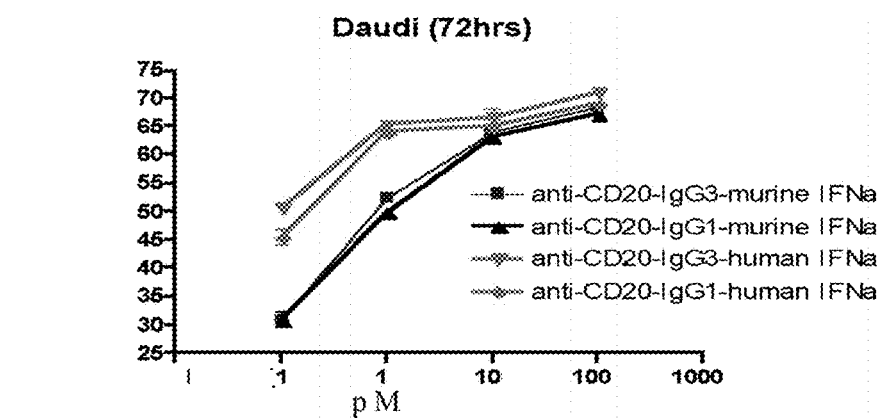

FIG. 20. Daudi cells were treated for 72 hours with various concentrations of fusion proteins. MTS solution was added to quantitate cell viability.

FIG. 21. Daudi cells were incubated for 72 hours with 1 pM of anti-CD20-IgG3-hIFNα with the $Gly_4Ser$ linker (6) (Gly-Ser Linker) or with 1 pM of anti-CD20-IgG3-hIFNα with the alpha helical linker (Alpha helix Linker). Cell viability and apoptosis was determined following staining with Annexin V and PI and analysis by FLOW cytometry.

FIG. 22 shows survival of mice inoculated with 5000 38C13-CD20 cells and treated on days 1, 2 and 3 with HBSS or the indicated amounts of the anti-CD20-IFN-α fusion proteins.

Figure 23:
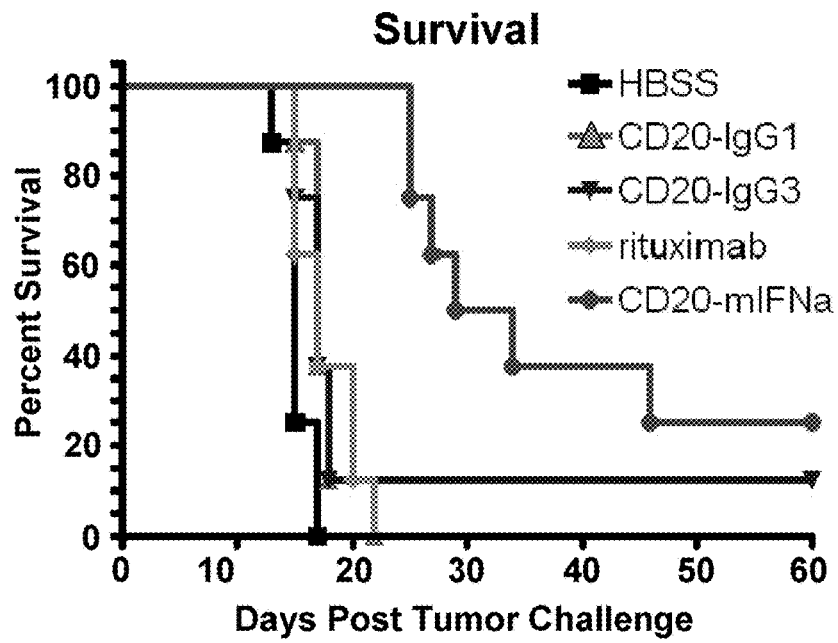

FIG. 23 shows survival of mice inoculated with 5000 38C13-CD20 cells and treated on days 5, 6 and 7 with 10 µg of anti-CD20-IgG1 (CD20-IgG1), anti-CD20-IgG3 (CD20-IgG3), rituximab or anti-CD20-IgG3-mIFNα (CD20-mIFNα) or HBSS.

Figure 24:
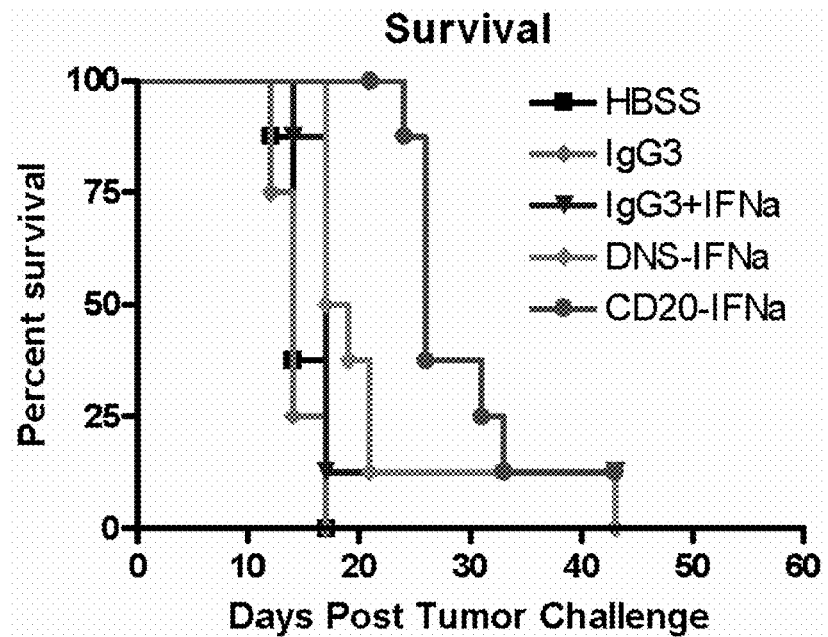

FIG. 24 shows survival of mice inoculated with 5000 38C13-CD20 cells and treated on days 5, 6 and 7 with 10 µg of anti-CD20-IgG3 (IgG3), anti-CD20-IgG3+IFNα☐ (IgG3+IFNα), anti-DNS-IgG3-mIFNα (DNS-IFNα), anti-CD20-IgG3-mIFNα (CD20-IFNα) or HBSS.

Figure 25:
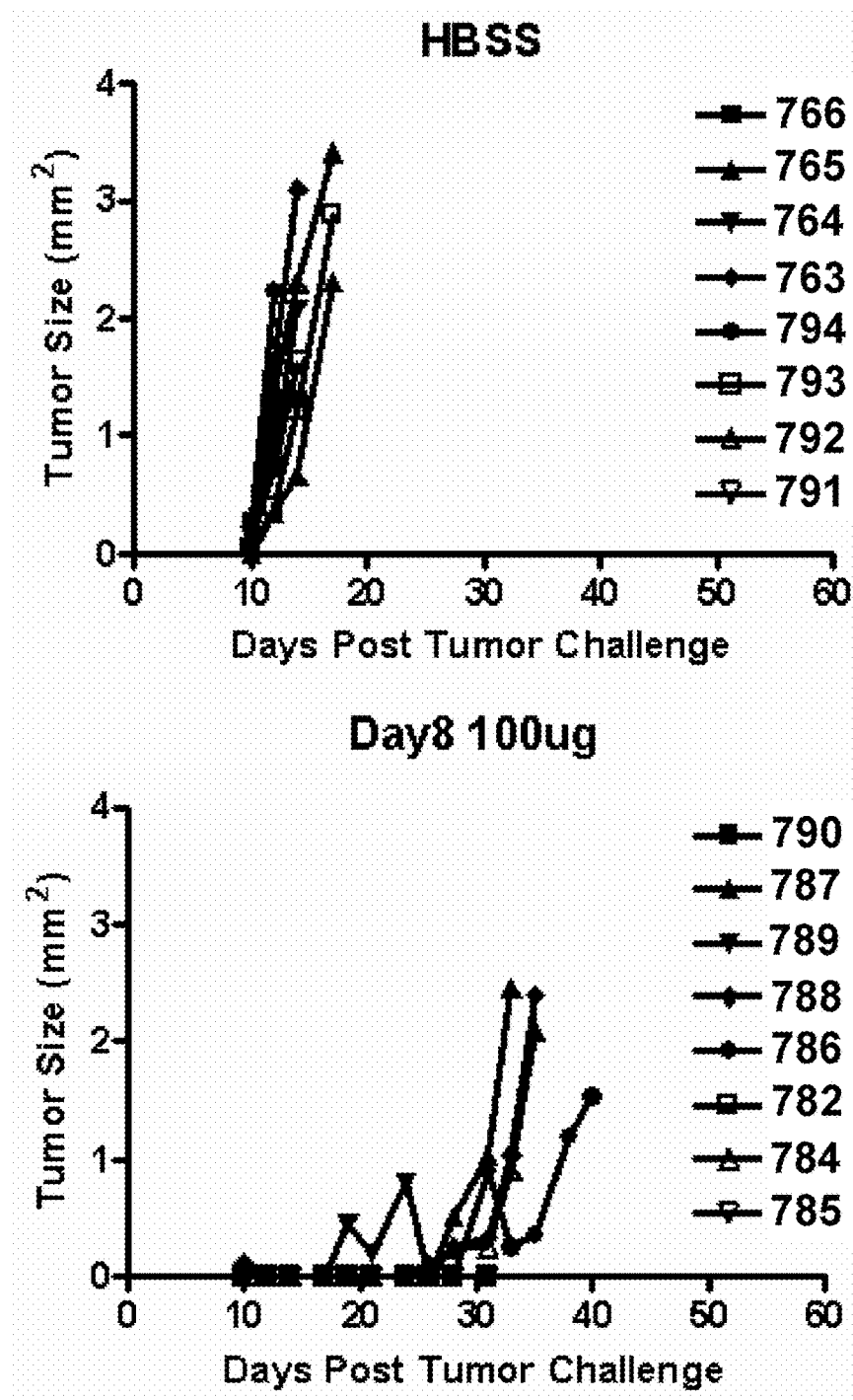

FIG. 25. Groups of eight mice were injected with 5000 38C13-CD20 cells on day 0. On days 8, 9 and 10 they were treated with HBSS or 100 µg of anti-CD20-IgG3-mIFNα. Tumor growth was monitored over time.

Figure 26:
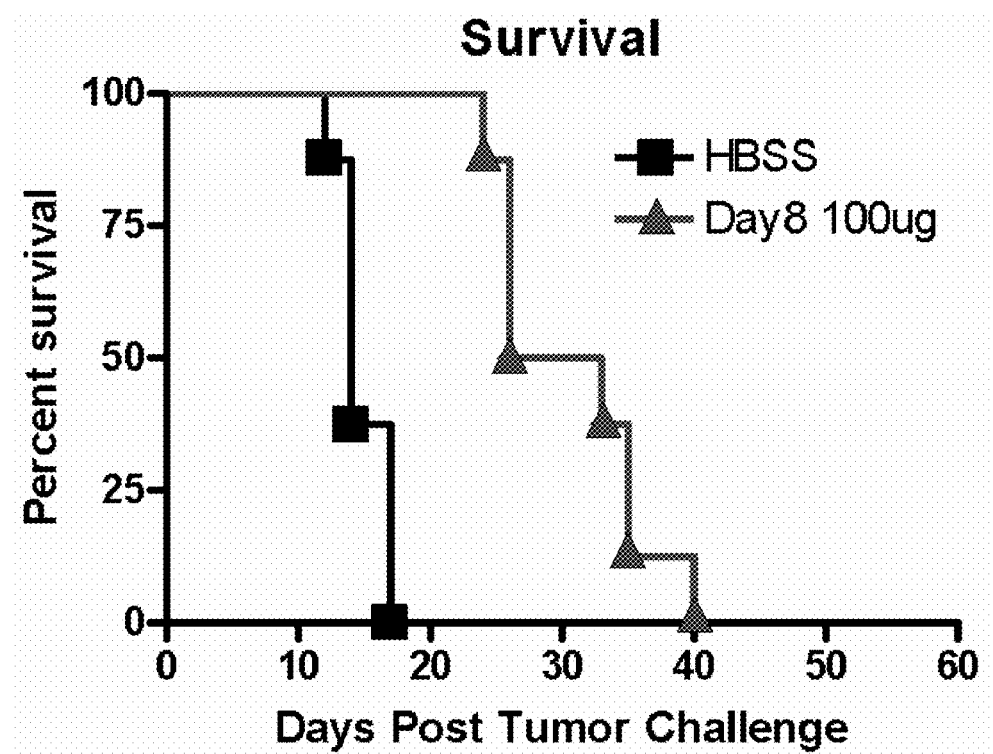

FIG. 26. Groups of eight mice were injected with 5000 38C13-CD20 cells on day 0. On days 8, 9 and 10 they were treated with HBSS or 100 µg of anti-CD20-IgG3-mIFNα. Survival was monitored over time.

Figure 27:
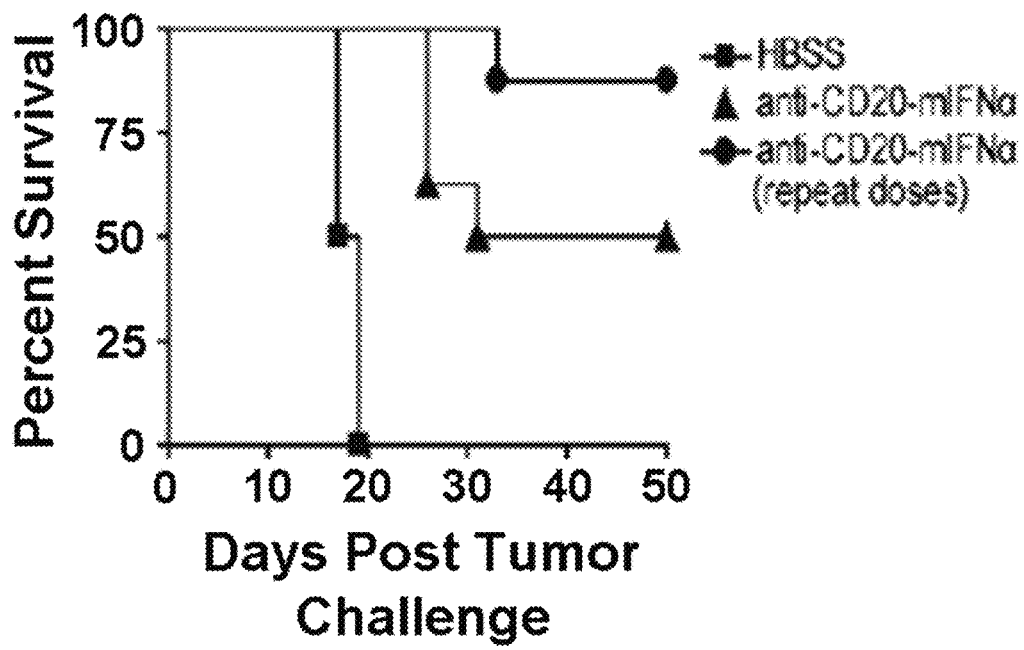

FIG. 27 shows that repeat dosing enhanced the efficacy of anti-CD20-mIFNα. Moreover, the data show the surprising result that attachment of a targeting moiety (e.g., anti-CD20) increased the efficacy of the fusion protein. Mice (n=8 per group) were treated with 10 µg of anti-CD-20-mIFNα 5, 6 and 7 days post tumor inoculation. One group of 8 was given additional doses of 30 µg of fusion protein 12 and 19 days post tumor inoculation (repeat doses). Mice were followed for survival and sacrificed when tumors reached 1.4 cm in diameter as per institutional guidelines. Mice treated with HBSS were used as controls.

Figure 28:
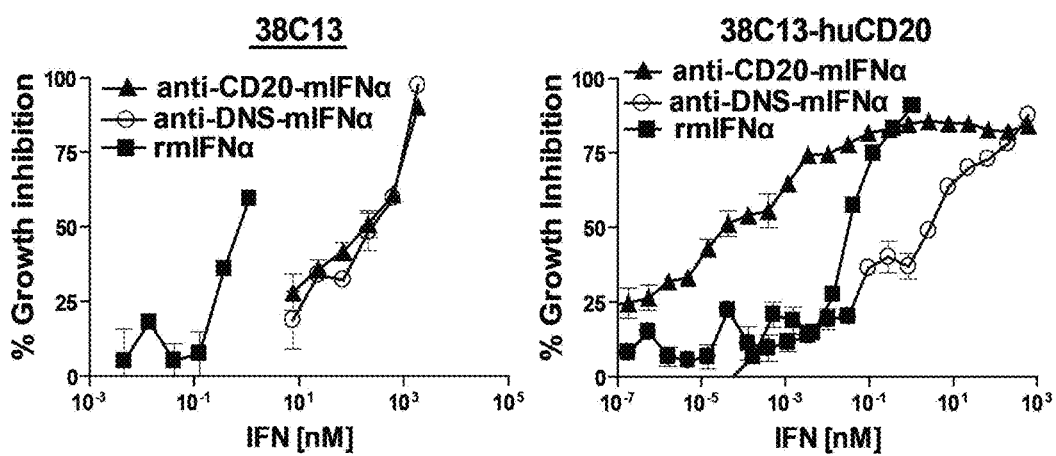

FIG. 28 shows the effect of the fusion protein on cell proliferation. The fusion protein has interferon activity as measured by the inhibition of cell proliferation which is improved by targeting. Cells were incubated with the indicated proteins for 48 hours. Cell proliferation was measured using the MTS assay and % growth inhibition calculated as [1-(ODexp/ODuntreated0]*100.

Figure 29:
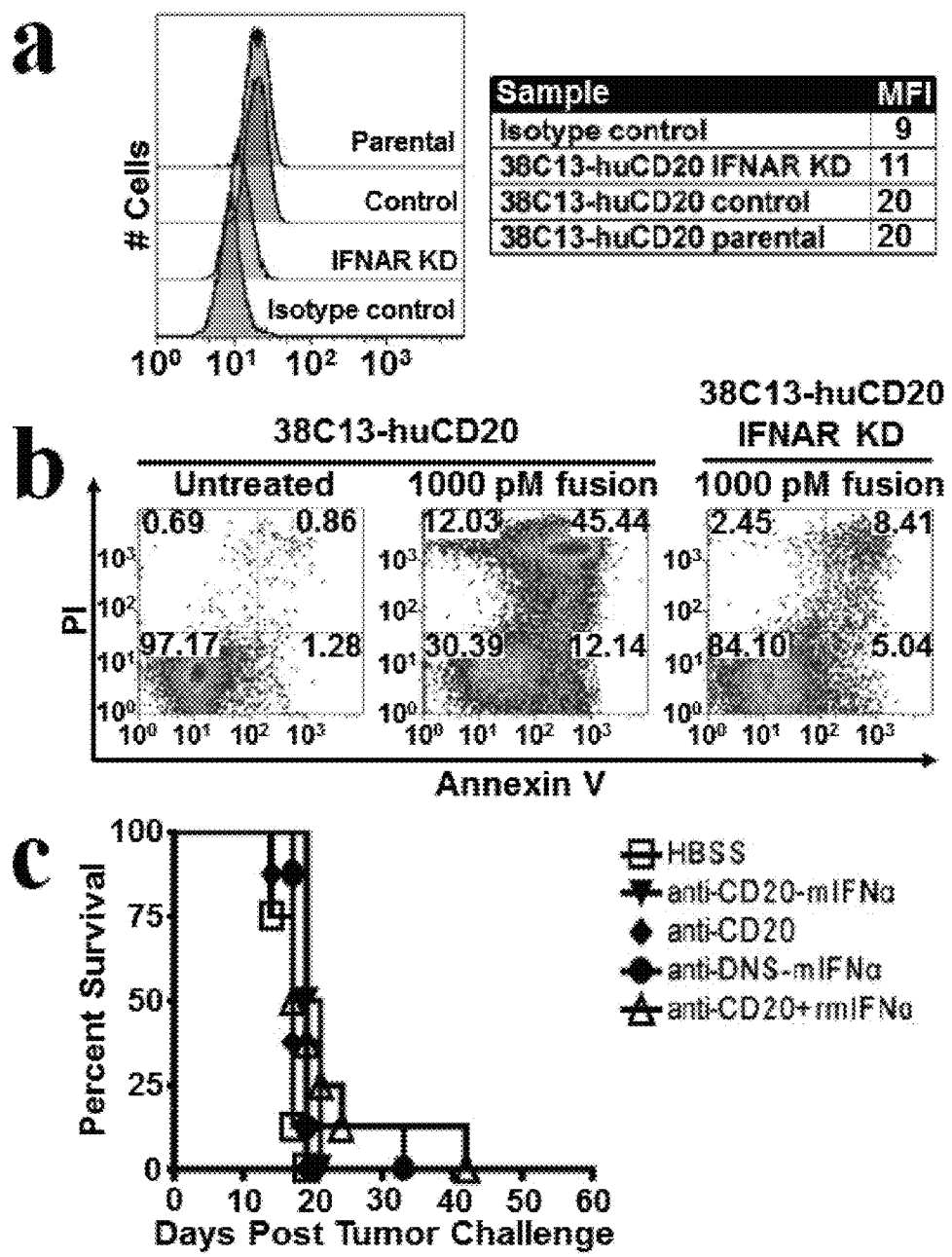

FIG. 29, panels A-C, show that anti-tumor efficacy of anti-CD20 requires IFNAR expression. Panel A: Flow cytometry analysis of IFNAR expression. 38C13-CD20 transduced with IFNAR-specific shRNA (38C13-huCD20IFNAR KD), 38C13 transduced with nonspecific shRNA (38C13-huCD20 control) and 38C13-CD20 parental cells stained with anti-IFNAR-biotin primary antibody (clone MAR1-5Ac) and detected with streptavidin-PE. Biotinylated IgG1 isotype stained control is also shown. Panel B: Apoptosis assay using parental 38C13-huCD20 and 38C13-huCD20IFNAR KD. Cell lines were treated with 1000 pM of anti-CD20-mIFNα and stained with Annexin V/PI 48 hours later. Panel C: Tumor challenge with 38C13-huCD20IFNAR KD cells. Mice (n=8) were treated 5, 6 and 7 days after tumor inoculation with 10 μg of anti-CD20 mIFNα or the molar equivalent of the indicated proteins. Mice were followed for survival and sacrificed when tumors reached 1.4 cm in diameter as per institutional guidelines. Mice treated with HBSS were used as control.

Figure 30:
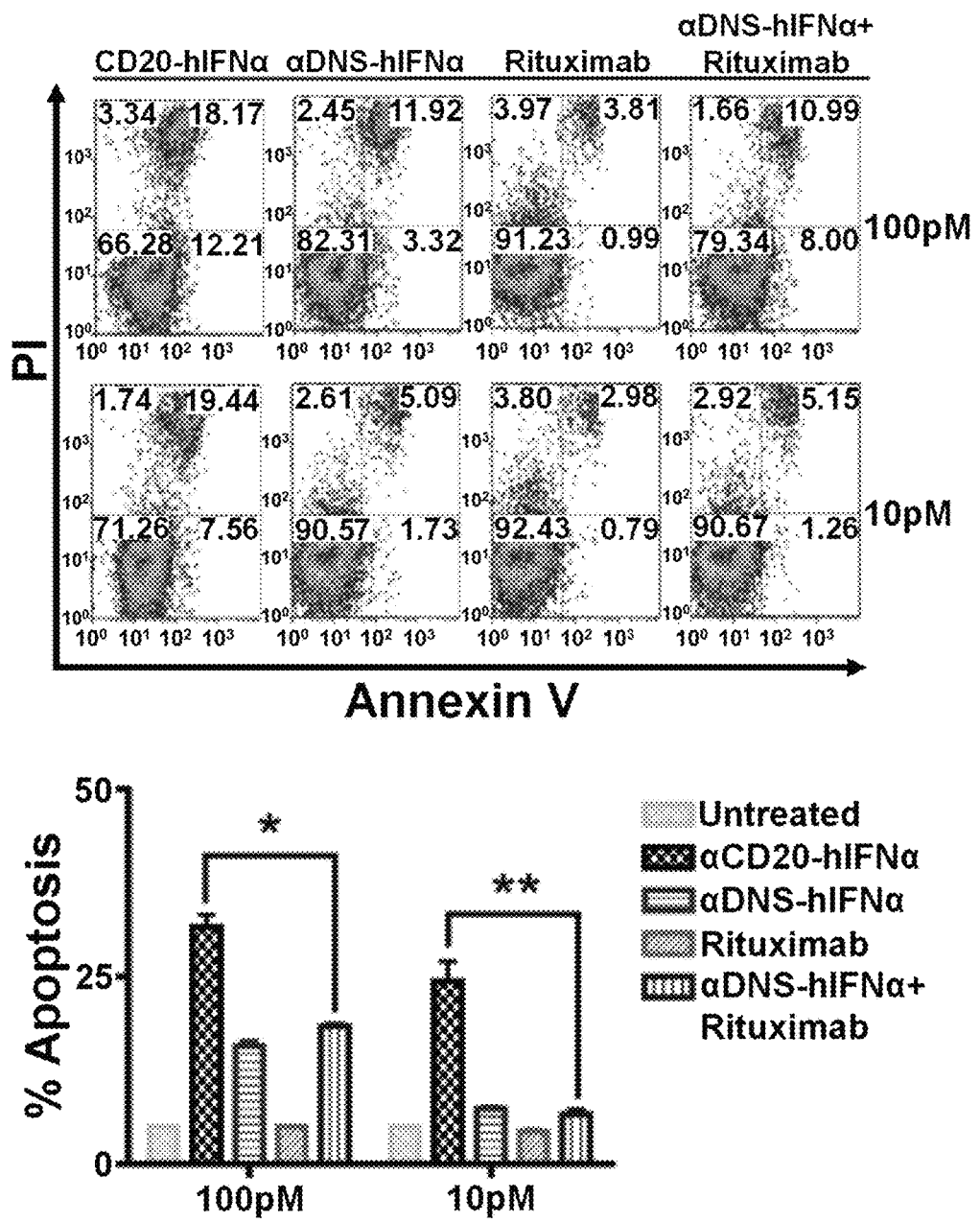

FIG. 30 shows that anti-CD20-hIFNα has proapoptotic activity against the human B-cell lymphoma Daudi. Cells were incubated with varying concentrations of the indicated proteins for 72 hours. Staining with AnnexinV-FITC and PI was performed to distinguish necrotic (Annexin$^-$PI$^+$), early apoptotic (Annexin$^+$PI$^-$) and late apoptotic (Annexin$^+$PI$^+$) cell populations. The percentage of total apoptotic cells was quantified for each sample as the sum of early apoptotic and late apoptotic cells. Experiments were performed in triplicate and error bars indicate mean±SD. *p=0.0014. **p=0.003.

Figure 31:
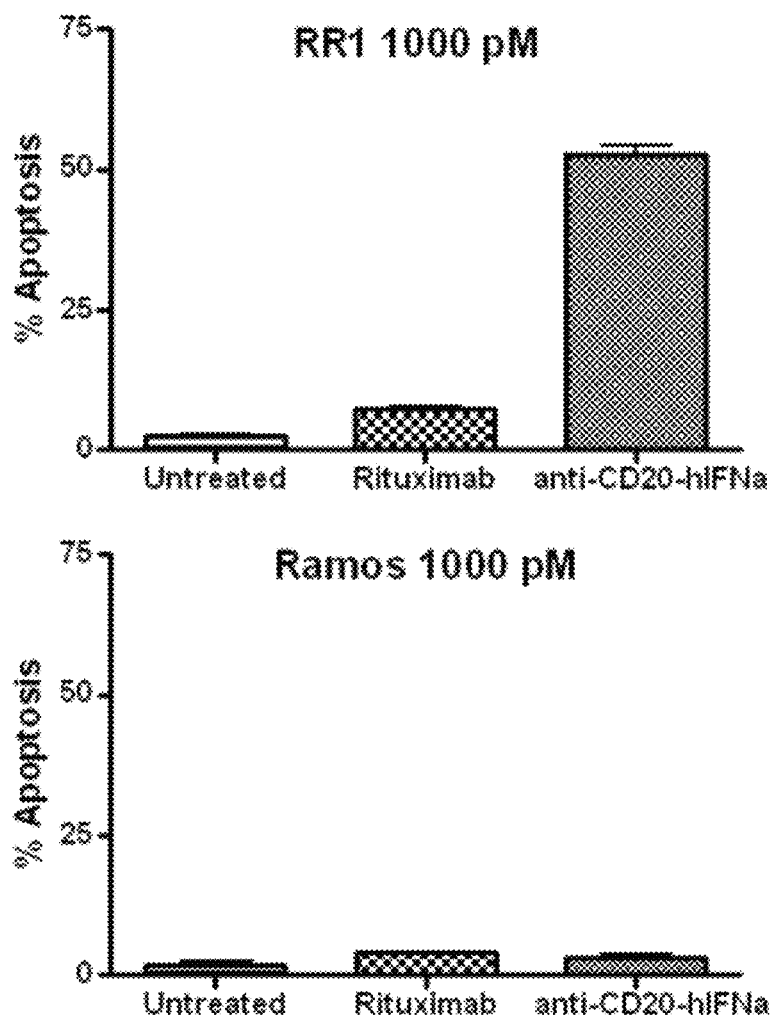

FIG. 31 shows that anti-CD20-IgG3-huIFNα is effective against rituximab resistant human cell lines. RR1 (Ramos rituximab-resistant) and Ramos cells were treated with 1000 pM of anti-CD20-IgG3-huIFNα for 72 hours. They were then stained with Annexin V-Alexa488 and PI (propidium iodide) to determine % apoptotic cells.

Figure 32:
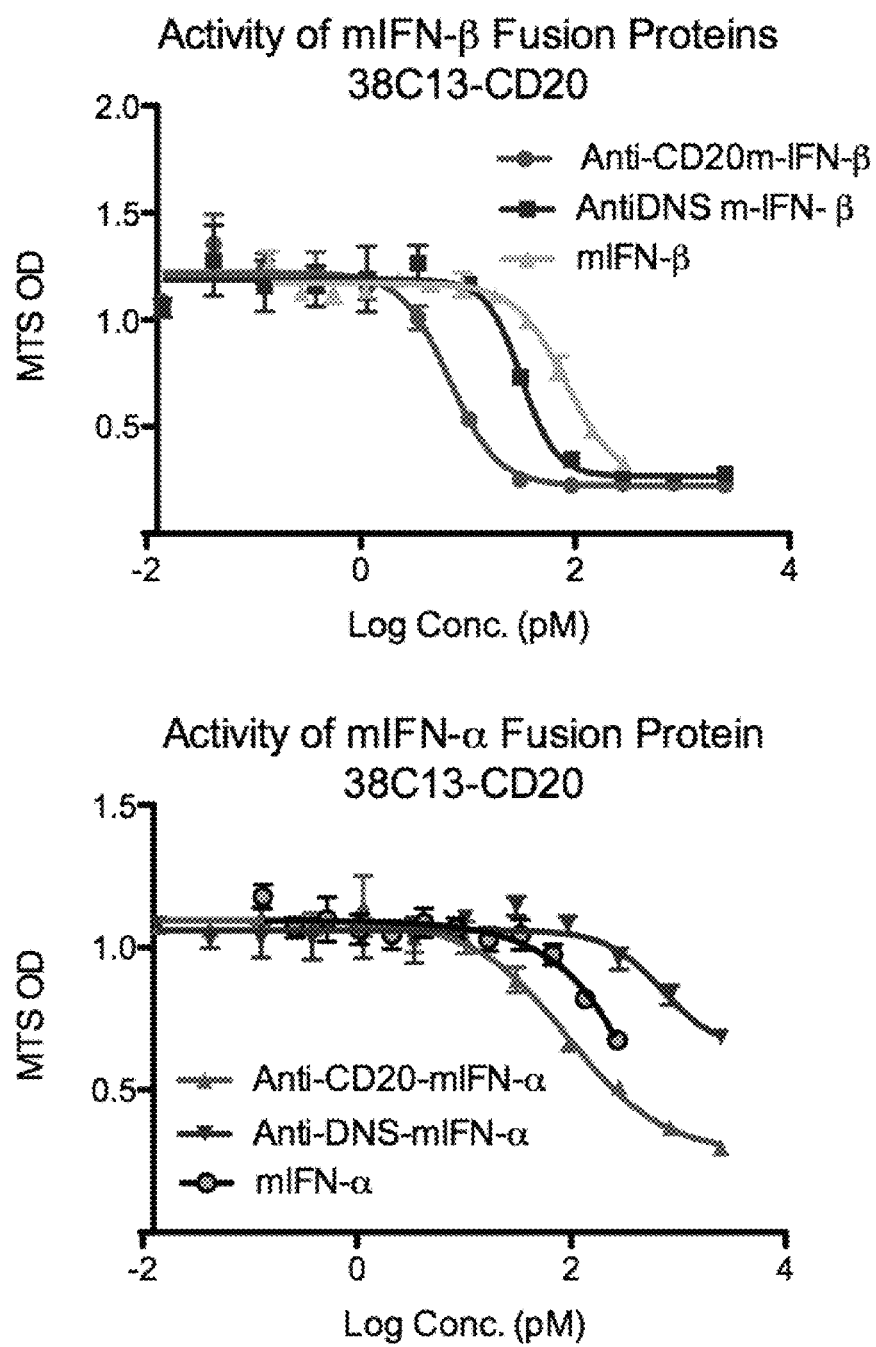

FIG. 32 shows the activity of IFN-α and IFN-β fusion proteins. 38C13-CD20 cells were incubated with the various treatments at 37° C. in a 5% CO$_2$ atmosphere for 72 hours. Cell viability was quantified using the MTS assay (Promega) by measuring absorbance at 490 nm using a Synergy HT Multi-Detection Microplate Reader. Data were analyzed by non-linear regression analysis using Prism GraphPad.

Figure 33:
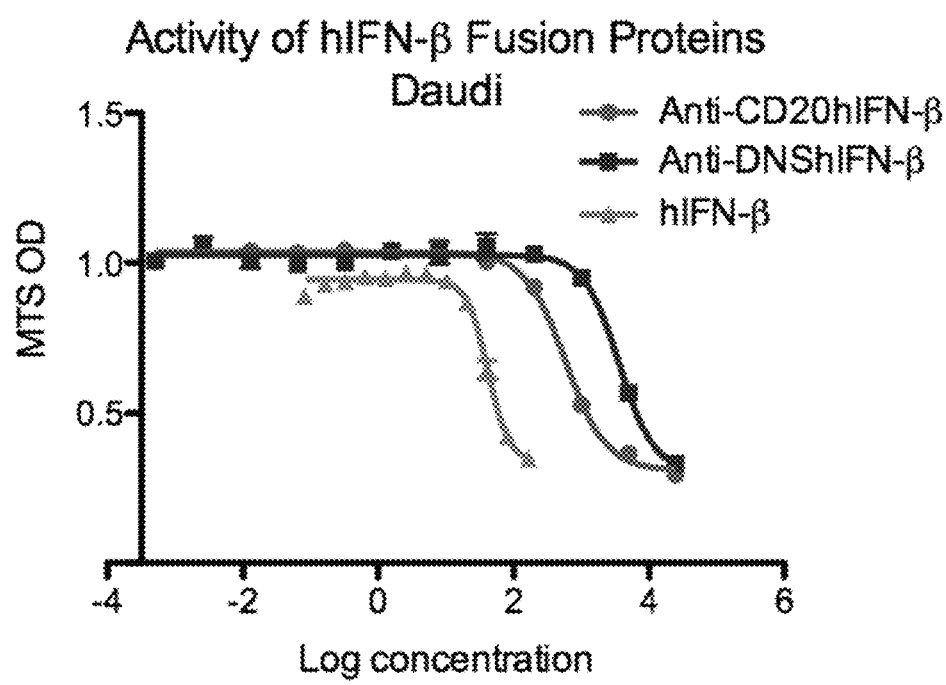

FIG. 33 shows that anti-CD20-hIFNβ is effective against human cells. Daudi cells were incubated with the various treatment at 37° C. in a 5% CO$_2$ atmosphere for 96 hours. Cell viability was quantified using the MTS assay (Promega) by measuring absorbance at 490 nm using a Synergy HT Multi-Detection Microplate Reader. Data were analyzed by non-linear regression analysis using Prism GraphPad.

Figure 34:
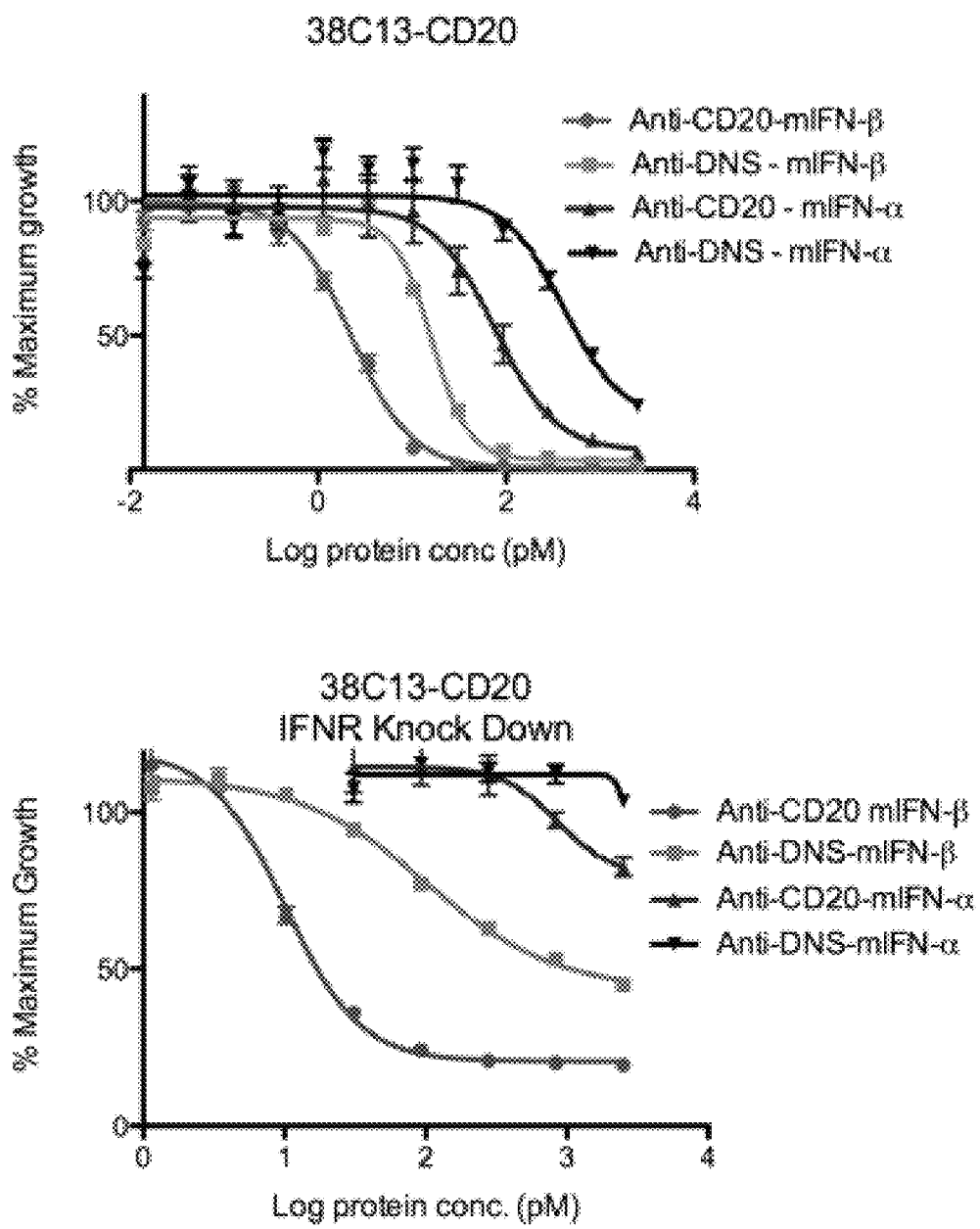

FIG. 34 shows that anti-CD20-mIFNβ is effective against cells expressing low levels of the IFN receptor. 38C13-CD20 cells or 38C13-CD20 cells in which the expression of the IFN receptor had been decreased (Knock Down) using shRNA were incubated with the indicated proteins at various concentrations for 48 hours. Cell viability was then quantified using the MTS assay. Data were analyzed by non-linear regression using Prism GraphPad.

Figure 35:
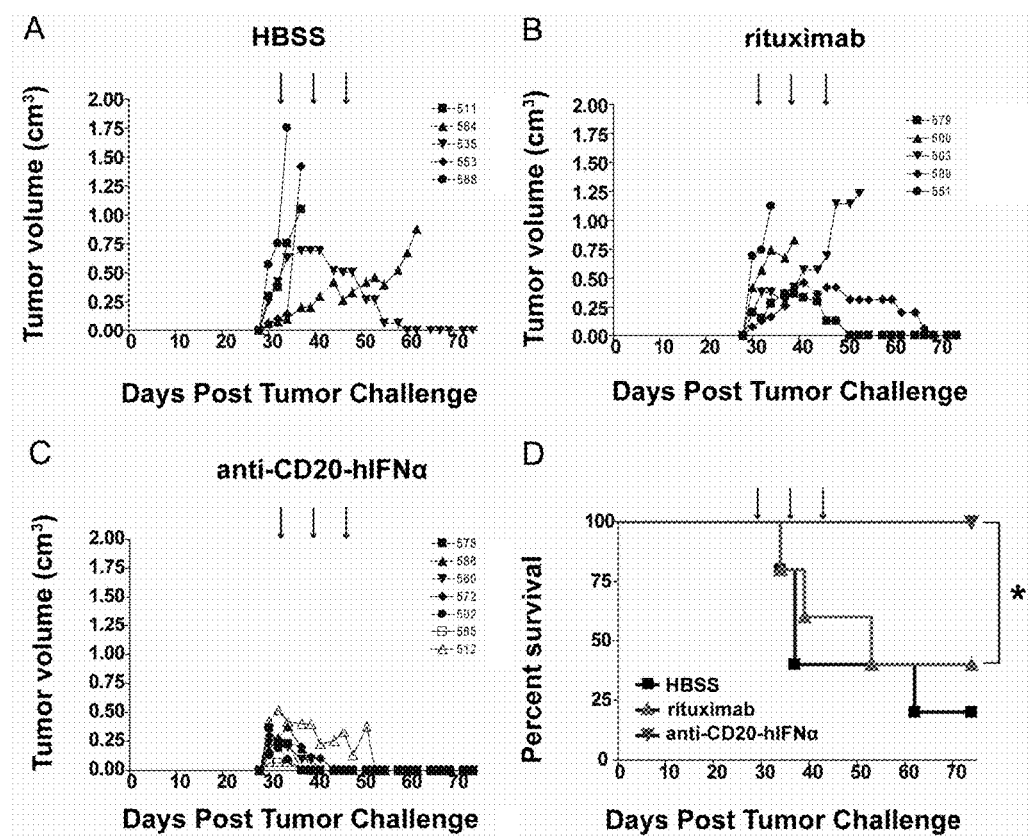

FIG. 35, panels A-D, show that anti-CD20-hIFNα completely cures established human xenograft tumors. Panels A-C: Tumor growth in mice (n=5-7 per group) inoculated subcutaneously with Daudi cells and treated as indicated with three weekly doses of 30 μg fusion protein, the equivalent molar concentration of rituximab, or HBSS. Treatment was administered 30, 37 and 44 days post tumor inoculation (arrows) to mice with tumors at least 0.5 cm in diameter. HBSS was injected as a control. Symbols represent individual mice. Panel D: Survival curves for the mice whose tumor growth is shown in panels A-C. *P=0.02.

DETAILED DESCRIPTION

Interferon is an important cytokine in initiating the innate immune response and also demonstrates a wide spectrum of anti-tumor activities. The clinical use of interferon (e.g., IFN-α) as an anticancer drug, however, is hampered by its short half-life, which significantly compromises its therapeutic effect. In certain embodiments this invention pertains to the discovery that the therapeutic index and actual activity (even in vitro) of interferon can be improved by attaching the interferon to a targeting moiety that specifically/preferentially binds a marker on or associated with the target cell (e.g., a tumor cell). This permits the deliver of higher doses of interferon to the target site with fewer systemic complications and the greater innate activity of the construct provides a greater therapeutic window. This was illustrated, in certain, by the construction and use of a fusion protein consisting of an anti-HER2/neu IgG3 and IFN-α or IFN-β (e.g., anti-HER2/neu-IgG3-IFN-α) and in another embodiment by the construction and use of anti-CD20-IFN-α and anti-CD20-IFN-β fusion proteins.

The efficacy of the HER2/neu-IgG3-IFN constructs was tested on a murine B-cell lymphoma, 38C13, transduced with human HER2/neu. The anti-HER2/neu-IgG3-IFN fusion protein exhibited a potent effect in inhibiting the 38C13/HER2 tumor growth in vivo, and even administration of 1 μg anti-HER2/neu IgG3-IFN-α resulted in 88% of long-term survivors after tumor challenge.

Remarkably, anti-HER2/neu IgG3-IFN-α demonstrated a potent activity against established 38C13/HER2 tumors, and complete tumor remission was observed in 88% treated mice. This dramatic anti-tumor activity was mediated by IFN-α induced apoptosis and targeting IFN-α to 38C13/HER2 tumor cells by the anti-HER2/neu IgG3 antibody was essential to potentiate these effects.

Similar results were observed for the anti-CD20-IgG3-IFN-α constructs and anti-CD20-IFN-β constructs (see, Examples herein). These results indicate that attachment (e.g., fusion) of an interferon (e.g., IFN-α) to a targeting moiety (e.g., to a tumor specific antibody) produces an effective therapeutic that can be used to inhibit the growth and/or proliferation or even to kill target cell(s). Thus, for example, the exemplary constructs described herein can readily be used for treatment of B cell lymphoma and other cancers in clinic.

Thus, in certain embodiments, this invention provides constructs (e.g. chimeric moieties) comprising an interferon (e.g., IFN-α, IFN-β, etc.) attached to a targeting moiety (e.g., to an antibody that specifically binds a cancer specific marker on a cancer cell). The constructs include chemical conjugates as well as fusion proteins. Also provided are nucleic acids encoding the fusion proteins as well as cells transfected with the nucleic acids to express the fusion proteins. Also provided are methods of inhibiting growth and proliferation of cancer cells as well as kits comprising, e.g. the chimeric moieties described herein, for the treatment of various cancers.

I. Chimeric Constructs Comprising a Targeting Moiety Attached to an Interferon.

It was a surprising discovery that chimeric constructs comprising a targeting moiety (e.g., an anti-tumor marker antibody) attached to a native (wild type) or modified IFN (e.g., IFN-α, IFN-β, etc.) can be effectively used to inhibit the growth and/or proliferation of target cancer cells expressing or associated with the marker to which the targeting moiety is directed. In certain embodiments the targeting moieties are chemically conjugated to the interferon, while in other embodiments, the targeting moiety is expressed as a fusion protein with the interferon. When produced as a fusion protein the targeting moiety (e.g., antibody) component can be directly fused to the IFN-α or attached by means of a peptide linker (e.g., a (Gly$_4$Ser)$_3$ (SEQ ID NO:5) linker, a Gly$_4$Ser (SEQ ID NO:6) linker, an AEAAAKEAAAKA (SEQ ID NO:7) linker, and the like.

Illustrative nucleic acid and amino acid constructs used in the compositions and methods described herein are shown in FIG. 1 and in Table 1. It will be appreciated that while the constructs in this figure are shown with particular linkers, targeting moieties and interferons, in certain embodiments other linkers, other targeting moieties and other interferons can be substituted therefore as described herein.

TABLE 1

Various illustrative constructs used in certain embodiments described herein.

| Description and Sequence | SEQ ID NO: |
|---|---|
| αCD20 light chain - nucleic acid sequence: | |
| ATGAAGTTGCCTGTTAGGCTGTTGGTGCTGATGTTCTGGATTCCTGCTTCCAGCA GTCAAATTGTTCTCTCCCAGTCTCCAGCAATCCTGTCTGCATCTCCAGGGGAGAA GGTCACAATGACTTGCAGGGCCAGCTCAAGTGTAAGTTACATCCACTGGTTCCAG CAGAAGCCAGGATCCTCCCCCAAACCCTGGATTTATGCCACATCCAACCTGGCTT CTGGAGTCCCTGTTCGCTTCAGTGGCAGTGGGTCTGGGACTTCTTACTCTCTCAC AATCAGCAGAGTGGAGGCTGAAGATGCTGCCACTTATTACTGCCAGCAGTGGACT AGTAACCCACCCACGTTCGGAGGGGGGACCAAGCTGGAAATCAAA | 8 |
| αCD20 light chain - amino acid sequence: | |
| MKLPVRLLVLMFWIPASSSQIVLSQSPAILSASPGEKVTMTCRASSSVSYIHWFQ QKPGSSPKPWIYATSNLASGVPVRFSGSGSGTSYSLTISRVEAEDAATYYCQQWT SNPPTFGGGTKLEIK | 9 |
| αCD20-IgG3-muIFNα Gly$_4$Ser - nucleic acid sequence: | |
| ATGTACTTGGGACTGAACTGTGTAATCATAGTTTTTCTCTTAAAAGGTGTCCAGA GTCAGGTACAACTGCAGCAGCCTGGGGCTGAGCTGGTGAAGCCTGGGGCCTCAGT GAAGATGTCCTGCAAGGCTTCTGGCTACACATTTACCAGTTACAATATGCACTGG GTAAAACAGACACCTGGTCGGGGCCTGGAATGGATTGGAGCTATTTATCCCGGAA ATGGTGATACTTCCTACAATCAGAAGTTCAAAGGCAAGGCCACATTGACTGCAGA CAAATCCTCCAGCACAGCCTACATGCAGCTCAGCAGCCTGACATCTGAGGACTCT GCGGTCTATTACTGTGCAAGATCGACTTACTACGGCGGTGACTGGTACTTCAATG TCTGGGGCGCAGGGACCACGGTCACCGTCTCTGCAGCTAGCACCAAGGGCCCATC GGTCTTCCCCCTGGCGCCCTGCTCCAGGAGCACCTCTGGGGGCACAGCGGCCCTG GGCTGCCTGGTCAAGGACTACTTCCCCGAACCGGTGACGGTGTCGTGGAACTCAG GCGCCCTGACCAGCGGCGTGCACACCTTCCCGGCTGTCCTACAGTCCTCAGGACT CTACTCCCTCAGCAGCGTGGTGACCGTGCCCTCCAGCAGCTTGGGCACCCAGACC TACACCTGCAACGTGAATCACAAGCCCAGCAACACCAAGGTGGACAAGAGAGTTG AGCTCAAAACCCCACTTGGTGACACAACTCACACATGCCCACGGTGCCCAGAGCC CAAATCTTGTGACACACCTCCCCCGTGCCCAAGGTGCCCAGAGCCCAAATCTTGT GACACACCTCCCCCGTGCCCAAGGTGCCCAGAGCCCAAATCTTGTGACACACCTC CCCCGTGCCCAAGGTGCCCAGCACCTGAACTCCTGGGAGGACCGTCAGTCTTCCT CTTCCCCCCAAAACCCAAGGATACCCTTATGATTTCCCGGACCCCTGAGGTCACG TGCGTGGTGGTGGACGTGAGCCACGAAGACCCCGAGGTCCAGTTCAAGTGGTACG TGGACGGCGTGGAGGTGCATAATGCCAAGACAAAGCTGCGGGAGGAGCAGTACAA CAGCACGTTCCGTGTGGTCAGCGTCCTCACCGTCCTGCACCAGGACTGGCTGAAC GGCAAGGAGTACAAGTGCAAGGTCTCCAACAAAGCCCTCCCAGCCCCCATCGAGA AAACCATCTCCAAAGCCAAAGGACAGCCCCGAGAACCACAGGTGTACACCCTGCC CCCATCCCGGGAGGAGATGACCAAGAACCAGGTCAGCCTGACCTGCCTGGTCAAA GGCTTCTACCCCAGCGACATCGCCGTGGAGTGGGAGAGCAATGGGCAGCCGGAGA ACAACTACAACACCACGCCTCCCATGCTGGACTCCGACGGCTCCTTCTTCCTCTA CAGCAAGCTCACCGTGGACAAGAGCAGGTGGCAGCAGGGGAACATCTTCTCATGC TCCGTGATGCATGAGGCTCTGCACAACCACTACACGCAGAAGAGCCTCTCCCTGT CTCCGGGTAAATCTGGTGGCGGTGGATCCTGTGACCTGCCTCAGACTCATAACCT CAGGAACAAGAGAGCCTTGACACTCCTGGTACAAATGAGGAGACTCTCCCCTCTC TCCTGCCTGAAGGACAGGAAGGACTTTGGATTCCCGCAGGAGAAGGTGGATGCCC AGCAGATCAAGAAGGCTCAAGCCATCCCTGTCCTGAGTGAGCTGACCCAGCAGAT CCTGAACATCTTCACATCAAAGGACTCATCTGCTGCTTGGAATGCAACCCTCCTA GACTCATTCTGCAATGACCTCCACCAGCAGCTCAATGACCTGCAAGGTTGTCTGA TGCAGCAGGTGGGGGTGCAGGAATTTCCCCTGACCCAGGAAGATGCCCTGCTGGC TGTGAGGAAATACTTCCACAGGATCACTGTGTACCTGAGAGAGAAGAAACACAGC CCCTGTGCCTGGGAGGTGGTCAGAGCAGAAGTCTGGAGAGCCCTGTCTTCCTCTG CCAATGTGCTGGGAAGACTGAGAGAAGAGAAA | 10 |

TABLE 1-continued

Various illustrative constructs used in certain embodiments described herein.

| Description and Sequence | SEQ ID NO: |
|---|---|
| αCD20-IgG3-muIFNα Gly$_4$Ser linker - Amino acid sequence: | |
| MYLGLNCVIIVFLLKGVQSQVQLQQPGAELVKPGASVKMSCKASGYTFTSYNMHW VKQTPGRGLEWIGAIYPGNGDTSYNQKFKGKATLTADKSSSTAYMQLSSLTSEDS AVYYCARSTYYGGDWYFNVWGAGTTVTVSAASTKGPSVFPLAPCSRSTSGGTAAL GCLVKDYFPEPVTVSWNSGALTSGVHTFPAVLQSSGLYSLSSVVTVPSSSLGTQT YTCNVNHKPSNTKVDKRVELKTPLGDTTHTCPRCPEPKSCDTPPPCPRCPEPKSC DTPPPCPRCPEPKSCDTPPPCPRCPAPELLGGPSVFLFPPKPKDTLMISRTPEVT CVVVDVSHEDPEVQFKWYVDGVEVHNAKTKLREEQYNSTFRVVSVLTVLHQDWLN GKEYKCKVSNKALPAPIEKTISKAKGQPREPQVYTLPPSREEMTKNQVSLTCLVK GFYPSDIAVEWESNGQPENNYNTTPPMLDSDGSFFLYSKLTVDKSRWQQGNIFSC SVMHEALHNHYTQKSLSLSPGKSGGGGSCDLPQTHNLRNKRALTLLVQMRRLSPL SCLKDRKDFGFPQEKVDAQQIKKAQAIPVLSELTQQILNIFTSKDSSAAWNATLL DSFCNDLHQQLNDLQGCLMQQVGVQEFPLTQEDALLAVRKYFHRITVYLREKKHS PCAWEVVRAEVWRALSSSANVLGRLREEK | 11 |
| αCD20-IgG3-muIFNα alpha helical linker - nucleic acid sequence: | |
| ATGTACTTGGGACTGAACTGTGTAATCATAGTTTTTCTCTTAAAAGGTGTCCAGA GTCAGGTACAACTGCAGCAGCCTGGGGCTGAGCTGGTGAAGCCTGGGGCCTCAGT GAAGATGTCCTGCAAGGCTTCTGGCTACACATTTACCAGTTACAATATGCACTGG GTAAAACAGACACCTGGTCGGGGCCTGGAATGGATTGGAGCTATTTATCCCGGAA ATGGTGATACTTCCTACAATCAGAAGTTCAAAGGCAAGGCCACATTGACTGCAGA CAAATCCTCCAGCACAGCCTACATGCAGCTCAGCAGCCTGACATCTGAGGACTCT GCGGTCTATTACTGTGCAAGATCGACTTACTACGGCGGTGACTGGTACTTCAATG TCTGGGGCGCAGGGACCACGGTCACCGTCTCTGCAGCTAGCACCAAGGGCCCATC GGTCTTCCCCCTGGCGCCCTGCTCCAGGAGCACCTCTGGGGGCACAGCGGCCCTG GGCTGCCTGGTCAAGGACTACTTCCCCGAACCGGTGACGGTGTCGTGGAACTCAG GCGCCCTGACCAGCGGCGTGCACACCTTCCCGGCTGTCCTACAGTCCTCAGGACT CTACTCCCTCAGCAGCGTGGTGACCGTGCCCTCCAGCAGCTTGGGCACCCAGACC TACACCTGCAACGTGAATCACAAGCCCAGCAACACCAAGGTGGACAAGAGAGTTG AGCTCAAAACCCCACTTGGTGACAACTCACACATGCCCACGGTGCCCAGAGCC CAAATCTTGTGACACACCTCCCCCGTGCCCAAGGTGCCCAGAGCCCAAATCTTGT GACACACCTCCCCCGTGCCCAAGGTGCCCAGCACCTGAACTCCTGGGAGGACCGTCAGTCTTCCT CTTCCCCCCAAAACCCAAGGATACCCTTATGATTTCCCGGACCCTGAGGTCACG TGCGTGGTGGTGGACGTGAGCCACGAAGACCCCGAGGTCCAGTTCAAGTGGTACG TGGACGGCGTGGAGGTGCATAATGCCAAGACAAAGCTGCGGGAGGAGCAGTACAA CAGCACGTTCCGTGTGGTCAGCGTCCTCACCGTCCTGCACCAGGACTGGCTGAAC GGCAAGGAGTACAAGTGCAAGGTCTCCAACAAAGCCCTCCCAGCCCCCATCGAGA AAACCATCTCCAAAGCCAAAGGACAGCCCCGAGAACCACAGGTGTACACCCTGCC CCCATCCCGGGAGGAGATGACCAAGAACCAGGTCAGCCTGACCTGCCTGGTCAAA GGCTTCTACCCCAGCGACATCGCCGTGGAGTGGGAGAGCAATGGGCAGCCGGAGA ACAACTACAACACCACGCCTCCCATGCTGGACTCCGACGGCTCCTTCTTCCTCTA CAGCAAGCTCACCGTGGACAAGAGCAGGTGGCAGCAGGGGAACATCTTCTCATGC TCCGTGATGCATGAGGCTCTGCACAACCACTACACGCAGAAGAGCCTCTCCCTGT CTCCGGGTAAAGCAGAGGCCGCAGCTAAAGAGGCCGCAGCCAAAGCGGGATCCTG TGACCTGCCTCAGACTCATAACCTCAGGAACAAGAGAGCCTTGACACTCCTGGTA CAAATGAGGAGACTCTCCCCTCTCTCCTGCCTGAAGGACAGGAAGGACTTTGGAT TCCCGCAGGAGAAGGTGGATGCCCAGCAGATCAAGAAGGCTCAAGCCATCCCTGT CCTGAGTGAGCTGACCCAGCAGATCCTGAACATCTTCACATCAAAGGACTCATCT GCTGCTTGGAATGCAACCCTCCTAGACTCATTCTGCAATGACCTCCACCAGCAGC TCAATGACCTGCAAGGTTGTCTGATGCAGCAGGTGGGGGTGCAGGAATTTCCCCT GACCCAGGAAGATGCCCTGCTGGCTGTGAGGAAATACTTCCACAGGATCACTGTG TACCTGAGAGAGAAGAAACACAGCCCCTGTGCCTGGGAGGTGGTCAGAGCAGAAG TCTGGAGAGCCCTGTCTTCCTCTGCCAATGTGCTGGGAAGACTGAGAGAAGAGAA A | 12 |
| αCD20-IgG3-muIFNα alpha helical linker - amino acid sequence: | |
| MYLGLNCVIIVFLLKGVQSQVQLQQPGAELVKPGASVKMSCKASGYTFTSYNMHW VKQTPGRGLEWIGAIYPGNGDTSYNQKFKGKATLTADKSSSTAYMQLSSLTSEDS AVYYCARSTYYGGDWYFNVWGAGTTVTVSAASTKGPSVFPLAPCSRSTSGGTAAL GCLVKDYFPEPVTVSWNSGALTSGVHTFPAVLQSSGLYSLSSVVTVPSSSLGTQT YTCNVNHKPSNTKVDKRVELKTPLGDTTHTCPRCPEPKSCDTPPPCPRCPEPKSC DTPPPCPRCPEPKSCDTPPPCPRCPAPELLGGPSVFLFPPKPKDTLMISRTPEVT CVVVDVSHEDPEVQFKWYVDGVEVHNAKTKLREEQYNSTFRVVSVLTVLHQDWLN GKEYKCKVSNKALPAPIEKTISKAKGQPREPQVYTLPPSREEMTKNQVSLTCLVK GFYPSDIAVEWESNGQPENNYNTTPPMLDSDGSFFLYSKLTVDKSRWQQGNIFSC SVMHEALHNHYTQKSLSLSPGKAEAAAKEAAAKAGSCDLPQTHNLRNKRALTLLV QMRRLSPLSCLKDRKDFGFPQEKVDAQQIKKAQAIPVLSELTQQILNIFTSKDSS AAWNATLLDSFCNDLHQQLNDLQGCLMQQVGVQEFPLTQEDALLAVRKYFHRITV YLREKKHSPCAWEVVRAEVWRALSSSANVLGRLREEK | 13 |

TABLE 1-continued

Various illustrative constructs used in
certain embodiments described herein.

| Description and Sequence | SEQ ID NO: |
|---|---|
| αCD20-IgG3-huIFNα Gly₄Ser linker - nucleic acid sequence: | |
| ATGTACTTGGGACTGAACTGTGTAATCATAGTTTTTCTCTTAAAAGGTGTCCAGA<br>GTCAGGTACAACTGCAGCAGCCTGGGGCTGAGCTGGTGAAGCCTGGGGCCTCAGT<br>GAAGATGTCCTGCAAGGCTTCTGGCTACACATTTACCAGTTACAATATGCACTGG<br>GTAAAACAGACACCTGGTCGGGGCCTGGAATGGATTGGAGCTATTTATCCCGGAA<br>ATGGTGATACTTCCTACAATCAGAAGTTCAAAGGCAAGGCCACATTGACTGCAGA<br>CAAATCCTCCAGCACAGCCTACATGCAGCTCAGCAGCCTGACATCTGAGGACTCT<br>GCGGTCTATTACTGTGCAAGATCGACTTACTACGGCGGTGACTGGTACTTCAATG<br>TCTGGGGCGCAGGGACCACGGTCACCGTCTCTGCAGCTAGCACCAAGGGCCCATC<br>GGTCTTCCCCCTGGCGCCCTGCTCCAGGAGCACCTCTGGGGGCACAGCGGCCCTG<br>GGCTGCCTGGTCAAGGACTACTTCCCCGAACCGGTGACGGTGTCGTGGAACTCAG<br>GCGCCCTGACCAGCGGCGTGCACACCTTCCCGGCTGTCCTACAGTCCTCAGGACT<br>CTACTCCCTCAGCAGCGTGGTGACCGTGCCCTCCAGCAGCTTGGGCACCCAGACC<br>TACACCTGCAACGTGAATCACAAGCCCAGCAACACCAAGGTGGACAAGAGAGTTG<br>AGCTCAAAACCCCACTTGGTGACACAACTCACACATGCCCACGGTGCCCAGAGCC<br>CAAATCTTGTGACACACCTCCCCCGTGCCCAAGGTGCCCAGAGCCCAAATCTTGT<br>GACACACCTCCCCCGTGCCCAAGGTGCCCAGAGCCCAAATCTTGTGACACACCTC<br>CCCCGTGCCCAAGGTGCCCAGCACCTGAACTCCTGGGAGGACCGTCAGTCTTCCT<br>CTTCCCCCCAAAACCCAAGGATACCCTTATGATTTCCCGGACCCCTGAGGTCACG<br>TGCGTGGTGGTGGACGTGAGCCACGAAGACCCCGAGGTCCAGTTCAAGTGGTACG<br>TGGACGGCGTGGAGGTGCATAATGCCAAGACAAAGCTGCGGGAGGAGCAGTACAA<br>CAGCACGTTCCGTGTGGTCAGCGTCCTCACCGTCCTGCACCAGGACTGGCTGAAC<br>GGCAAGGAGTACAAGTGCAAGGTCTCCAACAAAGCCCTCCCAGCCCCCATCGAGA<br>AAACCATCTCCAAAGCCAAAGGACAGCCCCGAGAACCACAGGTGTACACCCTGCC<br>CCCATCCCGGGAGGAGATGACCAAGAACCAGGTCAGCCTGACCTGCCTGGTCAAA<br>GGCTTCTACCCCAGCGACATCGCCGTGGAGTGGGAGAGCAATGGGCAGCCGGAGA<br>ACAACTACAACACCACGCCTCCCATGCTGGACTCCGACGGCTCCTTCTTCCTCTA<br>CAGCAAGCTCACCGTGGACAAGAGCAGGTGGCAGCAGGGGAACATCTTCTCATGC<br>TCCGTGATGCATGAGGCTCTGCACAACCACTACACGCAGAAGAGCCTCTCCCTGT<br>CTCCGGGTAAATCTGGTGGCGGTGGATCCTGTGATCTGCCTCAAACCCACAGCCT<br>GGGTAGCAGGAGGACCTTGATGCTCCTGGCACAGATGAGGAGAATCTCTCTTTTC<br>TCCTGCTTGAAGGACAGACATGACTTTGGATTTCCCCAGGAGGAGTTTGGCAACC<br>AGTTCCAAAAGGCTGAAACCATCCCTGTCCTCCATGAGATGATCCAGCAGATCTT<br>CAATCTCTTCAGCACAAAGGACTCATCTGCTGCTTGGGATGAGACCCTCCTAGAC<br>AAATTCTACACTGAACTCTACCAGCAGCTGAATGACCTGGAAGCCTGTGTGATAC<br>AGGGGGTGGGGGTGACAGAGACTCCCCTGATGAAGGAGGACTCCATTCTGGCTGT<br>GAGGAAATACTTCCAAAGAATCACTCTCTATCTGAAAGAAGAAATACAGCCCT<br>TGTGCCTGGGAGGTTGTCAGAGCAGAAATCATGAGATCTTTTTCTTTGTCAACAA<br>ACTTGCAAGAAAGTTTAAGAAGTAAGGAA | 14 |
| αCD20-IgG3-huIFNα Gly₄Ser linker - amino acid sequence: | |
| MYLGLNCVIIVFLLKGVQSQVQLQQPGAELVKPGASVKMSCKASGYTFTSYNMHW<br>VKQTPGRGLEWIGAIYPGNGDTSYNQKFKGKATLTADKSSSTAYMQLSSLTSEDS<br>AVYYCARSTYYGGDWYFNVWGAGTTVTVSAASTKGPSVFPLAPCSRSTSGGTAAL<br>GCLVKDYFPEPVTVSWNSGALTSGVHTFPAVLQSSGLYSLSSVVTVPSSSLGTQT<br>YTCNVNHKPSNTKVDKRVELKTPLGDTTHTCPRCPEPKSCDTPPPCPRCPEPKSC<br>DTPPPCPRCPEPKSCDTPPPCPRCPAPELLGGPSVFLFPPKPKDTLMISRTPEVT<br>CVVVDVSHEDPEVQFKWYVDGVEVHNAKTKLREEQYNSTFRVVSVLTVLHQDWLN<br>GKEYKCKVSNKALPAPIEKTISKAKGQPREPQVYTLPPSREEMTKNQVSLTCLVK<br>GFYPSDIAVEWESNGQPENNYNTTPPMLDSDGSFFLYSKLTVDKSRWQQGNIFSC<br>SVMHEALHNHYTQKSLSLSPGKS<u>GGGGS</u>CDLPQTHSLGSRRTLMLLAQMRRISLF<br>SCLKDRHDFGFPQEEFGNQFQKAETIPVLHEMIQQIFNLFSTKDSSAAWDETLLD<br>KFYTELYQQLNDLEACVIQGVGVTETPLMKEDSILAVRKYFQRITLYLKEKKYSP<br>CAWEVVRAEIMRSFSLSTNLQESLRSKE | 15 |
| αCD20-IgG3-huIFNα alpha helical linker - nucleic acid sequence: | |
| ATGTACTTGGGACTGAACTGTGTAATCATAGTTTTTCTCTTAAAAGGTGTCCAGA<br>GTCAGGTACAACTGCAGCAGCCTGGGGCTGAGCTGGTGAAGCCTGGGGCCTCAGT<br>GAAGATGTCCTGCAAGGCTTCTGGCTACACATTTACCAGTTACAATATGCACTGG<br>GTAAAACAGACACCTGGTCGGGGCCTGGAATGGATTGGAGCTATTTATCCCGGAA<br>ATGGTGATACTTCCTACAATCAGAAGTTCAAAGGCAAGGCCACATTGACTGCAGA<br>CAAATCCTCCAGCACAGCCTACATGCAGCTCAGCAGCCTGACATCTGAGGACTCT<br>GCGGTCTATTACTGTGCAAGATCGACTTACTACGGCGGTGACTGGTACTTCAATG<br>TCTGGGGCGCAGGGACCACGGTCACCGTCTCTGCAGCTAGCACCAAGGGCCCATC<br>GGTCTTCCCCCTGGCGCCCTGCTCCAGGAGCACCTCTGGGGGCACAGCGGCCCTG<br>GGCTGCCTGGTCAAGGACTACTTCCCCGAACCGGTGACGGTGTCGTGGAACTCAG<br>GCGCCCTGACCAGCGGCGTGCACACCTTCCCGGCTGTCCTACAGTCCTCAGGACT<br>CTACTCCCTCAGCAGCGTGGTGACCGTGCCCTCCAGCAGCTTGGGCACCCAGACC<br>TACACCTGCAACGTGAATCACAAGCCCAGCAACACCAAGGTGGACAAGAGAGTTG<br>AGCTCAAAACCCCACTTGGTGACACAACTCACACATGCCCACGGTGCCCAGAGCC<br>CAAATCTTGTGACACACCTCCCCCGTGCCCAAGGTGCCCAGAGCCCAAATCTTGT | 16 |

TABLE 1-continued

Various illustrative constructs used in
certain embodiments described herein.

| Description and Sequence | SEQ ID NO: |
|---|---|
| GACACACCTCCCCCGTGCCCAAGGTGCCCAGAGCCCAAATCTTGTGACACACCTC<br>CCCCGTGCCCAAGGTGCCCAGCACCTGAACTCCTGGGAGGACCGTCAGTCTTCCT<br>CTTCCCCCCAAAACCCAAGGATACCCTTATGATTTCCCGGACCCCTGAGGTCACG<br>TGCGTGGTGGTGGACGTGAGCCACGAAGACCCCGAGGTCCAGTTCAAGTGGTACG<br>TGGACGGCGTGGAGGTGCATAATGCCAAGACAAAGCCGCGGGAGGAGCAGTACAA<br>CAGCACGTTCCGTGTGGTCAGCGTCCTCACCGTCCTGCACCAGGACTGGCTGAAC<br>GGCAAGGAGTACAAGTGCAAGGTCTCCAACAAAGCCCTCCCAGCCCCCATCGAGA<br>AAACCATCTCCAAAGCCAAAGGACAGCCCCGAGAACCACAGGTGTACACCCTGCC<br>CCCATCCCGGGAGGAGATGACCAAGAACCAGGTCAGCCTGACCTGCCTGGTCAAA<br>GGCTTCTACCCCAGCGACATCGCCGTGGAGTGGGAGAGCAATGGGCAGCCGGAGA<br>ACAACTACAACACCACGCCTCCCATGCTGGACTCCGACGGCTCCTTCTTCCTCTA<br>CAGCAAGCTCACCGTGGACAAGAGCAGGTGGCAGCAGGGGAACATCTTCTCATGC<br>TCCGTGATGCATGAGGCTCTGCACAACCACTACACGCAGAAGAGCCTCTCCCTGT<br>CTCCGGGTAAAGCAGAGGCCGCAGCTAAAGAGGCCGCAGCCAAAGCGGGATCCTG<br>TGATCTGCCTCAAACCCACAGCCTGGGTAGCAGGAGGACCTTGATGCTCCTGGCA<br>CAGATGAGGAGAATCTCTCTTTTCTCCTGCTTGAAGGACAGACATGACTTTGGAT<br>TTCCCCAGGAGGAGTTTGGCAACCAGTTCCAAAAGGCTGAAACCATCCCTGTCCT<br>CCATGAGATGATCCAGCAGATCTTCAATCTCTTCAGCACAAAGGACTCATCTGCT<br>GCTTGGGATGAGACCCTCCTAGACAAATTCTACACTGAACTTACCAGCAGCTGA<br>ATGACCTGGAAGCCTGTGTGATACAGGGGGTGGGGGTGACAGAGACTCCCCTGAT<br>GAAGGAGGACTCCATTCTGGCTGTGAGGAAATACTTCCAAAGAATCACTCTCTAT<br>CTGAAAGAGAAGAAATACAGCCCTTGTGCCTGGGAGGTTGTCAGAGCAGAAATCA<br>TGAGATCTTTTTCTTTGTCAACAAACTTGCAAGAAAGTTTAAGAAGTAAGGAA | |

αCD20-IgG3-huIFNα alpha helical linker - amino acid sequence:

| | |
|---|---|
| MYLGLNCVIIVFLLKGVQSQVQLQQPGAELVKPGASVKMSCKASGYTFTSYNMHW<br>VKQTPGRGLEWIGAIYPGNGDTSYNQKFKGKATLTADKSSSTAYMQLSSLTSEDS<br>AVYYCARSTYYGGDWYFNVWGAGTTVTVSAASTKGPSVFPLAPCSRSTSGGTAAL<br>GCLVKDYFPEPVTVSWNSGALTSGVHTFPAVLQSSGLYSLSSVVTVPSSSLGTQT<br>YTCNVNHKPSNTKVDKRVELKTPLGDTTHTCPRCPEPKSCDTPPPCPRCPEPKSC<br>DTPPPCPRCPEPKSCDTPPPCPRCPAPELLGGPSVFLFPPKPKDTLMISRTPEVT<br>CVVVDVSHEDPEVQFKWYVDGVEVHNAKTKLREEQYNSTFRVVSVLTVLHQDWLN<br>GKEYKCKVSNKALPAPIEKTISKAKGQPREPQVYTLPPSREEMTKNQVSLTCLVK<br>GFYPSDIAVEWESNGQPENNYNTTPPMLDSDGSFFLYSKLTVDKSRWQQGNIFSC<br>SVMHEALHNHYTQKSLSLSPGKAEAAAKEAAAKAGSCDLPQTHSLGSRRTLMLLA<br>QMRRISLFSCLKDRHDFGFPQEEFGNQFQKAETIPVLHEMIQQIFNLFSTKDSSA<br>AWDETLLDKFYTELYQQLNDLEACVIQGVGVTETPLMKEDSILAVRKYFQRITLY<br>LKEKKYSPCAWEVVRAEIMRSFSLSTNLQESLRSKE | 17 |

αCD20-IgG1-muIFNα Gly₄Ser linker - nucleic acid sequence

| | |
|---|---|
| ATGTACTTGGGACTGAACTGTGTAATCATAGTTTTTCTCTTAAAAGGTGTCCAGA<br>GTCAGGTACAACTGCAGCAGCCTGGGGCTGAGCTGGTGAAGCCTGGGGCCTCAGT<br>GAAGATGTCCTGCAAGGCTTCTGGCTACACATTTACCAGTTACAATATGCACTGG<br>GTAAAACAGACACCTGGTCGGGGCCTGGAATGGATTGGAGCTATTTATCCCGGAA<br>ATGGTGATACTTCCTACAATCAGAAGTTCAAAGGCAAGGCCACATTGACTGCAGA<br>CAAATCCTCCAGCACAGCCTACATGCAGCTCAGCAGCCTGACATCTGAGGACTCT<br>GCGGTCTATTACTGTGCAAGATCGACTTACTACGGCGGTGACTGGTACTTCAATG<br>TCTGGGGCGCAGGGACCACGGTCACCGTCTCTGCAGCTAGCACCAAGGGCCCATC<br>GGTCTTCCCCCTGGCACCCTCCTCCAAGAGCACCTCTGGGGGCACAGCGGCCCTG<br>GGCTGCCTGGTCAAGGACTACTTCCCCGAACCGGTGACGGTGTCGTGGAACTCAG<br>GCGCCCTGACCAGCGGCGTGCACACCTTCCCGGCTGTCCTACAGTCCTCAGGACT<br>CTACTCCCTCAGCAGCGTGGTGACCGTGCCCTCCAGCAGCTTGGGCACCCAGACC<br>TACATCTGCAACGTGAATCACAAGCCCAGCAACACCAAGGTGGACAAGAAAGTTG<br>AGCCCAAATCTTGTGACAAAACTCACACATGCCCACCGTGCCCAGCACCTGAACT<br>CCTGGGGGGACCGTCAGTCTTCCTCTTCCCCCCAAAACCCAAGGACACCCTCATG<br>ATCTCCCGGACCCCTGAGGTCACATGCGTGGTGGTGGACGTGAGCCACGAAGACC<br>CTGAGGTCAAGTTCAACTGGTACGTGGACGGCGTGGAGGTGCATAATGCCAAGAC<br>AAAGCCGCGGGAGGAGCAGTACAACAGCACGTACCGTGTGGTCAGCGTCCTCACC<br>GTCCTGCACCAGGACTGGCTGAATGGCAAGGAGTACAAGTGCAAGGTCTCCAACA<br>AAGCCCTCCCAGCCCCCATCGAGAAAACCATCTCCAAAGCCAAAGGGCAGCCCCG<br>AGAACCACAGGTGTACACCCTGCCCCCATCCCGGGATGAGCTGACCAAGAACCAG<br>GTCAGCCTGACCTGCCTGGTCAAAGGCTTCTATCCCAGCGACATCGCCGTGGAGT<br>GGGAGAGCAATGGGCAGCCGGAGAACAACTACAAGACCACGCCTCCCGTGCTGGA<br>CTCCGACGGCTCCTTCTTCCTCTACAGCAAGCTCACCGTGGACAAGAGCAGGTGG<br>CAGCAGGGGAACGTCTTCTCATGCTCCGTGATGCATGAGGCTCTGCACAACCACT<br>ACACGCAGAAGAGCCTCTCCCTGTCTCCGGGTAAATCTGGTGGCGGTGGATCCTG<br>TGACCTGCCTCAGACTCATAACCTCAGGAACAAGAGCCTTGCACTCCTGGTA<br>CAAATGAGGAGACTCTCCCCTCTCCTGCCTGAAGGACAGGAAGGACTTTGGAT<br>TCCCGCAGGAGAAGGTGGATGCCCAGCAGATCAAGAAGGCTCAAGCCATCCCTGT<br>CCTGAGTGAGCTGACCCAGCAGATCCTGAACATCTTCACATCAAAGGACTCATCT<br>GCTCTTGGAATGCAACCCTCCTAGACTCATTCTGCAATGACCTCCACCAGCAGC<br>TCAATGACCTGCAAGGTTGTCTGATGCAGCAGGTGGGGGTGCAGGAATTTCCCCT | 18 |

TABLE 1-continued

Various illustrative constructs used in
certain embodiments described herein.

| Description and Sequence | SEQID NO: |
|---|---|
| GACCCAGGAAGATGCCCTGCTGGCTGTGAGGAAATACTTCCACAGGATCACTGTG<br>TACCTGAGAGAGAAGAAACACAGCCCCTGTGCCTGGGAGGTGGTCAGAGCAGAAG<br>TCTGGAGAGCCCTGTCTTCCTCTGCCAATGTGCTGGGAAGACTGAGAGAAGAGAA<br>A | |

αCD20-IgG1-muIFNα Gly₄Ser linker - amino acid sequence:

| | |
|---|---|
| MYLGLNCVIIVFLLKGVQSQVQLQQPGAELVKPGASVKMSCKASGYTFTSYNMHW<br>VKQTPGRGLEWIGAIYPGNGDTSYNQKFKGKATLTADKSSSTAYMQLSSLTSEDS<br>AVYYCARSTYYGGDWYFNVWGAGTTVTVSAASTKGPSVFPLAPSSKSTSGGTAAL<br>GCLVKDYFPEPVTVSWNSGALTSGVHTFPAVLQSSGLYSLSSVVTVPSSSLGTQT<br>YICNVNHKPSNTKVDKKVEPKSCDKTHTCPPCPAPELLGGPSVFLFPPKPKDTLM<br>ISRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKNQ<br>VSLTCLVKGFYPSDIAVEWESNGQPENNYKTTPPVLDSDGSFFLYSKLTVDKSRW<br>QQGNVFSCSVMHEALHNHYTQKSLSLSPGKSGGGGSCDLPQTHNLRNKRALTLLV<br>QMRRLSPLSCLKDRKDFGFPQEKVDAQQIKKAQAIPVLSELTQQILNIFTSKDSS<br>AAWNATLLDSFCNDLHQQLNDLQGCLMQQVGVQEFPLTQEDALLAVRKYFHRITV<br>YLREKKHSPCAWEVVRAEVWRALSSSANVLGRLREEK | 19 |

αCD20-IgG1-muIFNα alpha helical linker - nucleic acid sequence:

| | |
|---|---|
| ATGTACTTGGGACTGAACTGTGTAATCATAGTTTTTCTCTTAAAAGGTGTCCAGA<br>GTCAGGTACAACTGCAGCAGCCTGGGGCTGAGCTGGTGAAGCCTGGGGCCTCAGT<br>GAAGATGTCCTGCAAGGCTTCTGGCTACACATTTACCAGTTACAATATGCACTGG<br>GTAAAACAGACACCTGGTCGGGGCCTGGAATGGATTGGAGCTATTTATCCCGGAA<br>ATGGTGATACTTCCTACAATCAGAAGTTCAAAGGCAAGGCCACATTGACTGCAGA<br>CAAATCCTCCAGCACAGCCTACATGCAGCTCAGCAGCCTGACATCTGAGGACTCT<br>GCGGTCTATTACTGTGCAAGATCGACTTACTACGGCGGTGACTGGTACTTCAATG<br>TCTGGGGCGCAGGGACCACGGTCACCGTCTCTGCAGCTAGCACCAAGGGCCCATC<br>GGTCTTCCCCCTGGCACCCTCCTCAAGAGCACCTCTGGGGGCACAGCGGCCCTG<br>GGCTGCCTGGTCAAGGACTACTTCCCCGAACCGGTGACGGTGTCGTGGAACTCAG<br>GCGCCCTGACCAGCGGCGTGCACACCTTCCCGGCTGTCCTACAGTCCTCAGGACT<br>CTACTCCCTCAGCAGCGTGGTGACCGTGCCCTCCAGCAGCTTGGGCACCCAGACC<br>TACATCTGCAACGTGAATCACAAGCCCAGCAACACCAAGGTGGACAAGAAAGTTG<br>AGCCCAAATCTTGTGACAAAACTCACACATGCCCACCGTGCCCAGCACCTGAACT<br>CCTGGGGGGACCGTCAGTCTTCCTCTTCCCCCCAAAACCCAAGGACACCCTCATG<br>ATCTCCCGGACCCCTGAGGTCACATGCGTGGTGGTGGACGTGAGCCACGAAGACC<br>CTGAGGTCAAGTTCAACTGGTACGTGGACGGCGTGGAGGTGCATAATGCCAAGAC<br>AAAGCCGCGGGAGGAGCAGTACAACAGCACGTACCGGGTGGTCAGCGTCCTCACC<br>GTCCTGCACCAGGACTGGCTGAATGGCAAGGAGTACAAGTGCAAGGTCTCCAACA<br>AAGCCCTCCCAGCCCCCATCGAGAAAACCATCTCCAAAGCCAAAGGGCAGCCCCG<br>AGAACCACAGGTGTACACCCTGCCCCCATCCCGGGATGAGCTGACCAAGAACCAG<br>GTCAGCCTGACCTGCCTGGTCAAAGGCTTCTATCCCAGCGACATCGCCGTGGAGT<br>GGGAGAGCAATGGGCAGCCGGAGAACAACTACAAGACCACGCCTCCCGTGCTGGA<br>CTCCGACGGCTCCTTCTTCCTCTACAGCAAGCTCACCGTGGACAAGAGCAGGTGG<br>CAGCAGGGGAACGTCTTCTCATGCTCCGTGATGCATGAGGCTCTGCACAACCACT<br>ACACGCAGAAGAGCCTCTCCCTGTCTCCGGGTAAAGCAGAGGCCGCAGCTAAAGA<br>GGCCGCAGCCAAAGCGGGATCCTGTGACCTGCCTCAGACTCATAACCTCAGGAAC<br>AAGAGAGCCTTGACACTCCTGGTACAAATGAGGAGACTCTCCCCTCTCTCCTGCC<br>TGAAGGACAGGAAGGACTTTGGATTCCCGCAGGAGAAGGTGGATGCCCAGCAGAT<br>CAAGAAGGCTCAAGCCATCCCTGTCCTGAGTGAGCTGACCCAGCAGATCCTGAAC<br>ATCTTCACATCAAAGGACTCATCTGCTGCTTGGAATGCAACCCTCCTAGACTCAT<br>TCTGCAATGACCTCCACCAGCAGCTCAATGACCTGCAAGGTTGTCTGATGCAGCA<br>GGTGGGGGTGCAGGAATTTCCCCTGACCCAGGAAGATGCCCTGCTGGCTGTGAGG<br>AAATACTTCCACAGGATCACTGTGTACCTGAGAGAGAAGAAACACAGCCCCTGTG<br>CCTGGGAGGTGGTCAGAGCAGAAGTCTGGAGAGCCCTGTCTTCCTCTGCCAATGT<br>GCTGGGAAGACTGAGAGAAGAGAAATGA | 20 |

αCD20-IgG1-muIFNα alpha helical linker - amino acid sequence:

| | |
|---|---|
| MYLGLNCVIIVFLLKGVQSQVQLQQPGAELVKPGASVKMSCKASGYTFTSYNMHW<br>VKQTPGRGLEWIGAIYPGNGDTSYNQKFKGKATLTADKSSSTAYMQLSSLTSEDS<br>AVYYCARSTYYGGDWYFNVWGAGTTVTVSAASTKGPSVFPLAPSSKSTSGGTAAL<br>GCLVKDYFPEPVTVSWNSGALTSGVHTFPAVLQSSGLYSLSSVVTVPSSSLGTQT<br>YICNVNHKPSNTKVDKKVEPKSCDKTHTCPPCPAPELLGGPSVFLFPPKPKDTLM<br>ISRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKNQ<br>VSLTCLVKGFYPSDIAVEWESNGQPENNYKTTPPVLDSDGSFFLYSKLTVDKSRW<br>QQGNVFSCSVMHEALHNHYTQKSLSLSPGKAEAAAKEAAAKAGSCDLPQTHNLRN<br>KRALTLLVQMRRLSPLSCLKDRKDFGFPQEKVDAQQIKKAQAIPVLSELTQQILN<br>IFTSKDSSAAWNATLLDSFCNDLHQQLNDLQGCLMQQVGVQEFPLTQEDALLAVR<br>KYFHRITVYLREKKHSPCAWEVVRAEVWRALSSSANVLGRLREEK | 21 |

TABLE 1-continued

Various illustrative constructs used in
certain embodiments described herein.

| Description and Sequence | SEQID NO: |
|---|---|

αCD20-IgG1-huIFNα Gly₄Ser linker - nucleic acid sequence:

```
ATGTACTTGGGACTGAACTGTGTAATCATAGTTTTTCTCTTAAAAGGTGTCCAGA      22
GTCAGGTACAACTGCAGCAGCCTGGGGCTGAGCTGGTGAAGCCTGGGGCCTCAGT
GAAGATGTCCTGCAAGGCTTCTGGCTACACATTTACCAGTTACAATATGCACTGG
GTAAAACAGACACCTGGTCGGGGCCTGGAATGGATTGGAGCTATTTATCCCGGAA
ATGGTGATACTTCCTACAATCAGAAGTTCAAAGGCAAGGCCACATTGACTGCAGA
CAAATCCTCCAGCACAGCCTACATGCAGCTCAGCAGCCTGACATCTGAGGACTCT
GCGGTCTATTACTGTGCAAGATCGACTTACTACGGCGGTGACTGGTACTTCAATG
TCTGGGGCGCAGGGACCACGGTCACCGTCTCTGCAGCTAGCACCAAGGGCCCATC
GGTCTTCCCCCTGGCACCCTCCTCCAAGAGCACCTCTGGGGGCACAGCGGCCCTG
GGCTGCCTGGTCAAGGACTACTTCCCCGAACCGGTGACGGTGTCGTGGAACTCAG
GCGCCCTGACCAGCGGCGTGCACACCTTCCCGGCTGTCCTACAGTCCTCAGGACT
CTACTCCCTCAGCAGCGTGGTGACCGTGCCCTCCAGCAGCTTGGGCACCCAGACC
TACATCTGCAACGTGAATCACAAGCCCAGCAACACCAAGGTGGACAAGAAAGTTG
AGCCCAAATCTTGTGACAAAACTCACACATGCCCACCGTGCCCAGCACCTGAACT
CCTGGGGGGACCGTCAGTCTTCCTCTTCCCCCCAAAACCCAAGGACACCCTCATG
ATCTCCCGGACCCCTGAGGTCACATGCGTGGTGGTGGACGTGAGCCACGAAGACC
CTGAGGTCAAGTTCAACTGGTACGTGGACGGCGTGGAGGTGCATAATGCCAAGAC
AAAGCCGCGGGAGGAGCAGTACAACAGCACGTACCGTGTGGTCAGCGTCCTCACC
GTCCTGCACCAGGACTGGCTGAATGGCAAGGAGTACAAGTGCAAGGTCTCCAACA
AAGCCCTCCCAGCCCCCATCGAGAAAACCATCTCCAAAGCCAAAGGGCAGCCCCG
AGAACCACAGGTGTACACCCTGCCCCCATCCCGGGATGAGCTGACCAAGAACCAG
GTCAGCCTGACCTGCCTGGTCAAAGGCTTCTATCCCAGCGACATCGCCGTGGAGT
GGGAGAGCAATGGGCAGCCGGAGAACAACTACAAGACCACGCCTCCCGTGCTGGA
CTCCGACGGCTCCTTCTTCCTCTACAGCAAGCTCACCGTGGACAAGAGCAGGTGG
CAGCAGGGGAACGTCTTCTCATGCTCCGTGATGCATGAGGCTCTGCACAACCACT
ACACGCAGAAGAGCCTCTCCCTGTCTCCGGGTAAATCTGGTGGCGGTGGATCCTG
TGATCTGCCTCAAACCCACAGCCTGGGTAGCAGGAGGACCTTGATGCTCCTGGCA
CAGATGAGGAGAATCTCTCTTTTCTCCTGCTTGAAGGACAGACATGACTTTGGAT
TTCCCCAGGAGGAGTTTGGCAACCAGTTCCAAAAGGCTGAAACCATCCCTGTCCT
CCATGAGATGATCCAGCAGATCTTCAATCTCTTCAGCACAAAGGACTCATCTGCT
GCTTGGGATGAGACCCTCCTAGACAAATTCTACACTGAACTCTACCAGCAGCTGA
ATGACCTGGAAGCCTGTGTGATACAGGGGGTGGGGGTGACAGAGACTCCCCTGAT
GAAGGAGGACTCCATTCTGGCTGTGAGGAAATACTTCCAAAGAATCACTCTCTAT
CTGAAAGAGAAGAAATACAGCCCTTGTGCCTGGGAGGTTGTCAGAGCAGAAATCA
TGAGATCTTTTTCTTTGTCAACAAACTTGCAAGAAAGTTTAAGAAGTAAGGAA
```

αCD20-IgG1-huIFNα Gly₄Ser linker - amino acid sequence:

```
MYLGLNCVIIVFLLKGVQSQVQLQQPGAELVKPGASVKMSCKASGYTFTSYNMHW       23
VKQTPGRGLEWIGAIYPGNGDTSYNQKFKGKATLTADKSSSTAYMQLSSLTSEDS
AVYYCARSTYYGGDWYFNVWGAGTTVTVSAASTKGPSVFPLAPSSKSTSGGTAAL
GCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLM
ISRTPEVTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLTVDKSRW
QQGNVFSCSVMHEALHNHYTQKSLSLSPGKSGGGGSCDLPQTHSLGSRRTLMLLA
QMRRISLFSCLKDRHDFGFPQEEFGNQFQKAETIPVLHEMIQQIFNLFSTKDSSA
AWDETLLDKFYTELYQQLNDLEACVIQGVGVTETPLMKEDSILAVRKYFQRITLY
LKEKKYSPCAWEVVRAEIMRSFSLSTNLQESLRSKE
```

αCD20-IgG1-huIFNα alpha helical linker - nucleic acid sequence:

```
ATGTACTTGGGACTGAACTGTGTAATCATAGTTTTTCTCTTAAAAGGTGTCCAGA      24
GTCAGGTACAACTGCAGCAGCCTGGGGCTGAGCTGGTGAAGCCTGGGGCCTCAGT
GAAGATGTCCTGCAAGGCTTCTGGCTACACATTTACCAGTTACAATATGCACTGG
GTAAAACAGACACCTGGTCGGGGCCTGGAATGGATTGGAGCTATTTATCCCGGAA
ATGGTGATACTTCCTACAATCAGAAGTTCAAAGGCAAGGCCACATTGACTGCAGA
CAAATCCTCCAGCACAGCCTACATGCAGCTCAGCAGCCTGACATCTGAGGACTCT
GCGGTCTATTACTGTGCAAGATCGACTTACTACGGCGGTGACTGGTACTTCAATG
TCTGGGGCGCAGGGACCACGGTCACCGTCTCTGCAGCTAGCACCAAGGGCCCATC
GGTCTTCCCCCTGGCACCCTCCTCCAAGAGCACCTCTGGGGGCACAGCGGCCCTG
GGCTGCCTGGTCAAGGACTACTTCCCCGAACCGGTGACGGTGTCGTGGAACTCAG
GCGCCCTGACCAGCGGCGTGCACACCTTCCCGGCTGTCCTACAGTCCTCAGGACT
CTACTCCCTCAGCAGCGTGGTGACCGTGCCCTCCAGCAGCTTGGGCACCCAGACC
TACATCTGCAACGTGAATCACAAGCCCAGCAACACCAAGGTGGACAAGAAAGTTG
AGCCCAAATCTTGTGACAAAACTCACACATGCCCACCGTGCCCAGCACCTGAACT
CCTGGGGGGACCGTCAGTCTTCCTCTTCCCCCCAAAACCCAAGGACACCCTCATG
ATCTCCCGGACCCCTGAGGTCACATGCGTGGTGGTGGACGTGAGCCACGAAGACC
CTGAGGTCAAGTTCAACTGGTACGTGGACGGCGTGGAGGTGCATAATGCCAAGAC
AAAGCCGCGGGAGGAGCAGTACAACAGCACGTACCGTGTGGTCAGCGTCCTCACC
GTCCTGCACCAGGACTGGCTGAATGGCAAGGAGTACAAGTGCAAGGTCTCCAACA
```

TABLE 1-continued

Various illustrative constructs used in
certain embodiments described herein.

| Description and Sequence | SEQID NO: |
|---|---|
| AAGCCCTCCCAGCCCCCATCGAGAAAACCATCTCCAAAGCCAAAGGGCAGCCCCG<br>AGAACCACAGGTGTACACCCTGCCCCCATCCCGGGATGAGCTGACCAAGAACCAG<br>GTCAGCCTGACCTGCCTGGTCAAAGGCTTCTATCCCAGCGACATCGCCGTGGAGT<br>GGGAGAGCAATGGGCAGCCGGAGAACAACTACAAGACCACGCCTCCCGTGCTGGA<br>CTCCGACGGCTCCTTCTTCCTCTACAGCAAGCTCACCGTGGACAAGAGCAGGTGG<br>CAGCAGGGGAACGTCTTCTCATGCTCCGTGATGCATGAGGCTCTGCACAACCACT<br>ACACGCAGAAGAGCCTCTCCCTGTCTCCGGGTAAAGCAGGGCCGCAGCTAAAGA<br>GGCCGCAGCCAAAGCGGGATCCTGTGATCTGCCTCAAACCCACAGCCTGGGTAGC<br>AGGAGGACCTTGATGCTCCTGGCACAGATGAGGAGAATCTCTCTTTTCTCCTGCT<br>TGAAGGACAGACATGACTTTGGATTTCCCCAGGAGGAGTTTGGCAACCAGTTCCA<br>AAAGGCTGAAACCATCCCTGTCCTCCATGAGATGATCCAGCAGATCTTCAATCTC<br>TTCAGCACAAAGGACTCATCTGCTGCTTGGGATGAGACCCTCCTAGACAAATTCT<br>ACACTGAACTCTACCAGCAGCTGAATGACCTGGAAGCCTGTGTGATACAGGGGGT<br>GGGGGTGACAGAGACTCCCCTGATGAAGGAGGACTCCATTCTGGCTGTGAGGAAA<br>TACTTCCAAAGAATCACTCTCTATCTGAAAGAGAAGAAATACAGCCCTTGTGCCT<br>GGGAGGTTGTCAGAGCAGAAATCATGAGATCTTTTTCTTTGTCAACAAACTTGCA<br>AGAAAGTTTAAGAAGTAAGGAATGA | |
| αCD20-IgG1-huIFNα alpha helical linker - amino acid sequence: | |
| MYLGLNCVIIVFLLKGVQSQVQLQQPGAELVKPGASVKMSCKASGYTFTSYNMHW<br>VKQTPGRGLEWIGAIYPGNGDTSYNQKFKGKATLTADKSSSTAYMQLSSLTSEDS<br>AVYYCARSTYYGGDWYFNVWGAGTTVTVSAASTKGPSVFPLAPSSKSTSGGTAAL<br>GCLVKDYFPEPVTVSWNSGALTSGVHTFPAVLQSSGLYSLSSVVTVPSSSLGTQT<br>YICNVNHKPSNTKVDKKVEPKSCDKTHTCPPCPAPELLGGPSVFLFPPKPKDTLM<br>ISRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKNQ<br>VSLTCLVKGFYPSDIAVEWESNGQPENNYKTTPPVLDSDGSFFLYSKLTVDKSRW<br>QQGNVFSCSVMHEALHNHYTQKSLSLSPGKAEAAAKEAAAKAGSCDLPQTHSLGS<br>RRTLMLLAQMRRISLFSCLKDRHDFGFPQEEFGNQFQKAETIPVLHEMIQQIFNL<br>FSTKDSSAAWDETLLDKFYTELYQQLNDLEACVIQGVGVTETPLMKEDSILAVRK<br>YFQRITLYLKEKKYSPCAWEVVRAEIMRSFSLSTNLQESLRSKE | 25 |
| αHer2/neu light chain - nucleic acid sequence: | |
| ATGGGATGGAGCTGGGTAATCCTCTTTCTCCTGTCAGTAACTGCAGGTGTCCACT<br>CCCAGTCTGTGTTGACGCAGCCGCCCTCAGTGTCTGCGGCCCCAGGACAGAAGGT<br>CACCATCTCCTGCTCTGGAAGCAGCTCCAACATTGGGAATAATTATGTATCCTGG<br>TACCAGCAGCTCCCAGGAACAGCCCCCAAACTCCTCATCTATGATCACACCAATC<br>GGCCCTCAGGGGTCCCTGACCGATTCTCTGGCTCCAAGTCTGGCACCTCAGCCTC<br>CCTGGCCATCAGTGGGTTCCGGTCCGAGGATGAGGCTGATTATTACTGTGCCTCC<br>TGGGACTACACCCTCTCGGGCTGGGTGTTCGGAGGAGGGACCAAGGTCACCGTCC<br>TAGGTCGAACTGTGGCTGCACCATCTGTCTTCATCTTCCCGCCATCTGATGAGCA<br>GTTGAAATCTGGAACTGCCTCTGTTGTGTGCCTGCTGAATAACTTCTATCCCAGA<br>GAGGCCAAAGTACAGTGGAAGGTGGATAACGCCCTCCAATCGGGTAACTCCCAGG<br>AGAGTGTCACAGAGCAGGACAGCAAGGACAGCACCTACAGCCTCAGCAGCACCCT<br>GACGCTGAGCAAAGCAGACTACGAGAAACACAAAGTCTACGCCTGCGAAGTCACC<br>CATCAGGGCCTGAGCTCGCCCGTCACAAAGAGCTTCAACAGGGGAGAGTGTTAG | 26 |
| αHer2/neu light chain - Amino acid sequence | |
| MGWSWVILFLLSVTAGVHSQSVLTQPPSVSAAPGQKVTISCSGSSSNIGNNYVSW<br>YQQLPGTAPKLLIYDHTNRPAGVPDRFSGSKSGTSASLAISGFRSEDEADYYCAS<br>WDYTLSGWVFGGGTKVTVLGRTVAAPSVFIFPPSDEQLKSGTASVVCLLNNFYPR<br>EAKVQWKVDNALQSGNSQESVTEQDSKDSTYSLSSTLTLSKADYEKHKVYACEVT<br>HQGLSSPVTKSFNRGEC | 27 |
| αHer2/neu-IgG1-muIFNα Gly$_4$Ser linker - Nucleic acid sequence: | |
| ATGGGATGGAGCTGGGTAATGCATCTTTCTCCTGTCAGTAACTGCGGTGTCCACT<br>CCCAGGTCCAGCTGGTGCAGTCTGGGGCAGAGGTGAAAAAGCCCGGGGAGTCTCT<br>GAAGATCCCTGTAAGGGTTCTGGATACAGCTTTACCAGCTACTGGATCGCCTGG<br>GTGCGCCAGATGCCCGGGAAAGGCCTGGAGTACATGGGGCTCATCTATCCTGGTG<br>ACTCTGACACCAAATACAGCCCGTCCTTCCAAGGCCAGGTCACCATCTCAGTCGA<br>CAAGTCCGTCAGCACTGCCTACTTGCAATGGAGCAGTCTGAAGCCCTCGGACAGC<br>GCCGTGTATTTTTGTGCGAGACATGACGTGGGATATTGCACCGACCGGACTTGCG<br>CAAAGTGGCCTGAATACTTCCAGCATTGGGGCCAGGGCACCCTGGTCACCGTCTC<br>CTCAGCTAGCACCAAGGGCCCATCGGTCTTCCCCCTGGCACCCTCCTCCAAGAGC<br>ACCTCTGGGGGCACAGCGGCCCTGGGCTGCCTGGTCAAGGACTACTTCCCCGAAC<br>CGGTGACGGTGTCGTGGAACTCAGGCGCCCTGACCAGCGGCGTGCACACCTTCCC<br>GGCTGTCCTACAGTCCTCAGGACTCTACTCCCTCAGCAGCGTGGTGACCGTGCCC<br>TCCAGCAGCTTGGGCACCCAGACCTACATCTGCAACGTGAATCACAAGCCCAGCA<br>ACACCAAGGTGGACAAGAAAGTTGAGCCCAAATCTTGTGACAAAACTCACACATG<br>CCCACCGTGCCCAGCACCTGAACTCCTGGGGGGACCGTCAGTCTTCCTCTTCCCC | 28 |

TABLE 1-continued

Various illustrative constructs used in
certain embodiments described herein.

| Description and Sequence | SEQ ID NO: |
|---|---|
| CCAAAACCCAAGGACACCCTCATGATCTCCCGGACCCCTGAGGTCACATGCGTGG<br>TGGTGGACGTGAGCCACGAAGACCCTGAGGTCAAGTTCAACTGGTACGTGGACGG<br>CGTGGAGGTGCATAATGCCAAGACAAAGCCGCGGGAGGAGCAGTACAACAGCACG<br>TACCGTGTGGTCAGCGTCCTCACCGTCCTGCACCAGGACTGGCTGAATGGCAAGG<br>AGTACAAGTGCAAGGTCTCCAACAAAGCCCTCCCAGCCCCCATCGAGAAAACCAT<br>CTCCAAAGCCAAAGGGCAGCCCCGAGAACCACAGGTGTACACCCTGCCCCCATCC<br>CGGGATGAGCTGACCAAGAACCAGGTCAGCCTGACCTGCCTGGTCAAAGGCTTCT<br>ATCCCAGCGACATCGCCGTGGAGTGGGAGAGCAATGGGCAGCCGGAGAACAACTA<br>CAAGACCACGCCTCCCGTGCTGGACTCCGACGGCTCCTTCTTCCTCTACAGCAAG<br>CTCACCGTGGACAAGAGCAGGTGGCAGCAGGGGAACGTCTTCTCATGCTCCGTGA<br>TGCATGAGGCTCTGCACAACCACTACACGCAGAAGAGCCTCTCCCTGTCTCCGGG<br>TAAATCTGGTGGCGGTGGATCCTGTGACCTGCCTCAGACTCATAACCTCAGGAAC<br>AAGAGAGCCTTGACACTCCTGGTACAAATGAGGAGACTCTCCCCTCTCCTGCC<br>TGAAGGACAGGAAGGACTTTGGATTCCCGCAGGAGAAGGTGGATGCCCAGCAGAT<br>CAAGAAGGCTCAAGCCATCCCTGTCCTGAGTGAGCTGACCCAGCAGATCCTGAAC<br>ATCTTCACATCAAAGGACTCATCTGCTGCTTGGAATGCAACCCTCCTAGACTCAT<br>TCTGCAATGACCTCCACCAGCAGCTCAATGACCTGCAAGGTTGTCTGATGCAGCA<br>GGTGGGGGTGCAGGAATTTCCCCTGACCCAGGAAGATGCCCTGCTGGCTGTGAGG<br>AAATACTTCCACAGGATCACTGTGTACCTGAGAGAGAAGAAACACAGCCCCTGTG<br>CCTGGGAGGTGGTCAGAGCAGAAGTCTGGAGAGCCCTGTCTTCCTCTGCCAATGT<br>GCTGGGAAGACTGAGAAGAGAAA | |

αHer2/neu-IgG1mIFNα Gly₄Ser linker amino acid sequence:

| | |
|---|---|
| MGWSWVMHLSPVSNCGVHSQVQLVQSGAEVKKPGESLKISCKGSGYSFTSYWIAW<br>VRQMPGKGLEYMGLIYPGDSDTKYSPSFQGQVTISVDKSVSTAYLQWSSLKPSDS<br>AVYFCARHDVGYCTDRTCAKWPEYFQHWGQGTLVTVSSASTKGPSVFPLAPSSKS<br>TSGGTAALGCLVKDYFPEPVTVSWNSGALTSGVHTFPAVLQSSGLYSLSSVVTVP<br>SSSLGTQTYICNVNHKPSNTKVDKKVEPKSCDKTHTCPPCPAPELLGGPSVFLFP<br>PKPKDTLMISRTPEVTCVVVDVSHEDPEVKFNWYVDGVEVHNAKTKPREEQYNST<br>YRVVSVLTVLHQDWLNGKEYKCKVSNKALPAPIEKTISKAKGQPREPQVYTLPPS<br>RDELTKNQVSLTCLVKGFYPSDIAVEWESNGQPENNYKTTPPVLDSDGSFFLYSK<br>LTVDKSRWQQGNVFSCSVMHEALHNHYTQKSLSLSPGKSGGGGSCDLPQTHNLRN<br>KRALTLLVQMRRLSPLSCLKDRKDFGFPQEKVDAQQIKKAQAIPVLSELTQQILN<br>IFTSKDSSAAWNATLLDSFCNDLHQQLNDLQGCLMQQVGVQEFPLTQEDALLAVR<br>KYFHRITVYLREKKHSPCAWEVVRAEVWRALSSSANVLGRLREEK | 29 |

αHer2/neu-IgG1-muIFNa alpha helix linker - Nucleic acid sequence:

| | |
|---|---|
| ATGGGATGGAGCTGGGTAATGCATCTTTCTCCTGTCAGTAACTGCGGTGTCCACT<br>CCCAGGTCCAGCTGGTGCAGTCTGGGGCAGAGGTGAAAAAGCCCGGGGAGTCTCT<br>GAAGATCTCCTGTAAGGGTTCTGGATACAGCTTTACCAGCTACTGGATCGCCTGG<br>GTGCGCCAGATGCCCGGGAAAGGCCTGGAGTACATGGGGCTCATCTATCCTGGTG<br>ACTCTGACACCAAATACAGCCCGTCCTTCCAAGGCCAGGTCACCATCTCAGTCGA<br>CAAGTCCGTCAGCACTGCCTACTTGCAATGGAGCAGTCTGAAGCCCTCGGACAGC<br>GCCGTGTATTTTTGTGCGAGACATGACGTGGGATATTGCACCGACCGGACTTGCG<br>CAAAGTGGCCTGAATACTTCCAGCATTGGGGCCAGGGCACCCTGGTCACCGTCTC<br>CTCAGCTAGCACCAAGGGCCCATCGGTCTTCCCCCTGGCACCCTCCTCCAAGAGC<br>ACCTCTGGGGGCACAGCGGCCCTGGGCTGCCTGGTCAAGGACTACTTCCCCGAAC<br>CGGTGACGGTGTCGTGGAACTCAGGCGCCCTGACCAGCGGCGTGCACACCTTCCC<br>GGCTGTCCTACAGTCCTCAGGACTCTACTCCCTCAGCAGCGTGGTGACCGTGCCC<br>TCCAGCAGCTTGGGCACCCAGACCTACATCTGCAACGTGAATCACAAGCCCAGCA<br>ACACCAAGGTGGACAAGAAAGTTGAGCCCAAATCTTGTGACAAAACTCACACATG<br>CCCACCGTGCCCAGCACCTGAACTCCTGGGGGGACCGTCAGTCTTCCTCTTCCCC<br>CCAAAACCCAAGGACACCCTCATGATCTCCCGGACCCCTGAGGTCACATGCGTGG<br>TGGTGGACGTGAGCCACGAAGACCCTGAGGTCAAGTTCAACTGGTACGTGGACGG<br>CGTGGAGGTGCATAATGCCAAGACAAAGCCGCGGGAGGAGCAGTACAACAGCACG<br>TACCGTGTGGTCAGCGTCCTCACCGTCCTGCACCAGGACTGGCTGAATGGCAAGG<br>AGTACAAGTGCAAGGTCTCCAACAAAGCCCTCCCAGCCCCCATCGAGAAAACCAT<br>CTCCAAAGCCAAAGGGCAGCCCCGAGAACCACAGGTGTACACCCTGCCCCCATCC<br>CGGGATGAGCTGACCAAGAACCAGGTCAGCCTGACCTGCCTGGTCAAAGGCTTCT<br>ATCCCAGCGACATCGCCGTGGAGTGGGAGAGCAATGGGCAGCCGGAGAACAACTA<br>CAAGACCACGCCTCCCGTGCTGGACTCCGACGGCTCCTTCTTCCTCTACAGCAAG<br>CTCACCGTGGACAAGAGCAGGTGGCAGCAGGGGAACGTCTTCTCATGCTCCGTGA<br>TGCATGAGGCTCTGCACAACCACTACACGCAGAAGAGCCTCTCCCTGTCTCCGGG<br>TAAAGCAGAGGCCGCAGCTAAAGAGGCCGCAGCCAAAGCGGGATCCTGTGACCTG<br>CCTCAGACTCATAACCTCAGGAACAAGAGAGCCTTGACACTCCTGGTACAAATGA<br>GGAGACTCTCCCCTCTCTCCTGCCTGAAGGACAGGAAGGACTTTGGATTCCCGCA<br>GGAGAAGGTGGATGCCCAGCAGATCAAGAAGGCTCAAGCCATCCCTGTCCTGAGT<br>GAGCTGACCCAGCAGATCCTGAACATCTTCACATCAAAGGACTCATCTGCTGCTT<br>GGAATGCAACCCTCCTAGACTCATTCTGCAATGACCTCCACCAGCAGCTCAATGA<br>CCTGCAAGGTTGTCTGATGCAGCAGGTGGGGGTGCAGGAATTTCCCCTGACCCAG<br>GAAGATGCCCTGCTGGCTGTGAGGAAATACTTCCACAGGATCACTGTGTACCTGA | 30 |

TABLE 1-continued

Various illustrative constructs used in
certain embodiments described herein.

| Description and Sequence | SEQID NO: |
|---|---|

GAGAGAAGAAACACAGCCCCTGTGCCTGGGAGGTGGTCAGAGCAGAAGTCTGGAG
AGCCCTGTCTTCCTCTGCCAATGTGCTGGGAAGACTGAGAGAAGAGAAA

αHer2/neu-IgG1mIFNa alpha helix linker amino acid sequence:

| | |
|---|---|
| MGWSWVMHLSPVSNCGVHSQVQLVQSGAEVKKPGESLKISCKGSGYSFTSYWIAW<br>VRQMPGKGLEYMGLIYPGDSDTKYSPSFQGQVTISVDKSVSTAYLQWSSLKPSDS<br>AVYFCARHDVGYCTDRTCAKWPEYFQHWGQGTLVTVSSASTKGPSVFPLAPSSKS<br>TSGGTAALGCLVKDYFPEPVTVSWNSGALTSGVHTFPAVLQSSGLYSLSSVVTVP<br>SSSLGTQTYICNVNHKPSNTKVDKKVEPKSCDKTHTCPPCPAPELLGGPSVFLFP<br>PKPKDTLMISRTPEVTCVVVDVSHEDPEVKFNWYVDGVEVHNAKTKPREEQYNST<br>YRVVSVLTVLHQDWLNGKEYKCKVSNKALPAPIEKTISKAKGQPREPQVYTLPPS<br>RDELTKNQVSLTCLVKGFYPSDIAVEWESNGQPENNYKTTPPVLDSDGSFFLYSK<br>LTVDKSRWQQGNVFSCSVMHEALHNHYTQKSLSLSPGK<u>AEAAAKEAAAKA</u>GSCDL<br>PQTHNLRNKRALTLLVQMRRLSPLSCLKDRKDFGFPQEKVDAQQIKKAQAIPVLS<br>ELTQQILNIFTSKDSSAAWNATLLDSFCNDLHQQLNDLQGCLMQQVGVQEFPLTQ<br>EDALLAVRKYFHRITVYLREKKHSPCAWEVVRAEVWRALSSSANVLGRLREEK | 31 |

αHer2/neu-IgG2hIFNα Gly₄Ser linker nuclei acid sequence:

| | |
|---|---|
| ATGGGATGGAGCTGGGTAATGCATCTTTCTCCTGTCAGTAACTGCGGTGTCCACT<br>CCCAGGTCCAGCTGGTGCAGTCTGGGGCAGAGGTGAAAAAGCCCGGGGAGTCTCT<br>GAAGATCTCCTGTAAGGGTTCTGGATACAGCTTTACCAGCTACTGGATCGCCTGG<br>GTGCGCCAGATGCCCGGGAAAGGCCTGGAGTACATGGGGCTCATCTATCCTGGTG<br>ACTCTGACACCAAATACAGCCCGTCCTTCCAAGGCCAGGTCACCATCTCAGTCGA<br>CAAGTCCGTCAGCACTGCCTACTTGCAATGGAGCAGTCTGAAGCCCTCGGACAGC<br>GCCGTGTATTTTTGTGCGAGACATGACGTGGGATATTGCACCGACCGGACTTGCG<br>CAAAGTGGCCTGAATACTTCCAGCATTGGGGCCAGGGCACCCTGGTCACCGTCTC<br>CTCAGCTAGCACCAAGGGCCCATCGGTCTTCCCCCTGGCACCCTCCTCCAAGAGC<br>ACCTCTGGGGGCACAGCGGCCCTGGGCTGCCTGGTCAAGGACTACTTCCCCGAAC<br>CGGTGACGGTGTCGTGGAACTCAGGCGCCCTGACCAGCGGCGTGCACACCTTCCC<br>GGCTGTCCTACAGTCCTCAGGACTCTACTCCCTCAGCAGCGTGGTGACCGTGCCC<br>TCCAGCAGCTTGGGCACCCAGACCTACATCTGCAACGTGAATCACAAGCCCAGCA<br>ACACCAAGGTGGACAAGAAAGTTGAGCCCAAATCTTGTGACAAAACTCACACATG<br>CCCACCGTGCCCAGCACCTGAACTCCTGGGGGGACCGTCAGTCTTCCTCTTCCCC<br>CCAAAACCCAAGGACACCCTCATGATCTCCCGGACCCCTGAGGTCACATGCGTGG<br>TGGTGGACGTGAGCCACGAAGACCCTGAGGTCAAGTTCAACTGGTACGTGGACGG<br>CGTGGAGGTGCATAATGCCAAGACAAAGCCGCGGGAGGAGCAGTACAACAGCACG<br>TACCGTGTGGTCAGCGTCCTCACCGTCCTGCACCAGGACTGGCTGAATGGCAAGG<br>AGTACAAGTGCAAGGTCTCCAACAAAGCCCTCCCAGCCCCCATCGAGAAAACCAT<br>CTCCAAAGCCAAAGGGCAGCCCCGAGAACCACAGGTGTACACCCTGCCCCCATCC<br>CGGGATGAGCTGACCAAGAACCAGGTCAGCCTGACCTGCCTGGTCAAAGGCTTCT<br>ATCCCAGCGACATCGCCGTGGAGTGGGAGAGCAATGGGCAGCCGGAGAACAACTA<br>CAAGACCACGCCTCCCGTGCTGGACTCCGACGGCTCCTTCTTCCTCTACAGCAAG<br>CTCACCGTGGACAAGAGCAGGTGGCAGCAGGGGAACGTCTTCTCATGCTCCGTGA<br>TGCATGAGGCTCTGCACAACCACTACACGCAGAAGAGCCTCTCCCTGTCTCCGGG<br>TAAATCTGGTGGCGGTGGATCCTGTGATCTGCCTCAAACCCACAGCCTGGGTAGC<br>AGGAGGACCTTGATGCTCCTGGCACAGATGAGGAGAATCTCTCTTTTCTCCTGCT<br>TGAAGGACAGACATGACTTTGGATTTCCCCAGGAGGAGTTTGGCAACCAGTTCCA<br>AAAGGCTGAAACCATCCCTGTCCTCCATGAGATGATCCAGCAGATCTTCAATCTC<br>TTCAGCACAAAGGACTCATCTGCTGCTTGGGATGAGACCCTCCTAGACAAATTCT<br>ACACTGAACTCTACCAGCAGCTGAATGACCTGGAAGCCTGTGTGATACAGGGGGT<br>GGGGGTGACAGAGACTCCCCTGATGAAGGAGGACTCCATTCTGGCTGTGAGGAAA<br>TACTTCCAAAGAATCACTCTCTATCTGAAAGAGAAGAAATACAGCCCTTGTGCCT<br>GGGAGGTTGTCAGAGCAGAAATCATGAGATCTTTTCTTTGTCAACAAACTTGCA<br>AGAAAGTTTAAGAAGTAAGGAA | 32 |

αHer2/neu-IgG2hIFNα Gly₄Ser linker amino acid sequence

| | |
|---|---|
| MGWSWVMHLSPVSNCGVHSQVQLVQSGAEVKKPGESLKISCKGSGYSFTSYWIAW<br>VRQMPGKGLEYMGLIYPGDSDTKYSPSFQGQVTISVDKSVSTAYLQWSSLKPSDS<br>AVYFCARHDVGYCTDRTCAKWPEYFQHWGQGTLVTVSSASTKGPSVFPLAPSSKS<br>TSGGTAALGCLVKDYFPEPVTVSWNSGALTSGVHTFPAVLQSSGLYSLSSVVTVP<br>SSSLGTQTYICNVNHKPSNTKVDKKVEPKSCDKTHTCPPCPAPELLGGPSVFLFP<br>PKPKDTLMISRTPEVTCVVVDVSHEDPEVKFNWYVDGVEVHNAKTKPREEQYNST<br>YRVVSVLTVLHQDWLNGKEYKCKVSNKALPAPIEKTISKAKGQPREPQVYTLPPS<br>RDELTKNQVSLTCLVKGFYPSDIAVEWESNGQPENNYKTTPPVLDSDGSFFLYSK<br>LTVDKSRWQQGNVFSCSVMHEALHNHYTQKSLSLSPGKS<u>GGGGS</u>CDLPQTHSLGS<br>RRTLMLLAQMRRISLFSCLKDRHDFGFPQEEFGNQFQKAETIPVLHEMIQQIFNL<br>FSTKDSSAAWDETLLDKFYTELYQQLNDLEACVIQGVGVTETPLMKEDSILAVRK<br>YFQRITLYLKEKKYSPCAWEVVRAEIMRSFSLSTNLQESLRSKE | 33 |

TABLE 1-continued

Various illustrative constructs used in
certain embodiments described herein.

| Description and Sequence | SEQID NO: |
|---|---|
| αHer2/neu-IgG1-huIFNα alpha helix linker - nucleic acid sequence: | |
| ATGGGATGGAGCTGGGTAATGCATCTTTCTCCTGTCAGTAACTGCGGTGTCCACT<br>CCCAGGTCCAGCTGGTGCAGTCTGGGGCAGAGGTGAAAAAGCCCGGGGAGTCTCT<br>GAAGATCTCCTGTAAGGGTTCTGGATACAGCTTTACCAGCTACTGGATCGCCTGG<br>GTGCGCCAGATGCCCGGGAAAGGCCTGGAGTACATGGGGCTCATCTATCCTGGTG<br>ACTCTGACACCAAATACAGCCCGTCCTTCCAAGGCCAGGTCACCATCTCAGTCGA<br>CAAGTCCGTCAGCACTGCCTACTTGCAATGGAGCAGTCTGAAGCCCTCGGACAGC<br>GCCGTGTATTTTTGTGCGAGACATGACGTGGGATATTGCACCGACCGGACTTGCG<br>CAAAGTGGCCTGAATACTTCCAGCATTGGGGCCAGGGCACCCTGGTCACCGTCTC<br>CTCAGCTAGCACCAAGGGCCCATCGGTCTTCCCCCTGGCACCCTCCTCCAAGAGC<br>ACCTCTGGGGGCACAGCGGCCCTGGGCTGCCTGGTCAAGGACTACTTCCCCGAAC<br>CGGTGACGGTGTCGTGGAACTCAGGCGCCCTGACCAGCGGCGTGCACACCTTCCC<br>GGCTGTCCTACAGTCCTCAGGACTCTACTCCCTCAGCAGCGTGGTGACCGTGCCC<br>TCCAGCAGCTTGGGCACCCAGACCTACATCTGCAACGTGAATCACAAGCCCAGCA<br>ACACCAAGGTGGACAAGAAAGTTGAGCCCAAATCTTGTGACAAAACTCACACATG<br>CCCACCGTGCCCAGCACCTGAACTCCTGGGGGGACCGTCAGTCTTCCTCTTCCCC<br>CCAAAACCCAAGGACACCCTCATGATCTCCCGGACCCCTGAGGTCACATGCGTGG<br>TGGTGGACGTGAGCCACGAAGACCCTGAGGTCAAGTTCAACTGGTACGTGGACGG<br>CGTGGAGGTGCATAATGCCAAGACAAAGCCGCGGGAGGAGCAGTACAACAGCACG<br>TACCGGGTGGTCAGCGTCCTCACCGTCCTGCACCAGGACTGGCTGAATGGCAAGG<br>AGTACAAGTGCAAGGTCTCCAACAAAGCCCTCCCAGCCCCCATCGAGAAAACCAT<br>CTCCAAAGCCAAAGGGCAGCCCCGAGAACCACAGGTGTACACCCTGCCCCCATCC<br>CGGGATGAGCTGACCAAGAACCAGGTCAGCCTGACCTGCCTGGTCAAAGGCTTCT<br>ATCCCAGCGACATCGCCGTGGAGTGGGAGAGCAATGGGCAGCCGGAGAACAACTA<br>CAAGACCACGCCTCCCGTGCTGGACTCCGACGGCTCCTTCTTCCTCTACAGCAAG<br>CTCACCGTGGACAAGAGCAGGTGGCAGCAGGGGAACGTCTTCTCATGCTCCGTGA<br>TGCATGAGGCTCTGCACAACCACTACACGCAGAAGAGCCTCTCCCTGTCTCCGGG<br>TAAAGCAGAGGCCGCAGCTAAAGAGGCCGCAGCCAAAGCGGGATCCTGTGATCTG<br>CCTCAAACCCACAGCCTGGGTAGCAGGAGGACCTTGATGCTCCTGGCACAGATGA<br>GGAGAATCTCTCTTTTCTCCTGCTTGAAGGACAGACATGACTTTGGATTTCCCCA<br>GGAGGAGTTTGGCAACCAGTTCCAAAAGGCTGAAACCATCCCTGTCCTCCATGAG<br>ATGATCCAGCAGATCTTCAATCTCTTCAGCACAAAGGACTCATCTGCTGCTTGGG<br>ATGAGACCCTCCTAGACAAATTCTACACTGAACTCTACCAGCAGCTGAATGACCT<br>GGAAGCCTGTGTGATACAGGGGGTGGGGGTGACAGAGACTCCCCTGATGAAGGAG<br>GACTCCATTCTGGCTGTGAGGAAATACTTCCAAAGAATCACTCTCTATCTGAAAG<br>AGAAGAAATACAGCCCTTGTGCCTGGGAGGTTGTCAGAGCAGAAATCATGAGATC<br>TTTTTCTTTGTCAACAAACTTGCAAGAAAGTTTAAGAAGTAAGGAATGA | 34 |
| αHer2/neu-IgG1hIFNα alpha helix linker amino acid sequence: | |
| MGWSWVMHLSPVSNCGVHSQVQLVQSGAEVKKPGESLKISCKGSGYSFTSYWIAW<br>VRQMPGKGLEYMGLIYPGDSDTKYSPSFQGQVTISVDKSVSTAYLQWSSLKPSDS<br>AVYFCARHDVGYCTDRTCAKWPEYFQHWGQGTLVTVSSASTKGPSVFPLAPSSKS<br>TSGGTAALGCLVKDYFPEPVTVSWNSGALTSGVHTFPAVLQSSGLYSLSSVVTVP<br>SSSLGTQTYICNVNHKPSNTKVDKKVEPKSCDKTHTCPPCPAPELLGGPSVFLFP<br>PKPKDTLMISRTPEVTCVVVDVSHEDPEVKFNWYVDGVEVHNAKTKPREEQYNST<br>YRVVSVLTVLHQDWLNGKEYKCKVSNKALPAPIEKTISKAKGQPREPQVYTLPPS<br>RDELTKNQVSLTCLVKGFYPSDIAVEWESNGQPENNYKTTPPVLDSDGSFFLYSK<br>LTVDKSRWQQGNVFSCSVMHEALHNHYTQKSLSLSPGKAEAAAKEAAAKAGSCDL<br>PQTHSLGSRRTLMLLAQMRRISLFSCLKDRHDFGFPQEEFGNQFQKAETIPVLHE<br>MIQQIFNLFSTKDSSAAWDETLLDKFYTELYQQLNDLEACVIQGVGVTETPLMKE<br>DSILAVRKYFQRITLYLKEKKYSPCAWEVVRAEIMRSFSLSTNLQESLRSKE | 35 |
| Nucleotide sequence of anti-CD20 IgG1 GS1 human IFN beta: | |
| ATGTACTTGGGACTGAACTGTGTAATCATAGTTTTTCTCTTAAAAGGTGTCCAGA<br>GTCAGGTACAACTGCAGCAGCCTGGGGCTGAGCTGGTGAAGCCTGGGGCCTCAGT<br>GAAGATGTCCTGCAAGGCTTCTGGCTACACATTTACCAGTTACAATATGCACTGG<br>GTAAAACAGACACCTGGTCGGGCCTGGAATGGATTGGAGCTATTTATCCCGGAA<br>ATGGTGATACTTCCTACAATCAGAAGTTCAAAGGCAAGGCCACATTGACTGCAGA<br>CAAATCCTCCAGCACAGCCTACATGCAGCTCAGCAGCCTGACATCTGAGGACTCT<br>GCGGTCTATTACTGTGCAAGATCGACTTACTACGGCGGTGACTGGTACTTCAATG<br>TCTGGGGCGCAGGGACCACGGTCACCGTCTCTGCAGCTAGCACCAAGGGCCCATC<br>GGTCTTCCCCCTGGCACCCTCCTCCAAGAGCACCTCTGGGGGCACAGCGGCCCTG<br>GGCTGCCTGGTCAAGGACTACTTCCCCGAACCGGTGACGGTGTCGTGGAACTCAG<br>GCGCCCTGACCAGCGGCGTGCACACCTTCCCGGCTGTCCTACAGTCCTCAGGACT<br>CTACTCCCTCAGCAGCGTGGTGACCGTGCCCTCCAGCAGCTTGGGCACCCAGACC<br>TACATCTGCAACGTGAATCACAAGCCCAGCAACACCAAGGTGGACAAGAAAGTTG<br>AGCCCAAATCTTGTGACAAAACTCACACATGCCCACCGTGCCCAGCACCTGAACT<br>CCTGGGGGACCGTCAGTCTTCCTCTTCCCCCCAAAACCCAAGGACACCCTCATG<br>ATCTCCCGGACCCCTGAGGTCACATGCGTGGTGGTGGACGTGAGCCACGAAGACC<br>CTGAGGTCAAGTTCAACTGGTACGTGGACGGCGTGGAGGTGCATAATGCCAAGAC<br>AAAGCCGCGGGAGGAGCAGTACAACAGCACGTACCGGGTGGTCAGCGTCCTCACC | 36 |

TABLE 1-continued

Various illustrative constructs used in
certain embodiments described herein.

| Description and Sequence | SEQID NO: |
|---|---|
| GTCCTGCACCAGGACTGGCTGAATGGCAAGGAGTACAAGTGCAAGGTCTCCAACA<br>AAGCCCTCCCAGCCCCCATCGAGAAAACCATCTCCAAAGCCAAAGGGCAGCCCCG<br>AGAACCACAGGTGTACACCCTGCCCCCATCCCGGGATGAGCTGACCAAGAACCAG<br>GTCAGCCTGACCTGCCTGGTCAAAGGCTTCTATCCCAGCGACATCGCCGTGGAGT<br>GGGAGAGCAATGGGCAGCCGGAGAACAACTACAAGACCACGCCTCCCGTGCTGGA<br>CTCCGACGGCTCCTTCTTCCTCTACAGCAAGCTCACCGTGGACAAGAGCAGGTGG<br>CAGCAGGGGAACGTCTTCTCATGCTCCGTGATGCATGAGGCTCTGCACAACCACT<br>ACACGCAGAAGAGCCTCTCCCTGTCTCCGGGTAAATCTGGTGGCGGTGGATCCAT<br>GAGCTACAACTTGCTTGGATTCCTACAAAGAAGCAGCAATTTTCAGTGTCAGAAG<br>CTCCTGTGGCAATTGAATGGGAGGCTTGAATACTGCCTCAAGGACAGGATGAACT<br>TTGACATCCCTGAGGAGATTAAGCAGCTGCAGCAGTTCCAGAAGGAGGACGCCGC<br>ATTGACCATCTATGAGATGCTCCAGAACATCTTTGCTATTTTCAGACAAGATTCA<br>TCTAGCACTGGCTGGAATGAGACTATTGTTGAGAACCTCCTGGCTAATGTCTATC<br>ATCAGATAAACCATCTGAAGACAGTCCTGGAAGAAAAACTGGAGAAAGAAGATTT<br>CACCAGGGGAAAACTCATGAGCAGTCTGCACCTGAAAAGATATTATGGGAGGATT<br>CTGCATTACCTGAAGGCCAAGGAGTACAGTCACTGTGCCTGGACCATAGTCAGAG<br>TGGAAATCCTAAGGAACTTTTACTTCATTAACAGACTTACAGGTTACCTCCGAAA<br>CTGA | |
| Amino acid sequence of anti-CD20 IgG1 GS1 human IFN beta: | |
| MYLGLNCVIIVFLLKGVQSQVQLQQPGAELVKPGASVKMSCKASGYTFTSYNMHW<br>VKQTPGRGLEWIGAIYPGNGDTSYNQKFKGKATLTADKSSSTAYMQLSSLTSEDS<br>AVYYCARSTYYGGDWYFNVWGAGTTVTVSAASTKGPSVFPLAPSSKSTSGGTAAL<br>GCLVKDYFPEPVTVSWNSGALTSGVHTFPAVLQSSGLYSLSSVVTVPSSSLGTQT<br>YICNVNHKPSNTKVDKKVEPKSCDKTHTCPPCPAPELLGGPSVFLFPPKPKDTLM<br>ISRTPEVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELTKNQ<br>VSLTCLVKGFYPSDIAVEWESNGQPENNYKTTPPVLDSDGSFFLYSKLTVDKSRW<br>QQGNVFSCSVMHEALHNHYTQKSLSLSPGKSGGGGSMSYNLLGFLQRSSNFQCQK<br>LLWQLNGRLEYCLKDRMNFDIPEEIKQLQQFQKEDAALTIYEMLQNIFAIFRQDS<br>SSTGWNETIVENLLANVYHQINHLKTVLEEKLEKEDFTRGKLMSSLHLKRYYGRI<br>LHYLKAKEYSHCAWTIVRVEILRNFYFINRLTGYLRN | 37 |
| Nucleotide sequence of anti-CD20 IgG3 GS1 human IFN beta: | |
| ATGTACTTGGGACTGAACTGTGTAATCATAGTTTTTCTCTTAAAAGGTGTCCAGA<br>GTCAGGTACAACTGCAGCAGCCTGGGGCTGAGCTGGTGAAGCCTGGGGCCTCAGT<br>GAAGATGTCCTGCAAGGCTTCTGGCTACACATTTACCAGTTACAATATGCACTGG<br>GTAAAACAGACACCTGGTCGGGGCCTGGAATGGATTGGAGCTATTTATCCCGGAA<br>ATGGTGATACTTCCTACAATCAGAAGTTCAAAGGCAAGGCCACATTGACTGCAGA<br>CAAATCCTCCAGCACAGCCTACATGCAGCTCAGCAGCCTGACATCTGAGGACTCT<br>GCGGTCTATTACTGTGCAAGATCGACTTACTACGGCGGTGACTGGTACTTCAATG<br>TCTGGGGCGCAGGGACCACGGTCACCGTCTCTGCAGCTAGCACCAAGGGCCCATC<br>GGTCTTCCCCCTGGCGCCCTGCTCCAGGAGCACCTCTGGGGGCACAGCGGCCCTG<br>GGCTGCCTGGTCAAGGACTACTTCCCCGAACCGGTGACGGTGTCGTGGAACTCAG<br>GCGCCCTGACCAGCGGCGTGCACACCTTCCCGGCTGTCCTACAGTCCTCAGGACT<br>CTACTCCCTCAGCAGCGTGGTGACCGTGCCCTCCAGCAGCTTGGGCACCCAGACC<br>TACACCTGCAACGTGAATCACAAGCCCAGCAACACCAAGGTGGACAAGAGAGTTG<br>AGCTCAAAACCCCACTTGGTGACACAACTCACACATGCCCACGGTGCCCAGAGCC<br>CAAATCTTGTGACACACCTCCCCCGTGCCCAAGGTGCCCAGAGCCCAAATCTTGT<br>GACACACCTCCCCCGTGCCCAAGGTGCCCAGAGCCCAAATCTTGTGACACACCTC<br>CCCCGTGCCCAAGGTGCCCAGCACCTGAACTCCTGGGAGGACCGTCAGTCTTCCT<br>CTTCCCCCCAAAACCCAAGGATACCCTTATGATTTCCCGGACCCCTGAGGTCACG<br>TGCGTGGTGGTGGACGTGAGCCACGAAGACCCCGAGGTCCAGTTCAAGTGGTACG<br>TGGACGGCGTGGAGGTGCATAATGCCAAGACAAAGCTGCGGGAGGAGCAGTACAA<br>CAGCACGTTCCGTGTGGTCAGCGTCCTCACCGTCCTGCACCAGGACTGGCTGAAC<br>GGCAAGGAGTACAAGTGCAAGGTCTCCAACAAAGCCCTCCCAGCCCCCATCGAGA<br>AAACCATCTCCAAAGCCAAGGACAGCCCCGAGAACCACAGGTGTACACCCTGCC<br>CCCATCCCGGGAGGAGATGACCAAGAACCAGGTCAGCCTGACCTGCCTGGTCAAA<br>GGCTTCTACCCCAGCGACATCGCCGTGGAGTGGGAGAGCAATGGGCAGCCGGAGA<br>ACAACTACAACACCACGCCTCCCATGCTGGACTCCGACGGCTCCTTCTTCCTCTA<br>CAGCAAGCTCACCGTGGACAAGAGCAGGTGGCAGCAGGGGAACATCTTCTCATGC<br>TCCGTGATGCATGAGGCTCTGCACAACCACTACACGCAGAAGAGCCTCTCCCTGT<br>CTCCGGGTAAATCTGGTGGCGGTGGATCCATGAGCTACAACTTGCTTGGATTCCT<br>ACAAAGAAGCAGCAATTTTCAGTGTCAGAAGCTCCTGTGGCAATTGAATGGGAGG<br>CTTGAATACTGCCTCAAGGACAGGATGAACTTTGACATCCCTGAGGAGATTAAGC<br>AGCTGCAGCAGTTCCAGAAGGAGGACGCCGCATTGACCATCTATGAGATGCTCCA<br>GAACATCTTTGCTATTTTCAGACAAGATTCATCTAGCACTGGCTGGAATGAGACT<br>ATTGTTGAGAACCTCCTGGCTAATGTCTATCATCAGATAAACCATCTGAAGACAG<br>TCCTGGAAGAAAAACTGGAGAAAGAAGATTTCACCAGGGGAAAACTCATGAGCAG<br>TCTGCACCTGAAAAGATATTATGGGAGGATTCTGCATTACCTGAAGGCCAAGGAG<br>TACAGTCACTGTGCCTGGACCATAGTCAGAGTGGAAATCCTAAGGAACTTTTACT<br>TCATTAACAGACTTACAGGTTACCTCCGAAACTGA | 38 |

TABLE 1-continued

Various illustrative constructs used in
certain embodiments described herein.

| Description and Sequence | SEQ ID NO: |
|---|---|
| Amino acid sequence of anti-CD20 IgG3 GS1 human IFN beta: | |

MYLGLNCVIIVFLLKGVQSQVQLQQPGAELVKPGASVKMSCKASGYTFTSYNMHW
VKQTPGRGLEWIGAIYPGNGDTSYNQKFKGKATLTADKSSSTAYMQLSSLTSEDS
AVYYCARSTYYGGDWYFNVWGAGTTVTVSAASTKGPSVFPLAPCSRSTSGGTAAL
GCLVKDYFPEPVTVSWNSGALTSGVHTFPAVLQSSGLYSLSSVVTVPSSSLGTQT
YTCNVNHKPSNTKVDKRVELKTPLGDTTHTCPRCPEPKSCDTPPPCPRCPEPKSC
DTPPPCPRCPEPKSCDTPPPCPRCPAPELLGGPSVFLFPPKPKDTLMISRTPEVT
CVVVDVSHEDPEVQFKWYVDGVEVHNAKTKLREEQYNSTFRVVSVLTVLHQDWLN
GKEYKCKVSNKALPAPIEKTISKAKGQPREPQVYTLPPSREEMTKNQVSLTCLVK
GFYPSDIAVEWESNGQPENNYNTTPPMLDSDGSFFLYSKLTVDKSRWQQGNIFSC
SVMHEALHNHYTQKSLSLSPGKS<u>GGGGS</u>MSYNLLGFLQRSSNFQCQKLLWQLNGR
LEYCLKDRMNFDIPEEIKQLQQFQKEDAALTIYEMLQNIFAIFRQDSSSTGWNET
IVENLLANVYHQINHLKTVLEEKLEKEDFTRGKLMSSLHLKRYYGRILHYLKAKE
YSHCAWTIVRVEILRNFYFINRLTGYLRN

39

| Nucleotide sequence of anti-CD20 IgG3 GS1 murine IFN beta: | |

ATGTACTTGGGACTGAACTGTGTAATCATAGTTTTTCTCTTAAAAGGTGTCCAGA
GTCAGGTACAACTGCAGCAGCCTGGGGCTGAGCTGGTGAAGCCTGGGGCCTCAGT
GAAGATGTCCTGCAAGGCTTCTGGCTACACATTTACCAGTTACAATATGCACTGG
GTAAAACAGACACCTGGTCGGGGCCTGGAATGGATTGGAGCTATTTATCCCGGAA
ATGGTGATACTTCCTACAATCAGAAGTTCAAAGGCAAGGCCACATTGACTGCAGA
CAAATCCTCCAGCACAGCCTACATGCAGCTCAGCAGCCTGACATCTGAGGACTCT
GCGGTCTATTACTGTGCAAGATCGACTTACTACGGCGGTGACTGGTACTTCAATG
TCTGGGGCGCAGGGACCACGGTCACCGTCTCTGCAGCTAGCACCAAGGGCCCATC
GGTCTTCCCCCTGGCGCCCTGCTCCAGGAGCACCTCTGGGGGCACAGCGGCCCTG
GGCTGCCTGGTCAAGGACTACTTCCCCGAACCGGTGACGGTGTCGTGGAACTCAG
GCGCCCTGACCAGCGGCGTGCACACCTTCCCGGCTGTCCTACAGTCCTCAGGACT
CTACTCCCTCAGCAGCGTGGTGACCGTGCCCTCCAGCAGCTTGGGCACCCAGACC
TACACCTGCAACGTGAATCACAAGCCCAGCAACACCAAGGTGGACAAGAGAGTTG
AGCTCAAAACCCCACTTGGTGACACAACTCACACATGCCCACGGTGCCCAGAGCC
CAAATCTTGTGACACACCTCCCCCGTGCCCAAGGTGCCCAGAGCCCAAATCTTGT
GACACACCTCCCCCGTGCCCAAGGTGCCCAGAGCCCAAATCTTGTGACACACCTC
CCCCGTGCCCAAGGTGCCCAGCACCTGAACTCCTGGGAGGACCGTCAGTCTTCCT
CTTCCCCCCAAAACCCAAGGATACCCTTATGATTTCCCGGACCCCTGAGGTCACG
TGCGTGGTGGTGGACGTGAGCCACGAAGACCCCGAGGTCCAGTTCAAGTGGTACG
TGGACGGCGTGGAGGTGCATAATGCCAAGACAAAGCTGCGGGAGGAGCAGTACAA
CAGCACGTTCCGTGTGGTCAGCGTCCTCACCGTCCTGCACCAGGACTGGCTGAAC
GGCAAGGAGTACAAGTGCAAGGTCTCCAACAAAGCCCTCCCAGCCCCCATCGAGA
AAACCATCTCCAAAGCCAAAGGACAGCCCCGAGAACCACAGGTGTACACCCTGCC
CCCATCCCGGGAGGAGATGACCAAGAACCAGGTCAGCCTGACCTGCCTGGTCAAA
GGCTTCTACCCCAGCGACATCGCCGTGGAGTGGGAGAGCAATGGGCAGCCGGAGA
ACAACTACAACACCACGCCTCCCATGCTGGACTCCGACGGCTCCTTCTTCCTCTA
CAGCAAGCTCACCGTGGACAAGAGCAGGTGGCAGCAGGGGAACATCTTCTCATGC
TCCGTGATGCATGAGGCTCTGCACAACCACTACACGCAGAAGAGCCTCTCCCTGT
CTCCGGGTAAATCTGGTGGCGGTGGATCCATCAACTATAAGCAGCTCCAGCTCCA
AGAAAGGACGAACATTCGGAAATGTCAGGAGCTCCTGGAGCAGCTGAATGGAAAG
ATCAACCTCACCTACAGGGCGGACTTTAAGATCCCTATGGAGATGACGGAGAAGA
TGCAGAAGAGTTACACTGCCTTTGCCATCCAAGAGATGCTCCAGAATGTCTTTCT
TGTCTTCAGAAACAATTTCTCCAGCACTGGGTGGAATGAGACTATTGTTGTACGT
CTCCTGGATGAACTCCACCAGCAGACAGTGTTTCTGAAGACAGTACTAGAGGAAA
AGCAAGAGGAAAGATTGACGTGGGAGATGTCCTCAACTGCTCTCCACTTGAAGAG
CTATTACTGGAGGGTGCAAAGGTACCTTAAACTCATGAAGTACAACAGCTACGCC
TGGATGGTGGTCCGAGCAGAGATCTTCAGGAACTTTCTCATCATTCGAAGACTTA
CCAGAAACTTCCAAAACTGA

40

| Amino acid sequence of anti-CD20 IgG3 GS1 murine IFN beta: | |

MYLGLNCVIIVFLLKGVQSQVQLQQPGAELVKPGASVKMSCKASGYTFTSYNMHW
VKQTPGRGLEWIGAIYPGNGDTSYNQKFKGKATLTADKSSSTAYMQLSSLTSEDS
AVYYCARSTYYGGDWYFNVWGAGTTVTVSAASTKGPSVFPLAPCSRSTSGGTAAL
GCLVKDYFPEPVTVSWNSGALTSGVHTFPAVLQSSGLYSLSSVVTVPSSSLGTQT
YTCNVNHKPSNTKVDKRVELKTPLGDTTHTCPRCPEPKSCDTPPPCPRCPEPKSC
DTPPPCPRCPEPKSCDTPPPCPRCPAPELLGGPSVFLFPPKPKDTLMISRTPEVT
CVVVDVSHEDPEVQFKWYVDGVEVHNAKTKLREEQYNSTFRVVSVLTVLHQDWLN
GKEYKCKVSNKALPAPIEKTISKAKGQPREPQVYTLPPSREEMTKNQVSLTCLVK
GFYPSDIAVEWESNGQPENNYNTTPPMLDSDGSFFLYSKLTVDKSRWQQGNIFSC
SVMHEALHNHYTQKSLSLSPGKS<u>GGGGS</u>INYKQLQLQERTNIRKCQELLEQLNGK
INLTYRADFKIPMEMTEKMQKSYTAFAIQEMLQNVFLVFRNNFSSTGWNETIVVR
LLDELHQQTVFLKTVLEEKQEERLTWEMSSTALHLKSYYWRVQRYLKLMKYNSYA
WMVVRAEIFRNFLIIRRLTRNFQN

41

TABLE 1-continued

Various illustrative constructs used in
certain embodiments described herein.

| Description and Sequence | SEQID NO: |
|---|---|
| Anti-HER2/neu IgG1 G/S hIFN alpha - nucleotide sequence: | |
| ATGGAATGCAGCTGGGTAATGCTCTTTCTCCTGTCAGTAACTGCAGGTGTCCACT<br>CCGAGGTTCAGCTGGTGGAGTCTGGCGGTGGCCTGGTGCAGCCAGGGGGCTCACT<br>CCGTTTGTCCTGTGCAGCTTCTGGCTTCAACATTAAAGACACCTATATACACTGG<br>GTGCGTCAGGCCCCGGGTAAGGGCCTGGAATGGGTTGCAAGGATTTATCCTACGA<br>ATGGTTATACTAGATATGCCGATAGCGTCAAGGGCCGTTTCACTATAAGCGCAGA<br>CACATCCAAAAACACAGCCTACCTGCAGATGAACAGCCTGCGTGCTGAGGACACT<br>GCCGTCTATTATTGTTCTAGATGGGGAGGGGACGGCTTCTATGCTATGGACTACT<br>GGGGTCAAGGAACCCTGGTCACCGTCTCCTCGGCTAGCACCAAGGGCCCATCGGT<br>CTTCCCCCTGGCACCCTCCTCCAAGAGCACCTCTGGGGGCACAGCGGCCCTGGGC<br>TGCCTGGTCAAGGACTACTTCCCCGAACCGGTGACGGTGTCGTGGAACTCAGGCG<br>CCCTGACCAGCGGCGTGCACACCTTCCCGGCTGTCCTACAGTCCTCAGGACTCTA<br>CTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGC<br>CCAAATCTTGTGACAAAACTCACACATGCCCACCGTGCCCAGCACCTGAACTCCT<br>GGGGGGACCGTCAGTCTTCCTCTTCCCCCCAAAACCCAAGGACACCCTCATGATC<br>TCCCGGACCCCTGAGGTCACATGCGTGGTGGTGGACGTGAGCCACGAAGACCCTG<br>AGGTCAAGTTCAACTGGTACGTGGACGGCGTGGAGGTGCATAATGCCAAGACAAA<br>GCCGCGGGAGGAGCAGTACAACAGCACGTACCGGGTGGTCAGCGTCCTCACCGTC<br>CTGCACCAGGACTGGCTGAATGGCAAGGAGTACAAGTGCAAGGTCTCCAACAAAG<br>CCCTCCCAGCCCCCATCGAGAAAACCATCTCCAAAGCCAAAGGGCAGCCCCGAGA<br>ACCACAGGTGTACACCCTGCCCCCATCCCGGGATGAGCTGACCAAGAACCAGGTC<br>AGCCTGACCTGCCTGGTCAAAGGCTTCTATCCCAGCGACATCGCCGTGGAGTGGG<br>AGAGCAATGGGCAGCCGGAGAACAACTACAAGACCACGCCTCCCGTGCTGGACTC<br>CGACGGCTCCTTCTTCCTCTACAGCAAGCTCACCGTGGACAAGAGCAGGTGGCAG<br>CAGGGGAACGTCTTCTCATGCTCCGTGATGCATGAGGCTCTGCACAACCACTACA<br>CGCAGAAGAGCCTCTCCCTGTCTCCGGGTAAATCTGGTGGCGGTGGATCCTGTGA<br>TCTGCCTCAAACCCACAGCCTGGGTAGCAGGAGGACCTTGATGCTCCTGGCACAG<br>ATGAGGAGAATCTCTCTTTTCTCCTGCTTAAGGACAGACATGACTTTGGATTTC<br>CCCAGGAGGAGTTTGGCAACCAGTTCCAAAAGGCTGAAACCATCCCTGTCCTCCA<br>TGAGATGATCCAGCAGATCTTCAATCTCTTCAGCACAAAGGACTCATCTGCTGCT<br>TGGGATGAGACCCTCCTAGACAAATTCTACACTGAACTCTACCAGCAGCTGAATG<br>ACCTGGAAGCCTGTGTGATACAGGGGGTGGGGGTGACAGAGACTCCCCTGATGAA<br>GGAGGACTCCATTCTGGCTGTGAGGAAATACTTCCAAAGAATCACTCTCTATCTG<br>AAAGAGAAGAAATACAGCCCTTGTGCCTGGGAGGTTGTCAGAGCAGAAATCATGA<br>GATCTTTTTCTTTGTCAACAAACTTGCAAGAAAGTTTAAGAAGTAAGGAATGA | 42 |
| Anti-HER2/neu IgG1 G/S huIFN alpha amino acid sequence: | |
| MECSWVMLFLLSVTAGVHSEVQLVESGGGLVQPGGSLRLSCAASGFNIKDTYIHW<br>VRQAPGKGLEWVARIYPTNGYTRYADSVKGRFTISADTSKNTAYLQMNSLRAEDT<br>AVYYCSRWGGDGFYAMDYWGQGTLVTVSSASTKGPSVFPLAPSSKSTSGGTAALG<br>CLVKDYFPEPVTVSWNSGALTSGVHTFPAVLQSSGLYSLSSVVTVPSSSLGTQTY<br>ICNVNHKPSNTKVDKKVEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLTV<br>LHQDWLNGKEYKCKVSNKALPAPIEKTISKAKGQPREPQVYTLPPSRDELTKNQV<br>SLTCLVKGFYPSDIAVEWESNGQPENNYKTTPPVLDSDGSFFLYSKLTVDKSRWQ<br>QGNVFSCSVMHEALHNHYTQKSLSLSPGKSGGGGSCDLPQTHSLGSRRTLMLLAQ<br>MRRISLFSCLKDRHDFGFPQEEFGNQFQKAETIPVLHEMIQQIFNLFSTKDSSAA<br>WDETLLDKFYTELYQQLNDLEACVIQGVGVTETPLMKEDSILAVRKYFQRITLYL<br>KEKKYSPCAWEVVRAEIMRSFSLSTNLQESLRSKE | 43 |
| Anti-HER/neu IgG1 G/S huIFN Beta nucleotide sequence: | |
| ATGGAATGCAGCTGGGTAATGCTCTTTCTCCTGTCAGTAACTGCAGGTGTCCACT<br>CCGAGGTTCAGCTGGTGGAGTCTGGCGGTGGCCTGGTGCAGCCAGGGGGCTCACT<br>CCGTTTGTCCTGTGCAGCTTCTGGCTTCAACATTAAAGACACCTATATACACTGG<br>GTGCGTCAGGCCCCGGGTAAGGGCCTGGAATGGGTTGCAAGGATTTATCCTACGA<br>ATGGTTATACTAGATATGCCGATAGCGTCAAGGGCCGTTTCACTATAAGCGCAGA<br>CACATCCAAAAACACAGCCTACCTGCAGATGAACAGCCTGCGTGCTGAGGACACT<br>GCCGTCTATTATTGTTCTAGATGGGGAGGGGACGGCTTCTATGCTATGGACTACT<br>GGGGTCAAGGAACCCTGGTCACCGTCTCCTCGGCTAGCACCAAGGGCCCATCGGT<br>CTTCCCCCTGGCACCCTCCTCCAAGAGCACCTCTGGGGGCACAGCGGCCCTGGGC<br>TGCCTGGTCAAGGACTACTTCCCCGAACCGGTGACGGTGTCGTGGAACTCAGGCG<br>CCCTGACCAGCGGCGTGCACACCTTCCCGGCTGTCCTACAGTCCTCAGGACTCTA<br>CTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGC<br>CCAAATCTTGTGACAAAACTCACACATGCCCACCGTGCCCAGCACCTGAACTCCT<br>GGGGGGACCGTCAGTCTTCCTCTTCCCCCCAAAACCCAAGGACACCCTCATGATC<br>TCCCGGACCCCTGAGGTCACATGCGTGGTGGTGGACGTGAGCCACGAAGACCCTG<br>AGGTCAAGTTCAACTGGTACGTGGACGGCGTGGAGGTGCATAATGCCAAGACAAA<br>GCCGCGGGAGGAGCAGTACAACAGCACGTACCGGGTGGTCAGCGTCCTCACCGTC<br>CTGCACCAGGACTGGCTGAATGGCAAGGAGTACAAGTGCAAGGTCTCCAACAAAG | 44 |

TABLE 1-continued

Various illustrative constructs used in
certain embodiments described herein.

| Description and Sequence | SEQ ID NO: |
|---|---|
| CCCTCCCAGCCCCCATCGAGAAAACCATCTCCAAAGCCAAAGGGCAGCCCCGAGA<br>ACCACAGGTGTACACCCTGCCCCCATCCCGGGATGAGCTGACCAAGAACCAGGTC<br>AGCCTGACCTGCCTGGTCAAAGGCTTCTATCCCAGCGACATCGCCGTGGAGTGGG<br>AGAGCAATGGGCAGCCGGAGAACAACTACAAGACCACGCCTCCCGTGCTGGACTC<br>CGACGGCTCCTTCTTCCTCTACAGCAAGCTCACCGTGGACAAGAGCAGGTGGCAG<br>CAGGGGAACGTCTTCTCATGCTCCGTGATGCATGAGGCTCTGCACAACCACTACA<br>CGCAGAAGAGCCTCTCCCTGTCTCCGGGTAAATCTGGTGGCGGTGGATCCATGAG<br>CTACAACTTGCTTGGATTCCTACAAAGAAGCAGCAATTTTCAGTGTCAGAAGCTC<br>CTGTGGCAATTGAATGGGAGGCTTGAATACTGCCTCAAGGACAGGATGAACTTTG<br>ACATCCCTGAGGAGATTAAGCAGCTGCAGCAGTTCCAGAAGGAGGACGCCGCATT<br>GACCATCTATGAGATGCTCCAGAACATCTTTGCTATTTTCAGACAAGATTCATCT<br>AGCACTGGCTGGAATGAGACTATTGTTGAGAACCTCCTGGCTAATGTCTATCATC<br>AGATAAACCATCTGAAGACAGTCCTGGAAGAAAACTGGAGAAAGAAGATTTCAC<br>CAGGGGAAAACTCATGAGCAGTCTGCACCTGAAAAGATATTATGGGAGGATTCTG<br>CATTACCTGAAGGCCAAGGAGTACAGTCACTGTGCCTGGACCATAGTCAGAGTGG<br>AAATCCTAAGGAACTTTTACTTCATTAACAGACTTACAGGTTACCTCCGAAACTG<br>A | |

Anti-HER/neu IgG1 G/S hIFN Beta amino acid sequence:

| MECSWVMLFLLSVTAGVHSEVQLVESGGGLVQPGGSLRLSCAASGFNIKDTYIHW<br>VRQAPGKGLEWVARIYPTNGYTRYADSVKGRFTISADTSKNTAYLQMNSLRAEDT<br>AVYYCSRWGGDGFYAMDYWGQGTLVTVSSASTKGPSVFPLAPSSKSTSGGTAALG<br>CLVKDYFPEPVTVSWNSGALTSGVHTFPAVLQSSGLYSLSSVVTVPSSSLGTQTY<br>ICNVNHKPSNTKVDKKVEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLTV<br>LHQDWLNGKEYKCKVSNKALPAPIEKTISKAKGQPREPQVYTLPPSRDELTKNQV<br>SLTCLVKGFYPSDIAVEWESNGQPENNYKTTPPVLDSDGSFFLYSKLTVDKSRWQ<br>QGNVFSCSVMHEALHNHYTQKSLSLSPGKSGGGGSMSYNLLGFLQRSSNFQCQKL<br>LWQLNGRLEYCLKDRMNFDIPEEIKQLQQFQKEDAALTIYEMLQNIFAIFRQDSS<br>STGWNETIVENLLANVYHQINHLKTVLEEKLEKEDFTRGKLMSSLHLKRYYGRIL<br>HYLKAKEYSHCAWTIVRVEILRNFYFINRLTGYLRN | 45 |

Anti-her2/neu IgG1 alpha helical huIFN alpha nucleic acid sequence:

| ATGGAATGCAGCTGGGTAATGCTCTTTCTCCTGTCAGTAACTGCAGGTGTCCACT<br>CCGAGGTTCAGCTGGTGGAGTCTGGCGGTGGCCTGGTGCAGCCAGGGGGCTCACT<br>CCGTTTGTCCTGTGCAGCTTCTGGCTTCAACATTAAAGACACCTATATACACTGG<br>GTGCGTCAGGCCCCGGGTAAGGGCCTGGAATGGGTTGCAAGGATTTATCCTACGA<br>ATGGTTATACTAGATATGCCGATAGCGTCAAGGGCCGTTTCACTATAAGCGCAGA<br>CACATCCAAAAACACAGCCTACCTGCAGATGAACAGCCTGCGTGCTGAGGACACT<br>GCCGTCTATTATTGTTCTAGATGGGGAGGGGACGGCTTCTATGCTATGGACTACT<br>GGGGTCAAGGAACCCTGGTCACCGTCTCCTCGGCTAGCACCAAGGGCCCATCGGT<br>CTTCCCCCTGGCACCCTCCTCCAAGAGCACCTCTGGGGGCACAGCGGCCCTGGGC<br>TGCCTGGTCAAGGACTACTTCCCCGAACCGGTGACGGTGTCGTGGAACTCAGGCG<br>CCCTGACCAGCGGCGTGCACACCTTCCCGGCTGTCCTACAGTCCTCAGGACTCTA<br>CTCCCTCAGCAGCGTGGTGACCGTGCCCTCCAGCAGCTTGGGCACCCAGACCTAC<br>ATCTGCAACGTGAATCACAAGCCCAGCAACACCAAGGTGGACAAGAAAGTTGAGC<br>CCAAATCTTGTGACAAAACTCACACATGCCCACCGTGCCCAGCACCTGAACTCCT<br>GGGGGGACCGTCAGTCTTCCTCTTCCCCCCAAAACCCAAGGACACCCTCATGATC<br>TCCCGGACCCCTGAGGTCACATGCGTGGTGGTGGACGTGAGCCACGAAGACCCTG<br>AGGTCAAGTTCAACTGGTACGTGGACGGCGTGGAGGTGCATAATGCCAAGACAAA<br>GCCGCGGGAGGAGCAGTACAACAGCACGTACCGGGTGGTCAGCGTCCTCACCGTC<br>CTGCACCAGGACTGGCTGAATGGCAAGGAGTACAAGTGCAAGGTCTCCAACAAAG<br>CCCTCCCAGCCCCCATCGAGAAAACCATCTCCAAAGCCAAAGGGCAGCCCCGAGA<br>ACCACAGGTGTACACCCTGCCCCCATCCCGGGATGAGCTGACCAAGAACCAGGTC<br>AGCCTGACCTGCCTGGTCAAAGGCTTCTATCCCAGCGACATCGCCGTGGAGTGGG<br>AGAGCAATGGGCAGCCGGAGAACAACTACAAGACCACGCCTCCCGTGCTGGACTC<br>CGACGGCTCCTTCTTCCTCTACAGCAAGCTCACCGTGGACAAGAGCAGGTGGCAG<br>CAGGGGAACGTCTTCTCATGCTCCGTGATGCATGAGGCTCTGCACAACCACTACA<br>CGCAGAAGAGCCTCTCCCTGTCTCCGGGTAAAGCAGAGGCCGCAGCTAAAGAGGC<br>CGCAGCCAAAGCGGGATCCTGTGATCTGCCTCAAACCCACAGCCTGGGTAGCAGG<br>AGGACCTTGATGCTCCTGGCACAGATGAGGAGAATCTCTCTTTTCTCCTGCTTGA<br>AGGACAGACATGACTTTGGATTTCCCCAGGAGGAGTTTGGCAACCAGTTCCAAAA<br>GGCTGAAACCATCCCTGTCCTCCATGAGATGATCCAGCAGATCTTCAATCTCTTC<br>AGCACAAAGGACTCATCTGCTGCTTGGGATGAGACCCTCCTAGACAAATTCTACA<br>CTGAACTCTACCAGCAGCTGAATGACCTGGAAGCCTGTGTGATACAGGGGGTGGG<br>GGTGACAGAGACTCCCCTGATGAAGGAGGACTCCATTCTGGCTGTGAGGAAATAC<br>TTCCAAAGAATCACTCTCTATCTGAAAGAGAAGAAATACAGCCCTTGTGCCTGGG<br>AGGTTGTCAGAGCAGAAATCATGAGATCTTTTCTTTGTCAACAAACTTGCAAGA<br>AAGTTTAAGAAGTAAGGAATGA | 46 |

TABLE 1-continued

Various illustrative constructs used in certain embodiments described herein.

| Description and Sequence | SEQ ID NO: |
|---|---|
| Anti-her2/neu IgG1 alpha helical huIFN alpha amino acid sequence: | |
| MECSWVMLFLLSVTAGVHSEVQLVESGGGLVQPGGSLRLSCAASGFNIKDTYIHW<br>VRQAPGKGLEWVARIYPTNGYTRYADSVKGRFTISADTSKNTAYLQMNSLRAEDT<br>AVYYCSRWGGDGFYAMDYWGQGTLVTVSSASTKGPSVFPLAPSSKSTSGGTAALG<br>CLVKDYFPEPVTVSWNSGALTSGVHTFPAVLQSSGLYSLSSVVTVPSSSLGTQTY<br>ICNVNHKPSNTKVDKKVEPKSCDKTHTCPPCPAPELLGGPSVFLFPPKPKDTLMI<br>SRTPEVTCVVVDVSHEDPEVKFNWYVDGVEVHNAKTKPREEQYNSTYRVVSVLTV<br>LHQDWLNGKEYKCKVSNKALPAPIEKTISKAKGQPREPQVYTLPPSRDELTKNQV<br>SLTCLVKGFYPSDIAVEWESNGQPENNYKTTPPVLDSDGSFFLYSKLTVDKSRWQ<br>QGNVFSCSVMHEALHNHYTQKSLSLSPGKAEAAAKEAAAKAGSCDLPQTHSLGSR<br>RTLMLLAQMRRISLFSCLKDRHDFGFPQEEFGNQFQKAETIPVLHEMIQQIFNLF<br>STKDSSAAWDETLLDKFYTELYQQLNDLEACVIQGVGVTETPLMKEDSILAVRKY<br>FQRITLYLKEKKYSPCAWEVVRAEIMRSFSLSTNLQESLRSKE | 47 |
| Anti-HER2/neu Light chain - nucleic acid sequence: | |
| ATGGAATGGAGCTGTGTCATGCTCTTTCTCCTGTCAGTAACTGCAGGTGTCCACT<br>CCGACATCCAGATGACCCAGTCCCCGAGCTCCCTGTCCGCCTCTGTGGGCGATAG<br>GGTCACCATCACCTGCCGTGCCAGTCAGGATGTGAATACTGCTGTAGCCTGGTAT<br>CAACAGAAACCAGGAAAAGCTCCGAAACTACTGATTTACTCGGCATCCTTCCTCT<br>ACTCTGGAGTCCCTTCTCGCTTCTCTGGATCCAGATCTGGGACGGATTTCACTCT<br>GACCATCAGCAGTCTGCAGCCGGAAGACTTCGCAACTTATTACTGTCAGCAACAT<br>TATACTACTCCTCCCACGTTCGGACAGGGTACCAAGGTGGAGATCAAACGAACTG<br>TGGCTGCACCATCTGTCTTCATCTTCCCGCCATCTGATGAGCAGTTGAAATCTGG<br>AACTGCCTCTGTTGTGTGCCTGCTGAATAACTTCTATCCCAGAGAGGCCAAAGTA<br>CAGTGGAAGGTGGATAACGCCCTCCAATCGGGTAACTCCCAGGAGAGTGTCACAG<br>AGCAGGACAGCAAGGACAGCACCTACAGCCTCAGCAGCACCCTGACGCTGAGCAA<br>AGCAGACTACGAGAAACACAAAGTCTACGCCTGCGAAGTCACCCATCAGGGCCTG<br>AGCTCGCCCGTCACAAAGAGCTTCAACAGGGGAGAGTGTTAG | 48 |
| Anti-HER2/neu Light chain - amino acid sequence: | |
| MEWSCVMLFLLSVTAGVHSDIQMTQSPSSLSASVGDRVTITCRASQDVNTAVAWY<br>QQKPGKAPKLLIYSASFLYSGVPSRFSGSRSGTDFTLTISSLQPEDFATYYCQQH<br>YTTPPTFGQGTKVEIKRTVAAPSVFIFPPSDEQLKSGTASVVCLLNNFYPREAKV<br>QWKVDNALQSGNSQESVTEQDSKDSTYSLSSTLTLSKADYEKHKVYACEVTHQGL<br>SSPVTKSFNRGEC | 49 |

While the constructs in this Table are shown with particular targeting moieties, particular linkers, and particular interferons, in certain embodiments other targeting moieties, linkers, and interferons can be substituted therefore as described herein.

A) Targeting Moieties.

In various embodiments, the targeting moiety is a molecule that specifically or preferentially binds a marker expressed by (e.g., on the surface of) or associated with the target cell(s). While essentially any cell can be targeted, certain preferred cells include those associated with a pathology characterized by hyperproliferation of a cell (i.e., a hyperproliferative disorder). Illustrative hyperproliferative disorders include, but are not limited to psoriasis, neutrophilia, polycythemia, thrombocytosis, and cancer.

Hyperproliferative disorders characterized as cancer include but are not limited to solid tumors, such as cancers of the breast, respiratory tract, brain, reproductive organs, digestive tract, urinary tract, eye, liver, skin, head and neck, thyroid, parathyroid and their distant metastases. These disorders also include lymphomas, sarcomas, and leukemias. Examples of breast cancer include, but are not limited to invasive ductal carcinoma, invasive lobular carcinoma, ductal carcinoma in situ, and lobular carcinoma in situ. Examples of cancers of the respiratory tract include, but are not limited to small-cell and non-small-cell lung carcinoma, as well as bronchial adenoma and pleuropulmonary blastoma. Examples of brain cancers include, but are not limited to brain stem and hypophtalmic glioma, cerebellar and cerebral astrocytoma, medulloblastoma, ependymoma, as well as neuroectodermal and pineal tumor. Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus. Tumors of the digestive tract include, but are not limited to anal, colon, colorectal, esophageal, gallbladder, gastric, pancreatic, rectal, small-intestine, and salivary gland cancers. Tumors of the urinary tract include, but are not limited to bladder, penile, kidney, renal pelvis, ureter, and urethral cancers. Eye cancers include, but are not limited to intraocular melanoma and retinoblastoma. Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma. Skin cancers include, but are not limited to squamous cell carcinoma, Kaposi's sarcoma, malignant melanoma, Merkel cell skin cancer, and non-melanoma skin cancer. Head-and-neck cancers include, but are not limited to laryngeal/hypopharyngeal/nasopharyngeal/oropharyngeal cancer, and lip and oral cavity cancer. Lymphomas include, but are not limited to AIDS-related lymphoma, non-Hodgkin's lymphoma, cutaneous T-cell lymphoma, Hodgkin's disease, and lymphoma of the central nervous system. Sarcomas include, but are not limited to sarcoma of the soft tissue, osteosarcoma, malignant fibrous histiocytoma, lymphosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

In certain embodiments, the targeting moiety is a moiety that binds a cancer marker (e.g., a tumor associated antigen). A wide variety of cancer markers are known to those of skill in the art. The markers need not be unique to cancer cells, but can also be effective where the expression of the marker is elevated in a cancer cell (as compared to normal healthy cells) or where the marker is not present at comparable levels in surrounding tissues (especially where the chimeric moiety is delivered locally).

Illustrative cancer markers include, for example, the tumor marker recognized by the ND4 monoclonal antibody. This marker is found on poorly differentiated colorectal cancer, as well as gastrointestinal neuroendocrine tumors (see, e.g., Tobi et al. (1998) *Cancer Detection and Prevention*, 22(2): 147-152). Other important targets for cancer immunotherapy are membrane bound complement regulatory glycoprotein: CD46, CD55 and CD59, which have been found to be expressed on most tumor cells in vivo and in vitro. Human mucins (e.g. MUC1) are known tumor markers as are gp100, tyrosinase, and MAGE, which are found in melanoma. Wild-type Wilms' tumor gene WT1 is expressed at high levels not only in most of acute myelocytic, acute lymphocytic, and chronic myelocytic leukemia, but also in various types of solid tumors including lung cancer.

Acute lymphocytic leukemia has been characterized by the TAAs HLA-Dr, CD1, CD2, CD5, CD7, CD19, and CD20. Acute myelogenous leukemia has been characterized by the TAAs HLA-Dr, CD7, CD13, CD14, CD15, CD33, and CD34. Breast cancer has been characterized by the markers EGFR, HER2, MUC1, Tag-72. Various carcinomas have been characterized by the markers MUC1, TAG-72, and CEA. Chronic lymphocytic leukemia has been characterized by the markers CD3, CD19, CD20, CD21, CD25, and HLA-DR. Hairy cell leukemia has been characterized by the markers CD19, CD20, CD21, CD25. Hodgkin's disease has been characterized by the Leu-M1 marker. Various melanomas have been characterized by the HMB 45 marker. Non-hodgkins lymphomas have been characterized by the CD20, CD19, and Ia marker. And various prostate cancers have been characterized by the PSMA and SE10 markers.

In addition, many kinds of tumor cells display unusual antigens that are either inappropriate for the cell type and/or its environment, or are only normally present during the organisms' development (e.g. fetal antigens). Examples of such antigens include the glycosphingolipid GD2, a disialoganglioside that is normally only expressed at a significant level on the outer surface membranes of neuronal cells, where its exposure to the immune system is limited by the blood-brain barrier. GD2 is expressed on the surfaces of a wide range of tumor cells including neuroblastoma, medulloblastomas, astrocytomas, melanomas, small-cell lung cancer, osteosarcomas and other soft tissue sarcomas. GD2 is thus a convenient tumor-specific target for immunotherapies.

Other kinds of tumor cells display cell surface receptors that are rare or absent on the surfaces of healthy cells, and which are responsible for activating cellular signaling pathways that cause the unregulated growth and division of the tumor cell. Examples include (ErbB2) HER2/neu, a constitutively active cell surface receptor that is produced at abnormally high levels on the surface of breast cancer tumor cells.

Other useful targets include, but are not limited to CD20, CD52, CD33, epidermal growth factor receptor and the like.

An illustrative, but not limiting list of suitable tumor markers is provided in Table 2. Antibodies to these and other cancer markers are known to those of skill in the art and can be obtained commercially or readily produced, e.g. using phage-display technology.

TABLE 2

Illustrative cancer markers and associated references, all of which are incorporated herein by reference for the purpose of identifying the referenced tumor markers.

| Marker | Reference |
|---|---|
| 5 alpha reductase | Délos et al. (1998) *Int J Cancer*, 75: 6 840-846 |
| α-fetoprotein | Esteban et al. (1996) *Tumour Biol.*, 17(5): 299-305 |
| AM-1 | Harada et al. (1996) *Tohoku J Exp Med.*, 180(3): 273-288 |
| APC | Dihlmannet al. (1997) *Oncol Res.*, 9(3) 119-127 |
| APRIL | Sordat et al. ('998) *J Exp Med.*, 188(6): 1185-1190 |
| BAGE | Boel et al. (1995) *Immunity*, 2: 167-175. |
| β-catenin | Hugh et al. (1999) *Int J Cancer*, 82(4): 504-11 |
| Bcl2 | Koty et al. (1999) *Lung Cancer*, 23(2): 115-127 |
| bcr-abl (b3a2) | Verfaillie et al.('996) *Blood*, 87(11): 4770-4779 |
| CA-125 | Bast et al. ('998) *Int J Biol Markers*, 13(4): 179-187 |
| CASP-8/FLICE | Mandruzzato et al. (1997) *J Exp Med.*, 186(5): 785-793. |
| Cathepsins | Thomssen et al.(1995) *Clin Cancer Res.*, 1(7): 741-746 |
| CD19 | Scheuermann et al. (1995) *Leuk Lymphoma*, 18(5-6): 385-397 |
| CD20 | Knox et al. (1996) *Clin Cancer Res.*, 2(3): 457-470 |
| CD21, CD23 | Shubinsky et al. (1997) *Leuk Lymphoma*, 25(5-6): 521-530 |
| CD22, CD38 | French et al. (1995) *Br J Cancer*, 71(5): 986-994 |
| CD33 | Nakase et al. (1996) *Am J Clin Pathol.*, 105(6): 761-768 |
| CD35 | Yamakawa et al. *Cancer*, 73(11): 2808-2817 |
| CD44 | Naot et al. (1997) *Adv Cancer Res.*, 71: 241-319 |
| CD45 | Buzzi et al. (1992) *Cancer Res.*, 52(14): 4027-4035 |
| CD46 | Yamakawa et al. (1994) *Cancer*, 73(11): 2808-2817 |
| CD5 | Stein et al. (1991) *Clin Exp Immunol.*, 85(3): 418-423 |
| CD52 | Ginaldi et al. (1998) *Leuk Res.*, 22(2): 185-191 |

TABLE 2-continued

Illustrative cancer markers and associated references, all of which are incorporated herein by reference for the purpose of identifying the referenced tumor markers.

| Marker | Reference |
| --- | --- |
| CD55 | Spendlove et al. (1999) *Cancer Res.*, 59: 2282-2286. |
| CD59 (791Tgp72) | Jarvis et al. (1997) *Int J Cancer*, 71(6): 1049-1055 |
| CDC27 | Wang et al. (1999) *Science*, 284(5418): 1351-1354 |
| CDK4 | Wölfel et al. (1995) *Science*, 269(5228): 1281-1284 |
| CEA | Kass et al. (1999) *Cancer Res.*, 59(3): 676-683 |
| c-myc | Watson et al. (1991) *Cancer Res.*, 51(15): 3996-4000 |
| Cox-2 | Tsujii et al. (1998) *Cell*, 93: 705-716 |
| DCC | Gotley et al. (1996) *Oncogene*, 13(4): 787-795 |
| DcR3 | Pitti et al. (1998) *Nature*, 396: 699-703 |
| E6/E7 | Steller et al. (1996) *Cancer Res.*, 56(21): 5087-5091 |
| EGFR | Yang et al. (1999) *Cancer Res.*, 59(6): 1236-1243. |
| EMBP | Shiina et al. (1996) *Prostate*, 29(3): 169-176. |
| Ena78 | Arenberg et al. (1998) *J. Clin. Invest.*, 102: 465-472. |
| FGF8b and FGF8a | Dorkin et al. (1999) *Oncogene*, 18(17): 2755-2761 |
| FLK-1/KDR | Annie and Fong (1999) *Cancer Res.*, 59: 99-106 |
| Folic Acid Receptor | Dixon et al. (1992) *J Biol Chem.*, 267(33): 24140-72414 |
| G250 | Divgi et al. (1998) *Clin Cancer Res.*, 4(11): 2729-2739 |
| GAGE-Family | De Backer et al. (1999) *Cancer Res.*, 59(13): 3157-3165 |
| gastrin 17 | Watson et al. (1995) *Int J Cancer*, 61(2): 233-240 |
| Gastrin-releasing hormone (bombesin) | Wang et al. (1996) *Int J Cancer*, 68(4): 528-534 |
| GD2/GD3/GM2 | Wiesner and Sweeley (1995) *Int J Cancer*, 60(3): 294-299 |
| GnRH | Bahk et al.(1998) *Urol Res.*, 26(4): 259-264 |
| GnTV | Hengstler et al. (1998) *Recent Results Cancer Res.*, 154: 47-85 |
| gp100/Pmel17 | Wagner et al. (1997) *Cancer Immunol Immunother.*, 44(4): 239-247 |
| gp-100-in4 | Kirkin et al. (1998) *APMIS*, 106(7): 665-679 |
| gp15 | Maeurer et al.(1996) *Melanoma Res.*, 6(1): 11-24 |
| gp75/TRP-1 | Lewis et al.(1995) *Semin Cancer Biol.*, 6(6): 321-327 |
| hCG | Hoermann et al. (1992) *Cancer Res.*, 52(6): 1520-1524 |
| Heparanase | Vlodaysky et al. (1999) *Nat Med.*, 5(7): 793-802 |
| Her2/neu Her3 | Lewis et al. (1995) *Semin Cancer Biol.*, 6(6): 321-327 |
| HMTV | Kahl et al.(1991) *Br J Cancer*, 63(4): 534-540 |
| Hsp70 | Jaattela et al. (1998) *EMBO J.*, 17(21): 6124-6134 |
| hTERT (telomerase) | Vonderheide et al. (1999) *Immunity*, 10: 673-679. 1999. |
| IGFR1 | Ellis et al. (1998) *Breast Cancer Res. Treat.*, 52: 175-184 |
| IL-13R | Murata et al. (1997) *Biochem Biophys Res Commun.*, 238(1): 90-94 |
| iNOS | Klotz et al. (1998) *Cancer*, 82(10): 1897-1903 |
| Ki 67 | Gerdes et al. (1983) *Int J Cancer*, 31: 13-20 |
| KIAA0205 | Guéguen et al. (1998) *J Immunol.*, 160(12): 6188-6194 |
| K-ras, H-ras, N-ras | Abrams et al. (1996) *Semin Oncol.*, 23(1): 118-134 |
| KSA (CO17-1A) | Zhang et al. (1998) *Clin Cancer Res.*, 4(2): 295-302 |
| LDLR-FUT | Caruso et al. (1998) *Oncol Rep.*, 5(4): 927-930 |
| MAGE Family (MAGE1, MAGE3, etc.) | Marchand et al. (1999) *Int J Cancer, 80(2):* 219-230 |
| Mammaglobin | Watson et al. (1999) *Cancer Res.*, 59: 13 3028-3031 |
| MAP17 | Kocher et al. (1996) *Am J Pathol.*, 149(2): 493-500 |
| Melan-A/ MART-1 | Lewis and Houghton (1995) *Semin Cancer Biol.*, 6(6): 321-327 |
| mesothelin | Chang et al. (1996) *Proc. Natl. Acad. Sci., USA*, 93(1): 136-140 |
| MIC A/B | Groh et al.(1998) *Science*, 279: 1737-1740 |
| MT-MMP's, such as MMP2, MMP3, MMP7, MMP9 | Sato and Seiki (1996) *J Biochem (Tokyo)*, 119(2): 209-215 |
| Mox1 | Candia et al. (1992) *Development*, 116(4): 1123-1136 |
| Mucin, such as MUC-1, MUC-2, MUC-3, and MUC-4 | Lewis and Houghton (1995) *Semin Cancer Biol.*, 6(6): 321-327 |
| MUM-1 | Kirkin et al. (1998) *APMIS*, 106(7): 665-679 |
| NY-ESO-1 | Jager et al. (1998) *J. Exp. Med.*, 187: 265-270 |
| Osteonectin | Graham et al. (1997) *Eur J Cancer*, 33(10): 1654-1660 |
| p15 | Yoshida et al. (1995) *Cancer Res.*, 55(13): 2756-2760 |
| P170/MDR1 | Trock et al. (1997) *J Natl Cancer Inst.*, 89(13): 917-931 |
| p53 | Roth et al. (1996) *Proc. Natl. Acad. Sci., USA*, 93(10): 4781-4786. |
| p97/melanotransferrin | Furukawa et al. (1989) *J Exp Med.*, 169(2): 585-590 |
| PAI-1 | Grøndahl-Hansen et al. (1993) *Cancer Res.*, 53(11): 2513-2521 |
| PDGF | Vassbotn et al. (1993) *Mol Cell Biol.*, 13(7): 4066-4076 |
| Plasminogen (uPA) | Naitoh et al. (1995) *Jpn J Cancer Res.*, 86(1): 48-56 |
| PRAME | Kirkin et al. (1998) *APMIS*, 106(7): 665-679 |
| Probasin | Matuo et al. (1985) *Biochem Biophys Res Commun.*, 130(1): 293-300 |

TABLE 2-continued

Illustrative cancer markers and associated references, all of which are incorporated herein by reference for the purpose of identifying the referenced tumor markers.

| Marker | Reference |
|---|---|
| Progenipoietin | — |
| PSA | Sanda et al. (1999) *Urology*, 53(2): 260-266. |
| PSM | Kawakami et al.(1997) *Cancer Res.*, 57(12): 2321-2324 |
| RAGE-1 | Gaugler et al.(1996) *Immunogenetics*, 44(5): 323-330 |
| Rb | Dosaka-Akita et al. (1997) *Cancer*, 79(7): 1329-1337 |
| RCAS1 | Sonoda et al.(1996) *Cancer*, 77(8): 1501-1509. |
| SART-1 | Kikuchi et al.(1999(Int J Cancer, 81(3): 459-466 |
| SSX gene family | Gure et al. (1997) *Int J Cancer*, 72(6): 965-971 |
| STAT3 | Bromberg et al. (1999) *Cell, 98(3): 295-303* |
| STn (mucin assoc.) | Sandmaier et al. (1999) *J Immunother.*, 22(1): 54-66 |
| TAG-72 | Kuroki et al. (1990) Cancer Res., 50(16): 4872-4879 |
| TGF-α | Imanishi et al. (1989) *Br J Cancer*, 59(5): 761-765 |
| TGF-β | Picon et al. (1998) *Cancer Epidemiol Biomarkers Prev*, 7(6): 497-504 |
| Thymosin β 15 | Bao et al. (1996) *Nature Medicine*. 2(12), 1322-1328 |
| IFN-α | Moradi et al. (1993) *Cancer*, 72(8): 2433-2440 |
| TPA | Maulard et al. (1994) *Cancer*, 73(2): 394-398 |
| TPI | Nishida et al.(1984) *Cancer Res* 44(8): 3324-9 |
| TRP-2 | Parkhurst et al. (1998) *Cancer Res.*, 58(21) 4895-4901 |
| Tyrosinase | Kirkin et al. (1998) *APMIS*, 106(7): 665-679 |
| VEGF | Hyodo et al. (1998) *Eur J Cancer*, 34(13): 2041-2045 |
| ZAG | Sanchez et al. (1999) *Science*, 283(5409): 1914-1919 |
| p16INK4 | Quelle et al. (1995) *Oncogene* Aug. 17, 1995; 11(4): 635-645 |
| Glutathione S-transferase | Hengstler (1998) et al. *Recent Results Cancer Res.*, 154: 47-85 |

Any of the foregoing markers can be used as targets for the targeting moieties comprising the interferon-targeting moiety constructs of this invention. In certain embodiments the target markers include, but are not limited to members of the epidermal growth factor family (e.g., HER2, HER3, EGF, HER4), CD1, CD2, CD3, CD5, CD7, CD13, CD14, CD15, CD19, CD20, CD21, CD23, CD25, CD33, CD34, CD38, 5E10, CEA, HLA-DR, HM 1.24, HMB 45, 1a, Leu-M1, MUC1, PMSA, TAG-72, phosphatidyl serine antigen, and the like.

The foregoing markers are intended to be illustrative and not limiting. Other tumor associated antigens will be known to those of skill in the art.

Where the tumor marker is a cell surface receptor, ligand to that receptor can function as targeting moieties. Similarly mimetics of such ligands can also be used as targeting moieties.

Antibodies.

In certain embodiments, the targeting moieties can comprise antibodies, unibodies, or affybodies that specifically or preferentially bind the tumor marker. Antibodies that specifically or preferentially bind tumor markers are well known to those of skill in the art. Thus, for example, antibodies that bind the CD22 antigen expressed on human B cells include HD6, RFB4, UV22-2, Tol5, 4KB128, a humanized anti-CD22 antibody (hLL2) (see, e.g., Li et al. (1989) *Cell. Immunol.* 111: 85-99; Mason et al. (1987) *Blood* 69: 836-40; Behr et al. (1999) *Clin. Cancer Res.* 5: 3304s-3314s; Bonardi et al. (1993) *Cancer Res.* 53: 3015-3021).

Antibodies to CD33 include for example, HuM195 (see, e.g., Kossman et al. (1999) *Clin. Cancer Res.* 5: 2748-2755), CMA-676 (see, e.g., Sievers et al., (1999) *Blood* 93: 3678-3684.

Antibodies to CD38 include for example, AT13/5 (see, e.g., Ellis et al. (1995) *J. Immunol.* 155: 925-937), HB7, and the like.

In certain embodiments the targeting moiety comprises an anti-HER2 antibody. The erb-b2 gene, more commonly known as (Her-2/neu), is an oncogene encoding a transmembrane receptor. Several antibodies have been developed against Her-2/neu, including trastuzumab (e.g., HERCEPTIN®; Fornier et al. (1999) *Oncology* (Huntingt) 13: 647-58), TAB-250 (Rosenblum et al. (1999) *Clin. Cancer Res.* 5: 865-874), BACH-250 (Id.), TA1 (Maier et al. (1991) *Cancer Res.* 51: 5361-5369), and the mAbs described in U.S. Pat. Nos. 5,772,997; 5,770,195 (mAb 4D5; ATCC CRL 10463); and U.S. Pat. No. 5,677,171

Illustrative anti-MUC-1 antibodies include, but are not limited to Mc5 (see, e.g., Peterson et al. (1997) *Cancer Res.* 57: 1103-1108; Ozzello et al. (1993) *Breast Cancer Res. Treat.* 25: 265-276), and hCTMO1 (see, e.g., Van Hof et al. (1996) *Cancer Res.* 56: 5179-5185).

Illustrative anti-TAG-72 antibodies include, but are not limited to CC49 (see, e.g., Pavlinkova et al. (1999) *Clin. Cancer Res.* 5: 2613-2619), B72.3 (see, e.g., Divgi et al. (1994) *Nucl. Med. Biol.* 21: 9-15), and those disclosed in U.S. Pat. No. 5,976,531.

Illustrative anti-HM1.24 antibodies include, but are not limited to a mouse monoclonal anti-HM1.24 $IgG_{2a}/κ$ and a humanized anti-HM1.24 $IgG_1/κ$. antibody (see, e.g., Ono et al. (1999) *Mol. Immunol.* 36: 387-395).

A number of antibodies have been developed that specifically bind HER2 and some are in clinical use. These include, for example, trastuzumab (e.g., HERCEPTIN®, Fornier et al. (1999) *Oncology* (Huntingt) 13: 647-658), TAB-250 (Rosenblum et al. (1999) *Clin. Cancer Res.* 5: 865-874), BACH-250 (Id.), TA1 (see, e.g., Maier et al. (1991) *Cancer Res.* 51: 5361-5369), and the antibodies described in U.S. Pat. Nos. 5,772,997; 5,770,195, and 5,677,171.

Other fully human anti-HER2/neu antibodies are well known to those of skill in the art. Such antibodies include, but are not limited to the C6 antibodies such as C6.5, DPL5, G98A, C6MH3-B1, B1D2, C6VLB, C6VLD, C6VLE, C6VLF, C6MH3-D7, C6MH3-D6, C6MH3-D5, C6MH3-D3, C6MH3-D2, C6MH3-D1, C6MH3-C4, C6MH3-C3, C6MH3-B9, C6MH3-B5, C6MH3-B48, C6MH3-B47, C6MH3-B46, C6MH3-B43, C6MH3-B41, C6MH3-B39, C6MH3-B34, C6MH3-B33, C6MH3-B31, C6MH3-B27, C6MH3-B25, C6MH3-B21, C6MH3-B20, C6MH3-B2, C6MH3-B16, C6MH3-B15, C6MH3-B11, C6MH3-B1, C6MH3-A3, C6MH3-A2, and C6ML3-9. These and other anti-HER2/neu antibodies are described in U.S. Pat. Nos. 6,512,097 and 5,977,322, in PCT Publication WO 97/00271, in Schier et al. (1996) *J Mol Biol* 255: 28-43, Schier et al. (1996) *J Mol Biol* 263: 551-567, and the like.

More generally, antibodies directed to various members of the epidermal growth factor receptor family are well suited for use as targeting moieties in the constructs of the present invention. Such antibodies include, but are not limited to anti-EGF-R antibodies as described in U.S. Pat. Nos. 5,844,093 and 5,558,864, and in European Patent No. 706,799A.). Other illustrative anti-EGFR family antibodies include, but are not limited to antibodies such as C6.5, C6ML3-9, C6MH3-B1, C6-B1D2, F5, HER3.A5, HER3.F4, HER3.H1, HER3.H3, HER3.E12, HER3.B12, EGFR.E12, EGFR.C10, EGFR.B11, EGFR.E8, HER4.B4, HER4.G4, HER4.F4, HER4.A8, HER4.B6, HER4.D4, HER4.D7, HER4.D11, HER4.D12, HER4.E3, HER4.E7, HER4.F8 and HER4.C7 and the like (see, e.g., U.S. Patent publications US 2006/0099205 A1 and US 2004/0071696 A1 which are incorporated herein by reference).

As described in U.S. Pat. Nos. 6,512,097 and 5,977,322 other anti-EGFR family member antibodies can readily be produced by shuffling light and/or heavy chains followed by one or more rounds of affinity selection. Thus in certain embodiments, this invention contemplates the use of one, two, or three CDRs in the VL and/or VH region that are CDRs described in the above-identified antibodies and/or the above identified publications.

In various embodiments the targeting moiety comprises an antibody that specifically or preferentially binds CD20. Anti-CD20 antibodies are well known to those of skill and include, but are not limited to rituximab, ibritumomab tiuxetan, and tositumomab, AME-133v (Applied Molecular Evolution), Ocrelizumab (Roche), Ofatumumab (Genmab), TRU-015 (Trubion) and IMMU-106 (Immunomedics).

The invention need not be limited to the use of the antibodies described above, and other such antibodies as they are known to those of skill in the art can be used in the compositions and methods described herein.

While the above discussion pertains to antibodies, it will be recognized that affybodies and/or unibodies can be used instead of antibodies.

Unibodies.

UniBody are antibody technology that produces a stable, smaller antibody format with an anticipated longer therapeutic window than certain small antibody formats. In certain embodiments unibodies are produced from IgG4 antibodies by eliminating the hinge region of the antibody. Unlike the full size IgG4 antibody, the half molecule fragment is very stable and is termed a uniBody. Halving the IgG4 molecule left only one area on the UniBody that can bind to a target. Methods of producing unibodies are described in detail in PCT Publication WO2007/059782, which is incorporated herein by reference in its entirety (see, also, Kolfschoten et al. (2007) *Science* 317: 1554-1557).

Affibodies.

Affibody molecules are class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody variants that target the desired molecules can be selected using phage display technology (see, e.g., Nord et al. (1997) *Nat. Biotechnol.* 15: 772-777; Ronmark et al. (2002) *Eur. J. Biochem.,* 269: 2647-2655.). Details of Affibodies and methods of production are known to those of skill (see, e.g., U.S. Pat. No. 5,831,012 which is incorporated herein by reference in its entirety).

It will be recognized that the antibodies described above can be provided as whole intact antibodies (e.g., IgG), antibody fragments, or single chain antibodies, using methods well known to those of skill in the art. In addition, while the antibody can be from essentially any mammalian species, to reduce immunogenicity, it is desirable to use an antibody that is of the species in which the construct (e.g., anti-HER2/neu-IFN-α chimera) is to be used. In other words, for use in a human, it is desirable to use a human, humanized, or chimeric human antibody.

B) Interferons

In various embodiments chimeric moieties of this invention comprise an interferon (e.g., IFN-α, IFN-β, etc.) joined to the targeting moiety (e.g., anti-HER2/neu antibody). The interferon can be a full length wild-type interferon (e.g. IFN-α, IFN-β, IFN-γ, etc.) an interferon fragment (e.g., an IFN-α fragment), and/or a mutated interferon. Typically the interferon fragment is one that possesses the endogenous activity of the native interferon, preferably at a level of at least 80%, more preferably at least 90% or 95%, most preferably at least 98%, 99%, 100%, or a level greater than the wild-type interferon.

Means of identifying such modified interferon molecules are routine to those of skill in the art. In one illustrative approach, a library of truncated and/or mutated IFN-α is produced and screened for IFN-α activity. Methods of producing libraries of polypeptide variants are well known to those of skill in the art. Thus, for example error-prone PCR can be used to create a library of mutant and/or truncated IFN-α (see, e.g., U.S. Pat. No. 6,365,408).

The resulting library members can then be screened according to standard methods know to those of skill in the art. Thus, for example, IFN-α activity can be assayed by measuring antiviral activity against a particular test virus. Kits for assaying for IFN-α activity are commercially available (see, e.g., ILITE™ alphabeta kit by Neutekbio, Ireland).

In various embodiments use of a mutated interferon alpha 2 (IFNα 2) is contemplated. Certain mutants include a mutation of the His at position 57, and/or the E at position 58, and/or the Q at position 61. In certain embodiments the mutants include the mutation H57Y, and/or E58N, and/or Q61S. In certain embodiments the mutants include a mutated IFNα 2 having the mutations H57Y, E58N, and Q61S (YNS) (see, e.g., Kalie et al. (2007) *J. Biol. Chem.,* 282: 11602-11611).

A mutated IFN-β comprising a serine substituted for the naturally occurring cysteine at amino acid 17 has also been demonstrated to show efficacy (see, e.g., Hawkins et al. (1985) *Cancer Res.,* 45, 5914-5920.

In various embodiments use of truncated interferons is also contemplated. Human INFα, for example, with deletions of the first 15 amino-terminal amino acid residues and/or the last 10-13 carboxyl-terminal amino acid residues, have been shown to exhibit virtually the same activity as the parent molecules (see, e.g., Ackerman (1984) *Proc. Natl. Acad. Sci., USA,* 81: 1045-1047). Accordingly the use of IFN-αs having 1, 2, 3, up to 13 caroxyl terminal amino acid residues deleted and/or 1, 2, 3, up to 15 amino terminal amino acid residues deleted are contemplated.

It has also been demonstrated that activity resides in huIFN-α fragment HuIFN-α (1-110) (Id.). Accordingly carboxyl truncated IFNs with truncations after residue 110 and/or with 1, 2, 3, up to 15 amino terminal amino acid residues deleted are contemplated.

Certain C-terminally truncated interferon betas (IFN-β) have been shown to have increased activity (see, e.g., U.S. Patent Publication 2009/0025106 A1). Accordingly, in certain embodiments the interferons used in the constructs described herein include the C-terminally truncated IFN-β described as IFN-Δ1, IFN-Δ2, IFN-Δ3, IFN-Δ4, IFN-Δ5, IFN-Δ6, IFN-Δ7, IFN-Δ8, IFN-Δ9, IFN-Δ10 in US 2009/0025106 A1. In certain embodiments the interferon is IFN-Δ7, IFN-Δ8, IFN-A9 (SEQ ID NOs: 57, 59, and 61 in US 2009/0025106 A1 (see, Table 3).

The use of chemically modified interferons is also contemplated. For example, in certain embodiments, the interferon is chemically modified to increase serum half-life. Thus, for example, (2-sulfo-9-fluorenylmethoxycarbonyl)$_7$-interferon-α2 undergoes time-dependent spontaneous hydrolysis, generating active interferon (see, e.g., Shechter et al. (2001) *Proc. Natl. Acad. Sci., USA,* 98(3): 1212-1217). Other modifications, include for example, N-terminal modifications in including, but not limited to the addition of PEG, protecting groups, and the like. U.S. Pat. No. 5,824,784, for example, described N-terminally chemically modified interferon.

The foregoing interferons are intended to be illustrative and not limiting. Using the teaching provided herein, other suitable modified interferons (e.g., modified IFN-α, IFN-β, IFN-γ, etc.) can be readily identified and produced.

C. Attachment of the Antibody (e.g., Anti-HER2/Neu) to the IFN-α.

Generally speaking, the targeting moiety (e.g., an anti-HER2/neu antibody, and anti-CD20 antibody, etc.) can be joined together in any order. Thus, for example, the antibody can be joined to either the amino or carboxy terminal of the interferon. The antibody can also be joined to an internal region of the interferon, or conversely, the interferon can be joined to an internal location or to any terminus of the antibody, as long as the attachment does not interfere with binding of the antibody to that target marker (e.g., the HER2/neu receptor).

The antibody (e.g., a C6 anti-HER2/neu, anti-CD20, etc.) and the interferon (e.g., IFN-α, IFN-β, etc.) can be attached by any of a number of means well known to those of skill in the art. In certain embodiments, the interferon is conjugated, either directly or through a linker (spacer), to the

TABLE 3

Truncated IFN-β showing enhanced activity (see U.S. Patent Publication 2009/0025106 A1).

| Truncated IFN | Amino Acid Sequence | SEQ ID NO |
|---|---|---|
| IFN-Δ7 | Met Gly Lys Met Ala Ser Leu Phe Ala Thr Phe Leu Val Val Leu Val Ser Leu Ser Leu Ala Ser Glu Ser Ser Ala Cys Asp Leu Pro Gln Thr His Ser Leu Gly Ser Arg Arg Thr Leu Met Leu Leu Ala Gln Met Arg Arg Ile Ser Leu Phe Ser Cys Leu Lys Asp Arg His Asp Phe Gly Phe Pro Gln Glu Glu Phe Gly Asn Gln Phe Gln Lys Ala Glu Thr Ile Pro Val Leu His Glu Met Ile Gln Gln Ile Phe Asn Leu Phe Ser Thr Lys Asp Ser Ser Ala Ala Trp Asp Glu Thr Leu Leu Asp Lys Phe Tyr Thr Glu Leu Tyr Gln Gln Leu Asn Asp Leu Glu Ala Cys Val Ile Gln Gly Val Gly Val Thr Glu Thr Pro Leu Met Lys Glu Asp Ser Ile Leu Ala Val Arg Lys Tyr Phe Gln Arg Ile Thr Leu Tyr Leu Lys Glu Lys Lys Tyr Ser Pro Cys Ala Trp Glu Val Val Arg Ala Glu Ile Met Arg Ser Phe Ser Leu Ser Thr Asn Leu Gln | 50 |
| IFN-Δ8 | Met Gly Lys Met Ala Ser Leu Phe Ala Thr Phe Leu Val Val Leu Val Ser Leu Ser Leu Ala Ser Glu Ser Ser Ala Cys Asp Leu Pro Gln Thr His Ser Leu Gly Ser Arg Arg Thr Leu Met Leu Leu Ala Gln Met Arg Arg Ile Ser Leu Phe Ser Cys Leu Lys Asp Arg His Asp Phe Gly Phe Pro Gln Glu Glu Phe Gly Asn Gln Phe Gln Lys Ala Glu Thr Ile Pro Val Leu His Glu Met Ile Gln Gln Ile Phe Asn Leu Phe Ser Thr Lys Asp Ser Ser Ala Ala Trp Asp Glu Thr Leu Leu Asp Lys Phe Tyr Thr Glu Leu Tyr Gln Gln Leu Asn Asp Leu Glu Ala Cys Val Ile Gln Gly Val Gly Val Thr Glu Thr Pro Leu Met Lys Glu Asp Ser Ile Leu Ala Val Arg Lys Tyr Phe Gln Arg Ile Thr Leu Tyr Leu Lys Glu Lys Lys Tyr Ser Pro Cys Ala Trp Glu Val Val Arg Ala Glu Ile Met Arg Ser Phe Ser Leu Ser Thr Asn Leu | 51 |
| IFN-Δ9 | Met Gly Lys Met Ala Ser Leu Phe Ala Thr Phe Leu Val Val Leu Val Ser Leu Ser Leu Ala Ser Glu Ser Ser Ala Cys Asp Leu Pro Gln Thr His Ser Leu Gly Ser Arg Arg Thr Leu Met Leu Leu Ala Gln Met Arg Arg Ile Ser Leu Phe Ser Cys Leu Lys Asp Arg His Asp Phe Gly Phe Pro Gln Glu Glu Phe Gly Asn Gln Phe Gln Lys Ala Glu Thr Ile Pro Val Leu His Glu Met Ile Gln Gln Ile Phe Asn Leu Phe Ser Thr Lys Asp Ser Ser Ala Ala Trp Asp Glu Thr Leu Leu Asp Lys Phe Tyr Thr Glu Leu Tyr Gln Gln Leu Asn Asp Leu Glu Ala Cys Val Ile Gln Gly Val Gly Val Thr Glu Thr Pro Leu Met Lys Glu Asp Ser Ile Leu Ala Val Arg Lys Tyr Phe Gln Arg Ile Thr Leu Tyr Leu Lys Glu Lys Lys Tyr Ser Pro Cys Ala Trp Glu Val Val Arg Ala Glu Ile Met Arg Ser Phe Ser Leu Ser Thr Asn | 52 | antibody. In certain embodiments, however, it is preferable to recombinantly express the chimeric moiety as a fusion protein.

i) Chemical Conjugation of the Targeting Moiety to the Interferon.

In certain embodiments, the targeting moiety (e.g., an anti-CD20 antibody such as rituximab, an anti-HER2/neu antibody such as C6.5, C6MH3-B1, G98A, ML3-9, H3B1, B1D2, etc.) is chemically conjugated to the interferon (e.g., IFN-α, IFN-β, etc.) molecule. Means of chemically conjugating molecules are well known to those of skill.

The procedure for conjugating two molecules varies according to the chemical structure of the agent. Polypeptides typically contain variety of functional groups; e.g., carboxylic acid (COOH) or free amine (—$NH_2$) groups, that are available for reaction with a suitable functional group on the other peptide, or on a linker to join the molecules thereto.

Alternatively, the antibody and/or the interferon can be derivatized to expose or attach additional reactive functional groups. The derivatization can involve attachment of any of a number of linker molecules such as those available from Pierce Chemical Company, Rockford Ill.

A "linker", as used herein, typically refers to a molecule that is used to join the antibody to the interferon. In various embodiments, the linker is capable of forming covalent bonds to both the antibody and to the interferon. Suitable linkers are well known to those of skill in the art and include, but are not limited to, straight or branched-chain carbon linkers, heterocyclic carbon linkers, or peptide linkers. In certain embodiments, the linker(s) can be joined to the constituent amino acids of the antibody and/or the interferon through their side groups (e.g., through a disulfide linkage to cysteine). In certain preferred embodiments, the linkers are joined to the alpha carbon amino and/or carboxyl groups of the terminal amino acids of the antibody and/or the interferon.

A bifunctional linker having one functional group reactive with a group on the antibody and another group reactive on the interferon, can be used to form the desired conjugate. Alternatively, derivatization can involve chemical treatment of the targeting moiety. Procedures for generation of, for example, free sulfhydryl groups on polypeptides, such as antibodies or antibody fragments, are known (See U.S. Pat. No. 4,659,839).

Many procedures and linker molecules for attachment of various compounds including radionuclide metal chelates, toxins and drugs to proteins such as antibodies are known. See, for example, European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071-4075. In particular, production of various immunotoxins is well-known within the art and can be found, for example in "Monoclonal Antibody-Toxin Conjugates: Aiming the Magic Bullet," Thorpe et al., *Monoclonal Antibodies in Clinical Medicine*, Academic Press, pp. 168-190 (1982); Waldmann (1991) *Science,* 252: 1657; U.S. Pat. Nos. 4,545,985 and 4,894,443, and the like.

ii) Production of Fusion Proteins.

In certain embodiments, a chimeric targeting moiety-interferon fusion protein is synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins (e.g. anti-HER2/neu-IFN-α, anti-HER2/neu-IFN-β, anti-CD20-IFN-α, anti-CD20-IFN-β, etc.) described herein can be prepared by any suitable method, including, for example, cloning and restriction of appropriate sequences or direct chemical synthesis by methods such as the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862); the solid support method of U.S. Pat. No. 4,458,066, and the like.

Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is limited to sequences of about 100 bases, longer sequences may be obtained by the ligation of shorter sequences.

Alternatively subsequences can be cloned and the appropriate subsequences cleaved using appropriate restriction enzymes. The fragments can then be ligated to produce the desired DNA sequence.

In certain embodiments, DNA encoding fusion proteins of the present invention can be cloned using DNA amplification methods such as polymerase chain reaction (PCR). Thus, for example, the gene for the interferon (e.g., IFN-α) is PCR amplified, using a sense primer containing the restriction site for, e.g., NdeI and an antisense primer containing the restriction site for HindIII. This can produce a nucleic acid encoding the mature interferon sequence and having terminal restriction sites. An antibody having "complementary" restriction sites can similarly be cloned and then ligated to the interferon and/or to a linker attached to the interferon. Ligation of the nucleic acid sequences and insertion into a vector produces a vector encoding the interferon joined to the antibody (e.g., anti-CD20).

While the two molecules can be directly joined together, one of skill will appreciate that the molecules can be separated by a peptide spacer consisting of one or more amino acids. Generally the spacer will have no specific biological activity other than to join the proteins or to preserve some minimum distance or other spatial relationship between them. In certain embodiments, however, the constituent amino acids of the spacer can be selected to influence some property of the molecule such as the folding, net charge, or hydrophobicity.

It was a surprising discovery, however, that certain linkers are unsuitable for preparation of fusion proteins of the present invention. Thus, for example, the ($Gly_4Ser$)$_3$ (SEQ ID NO:5) linker was not well suited for the production of an anti-CD20-IFN construct. Without being bound to a particular theory, it is believed the interferon was being removed from the fusion protein by proteolysis. Western blot analysis using anti-Fc and anti-interferon, confirmed that both of the upper bands were heavy chains, but only the largest contained interferon.

It was also a surprising discovery that proteolysis resistant linkers and in certain embodiments, "short" proteolysis resistant linkers produced a targeted interferon construct that had greater activity (even in vitro) against cells expressing the target moiety (e.g., CD20) than an untargeted construct.

Accordingly, in certain preferred embodiments, it is desirable to use a linker that is resistant to proteolysis. Certain preferred linkers are linkers that are not the ($Gly_4Ser$)$_3$ (SEQ ID NO:5) linker. Certain preferred linkers are linkers shorter than 15 amino acids, or linkers shorter than 14, 13, 12, 11, 10, 9, 8, 7, 6, 5, 4, 3, or 2 amino acids in length. In certain embodiments the linker is an alpha helical linker ranging in length up to about 12 or 13 or 14 amino acids in length. In certain embodiments the linker is a Gly$_4$Ser (SEQ ID NO:6) linker or a linker approximately equal to in length or shorter than a (Gly$_4$Ser)$_2$ (SEQ ID NO:53) more preferably a linker approximately equal to in length or shorter than a Gly$_4$Ser (SEQ ID NO:6) linker.

Certain illustrative proteolysis-resistant linkers well suited for use in the constructs of this invention are shown in Table 4.

TABLE 4

Illustrative proteolysis-resistant linkers.

| Linker Seq | SEQ ID NO |
|---|---|
| GGGGS | 6 |
| GGGGSGGGGS | 53 |
| AEAAAKEAAAKA | 7 |
| A(EAAAK)$_n$A where n = 1, | 54 |
| where n = 2 | 55 |
| where n = 3 | 56 |
| where n = 4, | 57 |
| where n = 5 | 58 |
| GGGGG | 59 |
| GGGGGGGG | 60 |
| GGAGG | 61 |
| GAGAGAGAGA | 62 |
| RPLSYRPPFPFGFPSVRP | 63 |
| YPRSIYIRRRHPSPSLTT | 64 |
| TPSHLSHILPSFGLPTFN | 65 |
| RPVSPFTFPRLSNSWLPA | 66 |
| SPAAHFPRSIPRPGPIRT | 67 |
| APGPSAPSHRSLPSRAFG | 68 |
| PRNSIHFLHPLLVAPLGA | 69 |
| MPSLSGVLQVRYLSPPDL | 70 |
| SPQYPSPLTLTLPPHPSL | 71 |
| NPSLNPPSYLHRAPSRIS | 72 |
| LPWRTSLLPSLPLRRRP | 73 |
| PPLFAKGPVGLLSRSFPP | 74 |
| VPPAPVVSLRSAHARPPY | 75 |
| LRPTPPRVRSYTCCPTP | 76 |
| PNVAHVLPLLTVPWDNLR | 77 |
| CNPLLPLCARSPAVRTFP | 78 |

It was also a surprising discovery, as illustrated in FIG. 29 anti-CD20-IFN showed a dramatic gain in tumor specific potency as compared to IFN and anti-DNS-IFN, even in vitro. Interestingly, both antibody-IFN fusion molecules (anti-CD20-IFN and anti-DNS-IFN) showed lower potency than unfused IFN as depicted in the left panel of the figure. Without being bound to a particular theory, it is believed this is due to the shorter linker causing a steric hindrance. In certain embodiments the targeting moiety-interferon construct shows at least 1.25, preferably at least 1.5, more preferably at least 2×, still more preferably at least 5×, 10×, 20×, 50×, or at least 100× greater activity than the corresponding interferon without a targeting moiety.

The nucleic acid sequences encoding the fusion proteins can be expressed in a variety of host cells, including E. coli, other bacterial hosts, yeast, and various higher eukaryotic cells such as the COS, CHO and HeLa cells lines and myeloma cell lines. The recombinant protein gene is typically operably linked to appropriate expression control sequences for each host. For E. coli this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for E. coli and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes (1982) *Protein Purification*, Springer-Verlag, N.Y.: Deutscher (1990) *Methods in Enzymology Vol. 182: Guide to Protein Purification*, Academic Press, Inc. N.Y., and the like). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the fusion protein (e.g., anti-HER2/neu-IFN-α, anti-CD20-IFN-α, etc.) may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (see, e.g., Debinski et al. (1993) *J. Biol. Chem.*, 268: 14065-14070; Kreitman and Pastan (1993) *Bioconjug. Chem.*, 4: 581-585; and Buchner, et al. (1992) *Anal. Biochem.*, 205: 263-270). Debinski et al., for example, describe the denaturation and reduction of inclusion body proteins in guanidine-DTE. The protein is then refolded in a redox buffer containing oxidized glutathione and L-arginine.

In certain embodiments a transient expression system can be used to express the chimeric constructs described herein. Although many cell lines potentially can be used, one cell line that works well for transient expression is 293T. For transient expression of 293T on Day 0, 9 million cells in 25 ml are seeded for each 150 mm tissue culture plate. A 1 mg/ml of PEI (Polyethylenimine) is made using sterile water. For the expression of a complete antibody or antibody fusion protein, 25 μg each of H and L (50 ug total) is used per plate. A volume of 5 ml is used for transfection of each 150 mm plate. The DNA is mixed with DMEM, the PEI is then added and the mixture is incubated at room temperature for 10 mins. 1.75 μg PEI is used for each ug of DNA. For transfection, the old medium is removed, discarded and replaced with 20 ml of fresh medium (Iscoves+5% calf serum). The transfection mix is added and the plate is swirled. On Day 2, the medium is replaced with 30 ml of Iscoves medium containing 1% FBS (fetal bovine serum) to minimize the amount of bovine Ig present. Supernatants are collected from the cells on Days 4, 6 and 13 by removing the medium and replacing it with 30 ml of fresh Iscoves containing 1% FBS.

The cloning and expression of an anti-HER2/neu-IFN-α fusion protein is illustrated herein in Example 1, while the cloning and expression of an anti-CD20-IFN-α fusion protein is shown in Example 2.

One of skill would recognize these expression methods are illustrative and not limiting. Modifications can be made to the fusion proteins described herein without diminishing their activity/efficacy. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

Other modifications can be made to increase serum half-life and/or bioavailability. Such modifications include, but are not limited to the incorporation of D amino acids (especially in the linker), the use of non-naturally occurring amino acids, pegylation of the fusion protein, and the like.

D. Other Multi-Valent Targeting Moieties.

In certain embodiments this invention contemplates the use of multivalent, preferably trivalent, quadravalent, pentavalent or greater targeting moieties (e.g., anti-HER2/neu antibodies, anti-CD20 antibodies, etc.) to target the interferon to a target cell.

For example, multivalent anti-HER2/neu moieties can be produced by any of a number of methods. For example, linkers having three, four, or more reactive sites can be reacted with anti-HER2/neu antibodies to form a trimer or greater conjugate.

In certain embodiments, phage display, yeast display, bacterial display, or other display systems can be used to express and display multiple copies (e.g., at least 3, at least 4, at least 5, at least 6 copies, etc.) of a targeting (e.g., anti-HER2/neu, anti-CD20, etc.) antibody and thereby effectively provide a multivalent targeting moiety.

In certain embodiments the use of diabodies and triabodies (e.g., comprising two domains that bind CD-20 or one domain that binds CD20 and another domain that binds, for example, a different member of the EGFR receptor family (e.g., EGFR, HER3, etc.). Typically, diabodies comprise a heavy (VH) chain variable domain connected to a light chain variable domain (VL) on the same polypeptide chain (VH-VL) connected by a peptide linker that is too short to allow pairing between the two domains on the same chain. This forces pairing with the complementary domains of another chain and promotes the assembly of a dimeric molecule with two functional antigen binding sites (see, e.g., Holliger et al. (1993) *Proc. Natl. Acad. Sci.*, 90: 6444-6448). In certain embodiments to construct bispecific diabodies the V-domains of antibody A and antibody B are fused to create the two chains VHA-VLB, VHB-VLA. Each chain is inactive in binding to antigen, but recreates the functional antigen binding sites of antibodies A and B on pairing with the other chain.

II. Combined Uses.

The chimeric constructs of this invention are useful for inhibiting the growth and/or proliferation of target cells (e.g., cancer cells). In various embodiments the chimeric moieties can be used to inhibit disease progression, to shrink tumor size, and/or to stabilize regression/remission.

Particularly, in the treatment of cancer, the compositions and methods of the invention may also include additional therapeutic and/or pharmacologically acceptable agents. For instance, the compositions or methods may involve other agents for the treatment of cancer. Such agents include, but are not limited to alkylating agents (e.g., mechlorethamine (Mustargen), cyclophosphamide (Cytoxan, Neosar), ifosfamide (Ifex), phenylalanine mustard; melphalen (Alkeran), chlorambucol (Leukeran), uracil mustard, estramustine (Emcyt), thiotepa (Thioplex), busulfan (Myerlan), lomustine (CeeNU), carmustine (BiCNU, BCNU), streptozocin (Zanosar), dacarbazine (DTIC-Dome), cis-platinum, cisplatin (Platinol, Platinol AQ), carboplatin (Paraplatin), altretamine (Hexalen), etc.), antimetabolites (e.g. methotrexate (Amethopterin, Folex, Mexate, Rheumatrex), 5-fluoruracil (Adrucil, Efudex, Fluoroplex), floxuridine, 5-fluorodeoxyuridine (FUDR), capecitabine (Xeloda), fludarabine: (Fludara), cytosine arabinoside (Cytaribine, Cytosar, ARA-C), 6-mercaptopurine (Purinethol), 6-thioguanine (Thioguanine), gemcitabine (Gemzar), cladribine (Leustatin), deoxycoformycin; pentostatin (Nipent), etc.), antibiotics (e.g. doxorubicin (Adriamycin, Rubex, Doxil, Daunoxome-liposomal preparation), daunorubicin (Daunomycin, Cerubidine), idarubicin (Idamycin), valrubicin (Valstar), mitoxantrone (Novantrone), dactinomycin (Actinomycin D, Cosmegen), mithramycin, plicamycin (Mithracin), mitomycin C (Mutamycin), bleomycin (Blenoxane), procarbazine (Matulane), etc.), mitotic inhibitors (e.g. paclitaxel (Taxol), docetaxel (Taxotere), vinblatine sulfate (Velban, Velsar, VLB), vincristine sulfate (Oncovin, Vincasar PFS, Vincrex), vinorelbine sulfate (Navelbine), etc.), chromatin function inhibitors (e.g., topotecan (Camptosar), irinotecan (Hycamtin), etoposide (VP-16, VePesid, Toposar), teniposide (VM-26, Vumon), etc.), hormones and hormone inhibitors (e.g. diethylstilbesterol (Stilbesterol, Stilphostrol), estradiol, estrogen, esterified estrogens (Estratab, Menest), estramustine (Emcyt), tamoxifen (Nolvadex), toremifene (Fareston) anastrozole (Arimidex), letrozole (Femara), 17-OH-progesterone, medroxyprogesterone, megestrol acetate (Megace), goserelin (Zoladex), leuprolide (Leupron), testosteraone, methyltestosterone, fluoxmesterone (Android-F, Halotestin), flutamide (Eulexin), bicalutamide (Casodex), nilutamide (Nilandron), etc.), inhibitors of synthesis (e.g., aminoglutethimide (Cytadren), ketoconazole (Nizoral), etc.), immunomodulators (e.g., rituximab (RITUXAN®), trastuzumab (Herceptin), denileukin diftitox (Ontak), levamisole (Ergamisol), bacillus Calmette-Guerin, BCG (TheraCys, TICE BCG), interferon alpha-2a, alpha 2b (Roferon-A, Intron A), interleukin-2, aldesleukin (ProLeukin), etc.) and other agents such as 1-aspariginase (Elspar, Kidrolase), pegaspasgase (Oncaspar), hydroxyurea (Hydrea, Doxia), leucovorin (Wellcovorin), mitotane (Lysodren), porfimer (Photofrin), tretinoin (Veasnoid), and the like.

III. Pharmaceutical Compositions.

In order to carry out the methods of the invention, one or more active agents (chimeric moieties) of this invention are administered, e.g. to an individual diagnosed as having a cancer. The active agent(s) can be administered in the "native" form or, if desired, in the form of salts, esters, amides, prodrugs, derivatives, and the like, provided the salt, ester, amide, prodrug or derivative is suitable pharmacologically, i.e., effective in the present method. Salts, esters, amides, prodrugs and other derivatives of the active agents can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

For example, acid addition salts are prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

Preparation of esters typically involves functionalization of hydroxyl and/or carboxyl groups which may be present within the molecular structure of the drug. The esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides and prodrugs can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety that results in a compound that is therapeutically inactive until modified by an individual's metabolic system.

The active agents identified herein are useful for parenteral, topical, oral, nasal (or otherwise inhaled), rectal, or local administration, such as by aerosol or transdermally, for prophylactic and/or therapeutic treatment of one or more of the pathologies/indications described herein (e.g., atherosclerosis and/or symptoms thereof). The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectables, implantable sustained-release formulations, lipid complexes, etc.

The active agents of this invention are typically combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

The excipients are preferably sterile and generally free of undesirable matter. These compositions may be sterilized by conventional, well-known sterilization techniques.

In therapeutic applications, the compositions of this invention are administered to a patient suffering e.g. from a cancer, or at risk of cancer (e.g. after surgical removal of a primary tumor) in an amount sufficient to prevent and/or cure and/or or at least partially prevent or arrest the disease and/or its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the active agents of the formulations of this invention to effectively treat (ameliorate one or more symptoms) the patient.

The concentration of active agent(s) can vary widely, and will be selected primarily based on fluid volumes, viscosities, body weight and the like in accordance with the particular mode of administration selected and the patient's needs. Concentrations, however, will typically be selected to provide dosages ranging from about 0.1 or 1 mg/kg/day to about 50 mg/kg/day and sometimes higher. Typical dosages range from about 3 mg/kg/day to about 3.5 mg/kg/day, preferably from about 3.5 mg/kg/day to about 7.2 mg/kg/day, more preferably from about 7.2 mg/kg/day to about 11.0 mg/kg/day, and most preferably from about 11.0 mg/kg/day to about 15.0 mg/kg/day. In certain preferred embodiments, dosages range from about 10 mg/kg/day to about 50 mg/kg/day. In certain embodiments, dosages range from about 20 mg to about 50 mg given orally twice daily. It will be appreciated that such dosages may be varied to optimize a therapeutic regimen in a particular subject or group of subjects.

In certain preferred embodiments, the active agents of this invention are administered orally (e.g. via a tablet) or as an injectable in accordance with standard methods well known to those of skill in the art. In other preferred embodiments, the peptides, may also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

In certain embodiments elevated serum half-life can be maintained by the use of sustained-release protein "packaging" systems. Such sustained release systems are well known to those of skill in the art. In one preferred embodiment, the ProLease™ biodegradable microsphere delivery system for proteins and peptides (see, e.g., Tracy (1998) *Biotechnol. Prog.* 14: 108; Johnson et al. (1996), *Nature Med.* 2: 795; Herbert et al. (1998), *Pharmaceut. Res.* 15, 357) a dry powder composed of biodegradable polymeric microspheres containing the active agent in a polymer matrix that can be compounded as a dry formulation with or without other agents.

The ProLease™ microsphere fabrication process was specifically designed to achieve a high encapsulation efficiency while maintaining integrity of the active agent. The process consists of (i) preparation of freeze-dried drug particles from bulk by spray freeze-drying the drug solution with stabilizing excipients, (ii) preparation of a drug-polymer suspension followed by sonication or homogenization to reduce the drug particle size, (iii) production of frozen drug-polymer microspheres by atomization into liquid nitrogen, (iv) extraction of the polymer solvent with ethanol, and (v) filtration and vacuum drying to produce the final dry-powder product. The resulting powder contains the solid form of the active agents, which is homogeneously and rigidly dispersed within porous polymer particles. The polymer most commonly used in the process, poly(lactide-co-glycolide) (PLG), is both biocompatible and biodegradable.

Encapsulation can be achieved at low temperatures (e.g., −40° C.). During encapsulation, the protein is maintained in the solid state in the absence of water, thus minimizing water-induced conformational mobility of the protein, preventing protein degradation reactions that include water as a reactant, and avoiding organic-aqueous interfaces where proteins may undergo denaturation. A preferred process uses solvents in which most proteins are insoluble, thus yielding high encapsulation efficiencies (e.g., greater than 95%).

In another embodiment, one or more components of the solution can be provided as a "concentrate", e.g., in a storage container (e.g., in a premeasured volume) ready for dilution, or in a soluble capsule ready for addition to a volume of water.

The foregoing formulations and administration methods are intended to be illustrative and not limiting. It will be appreciated that, using the teaching provided herein, other suitable formulations and modes of administration can be readily devised.

IV. Kits.

In certain embodiments, this invention provides for kits for the treatment a primary cancer and/or in an adjunct therapy. Kits typically comprise a container containing a chimeric moiety of the present invention (e.g., anti-HER2/neu-IFN-α, anti-CD20-IFN-α, etc.). The chimeric moiety can be present in a pharmacologically acceptable excipient.

In addition the kits can optionally include instructional materials disclosing means of use of the chimeric moiety (e.g. to treat a cancer and/or as an adjunct therapeutic). The instructional materials may also, optionally, teach preferred dosages, counter-indications, and the like.

The kits can also include additional components to facilitate the particular application for which the kit is designed. Thus, for example, and additionally comprise means for disinfecting a wound, for reducing pain, for attachment of a dressing, and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Anti-her2/Neu IgG3 and IFN-Alpha Fusion Protein Demonstrates Potent Apoptotic and Anti-Tumor Activities Against B Cell Lymphoma In the present study, we constructed a fusion protein consisting of anti-HER2/neu-IgG3 with the variable region of C6MH3-B1 (Schier et al. (1996) *J Mol. Biol.* 263: 551-567) and IFN-α, and investigated its effect on a murine B cell lymphoma, 38C13, expressing human HER2/neu (38C13/HER2). We chose to evaluate IFN-α targeting to tumor in this model given the responsiveness of this B cell lymphoma to IFN-α (Reid et al. (1989) *Cancer Res.* 49: 4163-4169). Fusion of IFN-α to an Ab significantly increased its in vivo half-life. Anti-HER2/neu-IgG3-IFN-α was found to be efficient in inhibiting the growth in vivo of both small and established 38C13/HER2 tumors with no signs of systemic toxicity observed at effective doses. Anti-HER2/neu-IgG3-IFN-α inhibited the growth of and induced apoptosis in 38C13/HER2 cells. These results indicate that fusion of IFN-α to a tumor-specific antibody results in an agent effective for the treatment of B cell lymphoma.

Materials and Methods

Cell Lines and Culture Conditions

38C13 is a highly malignant murine B cell lymphoma derived from C3H/HeN mice. The construction and characterization of 38C13 expressing human HER2/neu (38C13/HER2) has been previously described (Dela Cruz et al. (2000) Immunol. 165: 5112-5121). Both 38C13 and 38C13/HER2 were cultured in IMDM (Irvine Scientific) supplemented with 2 mM L-glutamine, 10 U/ml penicillin, 10 microg/ml streptomycin (GPS; Sigma-Aldrich) and 10% calf serum (Atlanta Biologicals). Murine myeloma P3X63Ag8.653 (American Type Culture Collection) and its derivatives expressing anti-HER2 IgG3-IFN-α or IgG3-IFN-α were grown in IMDM supplemented with 10% calf serum and GPS. L929 fibroblasts (American Type Culture Collection) were cultured in IMDM with 5% calf serum and GPS. The construction and characterization of CT26/HER2, a murine colon adenocarcinoma cell line overexpressing human HER2/neu, has been previously described (Id.). CT26/HER2 was cultured in IMDM with 5% calf serum and GPS.

Plasmid Construction

The H and L chain variable regions of C6MH3-B1, an anti-human HER2/neu scFv were inserted into the human γ3 H chain (pAH4802) and κ L chain (pAG4622) expression vectors, respectively (Coloma et al. (1992) Immunol. Methods 152: 89-104), and used to produce chimeric IgG3 of this specificity. To construct the anti-human HER2/neu-IgG3 (C6MH3-B1)-IFN-α fusion protein, PCR was first used to introduce a BamH1 restriction enzyme site upstream and XbaI restriction enzyme site downstream of the mature murine IFN-α gene amplified by PCR from genomic DNA of BALB/c mice with the forward primer 5'-CGC GGA TCC TGT GAC CTG CCT CAG ACT C-3 (SEQ ID NO:79) and the reverse primer 5'-GCT CTA GAT CAT TTC TCT TCT CTC AGT CTT C-3 (SEQ ID NO:80). The final PCR product was ligated into a TA vector. The resulting vector, after sequencing, was digested with BamH1 and XbaI to release the DNA fragment which was inserted into the vector pAH9612 containing the IgG3 constant region with the C6MH3-B1 H chain variable region and a GGGGSGGGGSGGGGS (SEQ ID NO:5) peptide linker at the end of $C_H3$. The final PCR product, pAH9616, contained anti-HER2/neu-IgG3 followed by a GGGGSGGGGSGGGGS (SEQ ID NO: 5) peptide linker and murine IFN-α.

Production and Purification of Recombinant Proteins

Plasmid encoding the IgG3 H chain with the C6MH3-B1 variable region fused to IFN-α was transfected into P3X63Ag8.653 cells expressing either L chain with the C6MH3-B1 variable region (Huang and Morrison (2005) J. Pharmacol. Exp. Ther. 316: 983-991) to produce anti-HER2/neu-IgG3-IFN-α or nonspecific L chain (4D5; Genentech) (Dela Cruz et al. (2000) Immunol. 165: 5112-5121) to produce IgG3-IFN-α by electroporation with a pulse of 960 μFd capacitance and 0.2 V. Transfectants producing anti-HER2/neu(C6MH3-B1)-IgG3, anti-HER2/neu(C6MH3-B1)-IgG3-IFN-α, or IgG3-IFN-α were selected and characterized as previously described (Id.). Anti-HER2/neu (C6MH3-B1)-IgG3 was purified from culture supernatants using protein G immobilized on Sepharose 4B fast flow (Sigma-Aldrich), and anti-HER2/neu(C6MH3-B1)-IgG3-IFN-α and IgG3-IFN-α were purified from culture supernatants using protein A immobilized on Sepharose 4B fast flow (Sigma-Aldrich). Purity and integrity were assessed by Coomassie blue staining of proteins separated by SDS-PAGE. The international reference standard for mouse IFN-α provided by the National Institutes of Health was used to determine IFN activity of the fusion proteins. rIFN-α was obtained from PBL Biomedical Laboratories.

FPLC Analysis of IgG3-IFN-α Fusion Protein

To determine whether the fusion protein exists as monomer and/or polymers in solution, 100 μg of IgG3-IFN-α mixed with 400 μg of OVA to provide an internal control was analyzed by gel filtration on a 30×1.5-cm Superose 6 column attached in a fast protein liquid chromatography (FPLC) using PBS and 0.5 ml/min flow rate. Gel filtration on the same column of IgA2m that exists predominantly as dimer Ab with a molecular mass of 350 kDa and a mixture of Miles IgG of molecular mass 150 kDa and OVA of molecular mass 45 kDa were used to provide molecular mass standards.

Flow Cytometry Analysis of HER2/Neu-Binding Activity

To detect the reactivity of various anti-HER2/neu fusion proteins with CT26/HER2 cells, $1 \times 10^6$ cells were incubated at 4° C. for 1 h with 10 pM of the fusion protein. For some experiments, the fusion proteins were preincubated with 900 U of heparin at 4° C. for 17 h before incubation with CT26/HER2 cells. Cells were then reacted with biotinylated rat anti-human IgG (BD Biosciences) diluted 1/100. The bound biotinylated Abs were detected with PE-labeled streptavidin (BD Biosciences) diluted 1/1500 and cells were analyzed by flow cytometry using a FACScan (BD Biosciences).

IFN-α Antiviral Activity

The L-929 fibroblast cell line sensitive to the vesicular stomatitis virus (VSV) infection was used to quantify the biological activity of IFN-α. L-929 cells were plated in a 96-well tissue culture plate (Falcon; BD Biosciences) at a density of $4 \times 10^4$ cells/well and incubated overnight at 37° C. in a 5% CO2 atmosphere. Afterward, serial dilutions of different IFN-α fusion proteins or standard IFN-α (international reference standard for mouse IFN-α; National Institutes of Health, Bethesda, Md.) were added and the plate was incubated at 37° C. for 24 h. Four thousand PFU of VSV was then added to each well and incubated at 37° C. for another 48 h. Surviving adherent cells were stained with 50 μl of crystal violet (0.05% in 20% ethanol) for 10 min. The plates were washed with water and the remaining dye was solubilized by the addition of 100 μl of 100% methanol. Plates were read using an ELISA reader at 595 nm.

Assay for the Antiproliferative Effect of Anti-HER2/Neu-IgG3-IFN-α

In brief, 38C13 or 38C13/HER2 cells were plated in a 96-well tissue culture plate at a density of $1.25 \times 10^4$ cells/well and serial dilutions of different fusion proteins were added. The plates were then incubated for 48 h at 37° C. in a 5% CO2 atmosphere. Plates were developed by addition of 20 μl of MTS solution (Promega) and analyzed at 490 nm using an ELISA reader. Inhibition of proliferation (percent) was calculated as: 100×[(ODexp−ODblank)/(ODmedium−ODblank)]×100.

Assay for Apoptosis

In brief, $1 \times 10^6$ cells were treated with different fusion proteins for 72 h. The cells were then washed with ice-cold PBS. The annexin V/propidium iodide (PI) assay was conducted following procedures suggested by the manufacturer using the Vybrant Apoptosis Assay Kit 2 (Molecular Probes).

Proliferation of CFSE-Labeled 38C13/HER2 Tumor Cells

In brief, $1 \times 10^6$ cells were incubated with 2.5 μM CFSE (Molecular Probes) for 10 min at 37° C. Cells were then treated with 1 nM of different fusion proteins for 48 h and analyzed by flow cytometry following procedures suggested by the manufacturer using the CellTrace CFSE Cell Proliferation Kit (Molecular Probes).

Mice

Female C3H/HeN mice 6-8 wk of age obtained from Taconic Farms were used. Animals were housed in a facility using autoclaved polycarbonate cages containing wood-shaving bedding. The animals received food and water ad libitum. Artificial light was provided under a 12/12-h light/dark cycle. The temperature of the facility was 20° C. with 10-15 air exchanges per hour.

Half-Life

Murine rIFN-α (PBL Biomedical Laboratories), IgG3-IFN-α, and anti-HER2/neu-IgG3-IFN-α were iodinated to 10 µCi/µg with $^{125}$I using Iodo-Beads (Pierce) according to the manufacturer's protocol. Mice were injected i.p. with 66 µCi of $^{125}$I-labeled proteins. At various intervals after injection of $^{125}$I-labeled rIFN-α, IgG3-IFN-α, or anti-HER2/neu-IgG3-IFN-α, residual radioactivity was measured using a mouse whole body counter (Wm. B. Johnson and Associates).

Tumor Challenge and Ab Therapy

C3H/HeN mice received 1000 38C13/HER2 tumor cells s.c. Treatment was given by i.p. injection either 1, 3, and 5 days or 12, 13, and 14 days after tumor challenge. Tumors were measured every other day, and the tumor volume (in cubic millimeters) was approximated using the following formula: [length (mm)×width (mm)×width (mm)]/2 (Carlsson et al. (1983)*J. Cancer Res. Clin. Oncol.* 105: 20-23). Animals were observed until the length of the s.c. tumor reached 15 mm or until any mouse was observed to be suffering or appeared to be moribund. Animals under these conditions were euthanized humanely according to institutional policy.

Western Blot Analysis and Ab

In brief, 38C13/HER2 cells were treated with different fusion proteins for the indicated times, washed with ice-cold PBS, and lysed on ice for 10 min in lysis buffer (0.125% Nonidet P-40, 0.875% Brij 97, 10 mM Tris-HCl (pH 7.5), 2 mM EDTA, 0.15 M NaCl, 0.4 mM Na3VO4, 0.4 mM NaF, 1 mM PMSF, 2.5 µM leupeptin, and 2.5 µM aprotinin). Cell lysates were clarified at 10,000×g for 10 min at 4° C. Protein samples were then boiled in sample buffer before separation on 8% SDS-PAGE gels and transferred onto polyvinylidene fluoride microporous membranes (Millipore). After blocking with 3% BSA in 150 mM NaCl, 50 mM Tris-HCl (pH 7.6; TBS) for 1 h at room temperature, blots were probed with the indicated primary Abs overnight at 4° C. The blots were then washed three times at room temperature with 0.05% Tween 20 in TBS, incubated with the appropriate secondary Abs conjugated with HRP, and detected by a peroxidase-catalyzed ECL detection system (ECL; Pierce). Polyclonal rabbit antiphosphoSTAT1 was obtained from Cell Signaling Technology. Polyclonal HRP-conjugated donkey anti-rabbit IgG was obtained from Amersham Biosciences. Polyclonal rabbit anti-GAPDH was obtained from Abcam.

Statistical Analysis

Statistical analyses were performed using a two-tailed Student's t test for in vitro studies and log-rank (Mantel-Cox) analysis for animal survival curves.

Results

Production and Characterization of Anti-HER2/Neu-IgG3-IFN-α

Figure 2A:
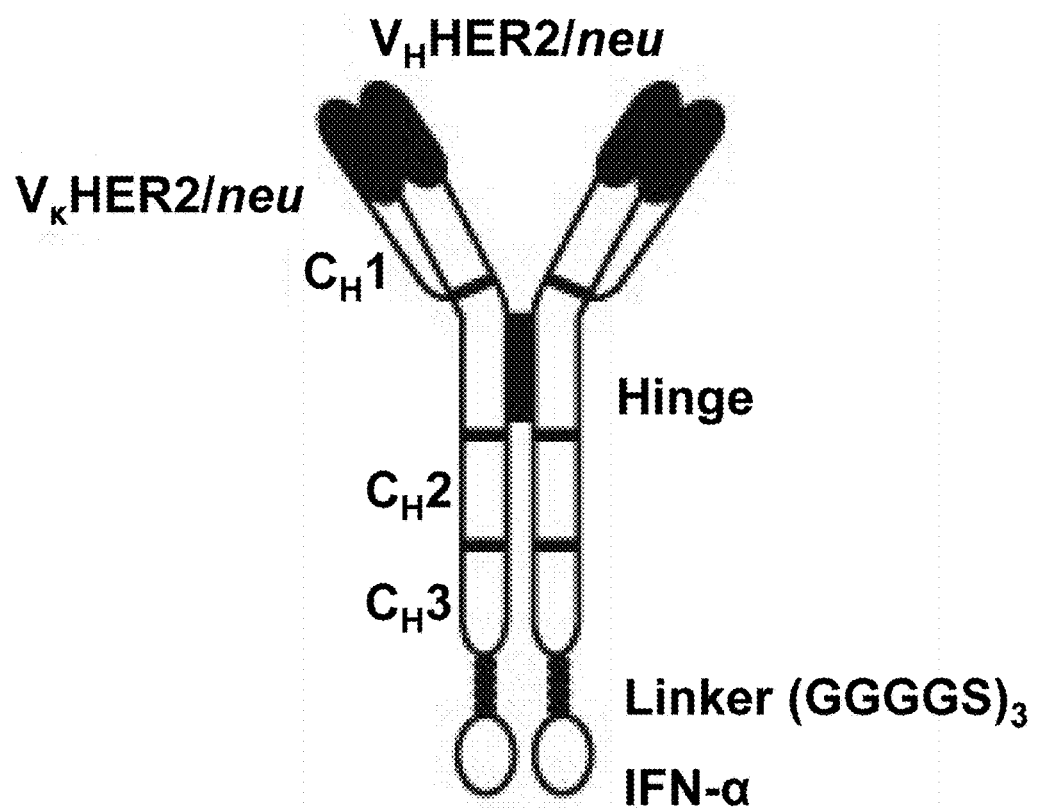
FIGS. 2A, 2B, 2C, and 2D illustrate the construction and characterization of anti-HER2/neu IgG3-IFN-α.
Figure 2B:
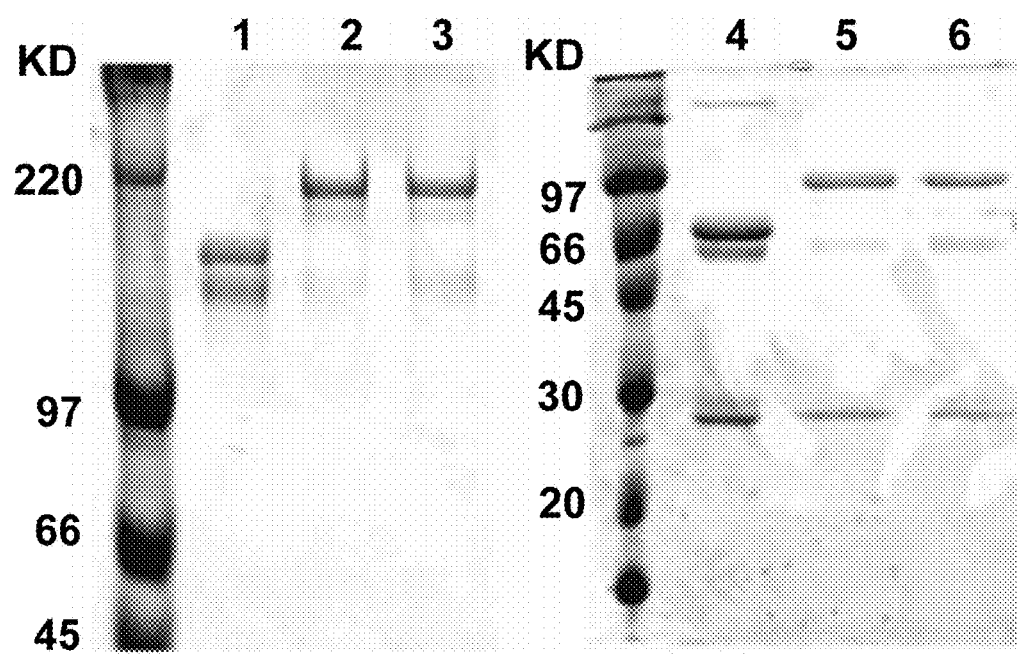

The construction and expression of anti-HER2/neu-IgG3 with the C6MH3-B1 (20) variable region has been described previously (Huang and Morrison (2005) *J. Pharmacol. Exp. Ther.* 316: 983-991). The amino-terminal end of mature murine IFN-α was fused to the carboxyl-terminal end of anti-HER2/neu-IgG3 separated by a flexible [(Gly$_4$)Ser]$_3$ (SEQ ID NO:5) linker (FIG. 2A). An identical fusion protein, IgG3-IFN-α, lacking HER2/neu specificity was constructed by replacing the C6MH3-B1 L chain with the 4D5 (rhuMab HER2, herceptin; Genentech) L chain. The proteins purified from culture supernatants using protein G were analyzed by SDS-PAGE under nonreducing and reducing conditions (FIG. 2B). In the absence of reducing agents, anti-HER2/neu-IgG3 (FIG. 2B, lane 1) migrates with a molecular mass of 170 kDa, whereas anti-HER2/neu-IgG3-IFN-α (FIG. 2B, lane 2) and IgG3-IFN-α (FIG. 2B, lane 3) are 210 kDa, the size expected for a complete IgG3 with two molecules of murine IFN-α attached (FIG. 2A). After treatment with the reducing agent, L chains migrating with a molecular mass of 25 kDa are seen for these proteins (FIG. 2B, lanes 4-6). However, the anti-HER2/neu-IgG3 has an H chain with a molecular mass of 60 kDa (FIG. 2B, lane 4), whereas IgG3-IFN-α (FIG. 2B, lane 5) and anti-HER2/neu-IgG3-IFN-α (FIG. 2B, lane 6) have an H chain with a molecular mass of 80 kDa as expected. The lower band in lane 1 (FIG. 2B) is bovine IgG which also bound to the protein G column; the bovine H and L chains are also seen in lane 4 (FIG. 2B) and to a lesser degree in lanes 5 and 6 (FIG. 2B). FPLC analysis showed that the IgG3-IFN-α fusion protein existed as a monomer in solution (data not shown).

Ag Binding and Antiviral Activity of Anti-HER2/Neu-IgG3-IFN-α

Figure 2C:
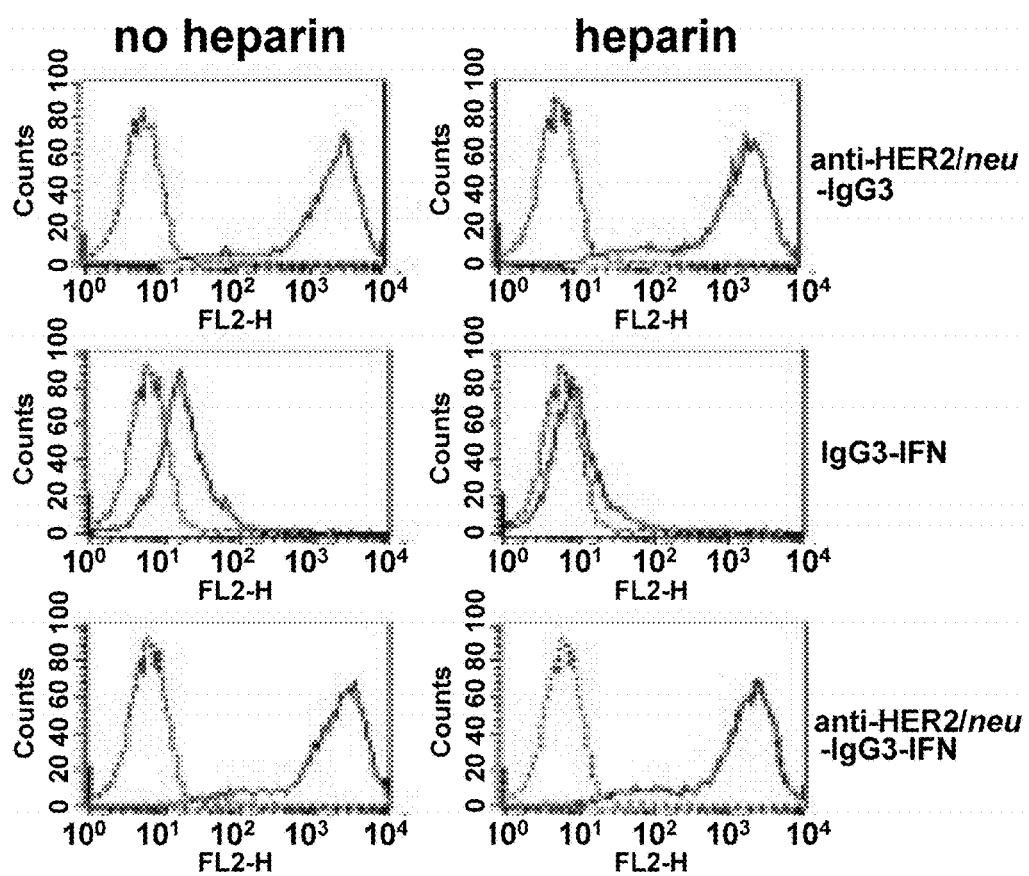

Both anti-HER2/neu-IgG3 and anti-HER2/neu-IgG3-IFN-α bound CT26/HER2 cells, which express high levels of human HER2/neu, while IgG3-IFN-α bound CT26/HER2 weakly (FIG. 2C). Many cytokines including IL-1, IL-2, IL-6 (Ramsden and Rider (1992) *Eur. J. Immunol.* 22: 3027-3031) and IFN-α (Fernandez-Botran et al. (1999) *Cytokine* 11: 313-325) have been shown to interact with heparin. To determine whether the weak interaction between IgG3-IFN-α and CT26/HER2 is due to the heparin binding, proteins were incubated with heparin before the addition to CT26/HER2. Heparin inhibited the binding of IgG3-IFN-α to CT26/HER2 cells but did not inhibit the binding of anti-HER2/neu-IgG3 and anti-HER2/neu-IgG3-IFN-α (FIG. 2C).

Figure 2D:
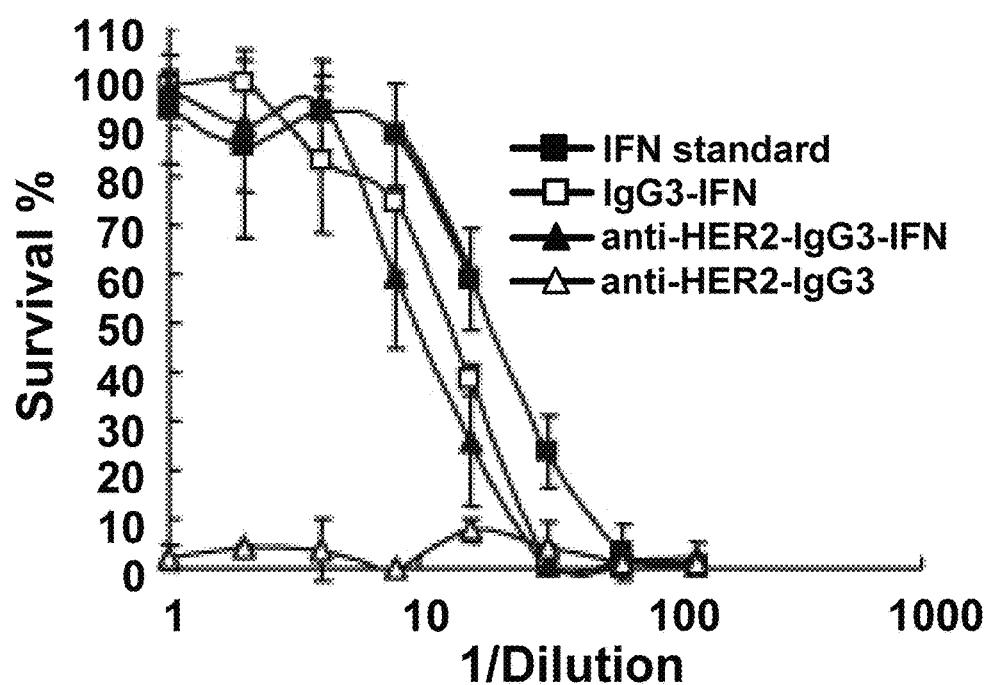

These results demonstrated that anti-HER2/neu-IgG3-IFN-α retained its ability to bind Ag and IgG3-IFN-α does not recognize HER2/neu. The L-929 fibroblast cell line sensitive to VSV infection was used to quantify the IFN-α biological activity of the fusion proteins in comparison to an IFN-α standard. Both anti-HER2/neu-IgG3-IFN-α and IgG3-IFN-α exhibited ~2400 U of IFN-α activity/µg activity against VSV-induced cytotoxicity in L-929 cells, while anti-HER2/neu-IgG3 exhibited no anti-viral activity (FIG. 2D).

In Vivo Antitumor Activity of Fusion Proteins

Figure 3A:
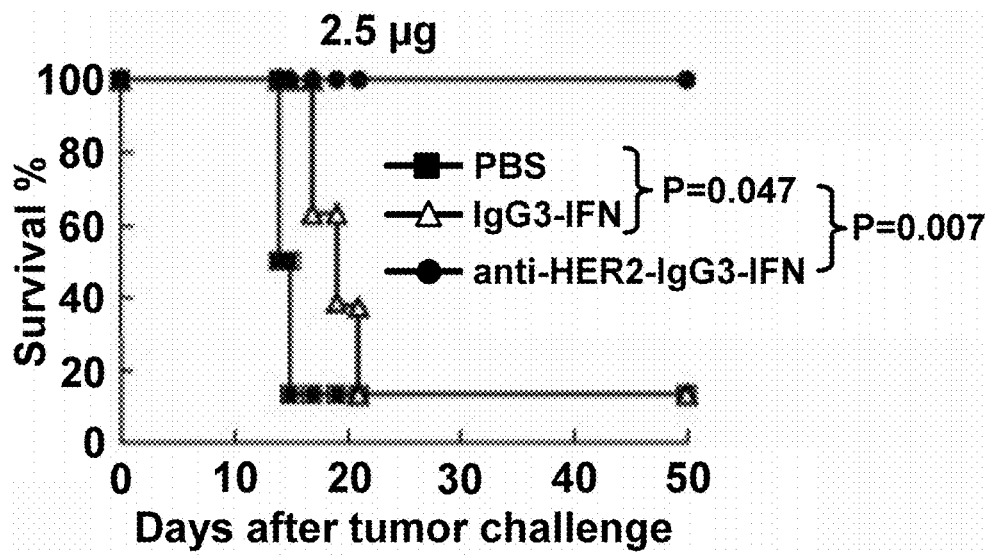
FIGS. 3A and 3B show in vivo antitumor activity of different IFN-α fusion proteins and rIFN-α. C3H/HeN mice were s.c. challenged with 1×10$^3$ 38C13/HER2 cells and i.p. treated with either 2.5 μg (FIG. 3A) or 1 (FIG. 3B) of the indicated proteins at days 1, 3, and 5 after tumor challenge. The tumor volume of each mouse is measured. Animals were observed until the diameter of the s.c. tumor reached 15 mm.
Figure 3B:
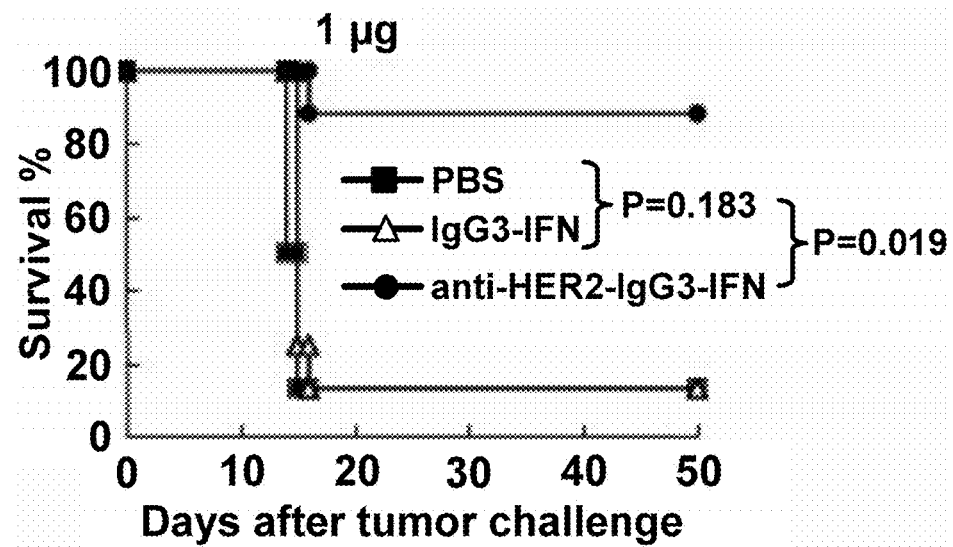

To determine the in vivo anti-tumor activity of anti-HER2/neu-IgG3-IFN-α, syngeneic mice were inoculated s.c. with 1×10$^3$ 38C13/HER2 tumor cells and treated on days 1, 3, and 5 after tumor challenge by i.p. administration of different doses of protein (FIG. 3A-3B). Mice treated with 2.5 µg of IgG3-IFN-α showed some regression of tumor growth, with one (13%) of eight mice alive after 50 days (FIG. 3A). However, in vivo targeting of IFN-α to tumors using a tumor-specific Ab dramatically improved its antitumor effect. All mice treated with 2.5 µg (FIG. 3A) of anti-HER2/neu-IgG3-IFN-α remained tumor free 50 days after tumor challenge (p=0.0048 compared with PBS control), and none of the treated mice showed evidence of toxicity. Thus, targeting of IFN-α to the tumor cell surface resulted in significant antitumor activity compared with IFN-α linked to a nonspecific Ab (p=0.007). Targeted anti-HER2/neu-IgG3-IFN-α continued to show potent antitumor activity when a lower dose was used. Seven (88%) of eight mice treated with 1 (FIG. 3B) of anti-HER2/neu-IgG3-IFN-α remained tumor free after 50 days. In marked contrast, at this lower dose mice treated with IgG3-IFN-α showed tumor growth similar to mice treated with PBS (p=0.183) and only one (13%) of eight mice survived. When the treatment was increased to three doses of 5 µg, both anti-HER2/neu-IgG3-IFN-α and IgG3-IFN-α were effective in preventing tumor growth (data not shown) undoubtedly reflecting the fact that 38C13 cells are sensitive to IFN-α treatment (Reid et al. (1989) *Cancer Res.* 49: 4163-4169; Basham et al. (1986) *J. Immunol.* 137: 3019-3024; Basham et al. (1988) *J. Immunol.* 141: 2855-2860). Tumor growth in mice treated with 5 µg of anti-HER2/neu-IgG3 Ab was the same as the PBS control, suggesting that Ab alone has no antitumor effect in vivo (data not shown). These results indicated that targeting of IFN-α to the tumor cells by a tumor-specific Ab can dramatically potentiate its effectiveness which was most clearly seen when low doses were administered. Importantly, this antitumor activity can be achieved without any evident toxicity.

IFN-α Fused to an Ab Results in Improved Antitumor Activity Compared with Free IFN-α

Figure 4A:
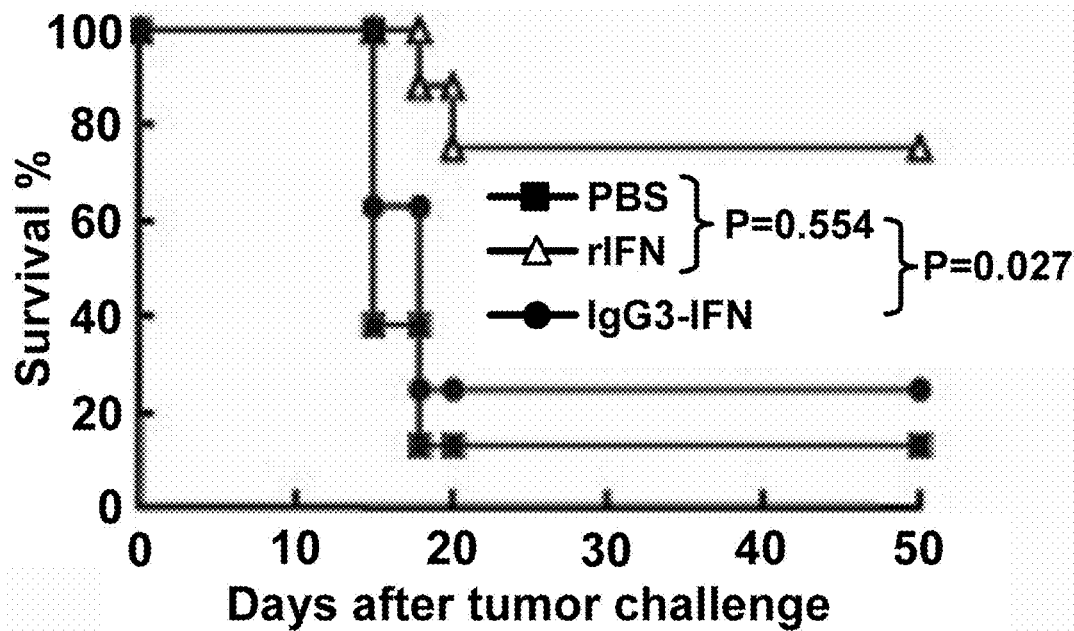
FIGS. 4A and 4B show that fusion of IgG3 to IFN-α improved its antitumor activity and increased its in vivo half-life.

As described above, we found that IFN-α fused to a non-tumor specific Ab exhibited antitumor activity. To compare its antitumor activity with that of soluble rIFN-α, mice were inoculated s.c. with $1 \times 10^3$ 38C13/HER2 tumor cells and treated 1 and 3 days after tumor challenge by i.p. administration of 9600 U (4 µg) of IgG3-IFN-α or 9600 U of rIFN-α (FIG. 4A). All mice treated with 9600 U of IgG3-IFN-α showed delayed tumor growth and 75% of the mice remained tumor free 50 days after tumor challenge (p=0.027). In contrast, mice treated with the same number of units of rIFN-α were not statistically different from PBS controls in their tumor growth pattern.

Figure 4B:
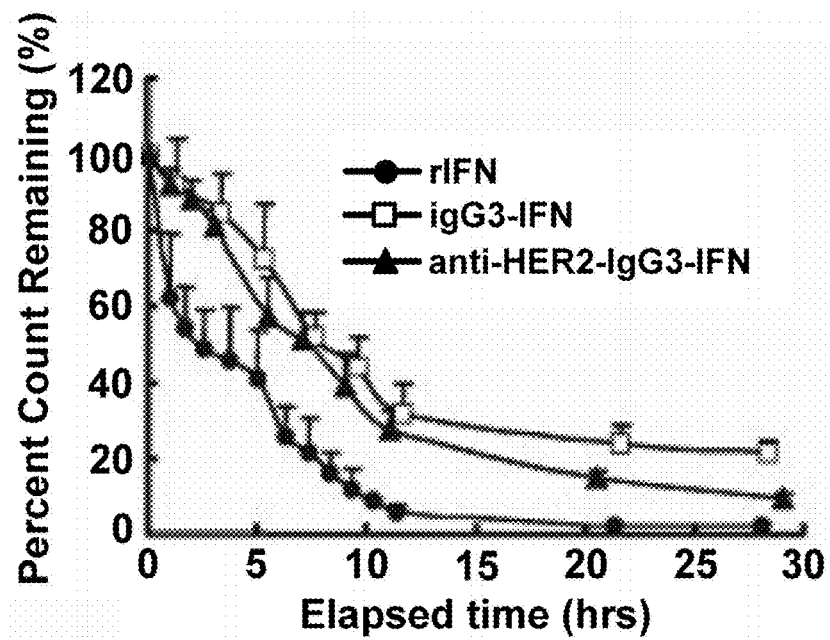

IFN-α has a very short in vivo half-life (Bailon et al. (2001) *Bioconjugate Chem.* 12: 195-202). In previous study, fusion of Abs to cytokines has been shown to increase their halflife (Dela Cruz et al. (2000) *Immunol.* 165: 5112-5121). The clearance of $^{125}$I-labeled rIFN-α, IgG3-IFN-α, or anti-HER2/neu-IgG3-IFN-α was examined in C3H/HeN mice. Mice were injected i.p. with 66 µCi of $^{125}$I-labeled proteins and the residual radioactivity was measured using a mouse whole body counter. rIFN-α was cleared rapidly with 50% eliminated by ~2.5 h (FIG. 4B). In contrast, both anti-HER2/neu-IgG3-IFN-α and IgG3-IFN-α exhibited significantly increased in vivo half-life with ~8 h required for elimination of 50% of the injected radioactivity. This increased half-life may contribute to the antitumor efficacy of the IFN-α fusion proteins. Thus, fusion of an IgG3 Ab to IFN-α can significantly improve its in vivo antitumor activity. However, this antitumor activity can be further improved by targeting the IFN-α to the tumor, making it effective at lower doses.

Anti-HER2/Neu-IgG3-IFN-α Inhibited Proliferation of Tumor Cells In Vitro

IFN-α has multiple activities including activation of the immune response and direct cytotoxicity against tumors. To investigate potential mechanisms of the antitumor effects seen using either anti-HER2/neu-IgG3-IFN-α or IgG3-IFN-α, the eight mice remaining tumor free (see FIG. 3A) were challenged with $1 \times 10^3$ 38C13/HER2 tumor cells. Surprisingly, all mice resembled untreated mice and quickly developed bulky tumors (data not shown). These results imply that under these experimental conditions of low tumor burden the IFN-α fusion proteins did not initiate a protective adaptive immune response, but instead the potent antitumor activity of the IFN-α fusion proteins is mediated either by the innate immune system or by a direct cytotoxic effect on tumor cells.

Figure 5A:
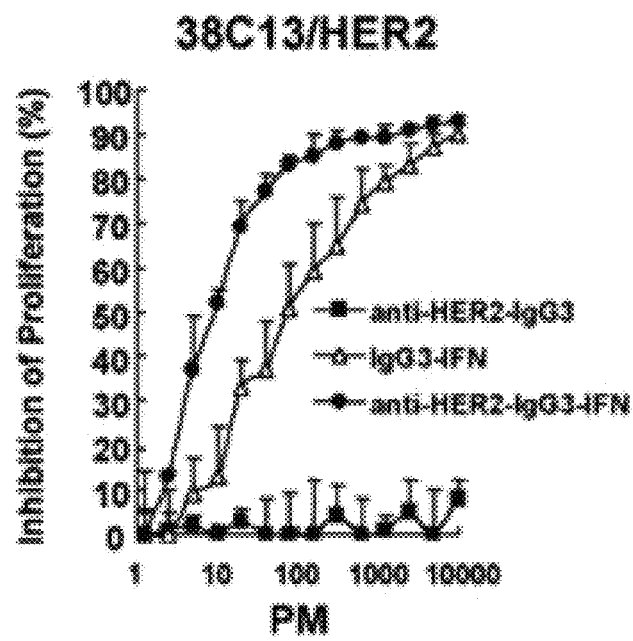
FIGS. 5A, 5B, 5C, and 5D show that IFN-α fusion proteins inhibited cell proliferation and induced apoptosis in 38C13/HER2 cells in vitro. IFN-α fusion proteins inhibited tumor cell proliferation. After incubation for 48 h with different doses of the different fusion proteins, viable 38C13/HER2 (FIG. 5A) or 38C13 (FIG. 5B) cells were measured using the MTS assay. These experiments were performed three times in triplicate; error bars, SD of the measurements.
Figure 5B:
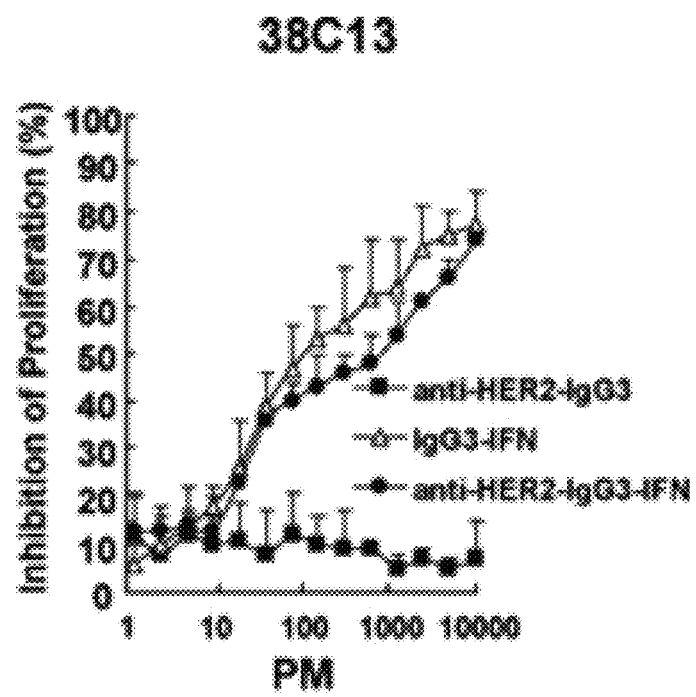

To determine whether IFN-α fusion proteins are directly cytotoxic to tumor cells, the 38C13/HER2 or parental 38C13 tumor cells were incubated with different proteins for 48 h and cell proliferation measured using the MTS assay. Treatment with anti-HER2/neu-IgG3 did not significantly inhibit the proliferation of either 38C13/HER2 or parental 38C13 tumor cells (FIGS. 5A and 5B). Although both anti-HER2/neu-IgG3-IFN-α and IgG3-IFN-α inhibited the proliferation of 38C13/HER2 tumor cells, anti-HER2/neu-IgG3-IFN-α was more effective than IgG3-IFN-α with IPSO values of 10 and 100 pM for anti-HER2/neu-IgG3-IFN-α and IgG3-IFN-α, respectively (FIG. 5A). In contrast, anti-HER2/neu-IgG3-IFN-α and IgG3-IFN-α exhibited similar antiproliferative activity against parental 38C13 tumor cells. These results provided evidence that IFN-α fusion proteins can directly inhibit the proliferation of the B cell lymphoma 38C13, and targeting IFN-α to tumor cells potentiated this effect.

Anti-HER2/Neu-IgG3-IFN-α Induced Apoptosis in Tumor Cells In Vitro

Figure 5C:
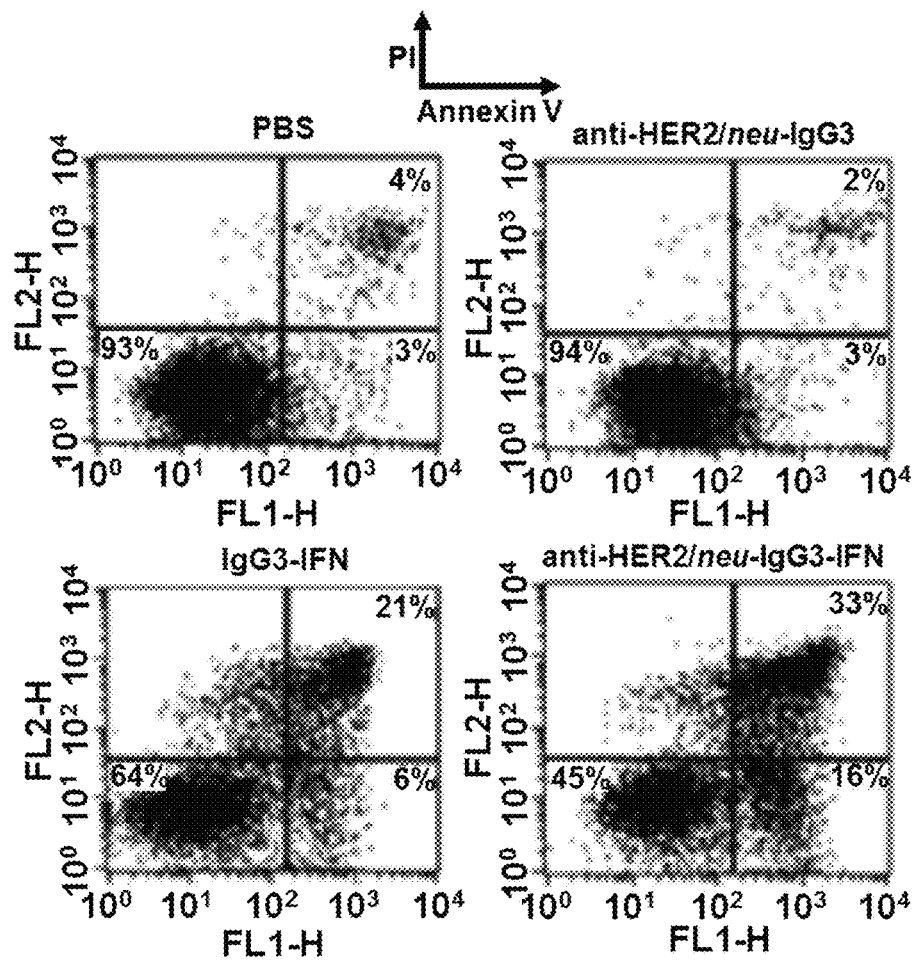

IFN-α signaling can induce apoptosis in some tumor cell lines. To determine whether apoptosis contributed to the antiproliferative effect we observed, 38C13/HER2 cells treated with different proteins were assayed for the translocation of phosphatidylserine from the inner to the outer leaflet of the plasma membrane using the annexin V-affinity assay (Koopman et al (1994) *Blood* 84: 1415-1420). Dead cells were stained by PI, which enters cells with a disrupted plasma membrane and binds to DNA. Compared with the PBS control, there was no increase in the number of dead cells (annexin V/PI bright, 2%) or early apoptotic cells (annexin V bright, 3%) following treatment with anti-HER2/neu-IgG3 (FIG. 5C). In contrast, when cells were treated with $IgG_3$-IFN-α, there was a significant increase in the number of dead cells (21%) and early apoptotic cells (6%). Treatment with anti-HER2/neu-IgG3-IFN-α resulted in a further increase in both the number of dead cells (33%) and early apoptotic cells (16%). These results indicated that IFN-α can induce apoptosis in 38C13/HER2 tumor cells, and that targeting IFN-α to tumor cells can markedly increase this effect.

Figure 5D:
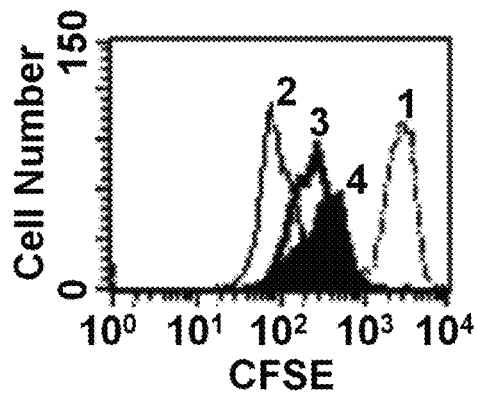

In addition to inducing apoptosis, IFN-α can directly inhibit the proliferation of tumor cells (Tiefenbrun et al. (1996) *Mol. Cell. Biol.* 16: 3934-3944). To determine whether both inhibition of proliferation and apoptosis were taking place in treated tumor cells, CF SE-labeled 38C13/HER2 cells were treated with different proteins for 48 h, the live cells were gated, and the level of CFSE was determined by flow cytometry. The CFSE signal in anti-HER2/neu-IgG3-treated cells (FIG. 5D, thin line) overlapped with the PBS-treated cells and was significantly less than that of cells fixed immediately after CFSE labeling (FIG. 5D, dotted line), indicating that anti-HER2/neu-IgG3 did not inhibit the proliferation of the 38C13/HER2. In contrast, IgG3-IFN-α significantly inhibited the proliferation of the surviving 38C13/HER2 cells (FIG. 5D, thick line), and targeting IFN-α to 38C13/HER2 cells by anti-HER2/neu-IgG3-IFN-α potentiated this effect (FIG. 5D, black area). These results indicated that although anti-HER2/neu-IgG3-IFN-α treatment did not result in complete cell death by 48 h, the surviving cells had a reduced ability to proliferate.

IFN-α Fusion Proteins Induce STAT1 Activation in Tumor Cells

Although engagement of the IFN-α receptor can initiate activation of multiple STAT proteins, STAT1 plays an obligate role in mediating IFN-α-dependent signaling (Meraz et al. (1996) Cell 84: 431-442). To investigate whether IFN-α fusion proteins initiate IFN-α signaling in 38C13/HER2 and that targeting IFN-α to tumor cells augments this effect, the phosphorylation of STAT1 following treatment was examined. As shown in FIG. 6A-6C, both anti-HER2/neu-IgG3-IFN-α and IgG3-IFN-α initiated robust STAT1 phosphorylation in 38C13/HER2 with STAT1 phosphorylation increasing 8-fold by 10 min. However, the phosphorylation of STAT1 induced by anti-HER2/neu-IgG3-IFN-α persisted for a longer period of time and greater STAT1 phosphorylation was seen at 30, 60, and 90 min in cells treated with anti-HER2/neu-IgG3-IFN-α. These results indicated that IFN-α fusion proteins can induce IFN-α signaling in 38C13 lymphoma cells and targeting IFN-α to tumor cells augments this effect.

Anti-HER2/Neu-IgG3-IFN-α Exhibited Potent Activity Against Established Tumors

Because anti-HER2/neu-IgG3-IFN-α exhibited potent cytotoxicity against 38C13/HER2 tumor cells, we investigated whether anti-HER2/neu-IgG3-IFN-α would be effective against established 38C13/HER2 tumors. Syngeneic mice were inoculated s.c. with $1\times10^3$ 38C13/HER2 tumor cells and i.p. treated with 5 (FIG. 7) of the indicated proteins on days 12, 13, and 14 after tumor challenge. The average tumor size on day 12 is 100 mm$^3$ and treatment with PBS or 10 μg of anti-HER2/neu-IgG3 (data not shown) did not inhibit tumor growth. Treatment with 5 μg of IgG3-IFN-α showed some effect in inhibiting tumor growth; however, all mice developed bulky tumors and none of them survived 32 days after tumor challenge. In contrast all mice treated with 5 μg of anti-HER2/neu-IgG3-IFN-α had delayed tumor growth, and three of eight mice had complete tumor regression and remained tumor free 50 days after tumor challenge (anti-HER2/neu-IgG3-IFN-α vs PBS, p=0.0001; anti-HER2/neu-IgG3-IFN-α vs IgG3-IFN-α, p=0.063). Thus, both IgG3-IFN-α and anti-HER2/neu-IgG3-IFN-α showed antitumor activity but anti-HER2/neu-IgG3-IFN-α was more effective in delaying tumor growth and complete tumor remission was observed only in mice treated with anti-HER2/neu-IgG3-IFN-α. When the treatment dose was increased to 10 μg of the fusion proteins, almost all mice treated with either anti-HER2/neu-IgG3-IFN-α or IgG3-IFN-α had complete tumor regression and remained tumor free after 50 days.

The mice that remained tumor free following treatment with three doses of 10 μg of fusion proteins were rechallenged with $1\times10^3$ 38C13/HER2 tumor cells on day 50. All mice remained tumor free (data not shown). These results suggest that an adaptive immune response with immunologic memory is initiated when larger, established tumors are treated with IFN-α fused to an Ab.

Discussion

Although rIFN-α has shown activity against B cell lymphoma and multiple myeloma, inconsistent efficacy and systemic toxicity have limited its usefulness (Oken (1992) Cancer 70: 946-948). The present work demonstrates that fusing IFN-α to an Ab improves its efficacy against tumors with further improvement seen when IFN-α is targeted to tumor cells by a tumor-specific Ab. This antitumor efficacy is seen without any apparent toxicity. These studies suggest that fusion of IFN-α with tumor-specific Ab may yield an effective biologic agent for the treatment of B cell lymphoma.

To test the hypothesis that directing IFN-α to tumor sites with Ab would result in improved efficacy, we chose a well-characterized murine B cell lymphoma engineered to express a common TAA, HER2/neu, to which Abs are available. Anti-HER2/neu-IgG3-IFN-α appears to be more effective in the treatment of the 38C13 B cell lymphoma than previously described immunotherapeutics, although in the present study a foreign Ag introduced by gene transduction was the target. Treatment with three 1 μg doses of anti-HER2/neu-IgG3-IFN-α beginning 1 day after tumor challenge appeared to be as effective in inhibiting tumor growth as treatment with 10 μg of anti-Id IgG1-IL-2 fusion protein for 5 days beginning 1 day after tumor challenge (Liu et al. (1998) Blood 92: 2103-2112). In addition, anti-HER2/neu-IgG3-IFN-α was effective against established tumors (FIG. 7) while anti-Id IgG1-IL-2 had little antitumor activity when treatment was begun either 3 or 7 days after tumor challenge (Id). The ability to cure established tumors also suggests that Ab-targeted IFN-α is a more powerful therapeutic agent than GM-CSF (Tao and Levy (1993) Nature 362: 755-758), CTLA-4 (Huang et al. (2000) Blood 96: 3663-3670), or CD40 ligand (Huang et al. (2004) Int. J. Cancer 108: 696-703) fused to the Id Ag since none of these vaccine strategies was effective against established tumors. Therefore, targeting IFN-α to tumor cells appears to be a promising approach for treating B cell lymphoma.

Targeting IFN-α to tumor cells with a tumor-specific Ab increases the antitumor efficacy of IFN-α. Anti-HER2/neu-IgG3-IFN-α is more effective in inhibiting proliferation and inducing apoptosis (FIG. 5A-5D) in 38C13/HER2 than IgG3-IFN-α and treatment with either 2.5 or 1 μg of anti-HER2/neu-IgG3-IFN-α was more effective in inhibiting growth of small tumors in vivo than the same doses of IgG3-IFN-α (FIGS. 3A and 3B). These results suggest that the tumor-specific Ab directs IFN-α to the tumor, thereby improving its therapeutic index with decreased systemic toxicity.

Remarkably, IgG3-IFN-α exhibits a more potent antitumor activity than rIFN-α (FIG. 4A). Although rIFN-α is effective in treatment of a variety of tumors (Gastl et al. (1985) Onkologie 8: 143-144; Atzpodien et al. (1991) Semin Oncol. 18: 108-112; Krown et al. (1992) J. Clin. Oncol. 10: 1344-1351), prolonged treatment with high doses is required to see effective antitumor activity in part because of the very short half-life of the cytokine. In this study, we demonstrated that fusion of an IgG3 Ab to IFN-α significantly increased its half-life (FIG. 4B), and this increased half-life may contribute to the increased in vivo antitumor activity of the fusion protein (FIG. 4A). In addition, the Fc region of the IgG3-IFN-α may help to target IFN-α to the Fc receptors present on B lymphoma cells and consequently increase the antitumor activity. Therefore, fusion of IFN-α to an IgG3 Ab may provide multiple advantages in improving the antitumor efficacy of IFN-α.

Although IFN-α has multiple activities, including activation of the immune response, it appears that direct cytotoxicity plays an important role in the potent antitumor activity of anti-HER2/neu-IgG3-IFN-α. Both IFN-α fusion proteins exhibited apoptotic and antiproliferative activities against 38C13/HER2 with tumor targeting significantly increasing these effects (FIG. 5A-5D). Although the IFN-α fusion proteins were very effective in treating small tumors (FIGS. 3A and 3B), none of the survivors developed an immune response that protected against second tumor challenge, suggesting that the direct cytotoxicity of the IFN-α fusion proteins was very effective in killing the tumor cells and that the adaptive immunity did not play a role when there was a small tumor burden. Because 38C13 is an extremely malignant B lymphoma cell line and mice injected with as few as 200 cells can develop bulky tumors within 20 days (Huang et al. (2000) *Blood* 96: 3663-3670), the IFN-α fusion proteins must be very effective in killing most of the inoculated tumor cells to result in long-term survivors. Multiple mechanisms, including down-regulation of NF-κB (Rath and Aggarwal (2001) *J. Interferon Cytokine Res.* 21: 523-528), induction of apoptosis by activating caspase-3 (Yanase et al. (2000) *J. Interferon Cytokine Res.* 20: 1121-1129), and up-regulation of both TRAIL and TRAIL receptors (Oshima et al. (2001) *Cytokine* 14: 193-201), have been shown to be involved in IFN-α-mediated cytotoxicity against tumor cells, and we would expect these mechanisms to contribute to the direct cytotoxicity against tumor cells seen with Ab-IFN-α fusion proteins. Consistent with this, we observed STAT1 activation following treatment of tumor cells with the fusion proteins (FIG. 6A-6C).

Although IFN-α fusion proteins failed to initiate a memory immune response when mice were treated beginning one day after tumor inoculation, IFN-α fusion proteins initiated an immune response that protected against second tumor challenge when mice were treated beginning 12 days after tumor inoculation. Therefore, IFN-α fusion proteins can activate protective adaptive immunity in the presence of a sizable tumor burden. Because IFN-α is capable of activating adaptive immunity via stimulation of DC differentiation and maturation (Santini et al. (2000) *J. Exp. Med.* 191: 1777-1788), it is possible that the established tumors provide more TAAs for DC activation in the presence of IFN-α. In addition, the foreign Ag human HER2/neu may contribute to the antitumor immunity by increasing the immunogenicity of the tumor cells in this model.

CD20, an Ag expressed by B cells, is expressed in most B cell lymphomas (Riley and Sliwkowski (2000) *Semin. Oncol.* 27: 17-24), and anti-CD20 (rituximab, Genentech) is one of the most successful cancer therapeutics, having tremendous efficacy against lymphoma with little toxicity (McLaughlin et al. (1998) *J. Clin. Oncol.* 16: 2825-2833). Although anti-HER2/neu IgG3-IFN-α is very effective against 38C13/HER2, HER2/neu is not normally expressed in lymphoma cells and therefore, it probably has limited therapeutic application in the treatment of lymphoma but should be effective in the treatments of cancers that express HER2/neu. In contrast, fusion of IFN-α to anti-CD20 is expected to yield a fusion protein effective against lymphoma with even greater antitumor activity by combining the antilymphoma activity of anti-CD20 and the potent immunostimulatory and cytotoxic activity of IFN-α in one protein. Additionally, IFN-α may further up-regulate CD20 expression as was seen in patients with B cell lymphoma following IFN-α treatment (Sivaraman et al. (2000) *Cytokines Cell Mol. Ther.* 6: 81-87). We are currently studying the effects of anti-CD20-IFN-α fusion proteins in murine models of B cell lymphoma.

In summary, we have constructed and characterized a novel fusion protein in which IFN-α was linked to an antibody recognizing a TAA. Our results indicate that fusion of IFN-α to a tumor-specific antibody can dramatically increase the efficacy of IFN-α with antitumor activity observed without any apparent toxicity. Remarkably, the Ab-IFN-α fusion protein was effective against established tumors. Therefore, IFN (e.g., IFN-α) fused to a tumor-specific antibody shows promise for the treatment of B cell lymphoma.

Example 2

Anti-CD20-IFNα Fusion Proteins

Introduction

Out initials studies had indicated that a fusion protein with anti-HER2/neu joined to IFN-α was an effective therapeutic for the treatment of HER2/neu expressing lymphoma. We sought to extend these studies to show that fusion of IFN-α with anti-CD20 would be an effective therapeutic for treating CD20 expressing lymphomas. CD20 is present on virtually all lymphomas. However, it should be noted that HER2/neu is expressed on many cancers and it would be expected that the anti-HER2/neu fusion protein would be effective in treating these. In the anti-CD20 fusion protein, we would expect the IFN-α in the fusion protein to both exert a direct cytotoxic effect against the tumor cells and to help elicit an anti-tumor immune response.

Produce Recombinant Antibodies Specific for CD20.

The variable regions for anti-CD20 (rituximab) were amplified and cloned into expression vectors for the production of chimeric antibodies with human kappa light chains and gamma 3 heavy chains. Protein was produced and its ability to recognize CD20 examined using flow-cytometry and the human B-cell line Daudi. As shown in FIG. 8, the recombinant protein binds as well as rituximab a recombinant IgG1.

Produce Antibody Fusion Proteins with Human Interferon Joined to Antibodies Specific for CD20 a. Design of Fusion Protein

In our initial attempt to make a fusion protein we joined IFN-α to the carboxy-terminus of the human IgG3 gene using a flexible glycine-serine linker consisting of (Gly$_4$Ser)$_3$ (SEQ ID NO:5). The heavy chain is shown diagrammatically in FIG. 9.

After verifying that the fusion protein vector had the correct nucleotide sequence, it was transfected with the chimeric anti-CD20 light chain into NS0 cells. Transfectants were screened by ELISA for the production of IgG. The clone giving the highest signal was expanded and following sub-cloning was grown in roller bottles. Supernatants were then passed through protein A Sepharose columns, and the bound proteins eluted and analyzed by SDS-PAGE both unreduced and following reduction (see, FIG. 10). Although the isolated protein was assembled into H$_2$L$_2$ molecules, most of the isolated protein was smaller than expected. Following reduction, most of the heavy chains were smaller than expected and ran at the same position as a gamma-3 heavy chain lacking a fusion protein. It appeared that the interferon was being removed from the fusion protein by proteolysis. Western blot analysis using anti-Fc and anti-interferon, confirmed that both of the upper bands were heavy chains, but only the largest contained interferon.

Flexible linkers can be a target of proteolytic cleavage. Therefore, we shortened the linker to only one copy of Gly$_4$Ser (SEQ ID NO:6). These vectors and vectors with the extended linker were transiently transfected along with the appropriate light chain into HEK293T-cells. Cells were radiolabeled by growth in $^{35}$S-methionine, immunoglobulins precipitated with protein A and analyzed by SDS-PAGE (FIG. 11). Whereas cleavage of fusion proteins with extended linkers is readily apparent, cleavage does not take place when the linker consists of only one Gly$_4$Ser (SEQ ID NO:6). Therefore, the linker used to produce the fusion protein is important and can influence its stability.

b. Recognition of CD20 by the Fusion Proteins

To determine if the fusion protein recognizes CD20, the human cell line Daudi which expresses CD20 was incubated with RITUXAN®, anti-DNS/IgG3-hu-IFN-α or anti-CD20/IgG3-hu-IFN-α. The anti-CD20/IgG3-hu-IFN-α bound better than RITUXAN® (FIG. 12). The anti-DNS/IgG3-hu-IFN-α fusion also showed some binding, although less than either CD20 specific protein. We hypothesize that the binding of the anti-DNS/IgG3-hu-IFN-α and the enhanced binding of anti-CD20/IgG3-hu-IFN-α compared to RITUXAN® is because the hu-IFN-α moiety binds to IFN receptors expressed on the Daudi cells The Timmerman laboratory has produced a transfectant of the murine lymphoma 38C13 that expresses human CD20. Both RITUXAN® and anti-CD20/IgG3-mu-IFN-α bound the transfectant. Anti-DNS/IgG3-mu-IFN-α showed no binding (FIG. 13).

c. Anti-Viral Activity of the Fusion Proteins

To assess the anti-viral activity of the hu-IFN-α fusion proteins, HeLa cells were seeded at 2×10$^5$ cells/ml and treated with two-fold serial dilutions of fusion protein or Roferon (recombinant human interferon 2a) for 24 hrs. Cells were then infected with VSV (vesicular stomatitis virus) at a concentration of 4000 pfu/100 µl. After 72 hrs, cells were stained with 0.1% crystal violet. Protection against viral infection was determined either by quantitating the cells surviving the infection by staining with 0.1% crystal violet and determining the amount of dye in each well using a a spot densitometer of by counting the number of plaques. In both assays the fusion protein had significant IFN-α activity but was about 100-fold reduced in activity compared to Roferon.

Growth Inhibition and Killing of Daudi Lymphoma Cells with the Fusion Proteins.

Two methods were used to assess the growth inhibition/killing of lymphoma cells expressing CD20 by the fusion proteins. It should be noted that for these experiments a human cell line, Daudi, that naturally expresses CD20 was used. In the first approach Daudi cells were incubated with various concentrations of IFN-α, antibody or fusion protein for 72 hrs and growth inhibition assessed using the CellTiter 96 AQueous cell proliferation assay (FIG. 14). Although showing less IFN-α activity in the anti-viral assay, anti-CD20/IgG3-hu-IFN-α and Roferon showed a similar ability to inhibit lymphoma growth suggesting that targeting the IFN-α enhances its cytotoxic effect. Anti-CD20/IgG3+Roferon did not show enhanced activity compared to Roferon alone. Anti-DNS/IgG3-hIFN-α, RITUXAN® and anti-CD20/IgG3 only showed some growth inhibition at the highest concentration used. It should be noted that fusion protein was more active than RITUXAN® in preventing cell growth in this assay.

In the second approach, Daudi cells were incubated with various concentrations of IFN-α, antibody or fusion protein for 72 hrs and then stained with Annexin V and propidium iodide (PI) and analyzed by FLOW cytometry. Shown in FIG. 15 are the results obtained when 10 pM of the various proteins was used. Cells in the early phases of apoptosis are Annexin V$^+$PI$^-$; late apoptotic and dead cells are Annexin V$^+$PI$^+$.

These experiments demonstrate several things. RITUXAN® and anti-CD20/IgG3 both induce little to no apoptosis, even at the highest concentrations tested. As would be expected, murine IFN-α is less effective against the human cell line than is human recombinant IFN-α (Roferon) and anti-DNS/IgG3-mIFN α which would not target the tumor cells is approximately as effective as recombinant murine IFN-α. However, targeting murine IFN-α to tumor cells using anti-CD20/IgG3-mIFNα results in effective induction of cell death. Anti-CD20/IgG3-hIFNα is more effective than anti-DNS/IgG3-hIFN a, again demonstrating the contribution of cell targeting to cell killing. In this in vitro assay, Roferon and anti-CD20/IgG3-hIFNα exhibit similar activity causing cell death at concentrations as low as 1 pM (data not shown). However, it should be pointed out that in vivo CD20/IgG3-hIFNα will target and accumulate at the site of the tumor while Roferon will exhibit its activity throughout the body.

Growth Inhibition and Killing of 38C13-CD20 Lymphoma Cells with the Fusion Proteins As briefly mentioned above, the laboratory of Dr. John Timmerman has developed a murine lymphoma, 38C13-CD20, that expresses human CD20 and will grow in syngenic C3H/HeJ mice. The availability of this cell line makes it possible to examine the in vivo efficacy of our fusion proteins. 38C13-CD20 cells were incubated for 48 hours with various antibodies and fusion proteins. Killing and apoptosis were then determined by staining cells with Annexin V and PI and examining them using FLOW cytometry. When proteins were used at a concentration of 100 pM (data not shown) both recombinant mIFN-α and anti-CD20-IgG3-mIFN-α were very effective in causing apoptosis, with anti-CD20-IgG3-mIFN-α somewhat more effective that recombinant mIFN-α. Some apoptosis was induced by treating 38C13-CD20 cells with anti-DNS-IgG3-mIFN-α or RITUXAN®. Treatment with anti-CD20/IgG3 at this concentration had no effect on cell viability. When the treatment concentration was lowered to 10 pM (FIG. 16), recombinant mIFN-α and anti-CD20/IgG3-mIFN-α continued to be effective in causing apoptosis, with anti-CD20/IgG3-mIFN-α more effective that recombinant mIFN-α. Only a small amount of apoptosis was seen following treatment with anti-DNS-IgG3-mIFN-α indicating that targeting of IFN-α using anti-CD20-IgG3-mIFN-α resulted in a more effective therapeutic agent. At this concentration RITUXAN® caused little apoptosis, indicating the superiority of the anti-CD20-IgG3/mIFN-α fusion protein over the unfused anti-CD20 antibody. Again, treatment with anti-CD20/IgG3 had no effect on cell viability. At a treatment dose of 1 pM, only anti-CD20-IgG3-mIFN-α induced apoptosis in 38C13-CD20 (data not shown). At a dose of 0.1 pM, none of the treatments induced apoptosis (data not shown).

As an alternative approach, 38C13-CD20 cells were treated with the various proteins at different concentrations and inhibition of growth monitored using the MTS assay (FIG. 17). Anti-CD20/IgG3-mIFN-α was most effective in inhibiting cell growth, followed by recombinant mIFN-α. Some growth inhibition was observed with anti-DNS/IgG3-mIFN-α. Anti-CD20/IgG3 and RITUXAN® had little effect on cell growth. Thus, the results obtained in this assay mirrored what was observed when apoptosis was monitored.

Production and Characterization of Additional IgG-IFNα Fusion Proteins a. Anti-CD20-IgG1-mIFNα and Anti-CD20-IgG1-hIFNα

The initial proteins were made with IFN-α fused to a human IgG3 backbone. RITUXAN® is an IgG1. To determine if the immunoglobulin backbone influenced the properties of the fusion proteins, fusion proteins with m-IFN-α and hu-IFN-α fused to IgG1 have now been produced. They were of the expected molecular weight.

Anti-CD20/IgG1-mIFNα was evaluated for its ability to induce apoptosis of 38C13-CD20 (FIG. 18). The studies showed it to be effective, possibly even more effective than the IgG3 fusion protein.

Anti-CD20/IgG1-hIFNα was evaluated for its ability to induce apoptosis of Daudi cells. The studies showed it exhibits activity similar to anti-CD20/IgG3-hIFNα (FIG. 19).

The fusion proteins were evaluated for their ability to inhibit the growth of Daudi cells as shown in FIG. 20. IgG1 fusions with both murine and human IFNα resembled the IgG3 fusions in their ability to inhibit the growth of Daudi cells.

b. Fusion Proteins with IFN-α Joined to the IgG Backbone with an Alpha Helical Linker.

Fusion proteins were produced in which the GlySer linker was replaced with linker with the sequence A(EAAAK)$_2$A (SEQ ID NO:7). This sequence is proposed to fold as an alpha helix.

Protein was produced by transient expression in 293T cells and evaluated by SDS-PAGE. The protein assembled and was of the expected molecular weight. No cleavage of the linker was observed.

The fusion protein, anti-CD20-IgG3-hIFNα (α-helical linker) when used at the same concentration as the fusion protein with the Gly$_4$Ser (SEQ ID NO:6) linker, was found to effectively induce apoptosis of Daudi cells (FIG. 21).

In Vivo Treatment of Tumors

The 38C13 lymphoma that had been transduced by the Timmerman laboratory to express human CD20 was used for these studies. 38C13 is an aggressive lymphoma that grows in syngenic C3H/HeJ mice. The transductant, 38C13-CD20, exhibits the same growth characteristic. Thus it is possible to investigate fusion protein mediated protection in immune competent animals.

a. Treatment of Early Tumors

Mice (groups of 4) were injected subcutaneously with 5000 38C13-CD20 cells on day zero. On days 1, 2 and 3 they were treated intravenously with hepes buffered saline solution (HBSS) or 0.4 µg, 2 µg, or 10 µg of anti-CD20-m-IFN-α and tumor growth monitored. By day 20 all of the animals treated with HBSS had large tumors and had to be sacrificed. In contrast, no tumor growth was seen in animals treated with 10 µg of the fusion protein; after day 20 tumors began to grow in 3 of the four animals treated with 0.4 µg of the fusion protein and 1 of the mice treated with 2 µg. The results showed that the anti-CD20/IFN-α fusion proteins are very effective in inhibiting in vivo tumor growth and in increasing survival (see, e.g., FIG. 22).

b. The Anti-CD20-mIFNα Fusion Protein is More Effective than Either Rituximab or Anti-CD20/IgG3 in Treating Moderate Sized Tumors C3H/HeJ mice were inoculated with 5000 38C13-CD20 cells on day 0. On days 5, 6 and 7 they were treated with HBSS or 10 µg of anti-CD20-IgG1 (produced in 293T cells), anti-CD20-IgG3, rituximab or anti-CD20-IgG3-mIFNα. They were monitored for tumor growth and survival (see, e.g., FIG. 23). Anti-CD20/IgG3-mIFNα was much more effective than rituximab, anti-CD20/IgG3 or anti-CD20/IgG1 in preventing the growth of moderate sized tumors.

The Tumor Targeting Ability of the Fusion Protein Significantly Enhances its Efficacy in Vivo.

C3H/H3J mice were inoculated with 5000 38C13-CD20 cells on day 0 and treated on days 5, 6 and 7 with 10 µg of anti-CD20-IgG3, 10 µg of anti-CD20-IgG3+mIFN-α (dose chosen to be same moles as in fusion protein), anti-DNS-IgG3-IFNα, or anti-CD20-IgG3-mIFNα and followed for tumor growth and survival (see, e.g., FIG. 24). Anti-CD20-IgG3-IFNα significantly delayed tumor growth and promoted survival indicating that targeting the IFNα to the tumor using the antibody combining site makes it a more effective therapeutic than either a fusion protein that does not target the fused IFNα (anti-DNS-IgG3-IFNα) or the injection of anti-CD20 along with IFNα that is not covalently associated (anti-CD20-IgG3+mIFN-α).

Fusion Protein Treatment is Effective Against Established Tumors

Groups of eight C3H/HeJ mice were inoculated with 5000 38C13-CD20 cells and treated on days 8, 9 and 10 with 100 µg of anti-CD20-mIFNα or HBSS. Mice were monitored for tumor growth (see FIG. 25) and survival (see, FIG. 26). Mice inoculated with anti-CD20-mIFNα shows improved survival (FIG. 26).

Repeat Treatment with Fusion Protein Leads to Improved Efficacy

In the initial experiments, mice were treated with a single round of injections that significantly delayed tumor onset and enhanced survival. However, some animals eventually developed tumors. To determine if repeated dosing with anti-CD20-mIFNα could completely prevent tumor growth mice were treated with two additional doses of 30 µg of fusion protein twelve and nineteen days following the initial treatments. As shown in FIG. 27. Following the two additional treatments, 87% of the animals were tumor free after 60 days indicating that they had been cured of their tumor. Importantly, there was no evidence of IFN-mediated toxicity in the treated animals whose normal cells express the murine IFNR. These results suggest that with an optimized treatment schedule, 38C13-huCD20 tumor growth can be completely prevented and that appropriate application of the fusion protein in the clinic can cure clinical disease.

Targeting IFNα Results in an Improved Anti-Tumor Activity

To quantify the IFNα activity of the fusion protein, MTS assay measuring cell viability were performed on the non-CD20 expressing parental 38C13 cells. Using 38C13 cells, anti-CD20-IFNα and anti-DNS-mIFNα had equivalent ability to inhibit the proliferation of non-CD20 expressing 38C13 (FIG. 28). However, their activities were about 300-fold reduced compared to recombinant mIFNα. In contrast anti-CD20-mIFNα had 105-fold higher anti-proliferative activity than non-targeted control anti-DNS-mIFNα against 38C13 cells that expressed CD20 (38C13-CD20) indicating that targeting of IFNα significantly enhances its efficacy. Compared to recombinant murine IFNα, anti-CD20-mIFNa had 103-fold higher anti-proliferative activity against 38C13-CD20. These experiments illustrate two important points. First the fusion protein has reduced IFN activity which would be expected to decrease its toxicity. Secondly, targeting by the fusion protein enhances its activity so that it is more potent that recombinant IFNα in inhibiting cell proliferation.

IFNAR Expression is Required for Anti-Tumor Activity of Anti-CD20-mIFNα Activity IFNα has potent immunostimulatory and antitumor activities. It can act on tumor cells directly by inducing apoptosis upon binding to its receptor IFNAR on the cell surface, or indirectly by recruiting host immune cells such as NK cells into the tumor microenvironment to promote tumor killing. To distinguish between these possibilities, we used an shRNA approach to generate 38C13-huCD20 IFNAR KD, a cell line with decreased expression of IFNAR (MFI=11) compared to its parent 38C13-huCD20 (MFI=20) (FIG. 29A). Knockdown of IFNAR did not affect CD20 expression as determined by flow cytometry (data not shown). In vitro apoptosis studies showed that 38C13-huCD20 IFNAR KD had a decreased sensitivity to fusion protein treatment. At 48 hours post-treatment with 1000 pM of anti-CD20-mIFNα, 57% of parental 38C13-huCD20 cells were apoptotic compared to only 13% of the 38C13-huCD20 IFNAR KD cells (FIG. 29B). Strikingly, in animal studies, the treatment regimen which had previously been effective against 38C13-huCD20 failed to delay or prevent tumor onset in mice inoculated with 38C13-huCD20 IFNAR. The in vivo growth kinetics of 38C13-huCD20 IFNAR KD were similar to those of the parental cell line 38C13-huCD20 (data not shown). Thus, IFNAR expression is required for anti-CD20-mIFNα-mediated activity in vivo. Data from these in vivo studies suggest that the anti-tumor effect of anti-CD20-mIFNα is mediated primarily and possibly exclusively through the induction of tumor cell death via a direct interaction between targeted IFNα and its receptor present on the surface of tumor cells.

Anti-CD20-hIFNα is Active Against Human Cells and Completely Cures Established Human Xenograft Tumors.

In this example, the effect of anti-CD20-hIFNα on human xenografts tumors was investigated. Five to seven mice per group were inoculated subcutaneously with Daudi cells and treated as indicated in FIG. 35 with three weekly doses of 30 μg fusion protein, the equivalent molar concentration of rituximab, or HBSS. Treatment was administered 30, 37 and 44 days post tumor inoculation (arrows) to mice with tumors at least 0.5 cm in diameter. HBSS was injected as a control. Symbols represent individual mice. Panel D: Survival curves for the mice whose tumor growth is shown in panels A-C. *P=0.02.

When activity was evaluated using the human lymphoma Daudi, consistent with what had been observed in the murine tumor model, anti-CD20-hIFNα had far higher proapoptotic activity than rituximab or the combination of rituximab and hIFNα. Importantly, the fusion protein was effective at very low doses where rituximab treatment did not induce significant levels of apoptosis.

One problem with rituximab treatment is that a subset of treated patients become refractory to treatment. A goal is to find an effective treatment for this patient population. rituximab resistant (RR) resistant clones of the human B cell lymphoma Ramos have been isolated by growth in stepwise increasing concentrations of rituximab for 10 week after which single cell clones were isolated (Jazirehi et al. (2007) *Cancer Res.* 67:1270). Increased expression of Bcl-2, Bcl-xL, Mcl-1 and hyperactivation of the NF-kB and ERK1/2 pathways was seen in the RR clones. We have obtained these cells and show that RR1 is more sensitive to treatment with anti-CD20hIFNα than is Ramos (FIG. 31). Thus, anti-CD20hIFNα holds promise for the treatment of rituximab resistant patients although it is not certain that the rituximab resistance seen in the patients results from the same changes as those seen in the cultured cells.

Example 3

Evaluation of Targeted Interferon-β

All type I IFNs are recognized by a single shared receptor composed of two transmembrane proteins IFNAR1 and IFNAR2. At the level of receptor recruitment, a prominent feature of IFN-β compared to IFN-α2 is a stronger binding to the receptor. The half-life of the complex with IFNAR2-EC is about 20-fold higher for IFN-β compared to IFN-α2 and the affinity of IFNAR1-EC for IFN-β is two orders of magnitude higher than for IFN-α2. IFN-α2 and IFN-β have very similar anti-viral activity, but differ significantly in their antiproliferative activity, with IFN-β being significantly more potent. Like IFN-α, IFN-β shows activity against malignancies. IFN-β has frequently been found to be more effective than IFN-α against non-hematopoietic tumors such as melanoma. Because of these differences, especially the higher affinity of IFN-β for the IFN-receptor, we have now evaluated the efficacy of anti-CD20-IFN-β fusion proteins.

The data showed that fusion proteins with murine IFN-β are extremely effective in inhibiting lymphoma proliferation (FIG. 32). The untargeted anti-DNS-mIFN-β is more active than mIFN-β on a molar basis, although it should be noted that there are two molecules of IFN-β per mole of fusion protein. As is seen with the IFN-α fusion proteins, targeting the fusion protein to the antigen CD20 expressed on the surface of the lymphoma makes it even more potent. Comparison of the IFN-β fusion proteins with the IFN-α fusion proteins showed that the IFN-β fusion proteins are even more potent.

Anti-CD20hIFN-β is Effective in Preventing Growth of Human Lymphoma Cells.

The antibody fusion proteins are effective in preventing the proliferation of Daudi cell. Daudi expressed human CD20 and anti-CD20hIFN-β is more effective than anti-DNShIFN-β showing that targeting to antigens expressed on the surface of the lymphoma cells makes the fusion protein more potent (FIG. 33). In contrast to what was seen with the murine IFN-β, the fusion proteins are not as active as recombinant human IFN-β.

Anti-CD20-mIFNβ is Effective Against Cells Expressing Low Levels of the IFN Receptor.

As shown in FIG. 34 and Table 5, anti-CD20-mIFNβ☐ is effective against cells expressing low levels of the IFN receptor.

TABLE 5

Efficacy of fusion proteins against cells expressing low levels of the interferon receptor.

|  | Anti-CD20-mIFN-β | Anti-DNS-mIFN-β | Anti-CD20-mIFN-α | Anti-DNS-mIFN-α |
|---|---|---|---|---|
| IC$_{50}$ (pM) 38C13-CD20 | 2.2 | 16.12 | 76.4 | 409.3 |
| IC$_{50}$ (pM) 38C13-CD20 - IFNR Knock Down | 10.1 | 102.0 | 848.4 | Not calculated |

IC$_{50}$ (pM) of 38C13-CD20 and 38C13-CD20 IFNR Knock-Down cells treated with the indicated proteins.

In addition, anti-CD20-mIFNβ causes apoptosis in 38C13CD20 cells in which the level of IFN receptor expression has been decreased using shRNA. Targeted anti-CD20-mIFNβ is more effective than non-targeted anti-DNS-mIFNβ or recombinant mIFNβ at similar concentrations These studies show that targeted anti-CD20-mIFNβ is effective against cells that express only low levels of the IFNR. Targeted anti-CD20-mIFNα was not effective against these cells. This is consistent with the higher affinity of IFNβ for the IFNR and suggests that fusion proteins with IFNβ may be effective against cells that do not respond to IFNα treatment.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of inhibiting growth and/or proliferation of a rituximab-resistant cancer cell, said method comprising contacting said cancer cell with a chimeric construct comprising an interferon attached to an antibody that binds to a tumor-associated antigen, wherein said antibody is attached to said interferon by a linker where the amino acid sequence of said linker consists of the sequence SGGGGS (SEQ ID NO:81) or AEAAAKEAAAKAGS (SEQ ID NO:82), wherein said construct when contacted to said rituximab-resistant cancer cell results in the killing or inhibition of growth or proliferation of said cancer cell.

2. The method of claim 1, wherein said cancer cell is a metastatic cell.

3. The method of claim 1, wherein said cancer cell is in a solid tumor.

4. The method of claim 1, wherein said cancer cell is a breast cancer cell.

5. The method of claim 1, wherein said cancer cell is a B cell lymphoma.

6. The method of claim 1, wherein said cancer cell is cell produced by a cancer selected from the group consisting of a B cell lymphoma, lung cancer, a bronchus cancer, a colorectal cancer, a prostate cancer, a breast cancer, a pancreas cancer, a stomach cancer, an ovarian cancer, a urinary bladder cancer, a brain or central nervous system cancer, a peripheral nervous system cancer, an esophageal cancer, a cervical cancer, a melanoma, a uterine or endometrial cancer, a cancer of the oral cavity or pharynx, a liver cancer, a kidney cancer, a biliary tract cancer, a small bowel or appendix cancer, a salivary gland cancer, a thyroid gland cancer, an adrenal gland cancer, an osteosarcoma, a chondrosarcoma, a liposarcoma, a testes cancer, and a malignant fibrous histiocytoma.

7. The method of claim 1, wherein:
said contacting comprises systemically administering said chimeric moiety to a mammal; or
said contacting comprises administering said chimeric moiety directly into a tumor site; or
said contacting comprises intravenous administration of said chimeric moiety.

8. The method of claim 1, wherein said cancer cell is a cancer cell in a human.

9. The method of claim 1, wherein said cancer cell is a cancer cell in a non-human mammal.

10. The method of claim 1, wherein said interferon is an interferon alpha.

11. The method of claim 1, wherein said interferon is an interferon beta.

12. The method of claim 1, wherein said construct is a recombinantly expressed fusion protein.

13. The method of claim 1, wherein said antibody specifically binds a marker selected from the group consisting of CD20, HER3, HER2/neu, MUC-1, G250, mesothelin, gp100, tyrosinase, and MAGE.

14. The method of claim 1, wherein said antibody is an antibody that binds CD20.

15. The method of claim 14, wherein said antibody that comprises the complementarity determining regions (CDRs) of anti-CD20 (rituximab).

16. The method of claim 14, wherein said antibody comprises the variable regions of anti-CD20 (rituximab).

17. The method of claim 1, wherein said antibody is an antibody that binds HER2.

* * * * *